United States Patent
Li

(10) Patent No.: US 9,711,739 B2
(45) Date of Patent: Jul. 18, 2017

(54) TETRADENTATE METAL COMPLEXES CONTAINING INDOLOACRIDINE AND ITS ANALOGUES

(71) Applicant: Arizona Board of Regents on behalf of Arizona State University, Scottsdale, AZ (US)

(72) Inventor: Jian Li, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/168,910

(22) Filed: May 31, 2016

(65) Prior Publication Data

US 2016/0359120 A1    Dec. 8, 2016

Related U.S. Application Data

(60) Provisional application No. 62/170,049, filed on Jun. 2, 2015, provisional application No. 62/274,456, filed on Jan. 4, 2016.

(51) Int. Cl.
| | |
|---|---|
| C07F 15/00 | (2006.01) |
| H01L 51/50 | (2006.01) |
| H01L 51/00 | (2006.01) |
| C09K 11/06 | (2006.01) |
| H01L 51/42 | (2006.01) |

(52) U.S. Cl.
CPC ........ *H01L 51/0084* (2013.01); *C07F 15/006* (2013.01); *C07F 15/0086* (2013.01); *C09K 11/06* (2013.01); *H01L 51/0087* (2013.01); *C09K 2211/1029* (2013.01); *C09K 2211/185* (2013.01); *H01L 51/42* (2013.01); *H01L 51/5016* (2013.01)

(58) Field of Classification Search
CPC ................................ C07F 15/00; H01L 51/50
USPC ........................................... 546/10; 313/504
See application file for complete search history.

(56) References Cited

U.S. PATENT DOCUMENTS

| | | | |
|---|---|---|---|
| 4,769,292 A | 9/1988 | Tang et al. | |
| 5,707,745 A | 1/1998 | Forrest et al. | |
| 5,844,363 A | 12/1998 | Gu et al. | |
| 6,303,238 B1 | 10/2001 | Thompson et al. | |
| 6,780,528 B2 | 8/2004 | Tsuboyama et al. | |
| 7,002,013 B1 | 2/2006 | Chi et al. | |
| 7,037,599 B2 | 5/2006 | Culligan et al. | |
| 7,279,704 B2 | 10/2007 | Walters et al. | |
| 7,332,232 B2 | 2/2008 | Ma et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,947,383 B2 | 5/2011 | Ise et al. | |
| 8,389,725 B2 | 3/2013 | Li et al. | |
| 8,617,723 B2 | 12/2013 | Stoessel | |
| 8,816,080 B2 | 8/2014 | Li et al. | |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Wong; Challenges in organometallic research—Great opportunity for solar cells and OLEDs, Journal of Organometallic Chemistry, 2009, 694, 2644-2647.

(Continued)

*Primary Examiner* — Charanjit Aulakh
(74) *Attorney, Agent, or Firm* — Fish & Richardson P.C.

(57) ABSTRACT

Platinum, palladium, and gold tetradentate metal complexes of Formulas I and II including indoloacridine.

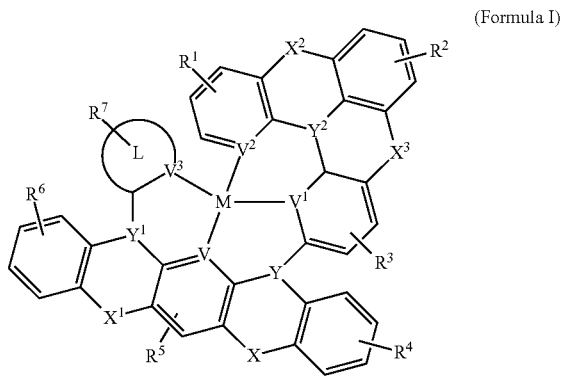

(Formula I)

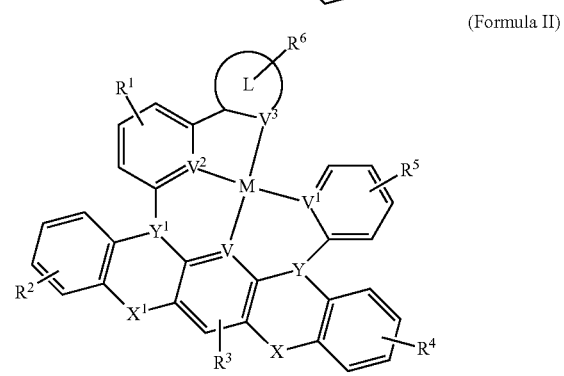

(Formula II)

The complexes are suitable for use as phosphorescent or delayed fluorescent and phosphorescent emitters in display and lighting applications.

19 Claims, 5 Drawing Sheets

(56) References Cited

U.S. PATENT DOCUMENTS

| | | | |
|---|---|---|---|
| 8,871,361 B2 | 10/2014 | Xia et al. | |
| 8,927,713 B2 | 1/2015 | Li et al. | |
| 8,946,417 B2 | 2/2015 | Jian et al. | |
| 9,059,412 B2 | 6/2015 | Zeng et al. | |
| 9,224,963 B2 | 12/2015 | Li et al. | |
| 9,238,668 B2 | 1/2016 | Li et al. | |
| 9,312,505 B2 * | 4/2016 | Brooks | C07F 15/0086 |
| 9,324,957 B2 | 4/2016 | Li et al. | |
| 9,382,273 B2 | 7/2016 | Li | |
| 9,385,329 B2 | 7/2016 | Li et al. | |
| 9,425,415 B2 | 8/2016 | Li et al. | |
| 9,461,254 B2 | 10/2016 | Tsai et al. | |
| 9,550,801 B2 | 1/2017 | Li et al. | |
| 2002/0068190 A1 | 6/2002 | Tsuboyama et al. | |
| 2003/0062519 A1 | 4/2003 | Yamazaki et al. | |
| 2005/0170207 A1 | 8/2005 | Ma et al. | |
| 2005/0260446 A1 | 11/2005 | Mackenzie et al. | |
| 2006/0073359 A1 | 4/2006 | Ise et al. | |
| 2006/0094875 A1 | 5/2006 | Itoh et al. | |
| 2006/0202197 A1 | 9/2006 | Nakayama et al. | |
| 2006/0210831 A1 | 9/2006 | Sano et al. | |
| 2006/0263635 A1 | 11/2006 | Ise | |
| 2006/0286406 A1 | 12/2006 | Igarashi et al. | |
| 2007/0057630 A1 | 3/2007 | Nishita et al. | |
| 2007/0059551 A1 | 3/2007 | Yamazaki | |
| 2007/0082284 A1 | 4/2007 | Stoessel et al. | |
| 2007/0103060 A1 | 5/2007 | Itoh et al. | |
| 2008/0001530 A1 | 1/2008 | Ise et al. | |
| 2008/0036373 A1 | 2/2008 | Itoh et al. | |
| 2008/0054799 A1 | 3/2008 | Satou | |
| 2008/0079358 A1 | 4/2008 | Satou | |
| 2008/0241518 A1 | 10/2008 | Satou et al. | |
| 2008/0241589 A1 | 10/2008 | Fukunaga et al. | |
| 2009/0026936 A1 | 1/2009 | Satou et al. | |
| 2009/0026939 A1 | 1/2009 | Kinoshita et al. | |
| 2009/0032989 A1 | 2/2009 | Karim et al. | |
| 2009/0039768 A1 | 2/2009 | Igarashi et al. | |
| 2009/0079340 A1 | 3/2009 | Kinoshita et al. | |
| 2009/0128008 A1 | 5/2009 | Ise et al. | |
| 2009/0218561 A1 | 9/2009 | Kitamura et al. | |
| 2009/0261721 A1 | 10/2009 | Murakami et al. | |
| 2009/0267500 A1 | 10/2009 | Kinoshita et al. | |
| 2010/0000606 A1 | 1/2010 | Thompson et al. | |
| 2010/0013386 A1 | 1/2010 | Thompson et al. | |
| 2010/0171111 A1 | 7/2010 | Takada et al. | |
| 2012/0095232 A1 | 4/2012 | Li et al. | |
| 2012/0181528 A1 | 7/2012 | Takada et al. | |
| 2012/0215001 A1 | 8/2012 | Li et al. | |
| 2012/0223634 A1 | 9/2012 | Xia et al. | |
| 2012/0302753 A1 | 11/2012 | Li | |
| 2013/0048963 A1 | 2/2013 | Beers et al. | |
| 2013/0168656 A1 | 7/2013 | Tsai et al. | |
| 2013/0203996 A1 | 8/2013 | Li et al. | |
| 2013/0237706 A1 | 9/2013 | Li et al. | |
| 2013/0341600 A1 | 12/2013 | Lin et al. | |
| 2014/0014922 A1 | 1/2014 | Lin et al. | |
| 2014/0027733 A1 | 1/2014 | Zeng et al. | |
| 2014/0084261 A1 | 3/2014 | Brooks et al. | |
| 2014/0114072 A1 | 4/2014 | Li et al. | |
| 2014/0203248 A1 | 7/2014 | Zhou et al. | |
| 2014/0330019 A1 | 11/2014 | Li et al. | |
| 2014/0364605 A1 | 12/2014 | Li et al. | |
| 2015/0008419 A1 | 1/2015 | Li | |
| 2015/0028323 A1 | 1/2015 | Xia et al. | |
| 2015/0069334 A1 | 3/2015 | Xia et al. | |
| 2015/0105556 A1 | 4/2015 | Li et al. | |
| 2015/0162552 A1 | 6/2015 | Li et al. | |
| 2015/0194616 A1 | 7/2015 | Li et al. | |
| 2015/0228914 A1 | 8/2015 | Li et al. | |
| 2015/0287938 A1 | 10/2015 | Li et al. | |
| 2015/0318500 A1 | 11/2015 | Li | |
| 2015/0349279 A1 | 12/2015 | Li et al. | |
| 2016/0028028 A1 | 1/2016 | Li et al. | |
| 2016/0043331 A1 | 2/2016 | Li et al. | |
| 2016/0072082 A1 | 3/2016 | Brooks et al. | |
| 2016/0133862 A1 | 5/2016 | Li et al. | |
| 2016/0197291 A1 | 7/2016 | Li et al. | |
| 2016/0285015 A1 | 9/2016 | Li et al. | |
| 2016/0359125 A1 | 12/2016 | Li et al. | |
| 2017/0005278 A1 | 1/2017 | Li et al. | |
| 2017/0012224 A1 | 1/2017 | Li et al. | |
| 2017/0047533 A1 | 2/2017 | Li et al. | |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |

(56) References Cited

FOREIGN PATENT DOCUMENTS

| JP | 5604505 | 10/2014 |
|---|---|---|
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| WO | WO0070655 | 11/2000 |
| WO | WO2004003108 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029186 | 2/2016 |

OTHER PUBLICATIONS

JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).

Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Barry O'Brien et al.: White organic light emitting diodes using Pt-based red, green and blue phosphorescent dopants. Proc. SPIE, vol. 8829, pp. 1-6, Aug. 25, 2013.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate $O^\wedge N^\wedge C^\wedge N$ Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate $O^\wedge N^\wedge C^\wedge N$ ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.

(56) References Cited

OTHER PUBLICATIONS

Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Murakami; JP 2007258550, English machine translation from EPO, Oct. 4, 2007. 80 pages.
Murakami; JP 2007324309, English machine translation from EPO, Dec. 13, 2007, 89 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.

\* cited by examiner

TETRADENTATE METAL COMPLEXES CONTAINING INDOLOACRIDINE AND ITS ANALOGUES

CROSS-REFERENCE TO RELATED APPLICATIONS

This application claims priority to U.S. Provisional Patent Application No. 62/170,049 entitled "TETRADENTATE METAL COMPLEXES CONTAINING INDOLOACRIDINE AND ITS ANALOGUES" filed on Jun. 2, 2015, and U.S. Provisional Patent Application No. 62/274,456 entitled "TETRADENTATE METAL COMPLEXES CONTAINING INDOLOACRIDINE AND ITS ANALOGUES" filed on Jan. 4, 2016, which are hereby incorporated by reference in their entirety.

TECHNICAL FIELD

The present disclosure relates to tetradentate metal complexes containing indoloacridine suitable for use as phosphorescent or delayed fluorescent and phosphorescent emitters in display and lighting applications.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, and devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting, and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

Tetradentate cyclometalated complexes containing indoloacridine having tunable emission wavelengths in the visible range are described. These emitters can be used in organic light emitting diodes (OLEDs), displays and lighting applications.

A first general aspect includes complexes of Formula I:

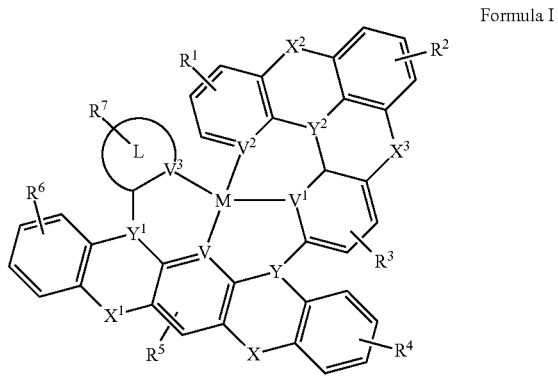

Formula I wherein:
M is Pt (II), Pd (II), or Au (III),
each of V, $V^1$, $V^2$, and $V^3$ is independently N, C, P, or Si,
each of X, $X^1$, $X^2$, and $X^3$ is independently present or absent, and each X, $X^1$, $X^2$, and $X^3$ present independently represents a single bond, $CR^8R^9$, C=O, $SiR^8R^9$, $GeR^8R^9$, $NR^8$, $PR^8$, $PR^8R^9$, $R^8P$=O, $AsR^8$, $R^8As$=O, O, S, S=O, $SO_2$, Se, Se=O, $SeO_2$, $BR^8$, $BR^8R^9$, $AlR^8$, $AlR^8R^9$, $R^8Bi$=O, or $BiR^8$,
each of Y, $Y^1$ and $Y^2$ is independently $CR^{10}$, $SiR^{10}$, $GeR^{10}$, N, P, P=O, As, As=O, B, Bi=O, or Bi,
L is a substituted or unsubstituted aryl, heteroaryl, or N-heterocyclic carbene,
each of $R^1$, $R^2$, $R^3$, $R^4$, $R^5$, $R^6$, and $R^7$ is independently absent or present as a single substituent or multiple substituents, valency permitting, and each $R^1$, $R^2$, $R^3$, $R^4$, $R^5$, $R^6$, and $R^7$ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and
each of $R^8$, $R^9$, and $R^{10}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Implementations of the first general aspect include the following.

When M is Pt or Pd and one of X, $X^1$, $X^2$, and $X^3$ is $BR^8R^9$ or $AlR^8R^9$, then one of V, $V^1$, $V^2$, and $V^3$ is C or Si.

When M is Pt or Pd and two of X, $X^1$, $X^2$, and $X^3$ are independently $BR^8R^9$ or $AlR^8R^9$, then each of V, $V^1$, $V^2$, and $V^3$ is independently N or P.

When M is Au and one of X, $X^1$, $X^2$, and $X^3$ is $BR^8R^9$ or $AlR^8R^9$, then two of V, $V^1$, $V^2$, and $V^3$ are independently C or Si.

When M is Au and two of X, $X^1$, $X^2$, and $X^3$ are independently $BR^8R^9$ or $AlR^8R^9$, then one of V, $V^1$, $V^2$, and $V^3$ is C or Si.

When M is Au and three of X, $X^1$, $X^2$, and $X^3$ are $BR^8R^9$ or $AlR^8R^9$, then each of V, $V^1$, $V^2$, and $V^3$ is independently N or P.

In some implementations of Formula I, V and $V^1$ are C; $V^2$ and $V^3$ are N; Y, $Y^1$, and $Y^2$ are N; and L is a substituted or unsubstituted pyridyl. In other implementations of Formula I, V and $V^1$ are C; $V^2$ and $V^3$ are N; Y, $Y^1$, and $Y^2$ are N; L is a substituted or unsubstituted pyridyl; X is $CR^8R^9$, and $X^1$ is a single bond.

A second general aspect includes complexes of Formula II:

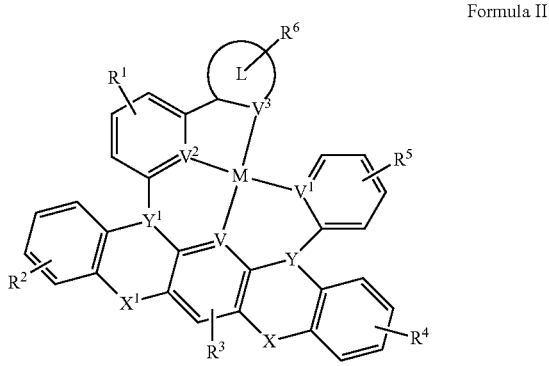

Formula II wherein:
M is Pt (II), Pd (II), or Au (III),
each of V, $V^1$, $V^2$, and $V^3$ is independently N, C, P, or Si,
each of X and $X^1$ is independently present or absent, and each X and $X^1$ present independently represents $CR^7R^8$, C=O, $SiR^7R^8$, $GeR^7R^8$, $PR^7$, $PR^7R^8$, $R^7P$=O, $AsR^7$, $R^7As$=O, O, S, S=O, $SO_2$, Se, Se=O, $SeO_2$, $BR^7$, $BR^7R^8$, $R^7Bi$=O, $BiR^7$, or a single bond,
each of Y and $Y^1$ is independently $CR^9$, $SiR^9$, $GeR^9$, N, P, P=O, As, As=O, B, Bi=O, or Bi,
L is a substituted or unsubstituted aryl, heteroaryl, or N-heterocyclic carbene,
each of $R^1$, $R^2$, $R^3$, $R^4$, $R^5$, and $R^6$ is independently absent or present as a single substituent or multiple substituents, valency permitting, and each $R^1$, $R^2$, $R^3$, $R^4$, $R^5$, and $R^6$ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and
each of $R^7$, $R^8$, and $R^9$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Implementations of the second general aspect include the following.

When M is Pt or Pd and one of X and $X^1$ is $BR^7R^8$ or $AlR^7R^8$, then one of V, $V^1$, $V^2$, and $V^3$ is C or Si.

When M is Pt or Pd and both of X and $X^1$ are independently $BR^7R^8$ or $AlR^7R^8$, then each of V, $V^1$, $V^2$, and $V^3$ is independently N or P.

When M is Au and one of X and $X^1$ is $BR^7R^8$ or $AlR^7R^8$, then two of V, $V^1$, $V^2$, and $V^3$ are independently C or Si.

When M is Au and both of X and $X^1$ are independently $BR^7R^8$ or $AlR^7R^8$, then one of V, $V^1$, $V^2$, and $V^3$ is C or Si.

In some implementations of Formula II, V and $V^2$ are C; $V^1$ and $V^3$ are N, Y and $Y^1$ are N; and L is a substituted or unsubstituted pyridyl. In other implementations of Formula II, V and $V^2$ are C; $V^1$ and $V^3$ are N, Y and $Y^1$ are N; L is a substituted or unsubstituted pyridyl; and X is a single bond. In still other implementations of Formula II, V and $V^2$ are C; $V^1$ and $V^3$ are N, Y and $Y^1$ are N; L is a substituted or unsubstituted pyridyl; X is a single bond; and $X^1$ is $CR^8R^9$.

The complexes of Formulas I and II are suitable for use as phosphorescent or delayed fluorescent and phosphorescent emitters in display and lighting applications.

A third general aspect includes one or more complexes the first and second general aspects or any combination thereof as an emitter in an organic light emitting device (OLED).

A fourth general aspect includes a lighting device, such as a photovoltaic device, an organic phototransistor, an organic photovoltaic cell, or an organic photodetector, or a luminescent display device, any one of which may include the OLED of the third general aspect.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

Figure 1:
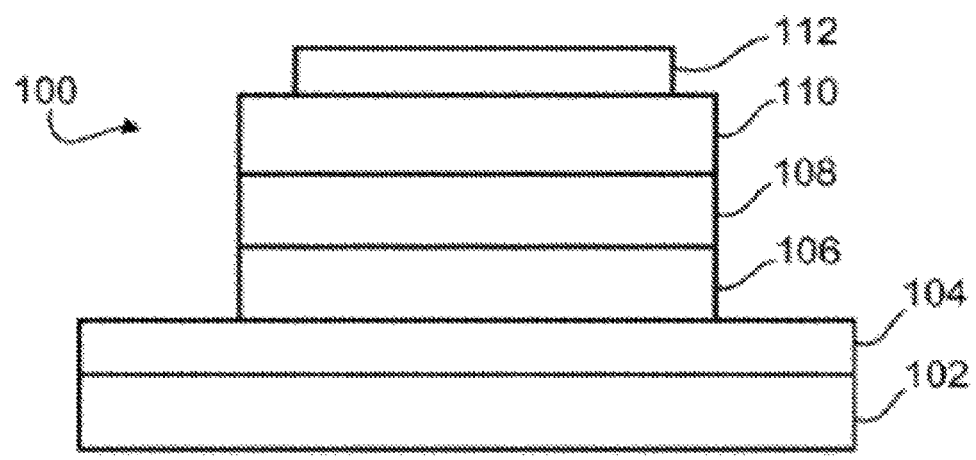
FIG. 1 depicts a cross section of an exemplary organic light-emitting diode (OLED).

Introducing an indoloacridine group to the ligand of metal complexes as described herein increases the stability of the metal complexes. Chemical structures of the emissive luminophores and the ligands may be modified, and the metal interchanged (e.g., platinum, palladium, or gold) to adjust the energy of the singlet states and the triplet states of the metal complexes, thereby allowing selection of desired optical properties of the metal complexes. The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group can connect two atoms such as, for example, a N atom and a C atom. A linking atom or group is in one aspect disclosed as X, Y, $Y^1$, $Y^2$, and/or Z herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A". "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula $-C(O)H$. Throughout this specification "C(O)" is a short hand notation for a carbonyl group, i.e., C=O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula $-NH(-alkyl)$ where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propyl amino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]$_n$—CH$_3$, and —[CH$_2$CH (COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

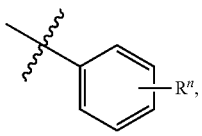

which is understood to be equivalent to a formula:

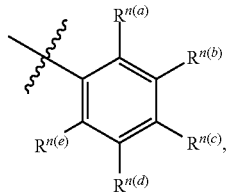

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Tetradentate cyclometalated complexes with 6-membered coordination rings represented by Formula I and Formula II are efficient emitters having tunable emission wavelengths in the visible range. These compounds have a high quantum efficiency of emission, which is proportional to the integral of the wavefunction of the ground state and the excited state, and favors a small difference in equilibrium geometry between the ground state and the excited state.

Complexes of Formula I are represented as shown below.

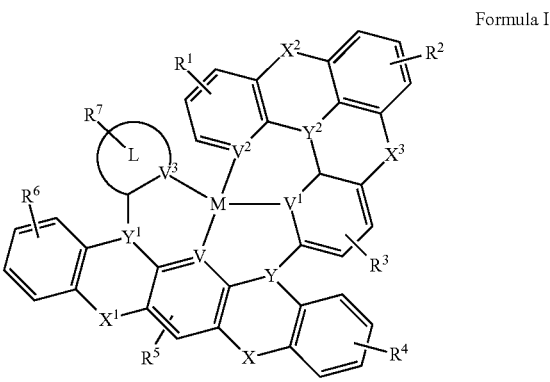

Formula I

In Formula I:
M is Pt (II), Pd (II), or Au (III),
each of V, $V^1$, $V^2$, and $V^3$ is independently N, C, P, or Si,
each of X, $X^1$, $X^2$, and $X^3$ is independently present or absent, and each X, $X^1$, $X^2$, and $X^3$ present independently represents $CR^8R^9$, C=O, $SiR^8R^9$, $GeR^8R^9$, $NR^8$, $PR^8$, $PR^8R^9$, $R^8P$=O, $AsR^8$, $R^8As$=O, O, S, S=O, $SO_2$, Se, Se=O, $SeO_2$, $BR^8$, $BR^8R^9$, $AlR^8$, $AlR^8R^9$, $R^8Bi$=O, $BiR^8$, or a single bond,
each of Y, $Y^1$ and $Y^2$ is independently $CR^{10}$, $SiR^{10}$, $GeR^{10}$, N, P, P=O, As, As=O, B, Bi=O, or Bi,
L is a substituted or unsubstituted aryl, heteroaryl, or N-heterocyclic carbene,
each of $R^1$, $R^2$, $R^3$, $R^4$, $R^5$, $R^6$, and $R^7$ is independently absent or present as a single substituent or multiple substituents, valency permitting, and each $R^1$, $R^2$, $R^3$, $R^4$, $R^5$, $R^6$, and $R^7$ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and
each of $R^8$, $R^9$, and $R^{10}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Complexes of Formula I include the following implementations.

When M is Pt or Pd and one of X, $X^1$, $X^2$, and $X^3$ is $BR^8R^9$ or $AlR^8R^9$, then one of V, $V^1$, $V^2$, and $V^3$ is C or Si.

When M is Pt or Pd and two of X, $X^1$, $X^2$, and $X^3$ are independently $BR^8R^9$ or $AlR^8R^9$, then each of V, $V^1$, $V^2$, and $V^3$ is independently N or P.

When M is Au and one of X, X², and X³ is BR⁸R⁹ or AlR⁸R⁹, then two of V, V¹, V², and V³ are independently C or Si.

When M is Au and two of X, X¹, X², and X³ are independently BR⁸R⁹ or AlR⁸R⁹, then one of V, V¹, V², and V³ is C or Si.

When M is Au and three of X, X¹, X², and X³ are BR⁸R⁹ or AlR⁸R⁹, then each of V, V¹, V², and V³ is independently N or P.

In some implementations of Formula I, V and V¹ are C; V² and V³ are N; Y, Y¹, and Y² are N; and L is a substituted or unsubstituted pyridyl. In other implementations of Formula I, V and V¹ are C; V² and V³ are N; Y, Y¹, and Y² are N; L is a substituted or unsubstituted pyridyl; X is CR⁸R⁹, and X¹ is a single bond.

Additional implementations of Formula I are shown below, in which above:

M is Pt(II), Pd(II), or Au(III), each U is independently CR⁸R⁹, C=O, SiR⁸R⁹, GeR⁸R⁹, NR⁸, PR⁸, PR⁸R⁹, R⁸P=O, AsR⁸, R⁸As=O, O, S, S=O, SO₂, Se, Se=O, SeO₂, BR⁸, BR⁸R⁹, AlR⁸, AlR⁸R⁹, R⁸Bi=O, or a single bond, each A is independently BR⁸R⁹ or AlR⁸R⁹, and

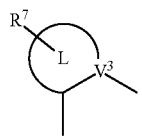

is one of

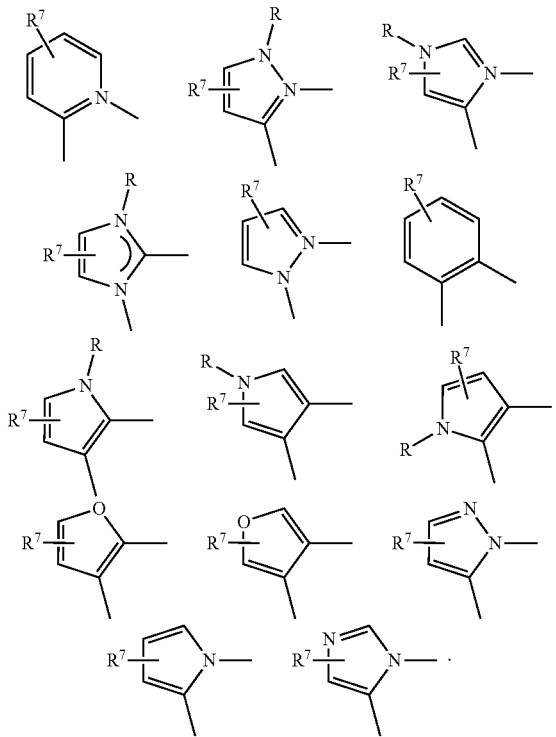

where R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

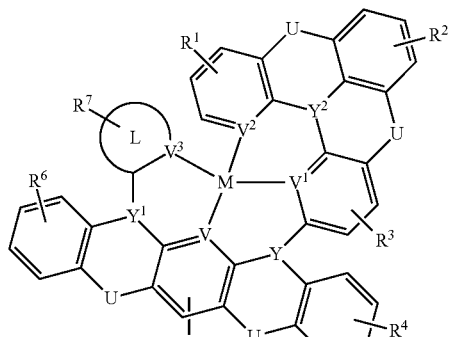

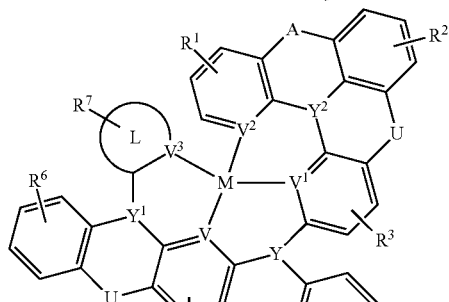

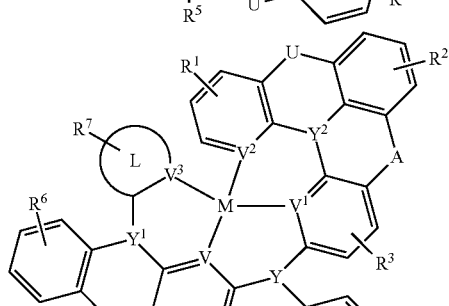

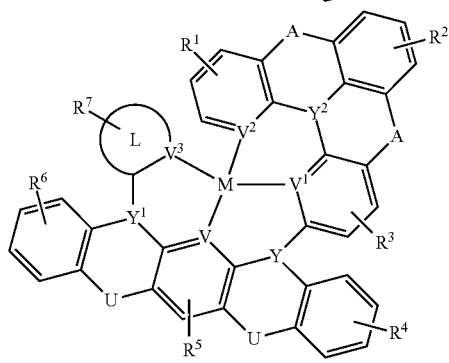

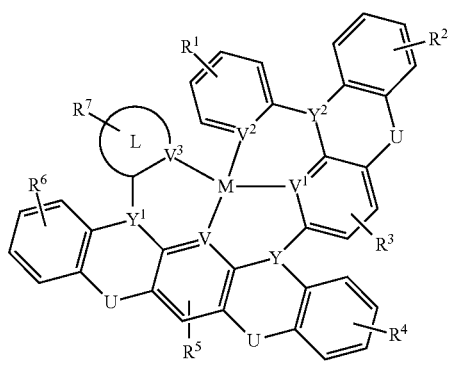
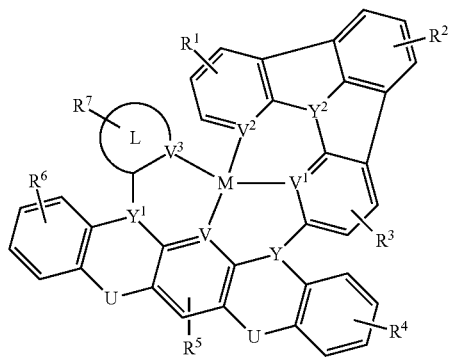
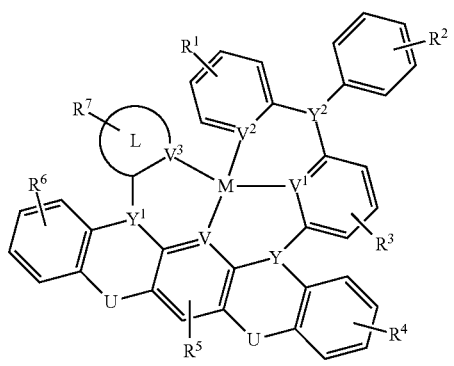
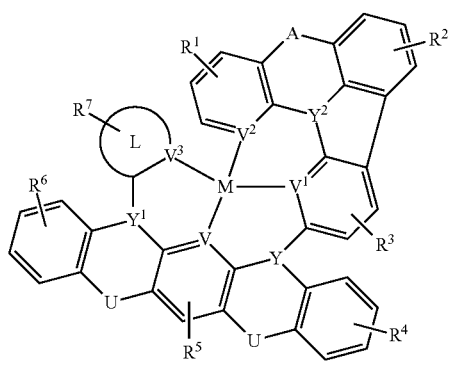
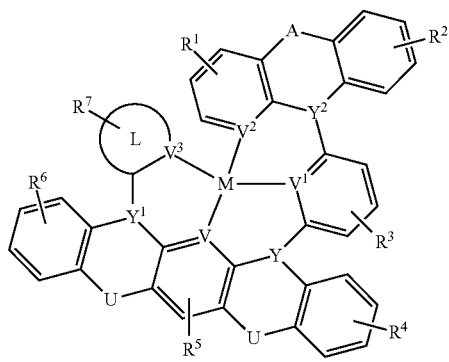
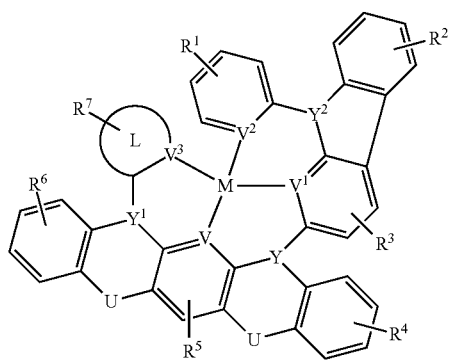

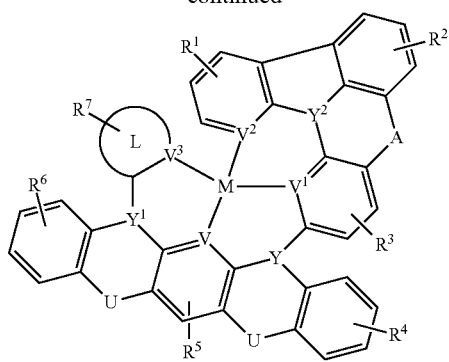
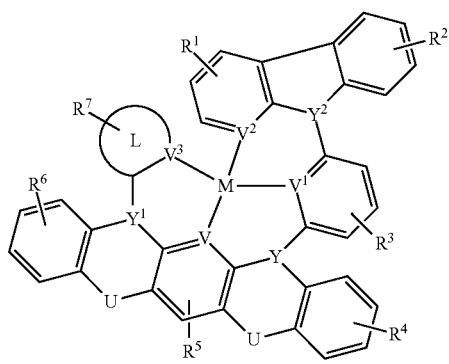
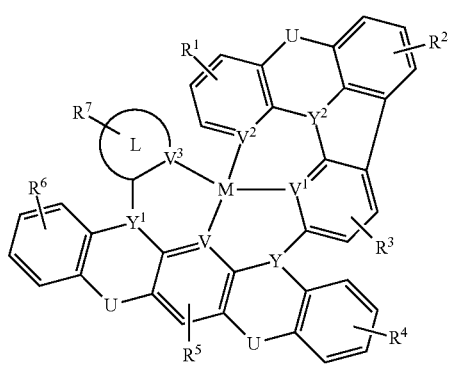
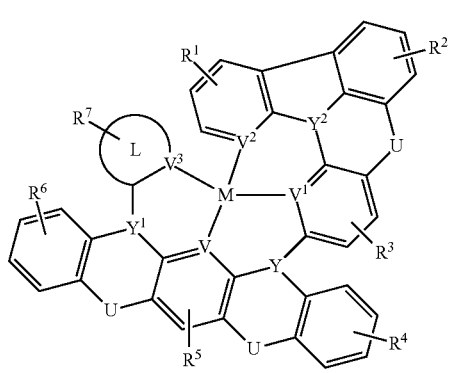
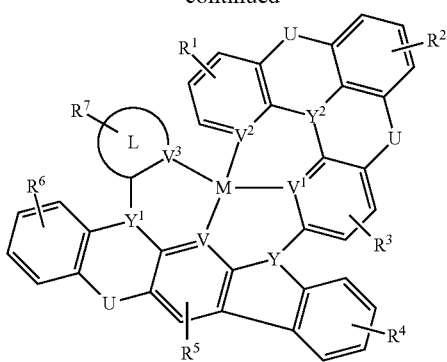
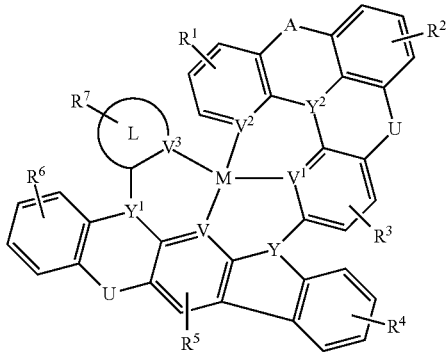
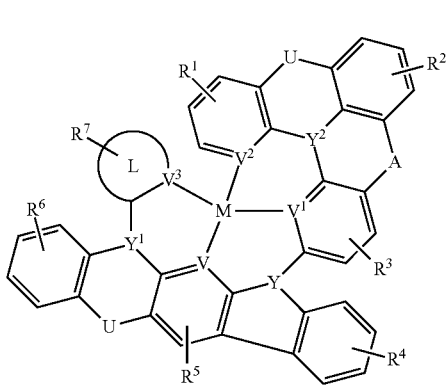
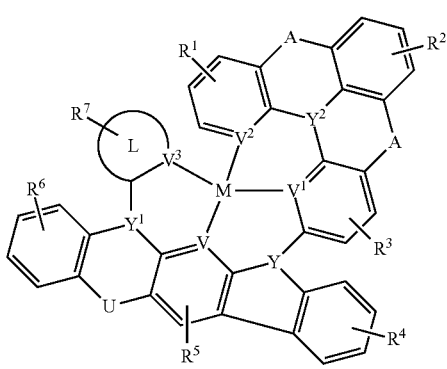

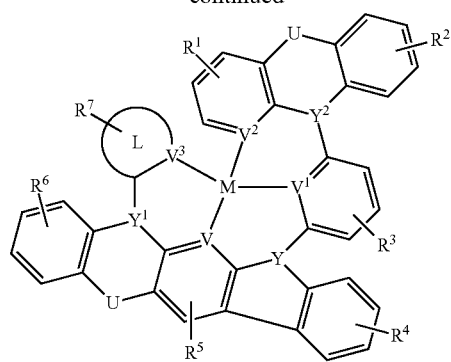
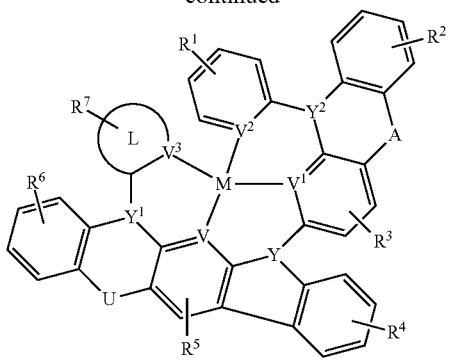
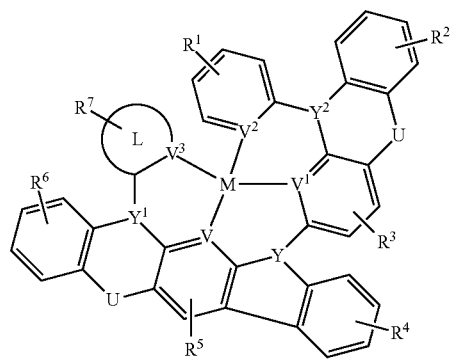
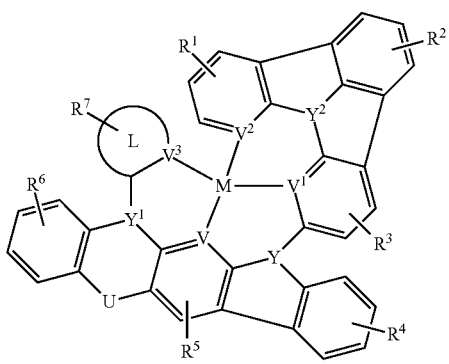
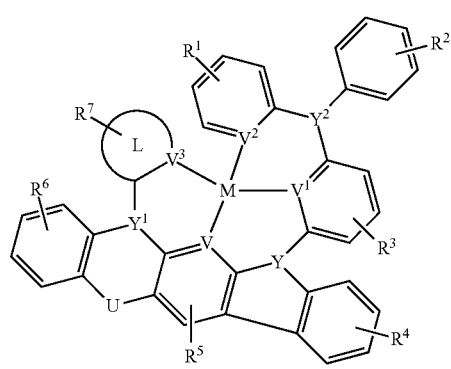
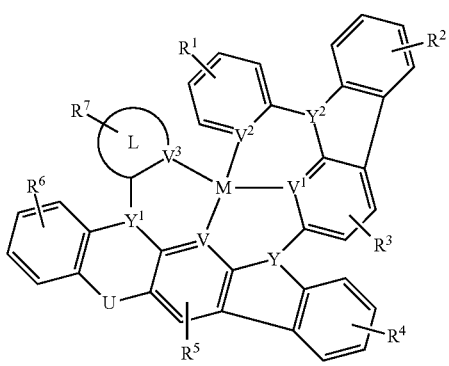
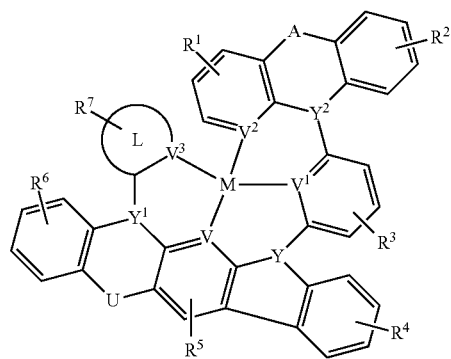

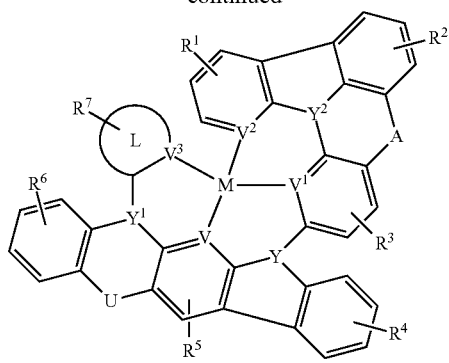
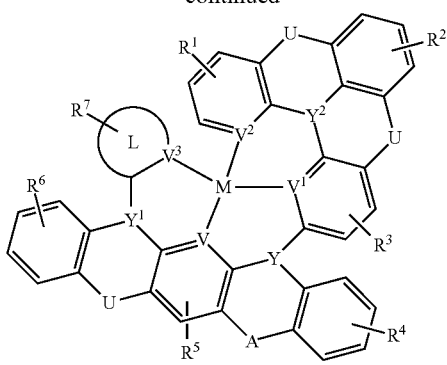
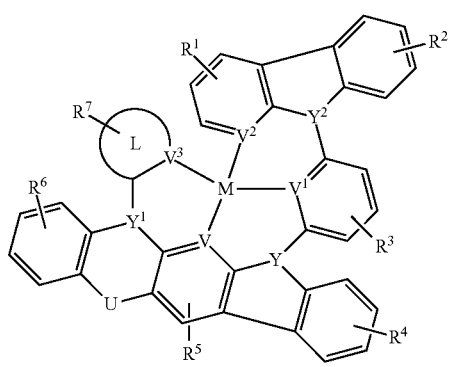
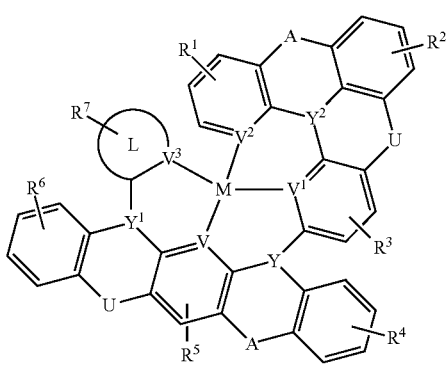
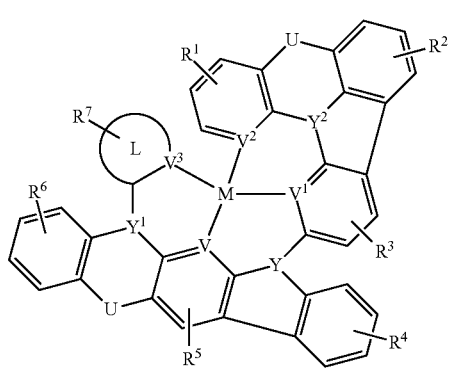
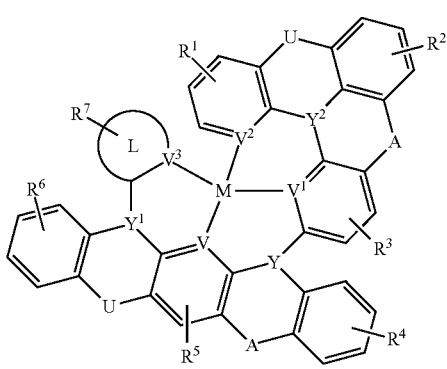
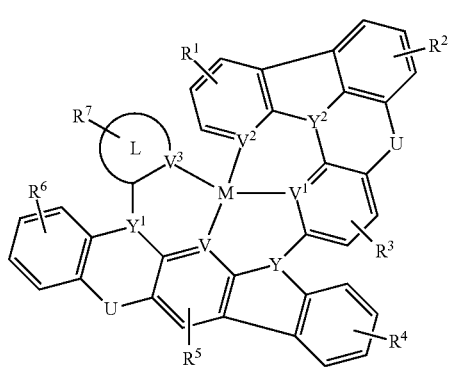
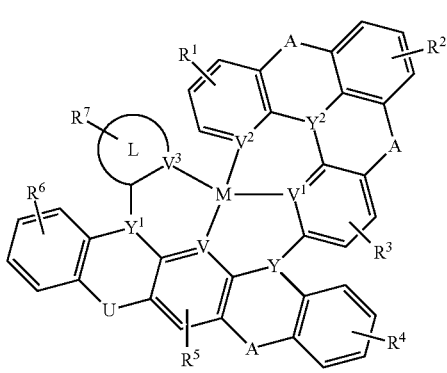

-continued
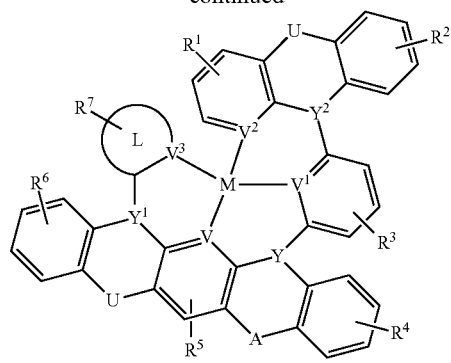
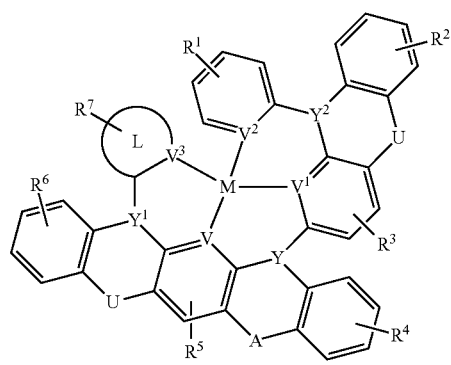
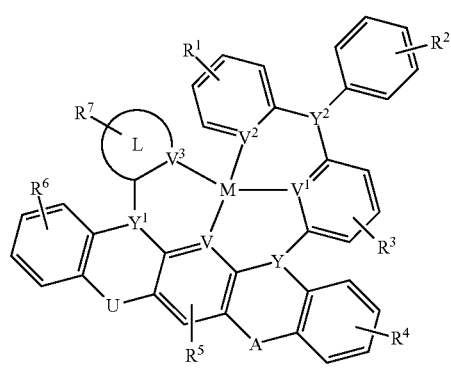
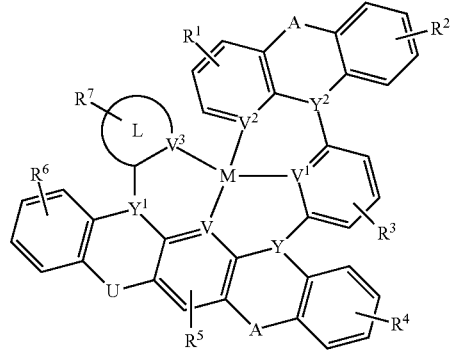
-continued
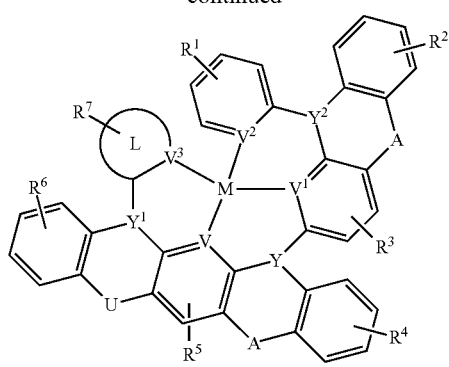
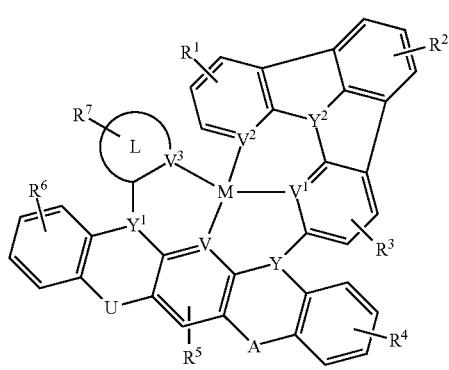
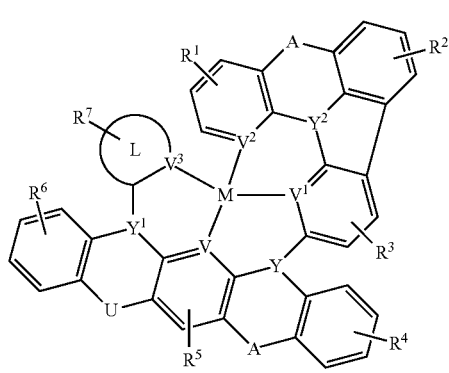
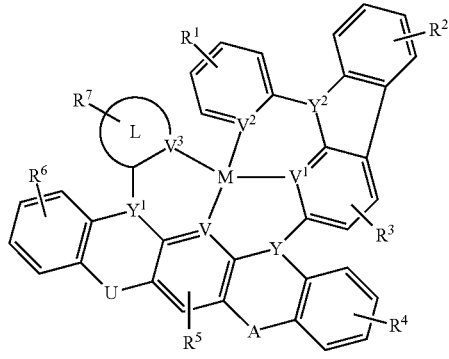

-continued
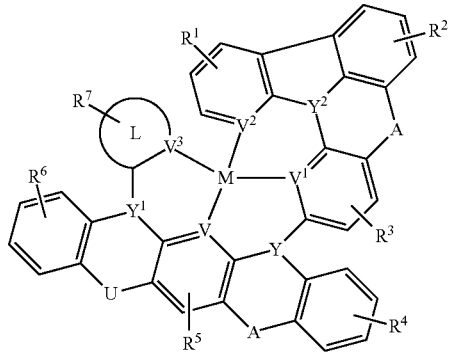
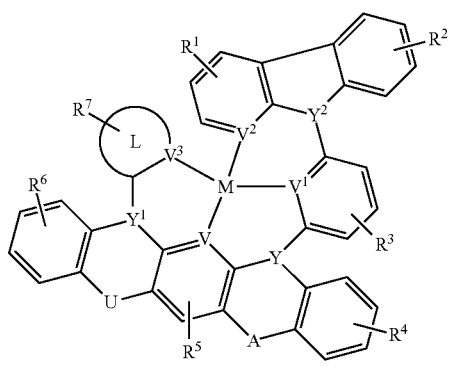
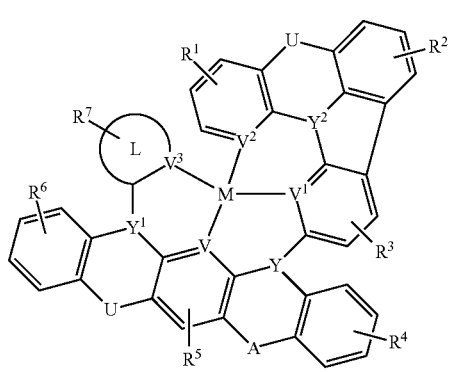
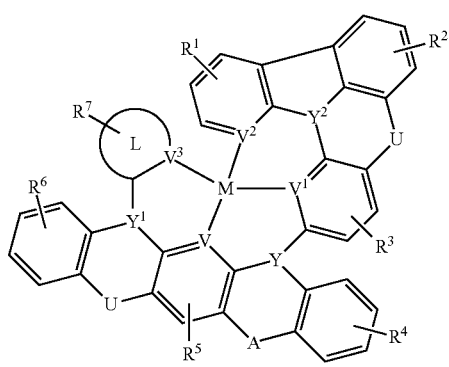
-continued
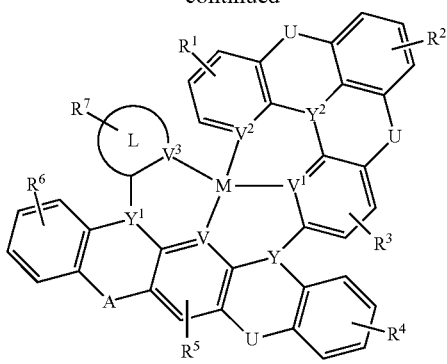
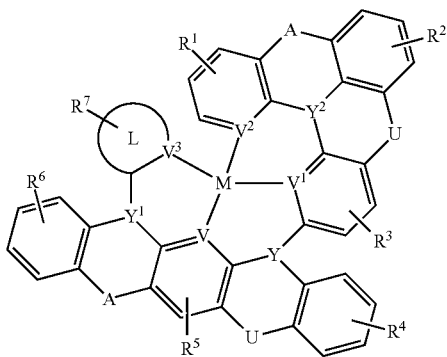
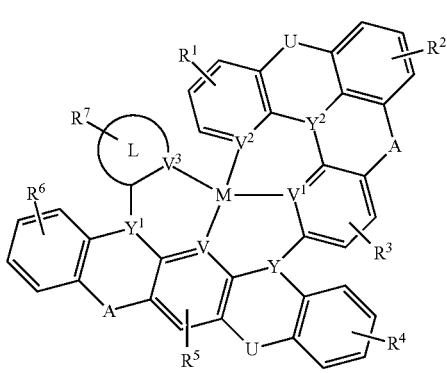
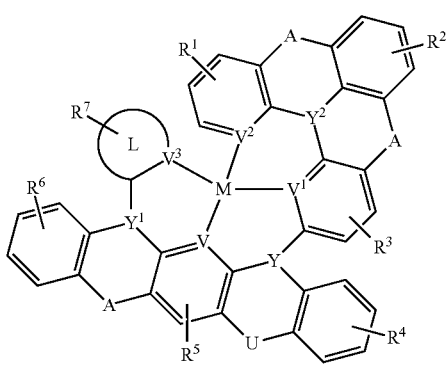

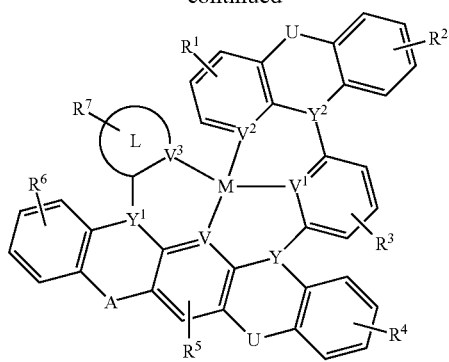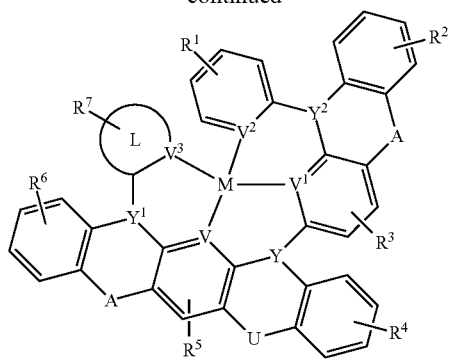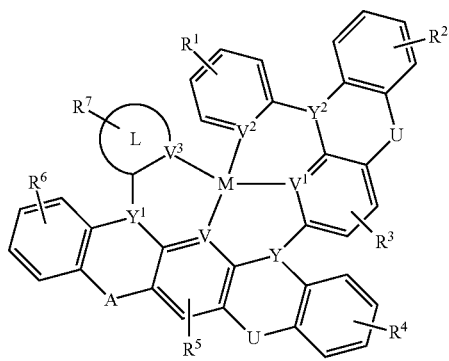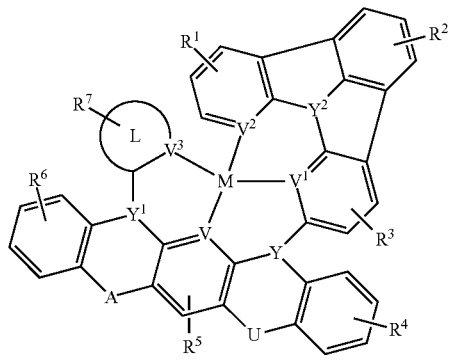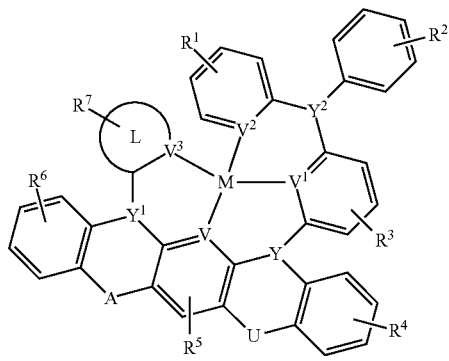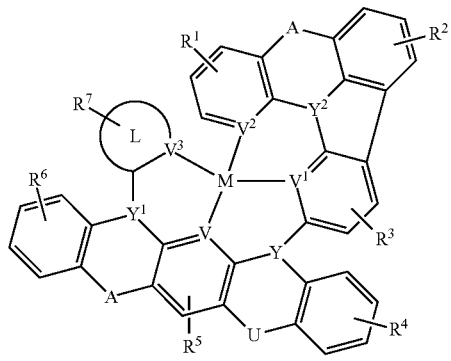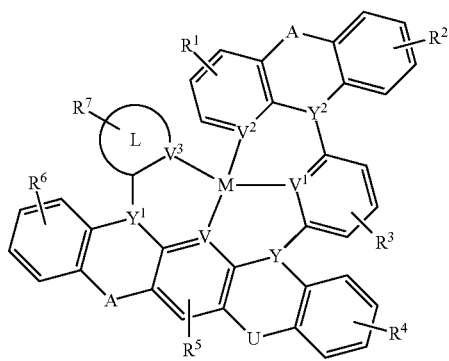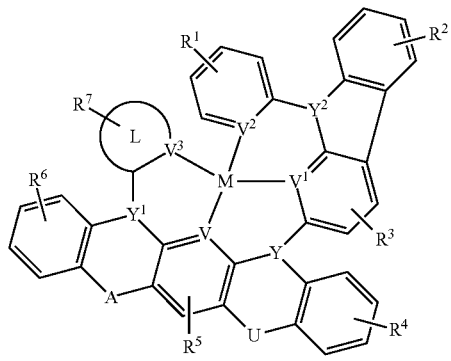

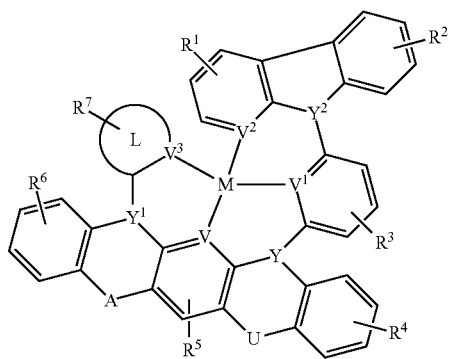
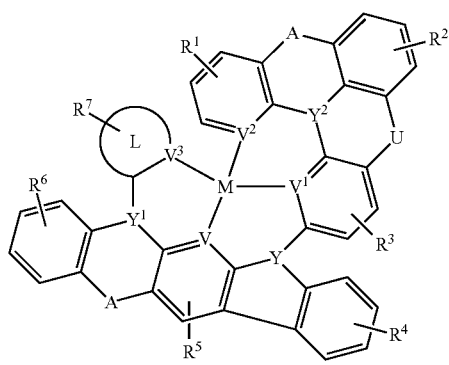
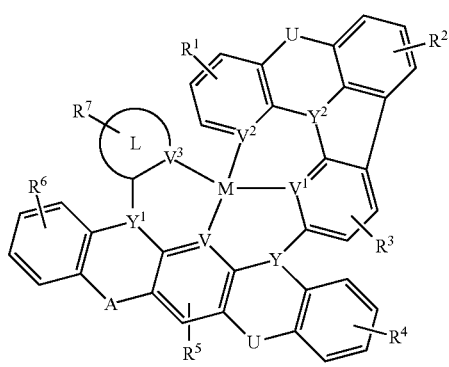
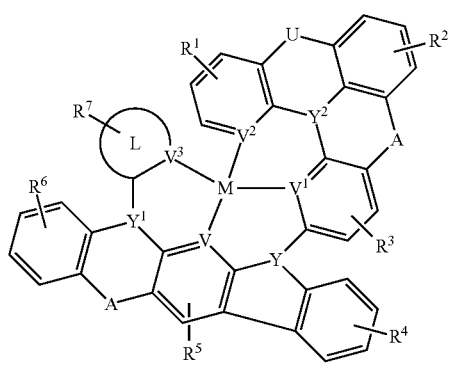

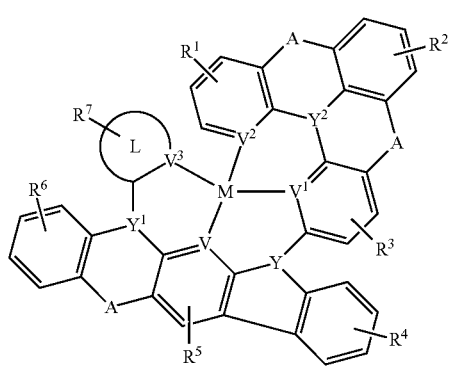

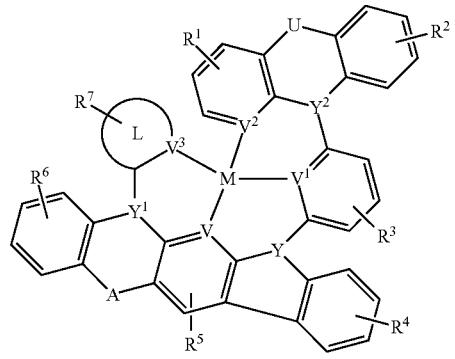
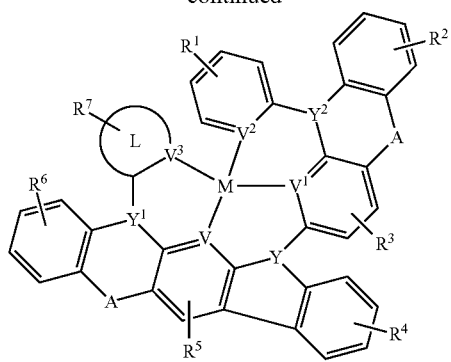

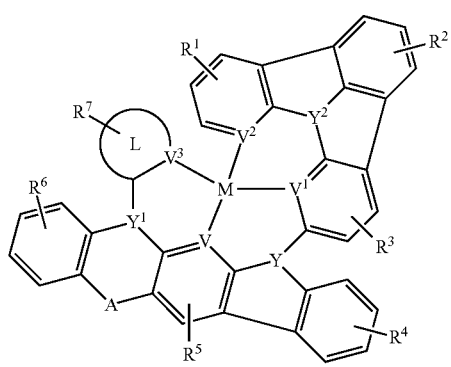

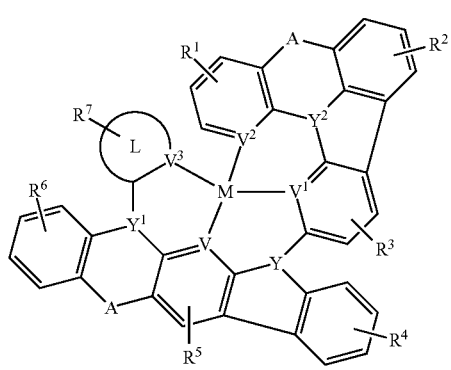
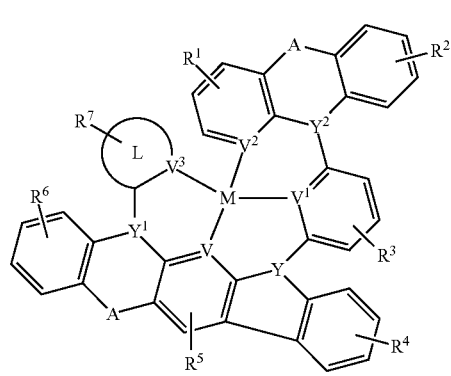
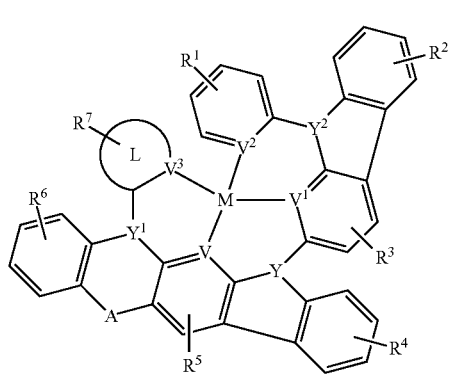

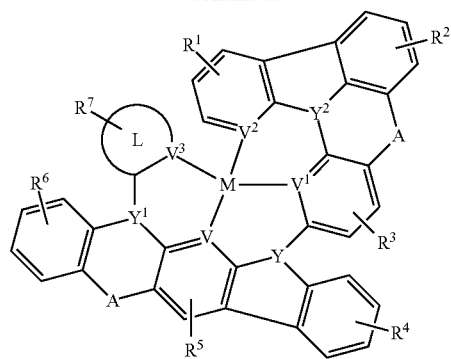
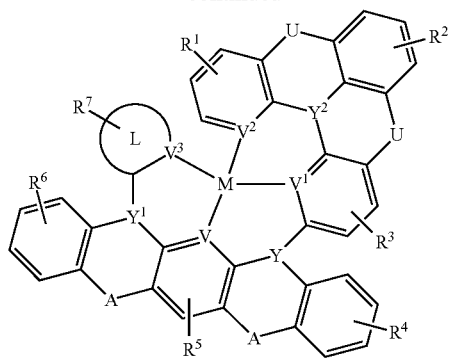
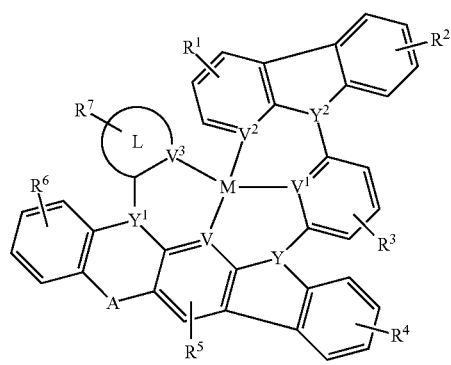
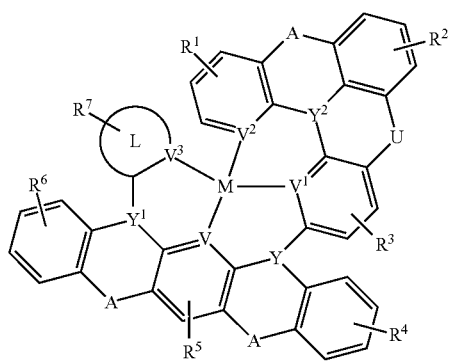
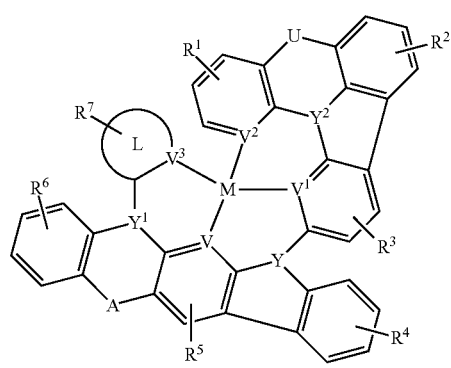
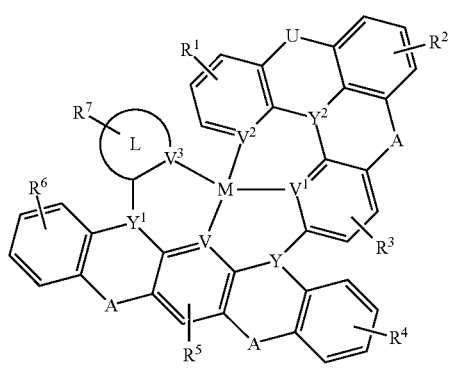
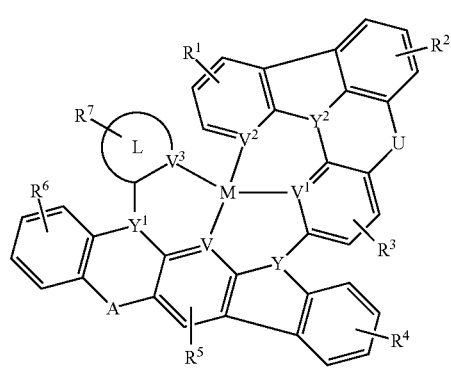
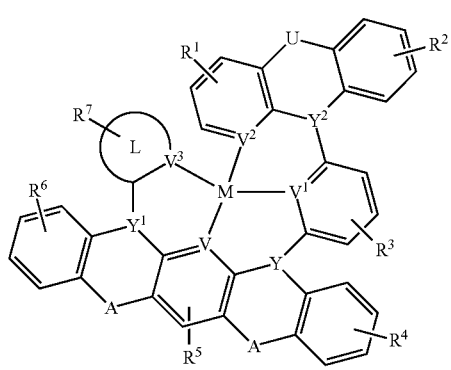

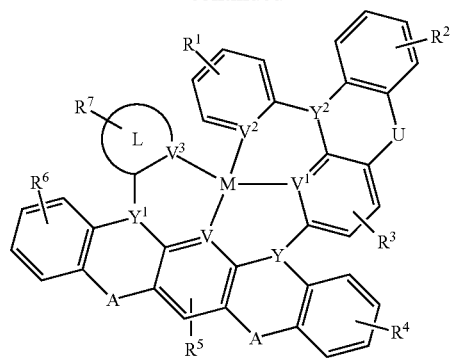
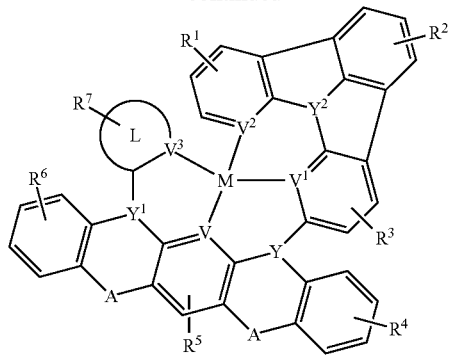

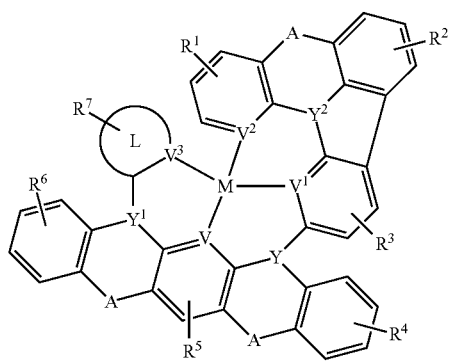

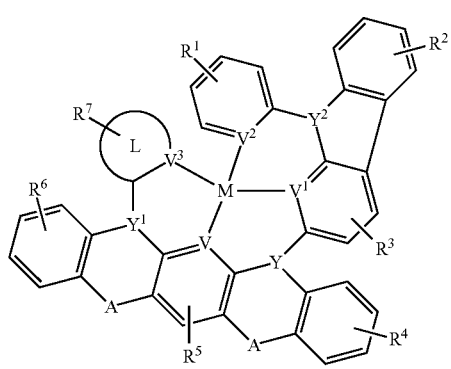
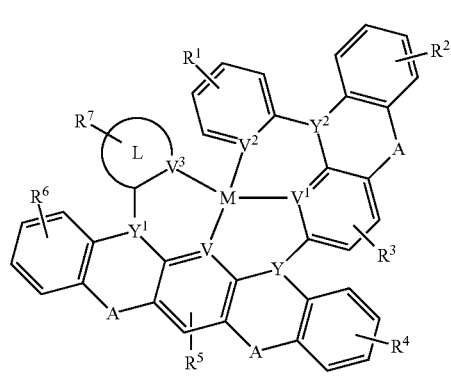
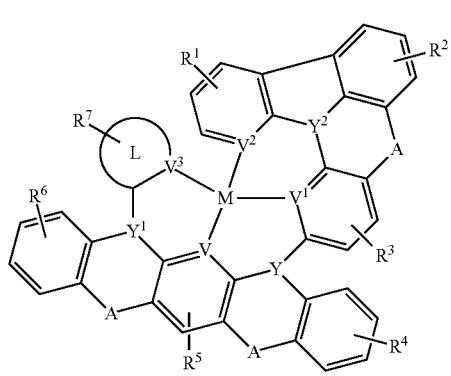

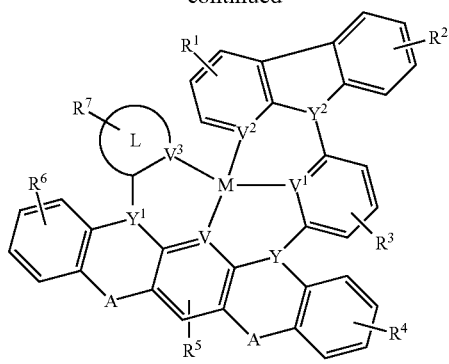
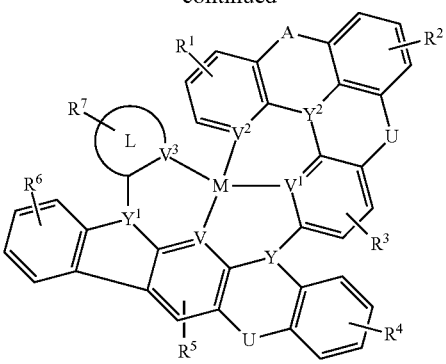
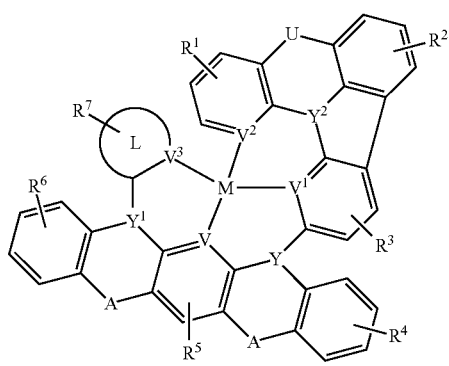
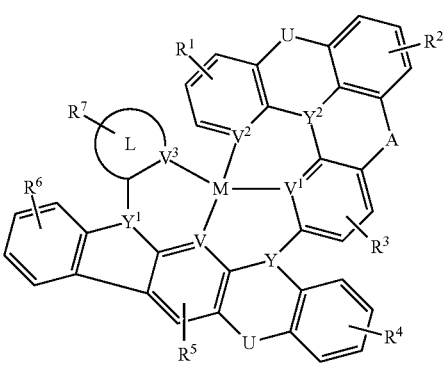
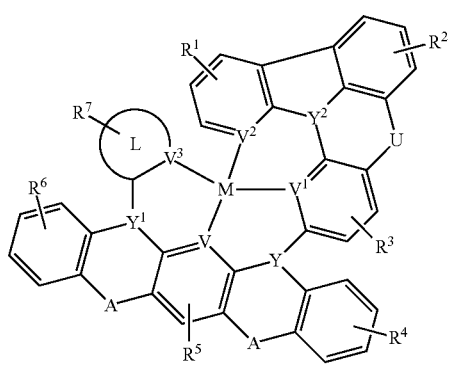
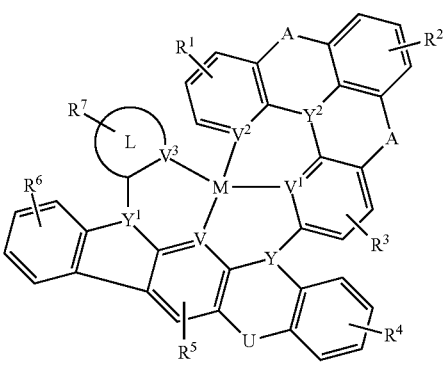
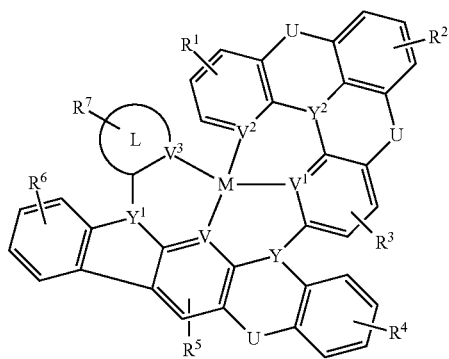
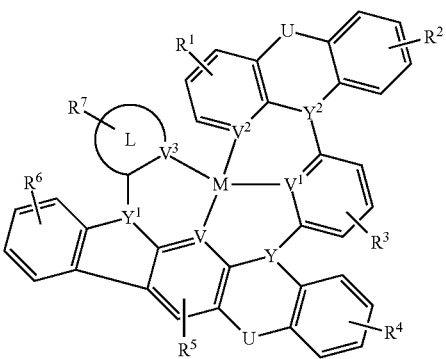

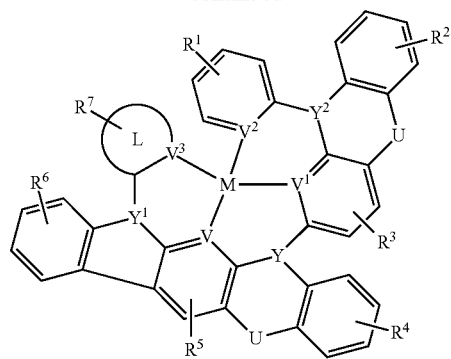
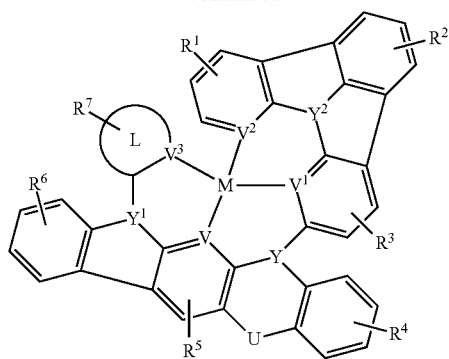
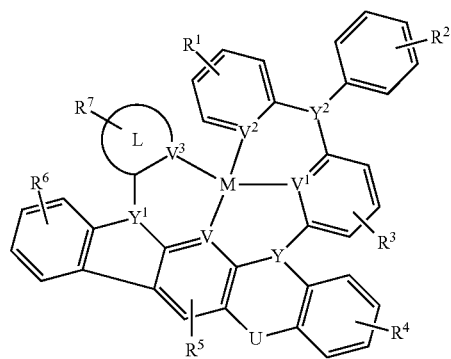
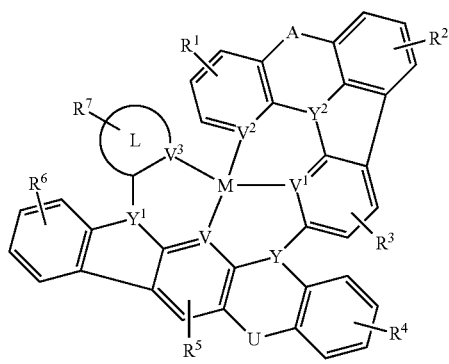
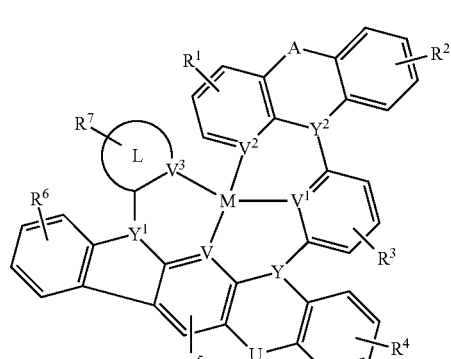
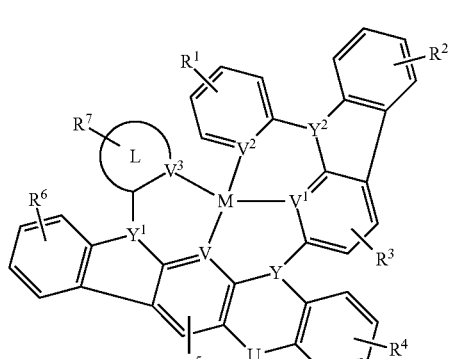
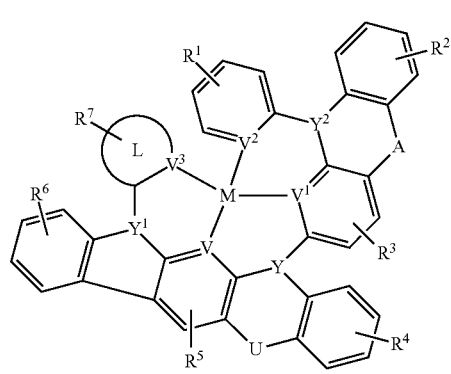
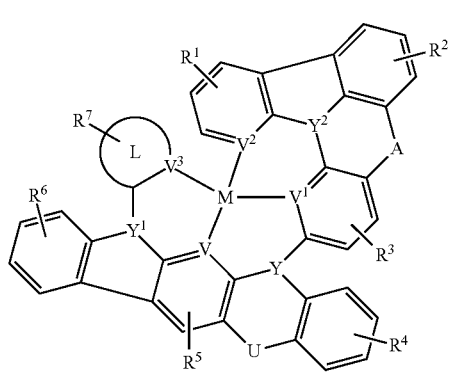

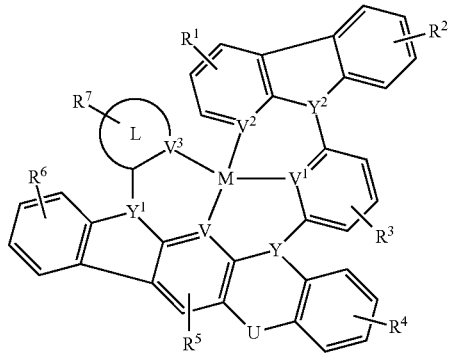
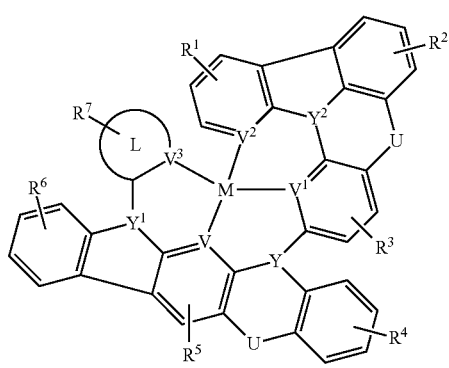
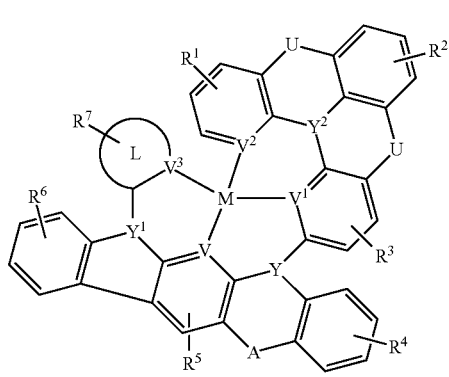
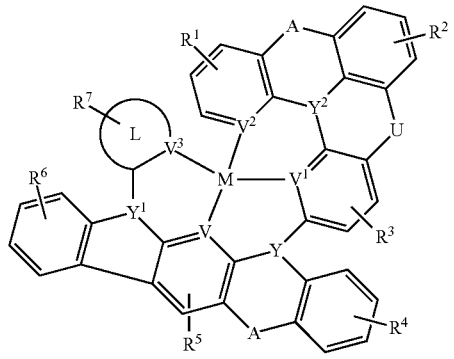
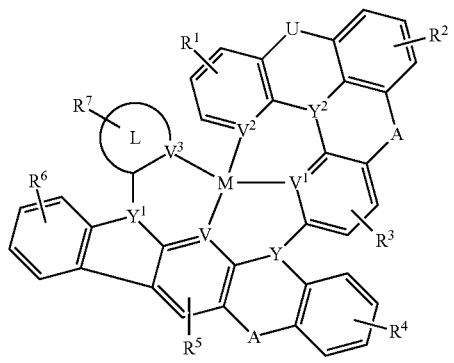
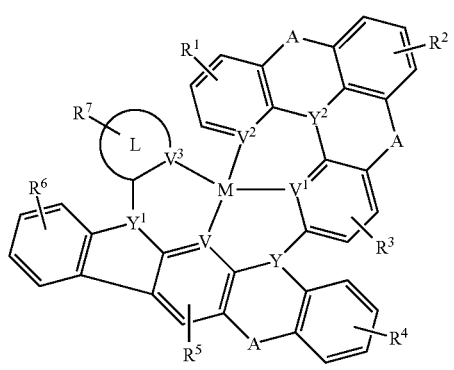
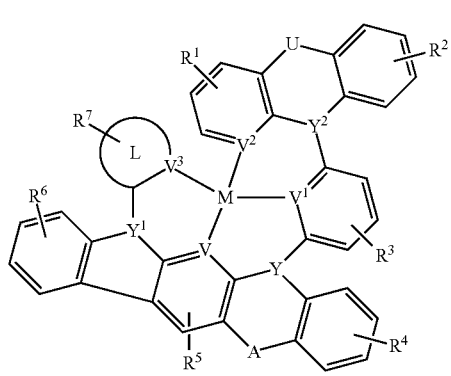

-continued
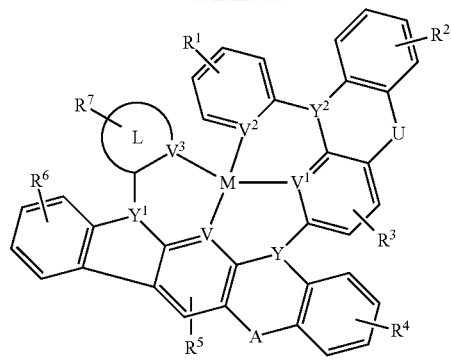
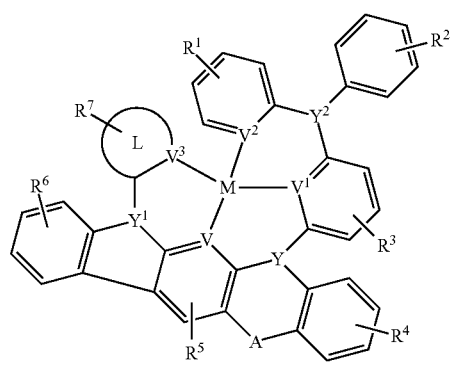
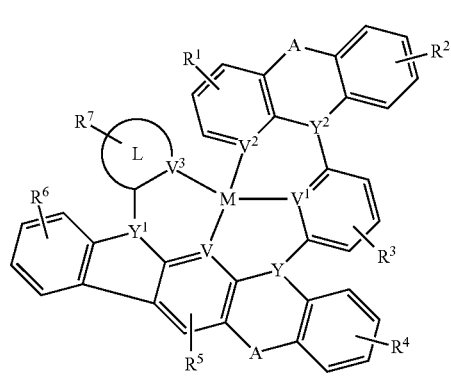
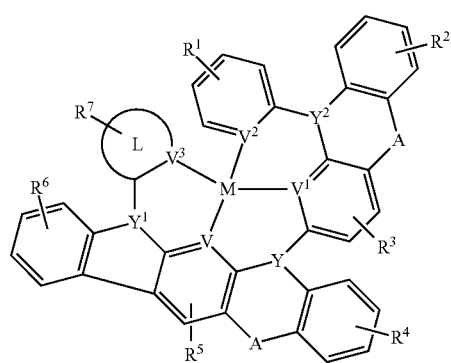
-continued
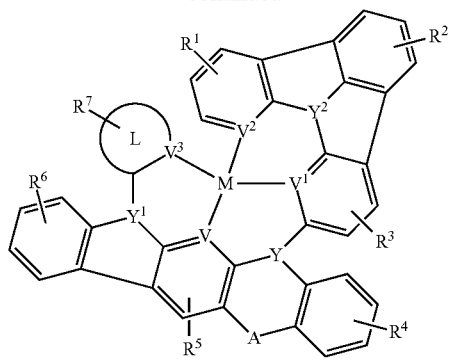
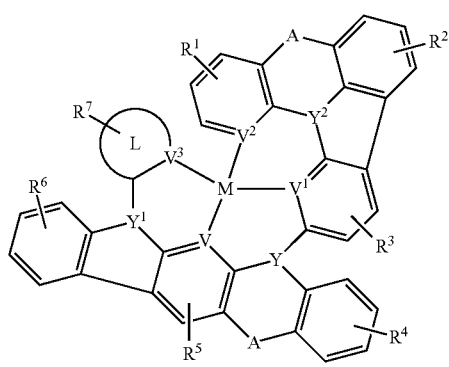
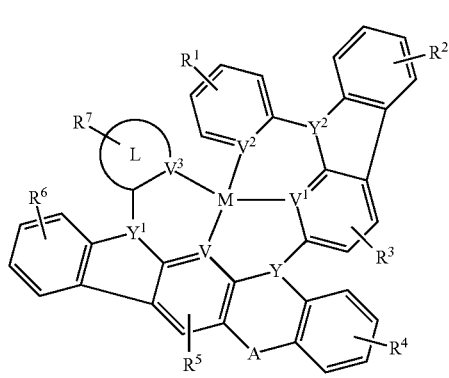
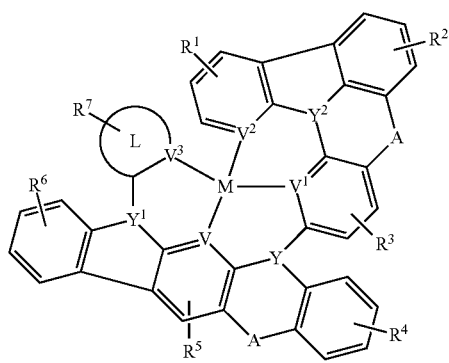

-continued
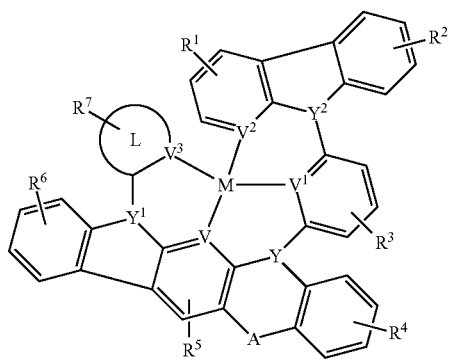
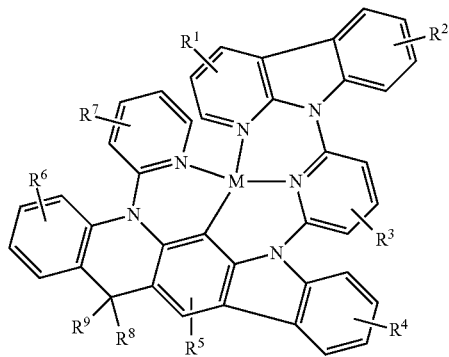
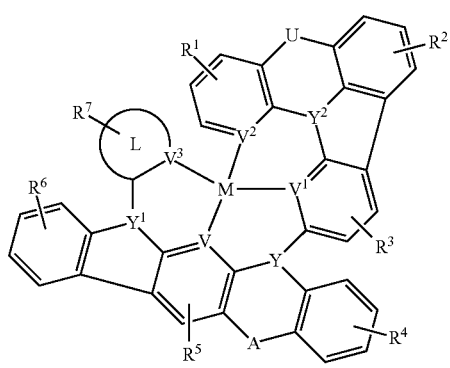
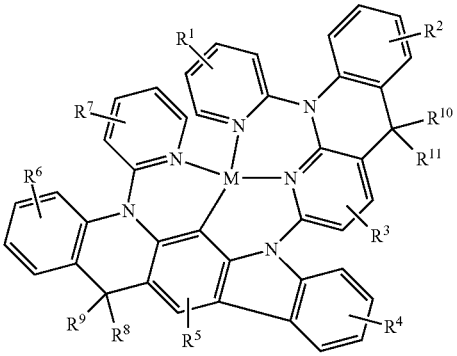
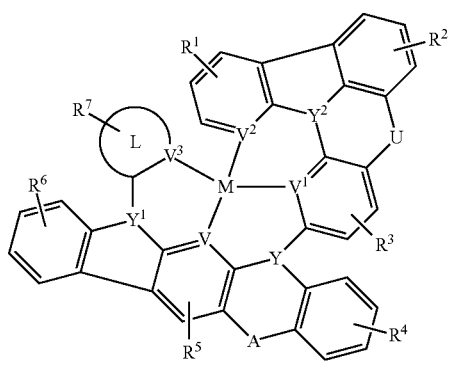
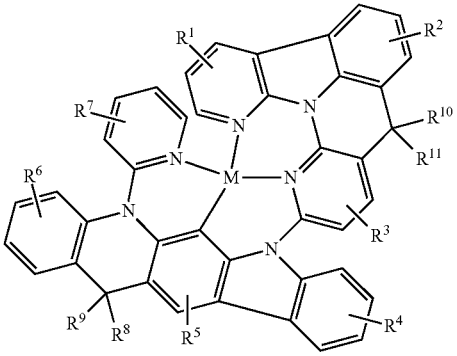
Further implementations of Formula I are shown below, in which M is Pt(II) or Pd(II).
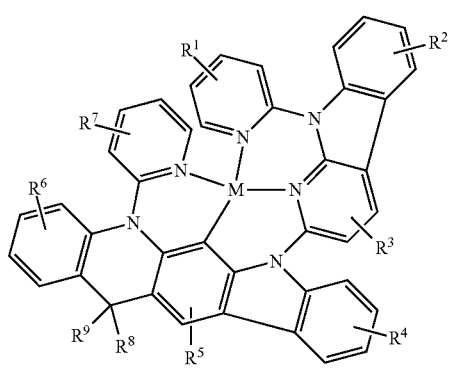
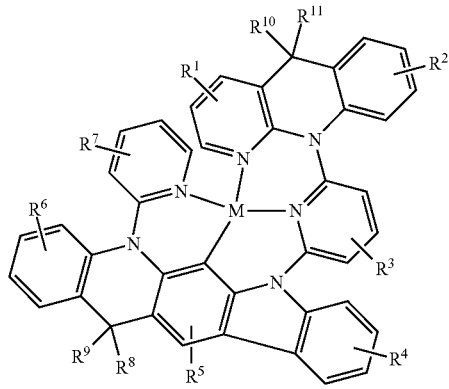

-continued
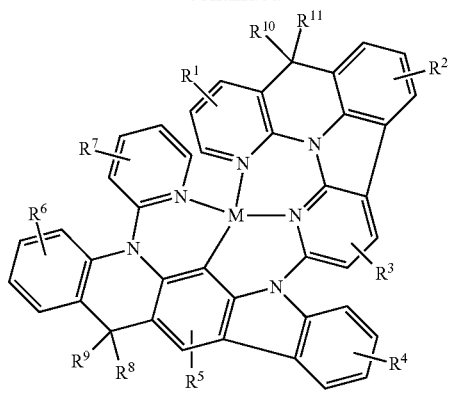
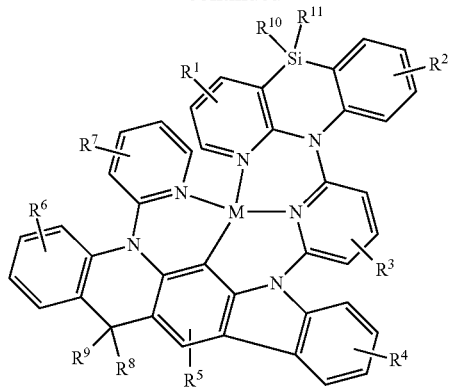
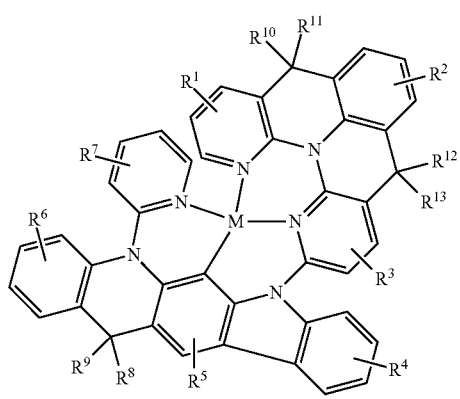
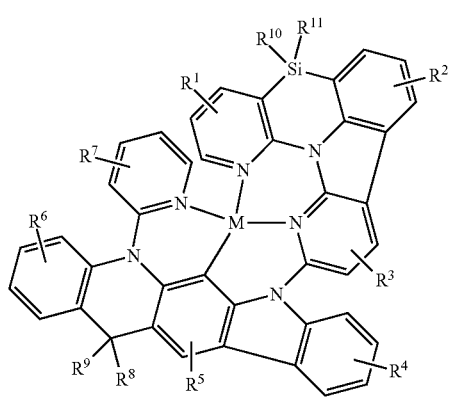
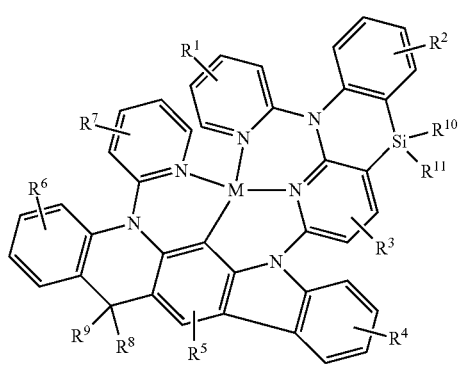
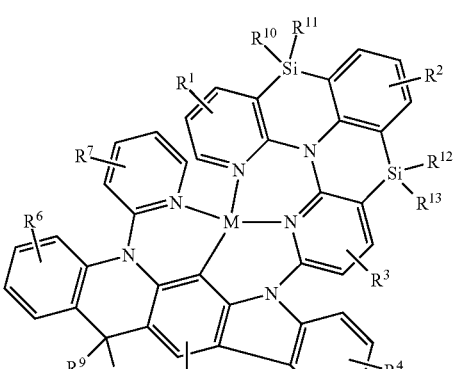
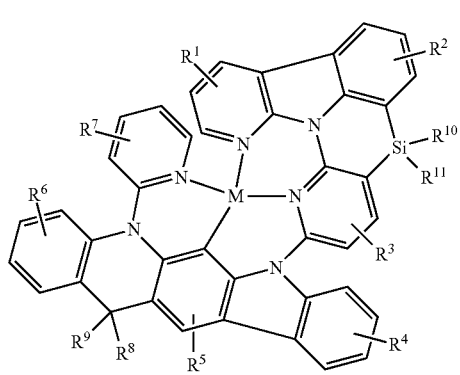
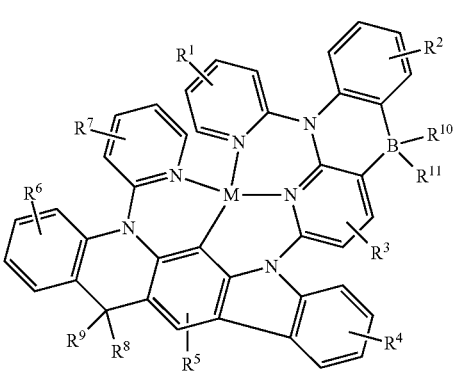

-continued
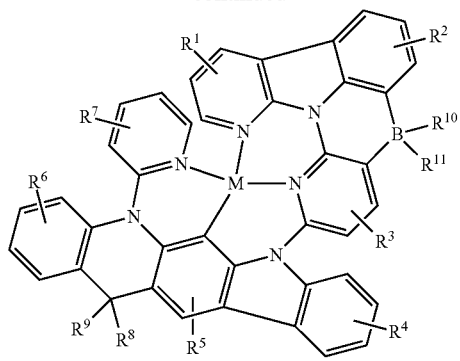
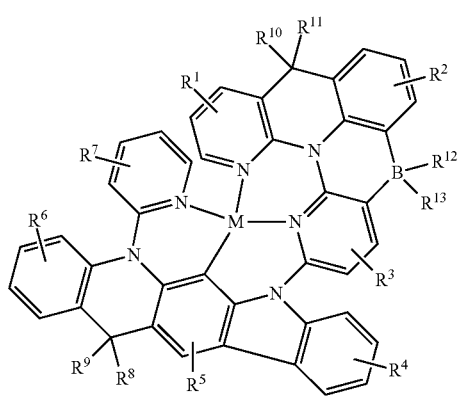
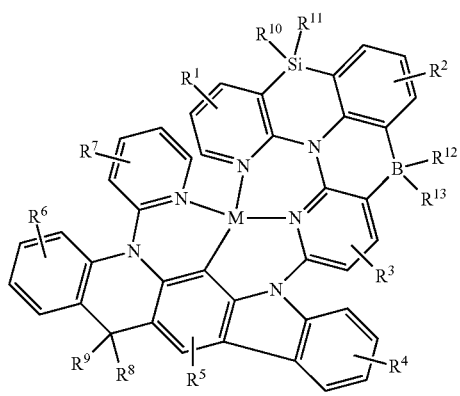
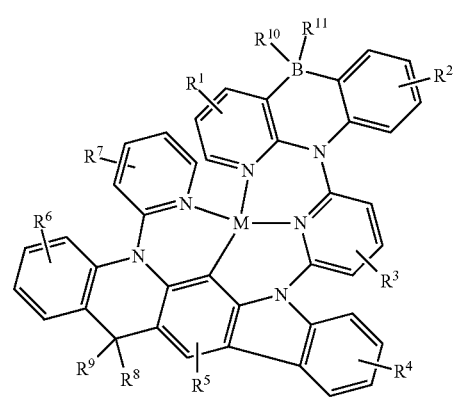
-continued
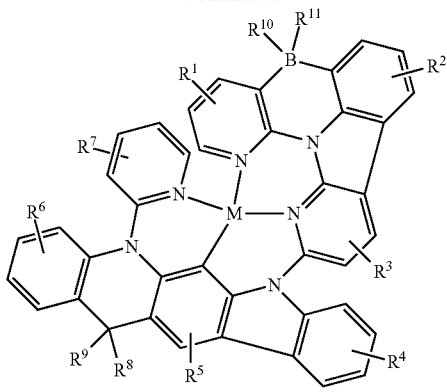
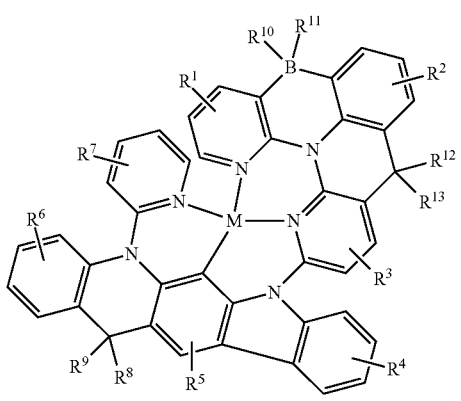
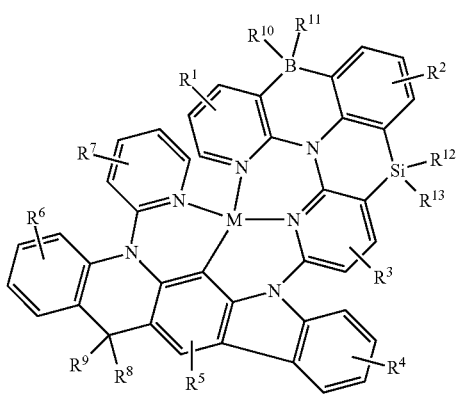
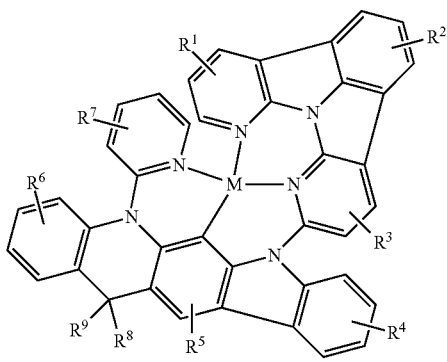

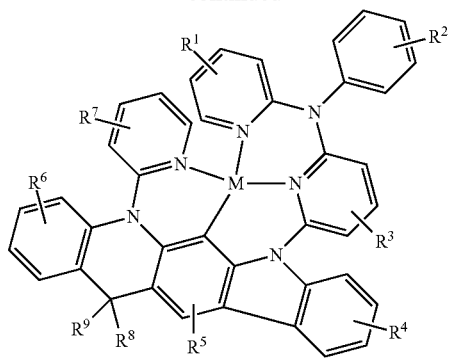
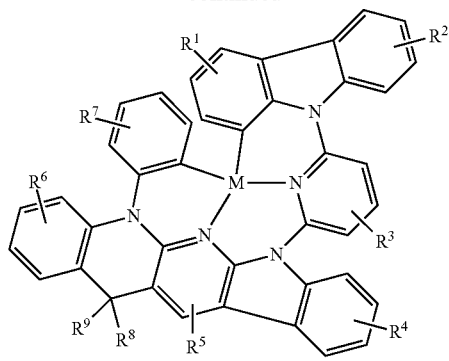
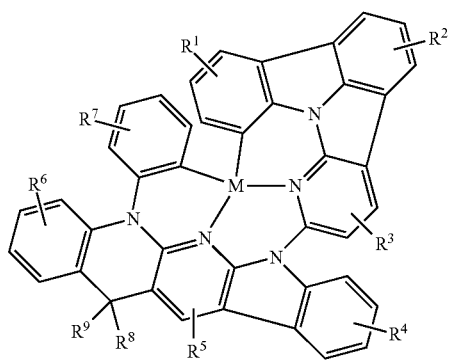
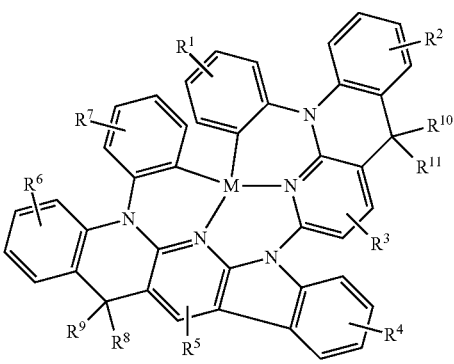
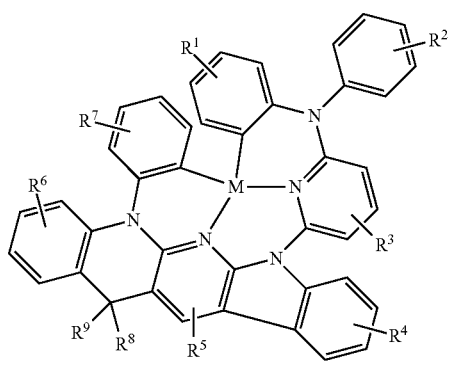
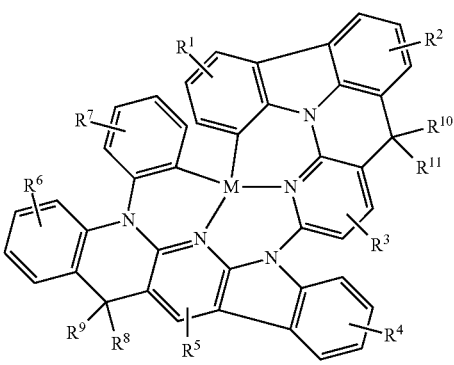
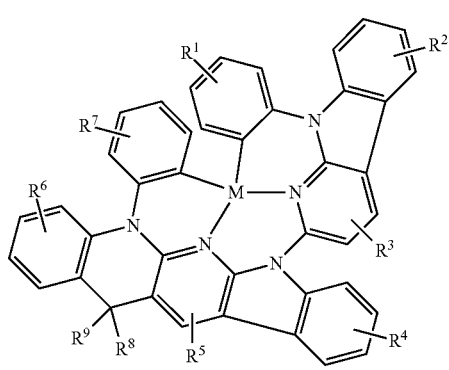
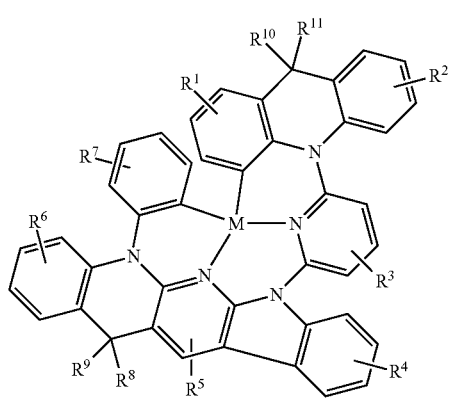

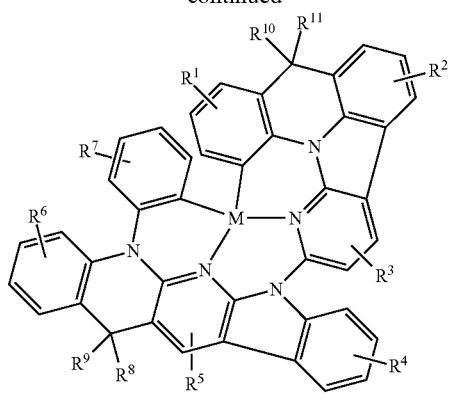
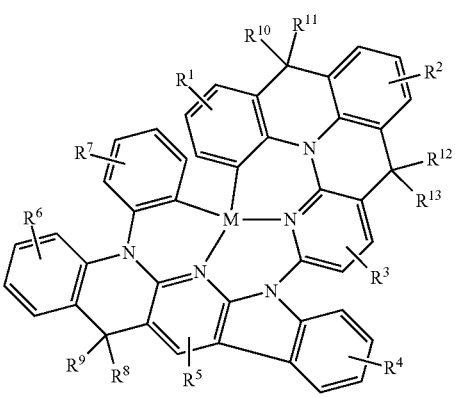
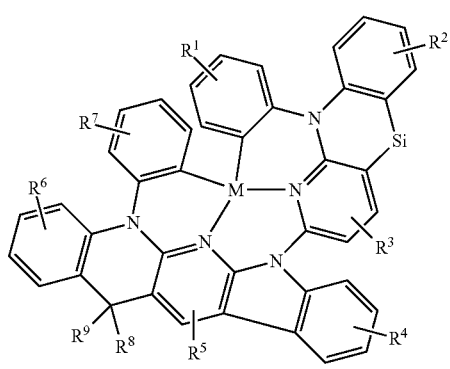
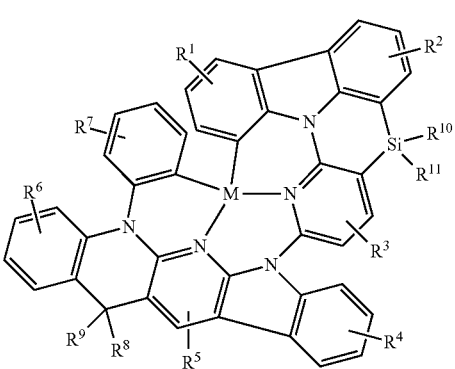
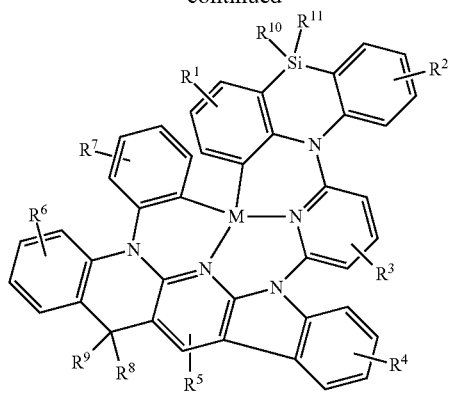
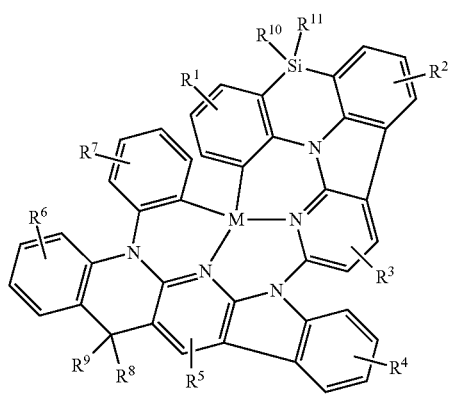
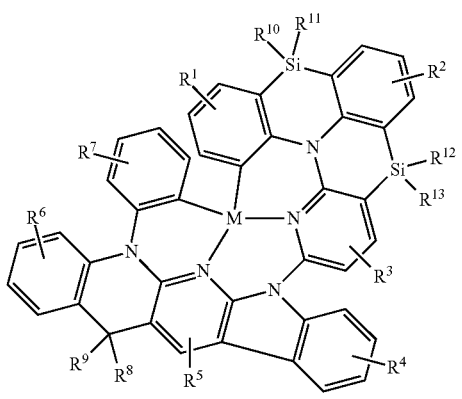
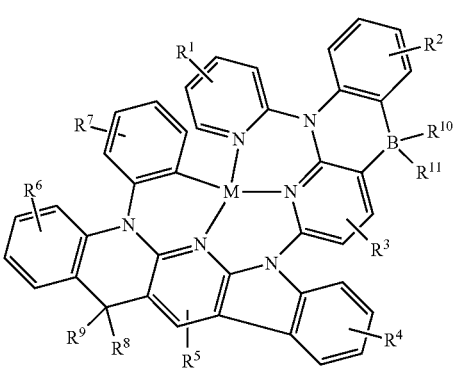

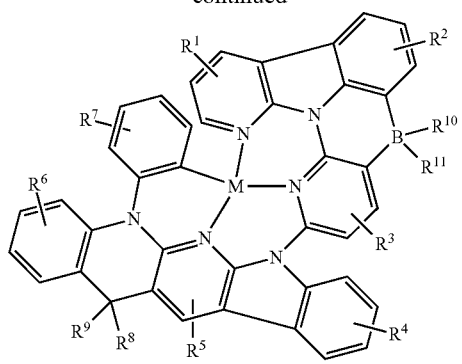
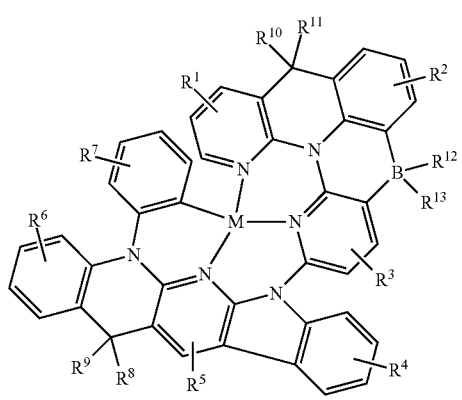
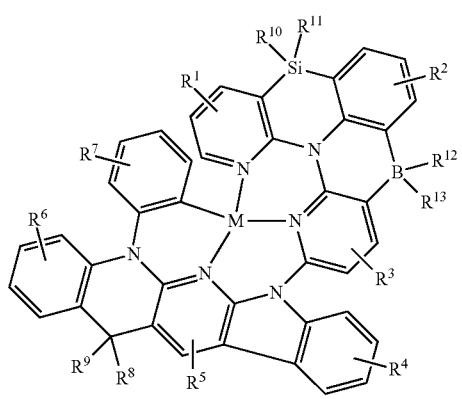
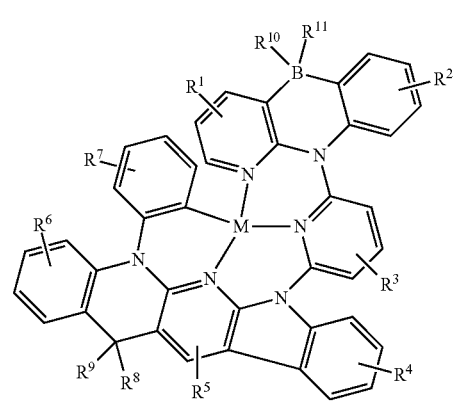
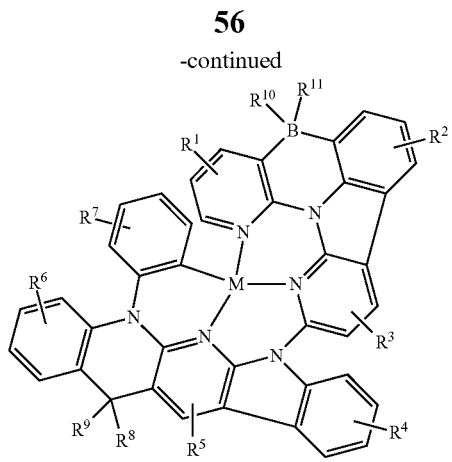
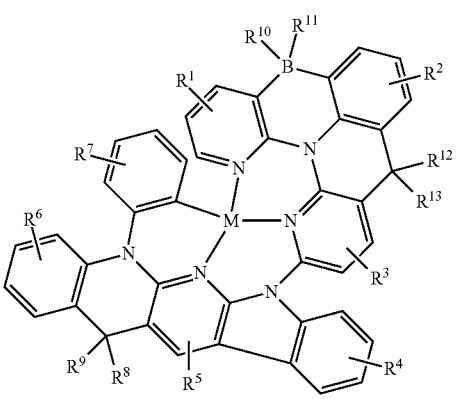
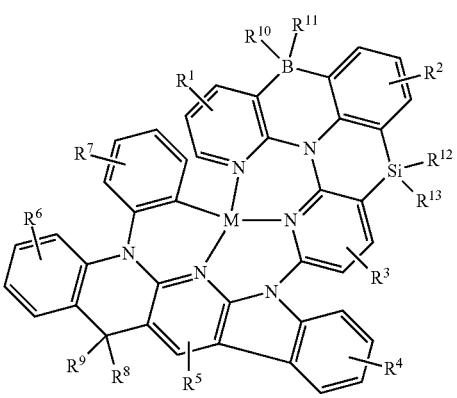
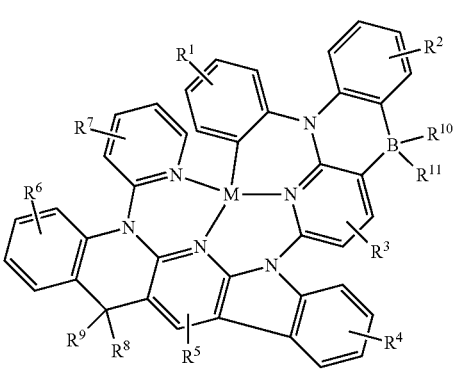

57
-continued
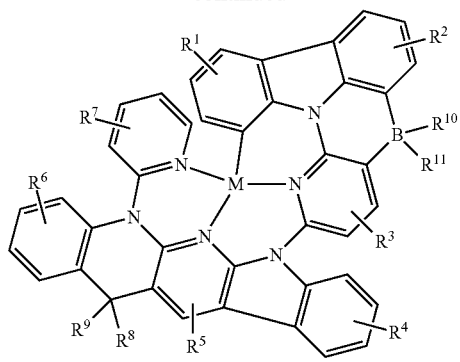
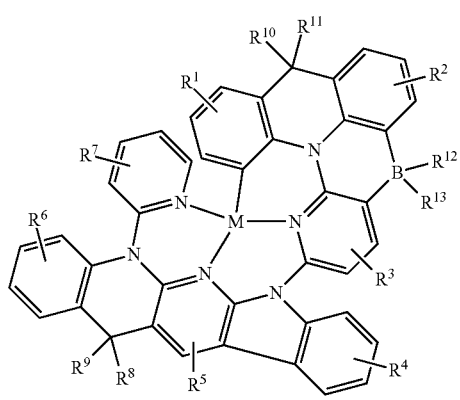
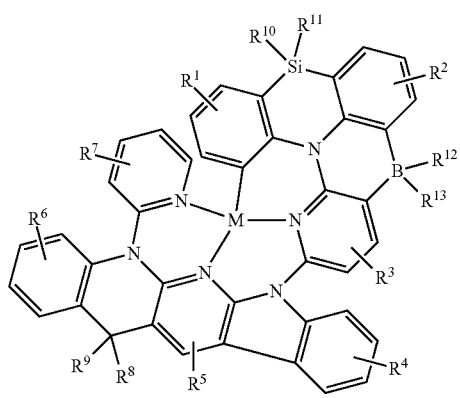
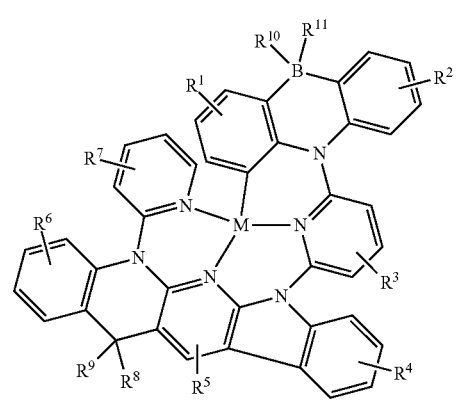
58
-continued
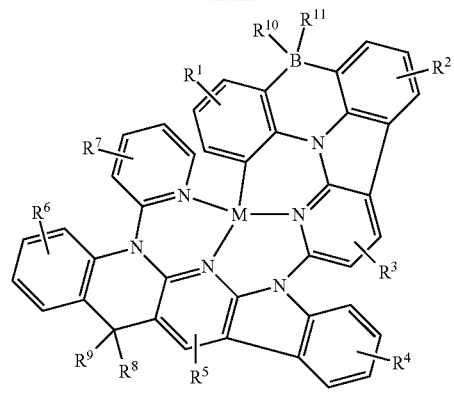
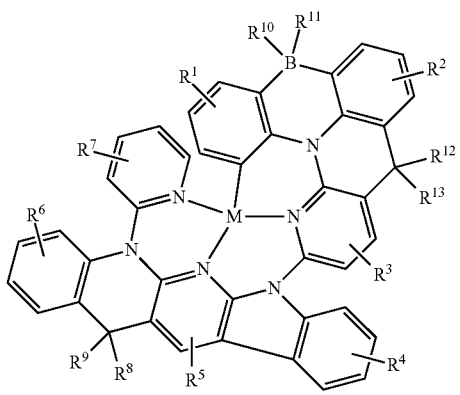
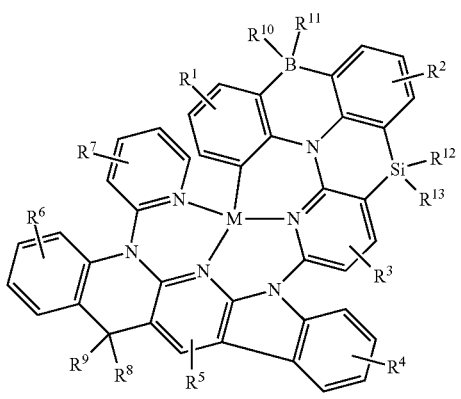
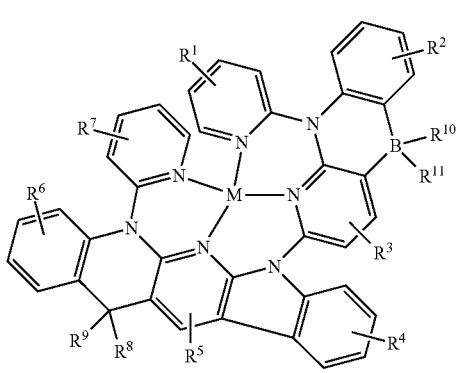

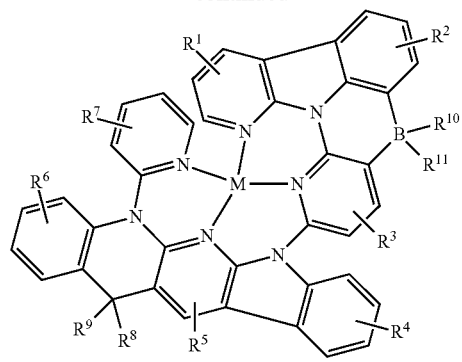
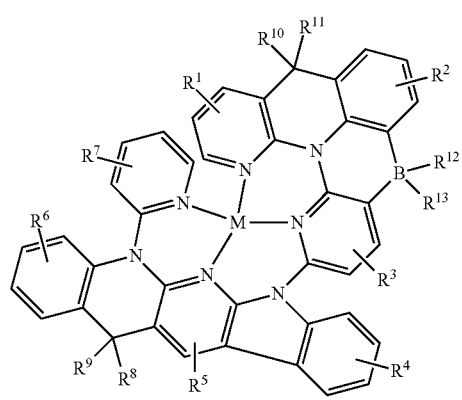
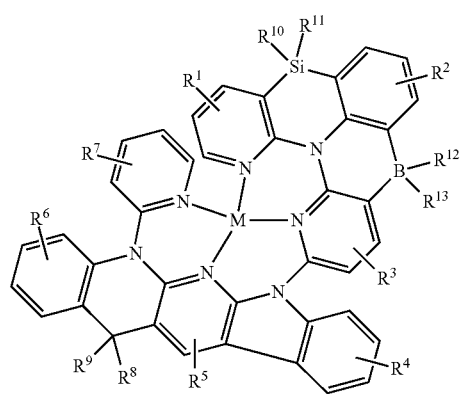
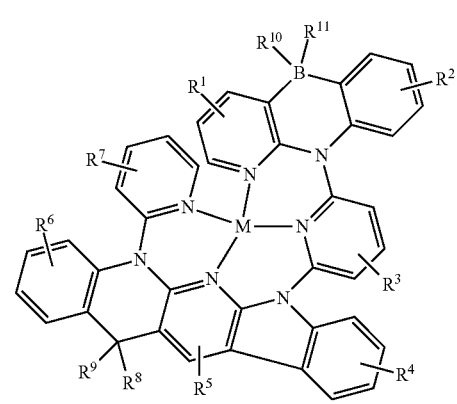
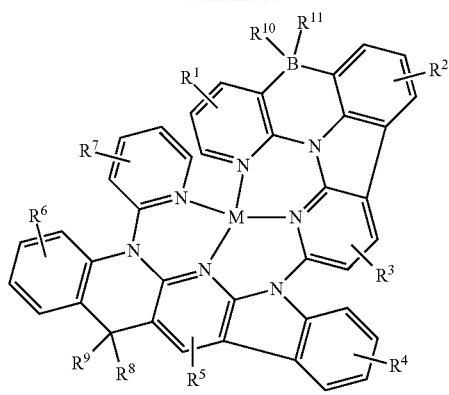
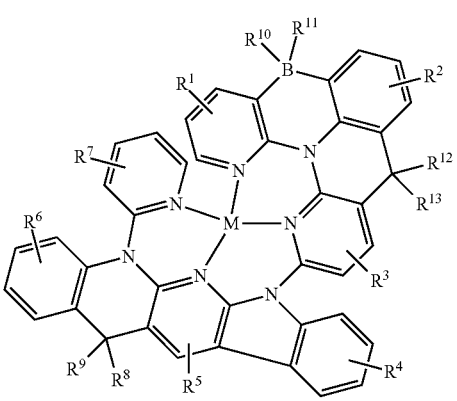
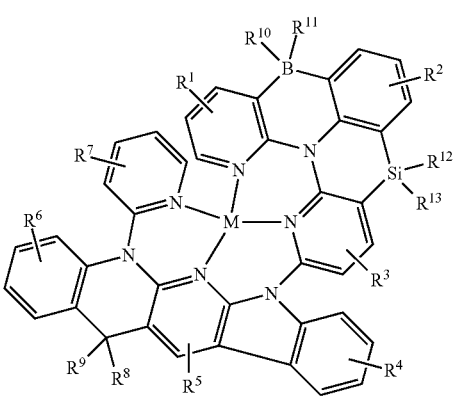
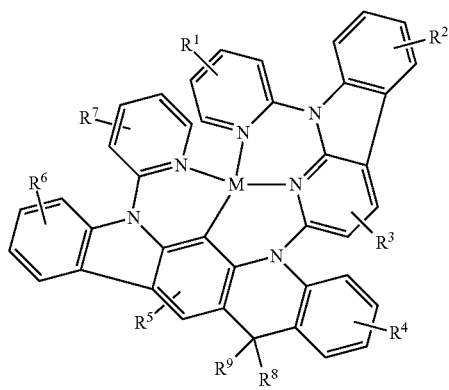

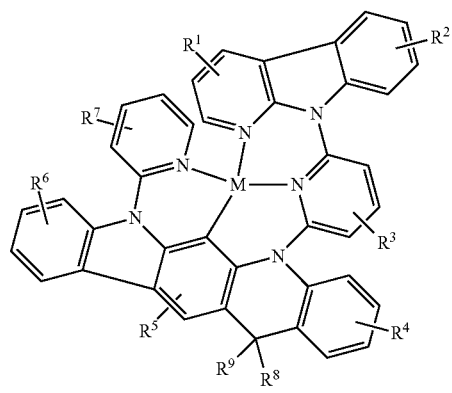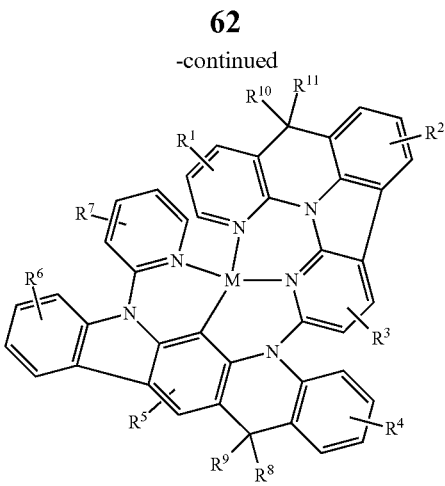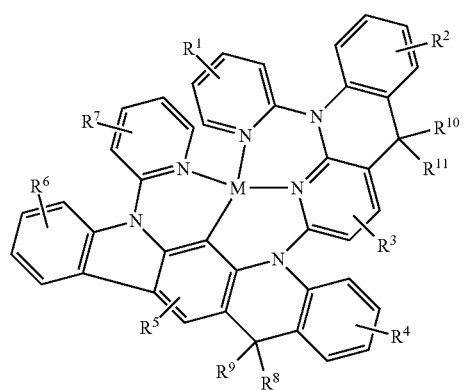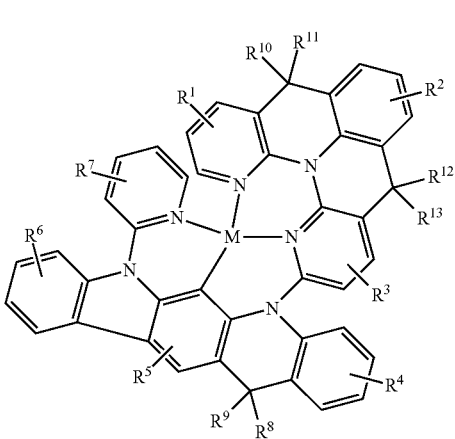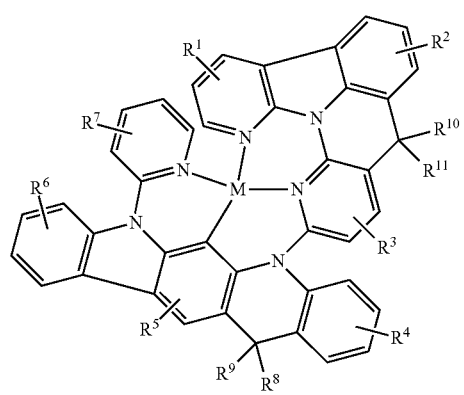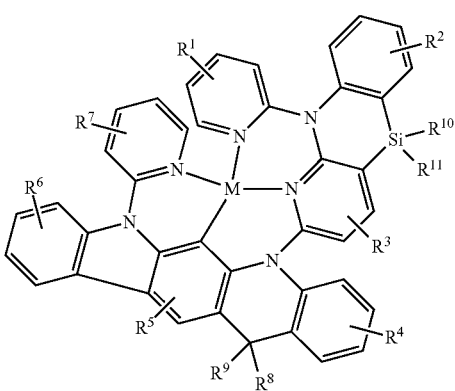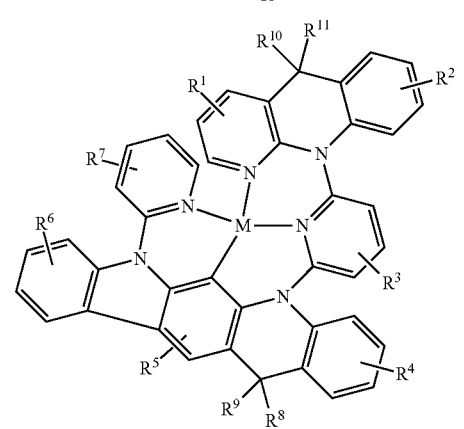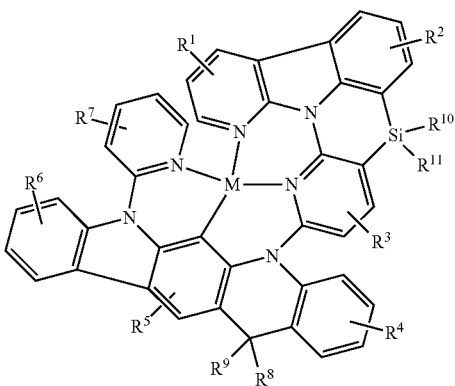

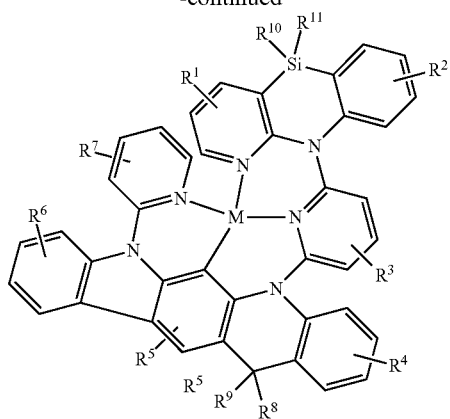
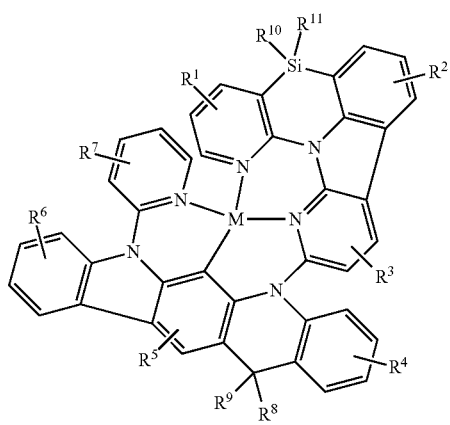
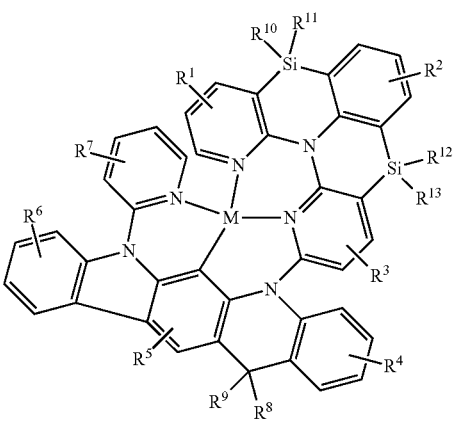
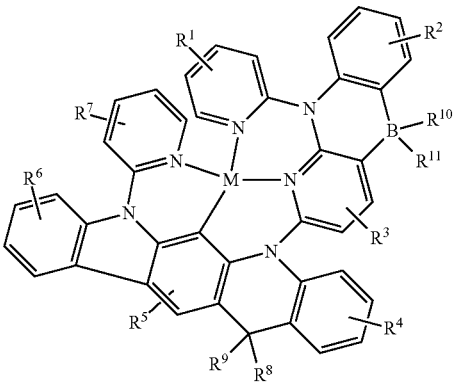
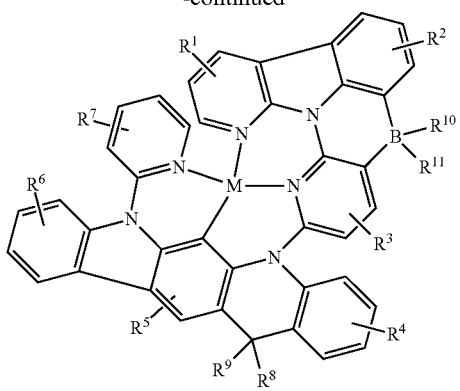
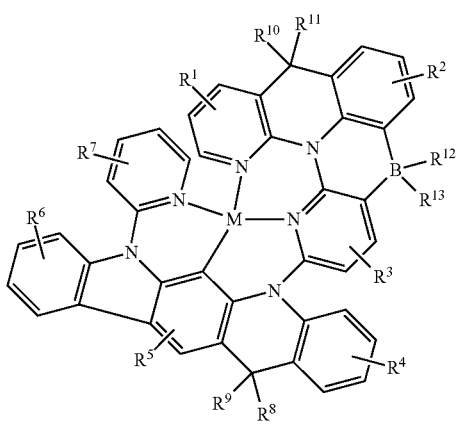
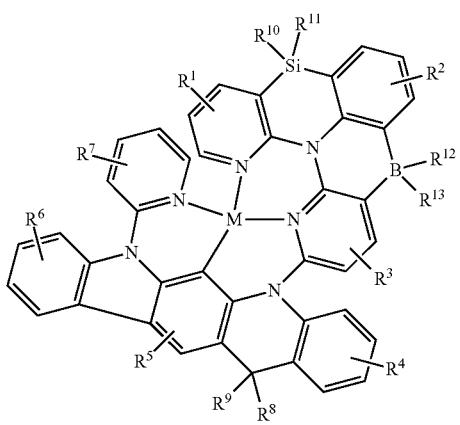
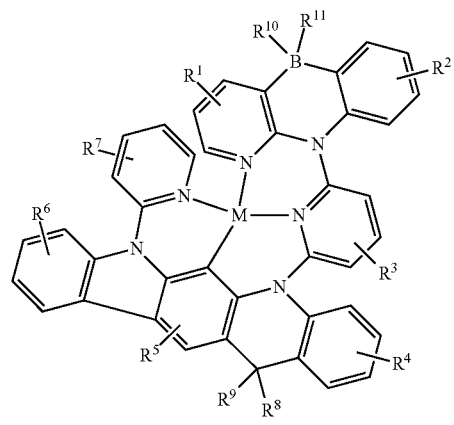

-continued
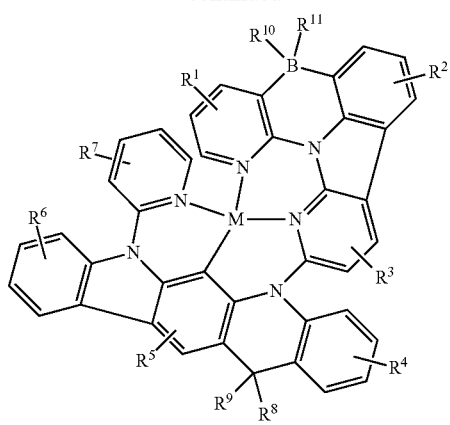
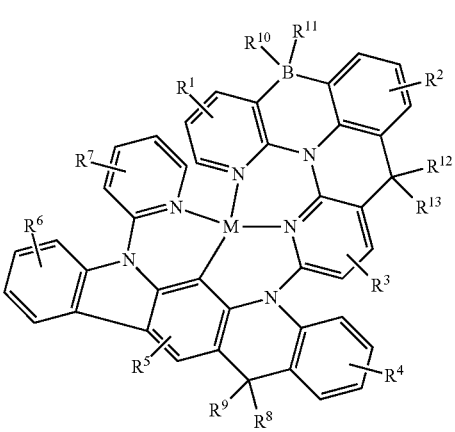
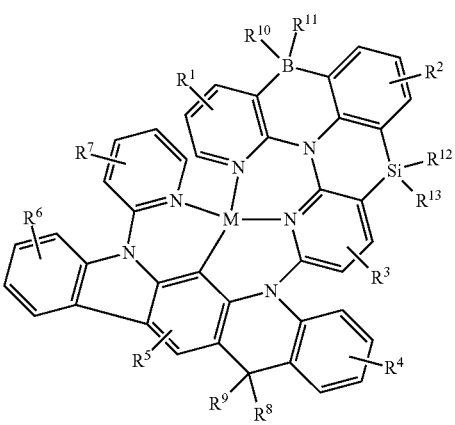
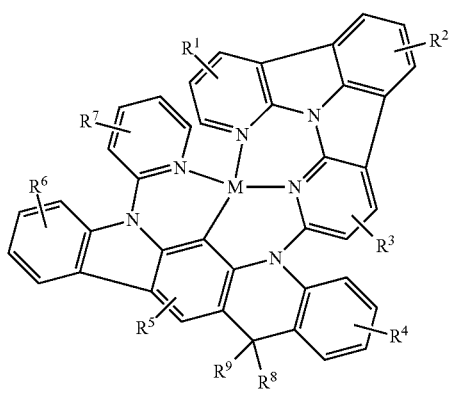
-continued
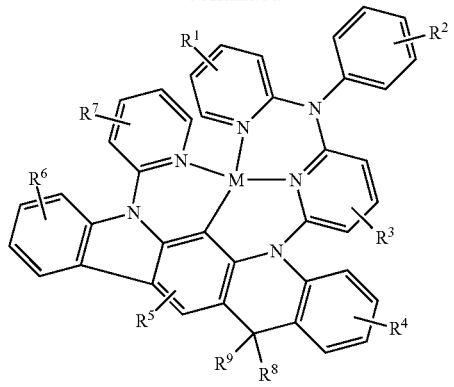
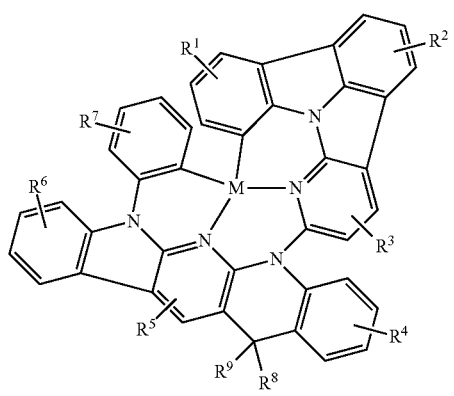
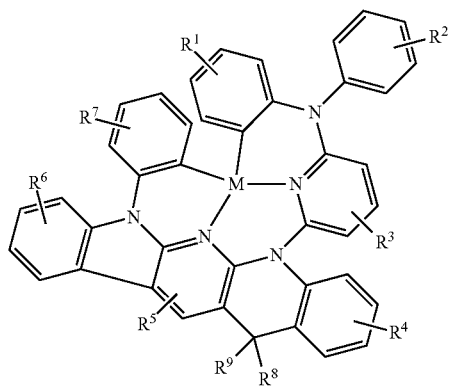
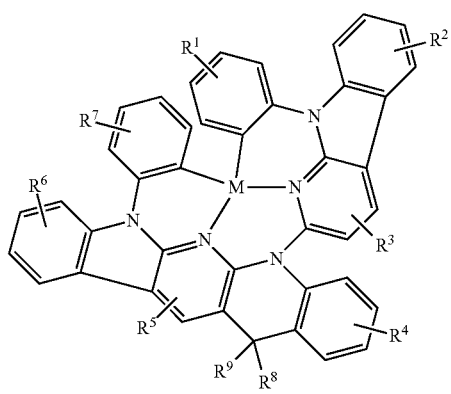

-continued
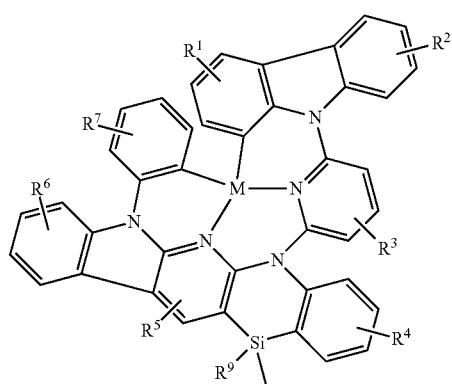
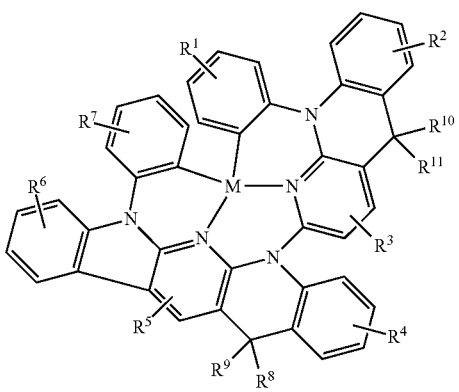
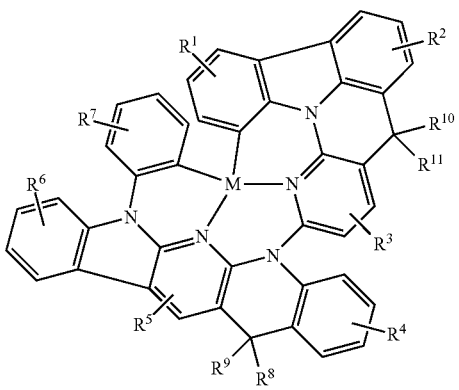
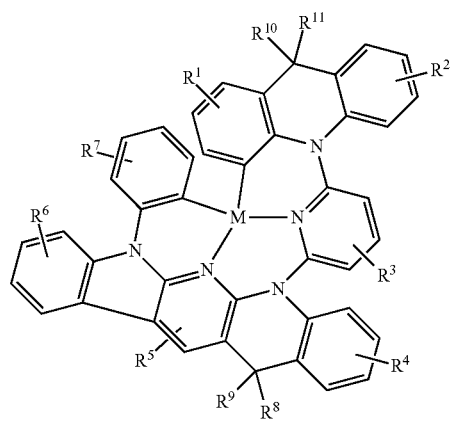
-continued
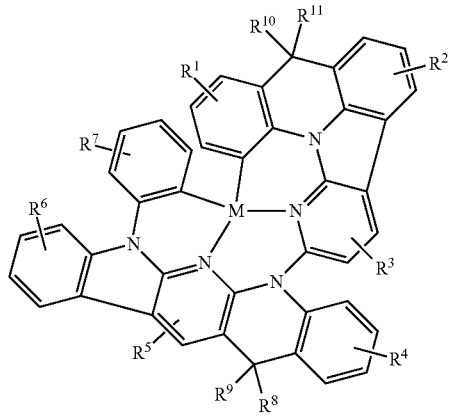
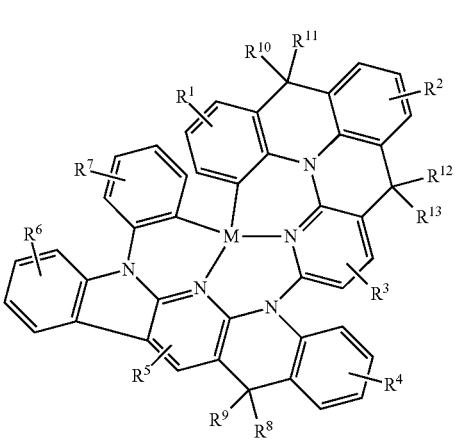
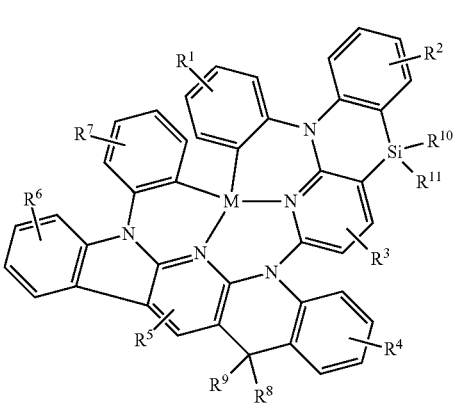
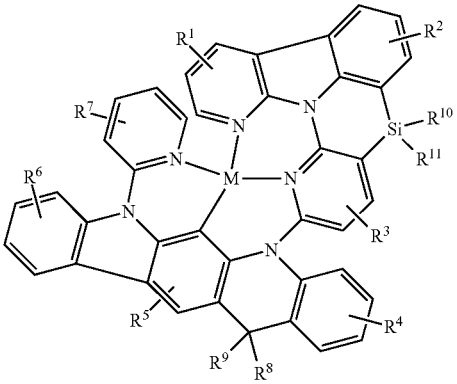

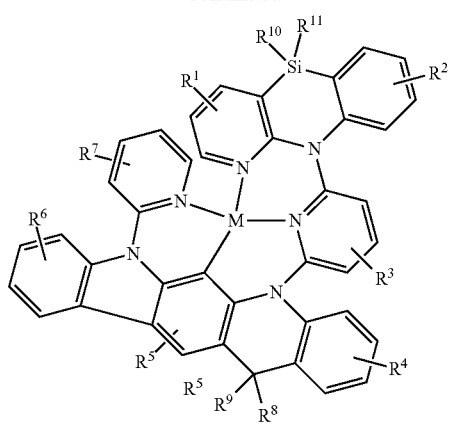
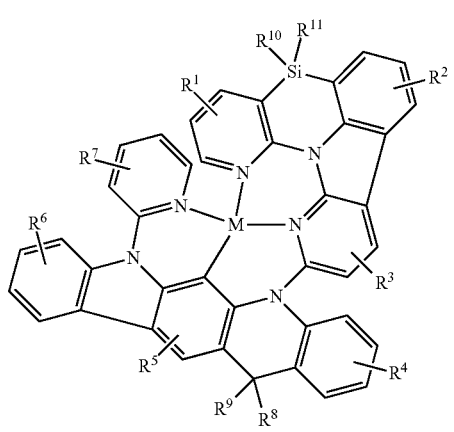
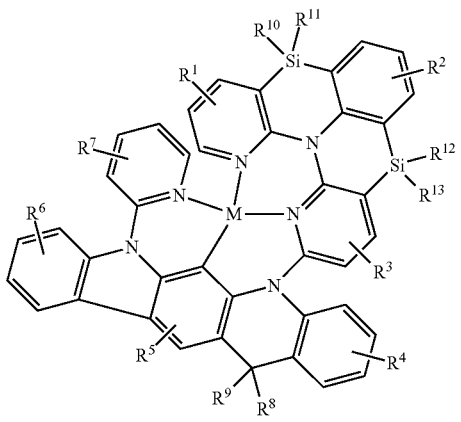
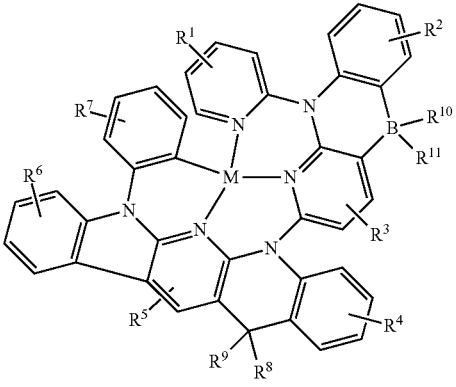
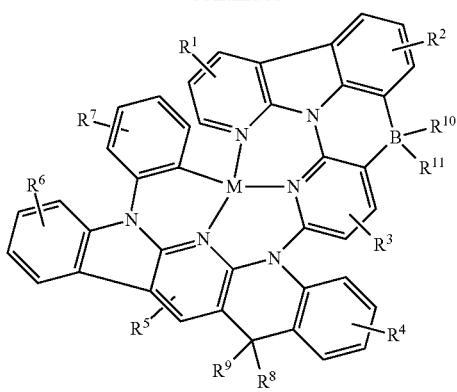
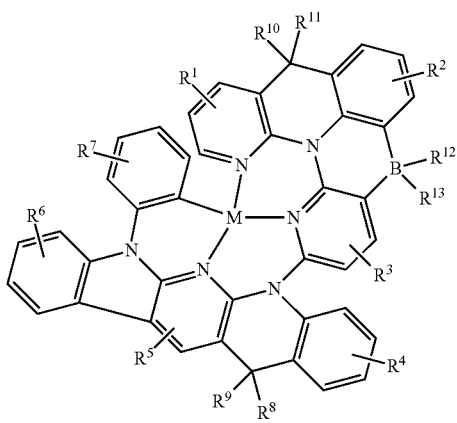
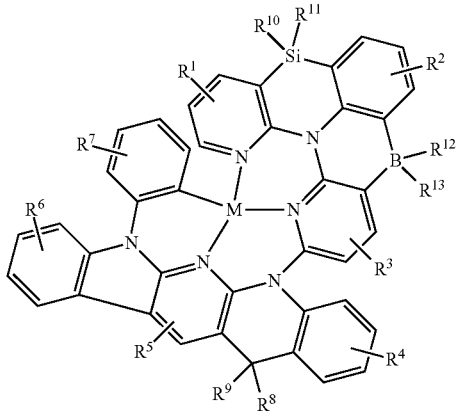
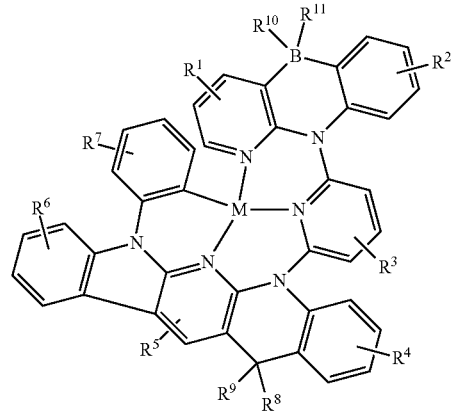

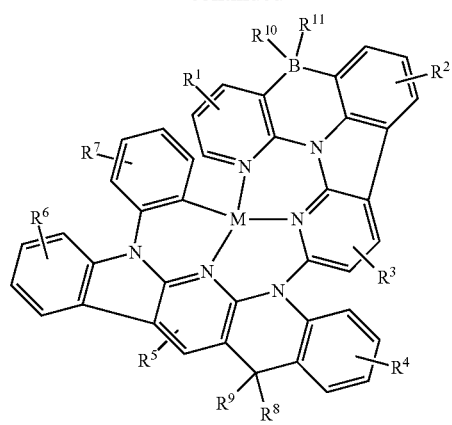
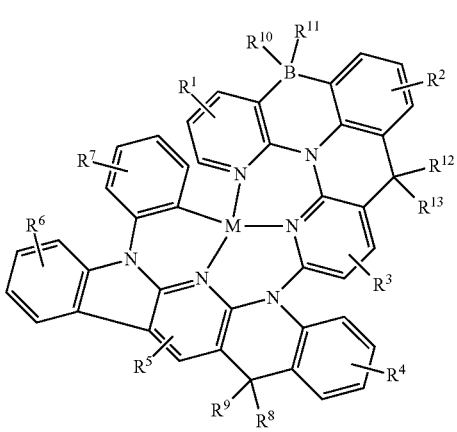
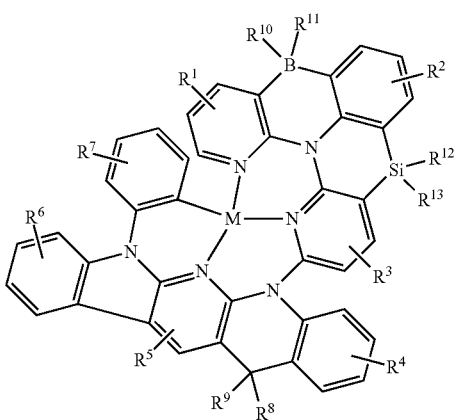
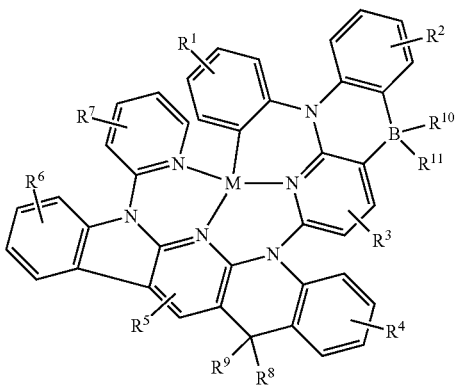
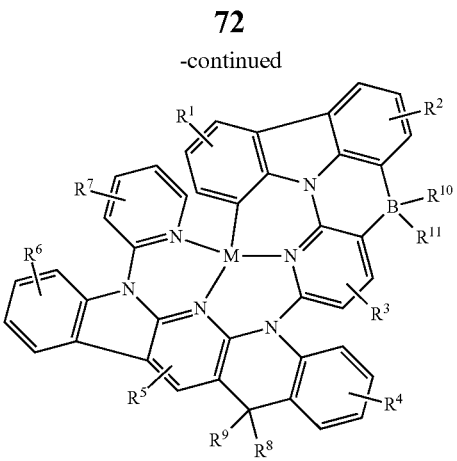
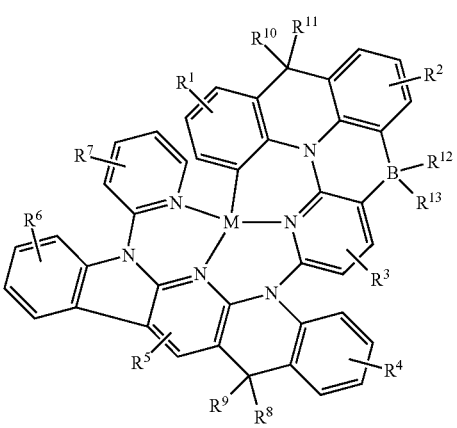
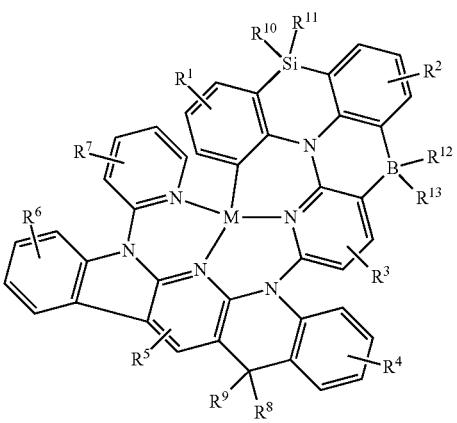
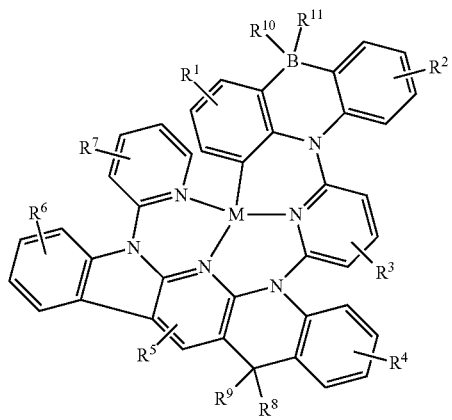

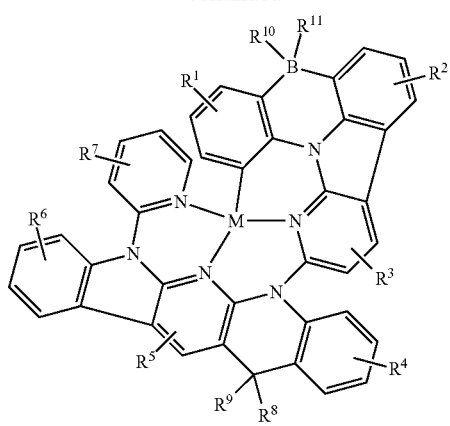
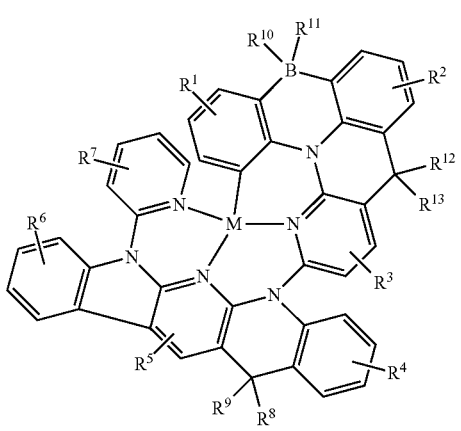
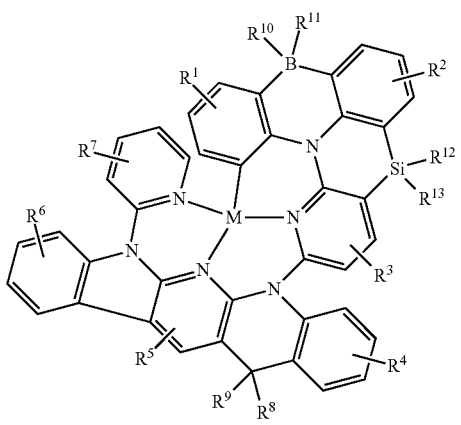
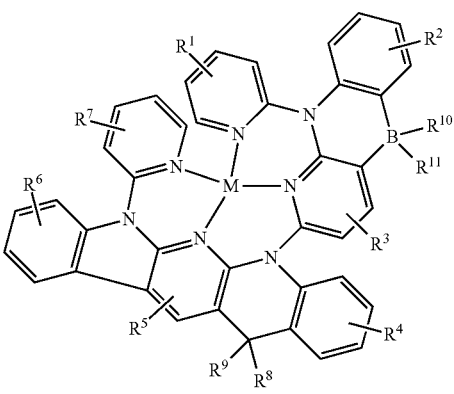
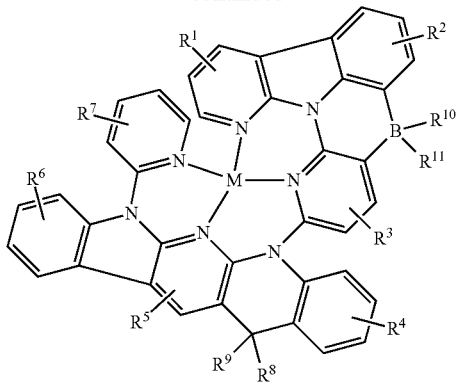
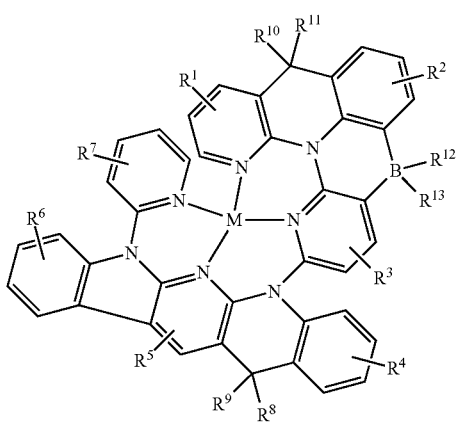
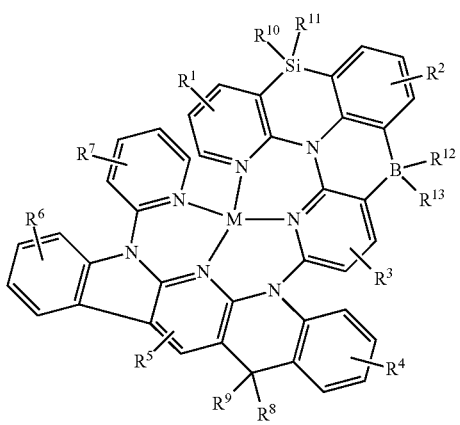
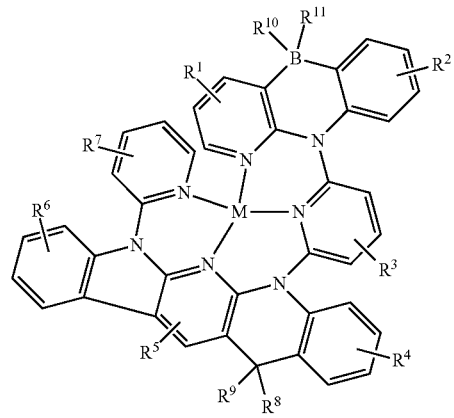

75
-continued
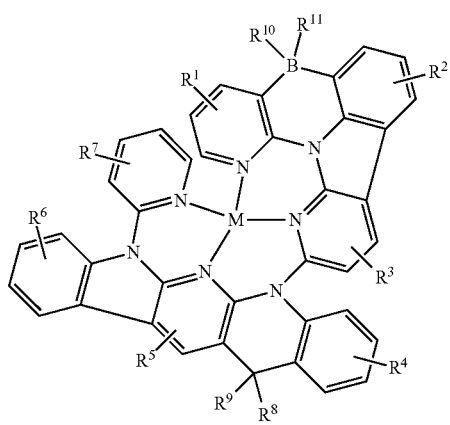
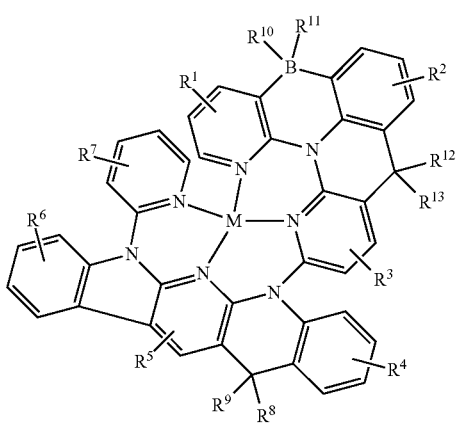
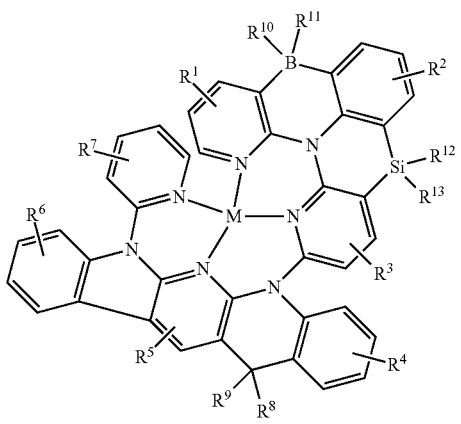
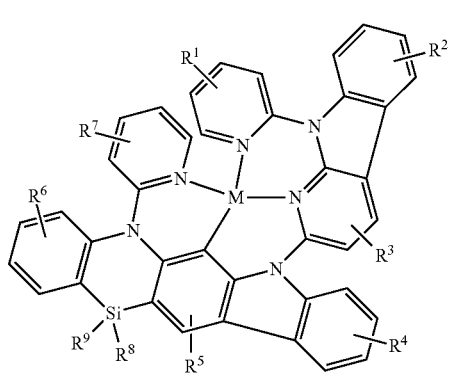
76
-continued
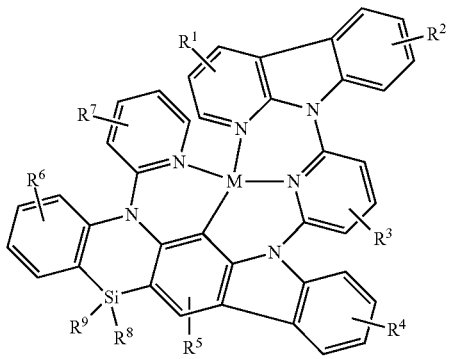
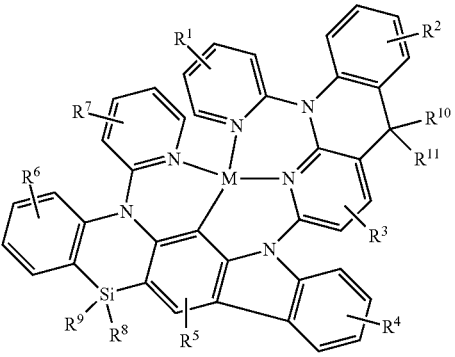
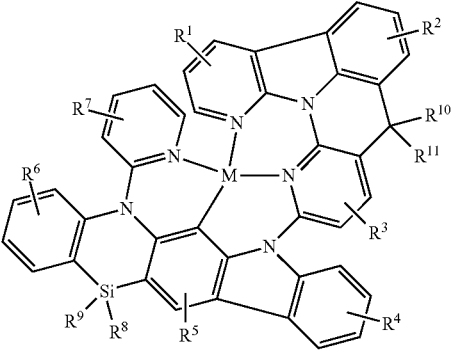
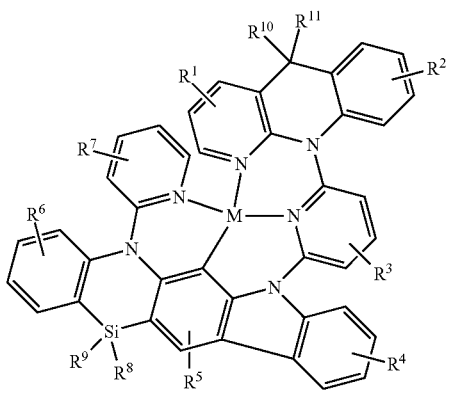

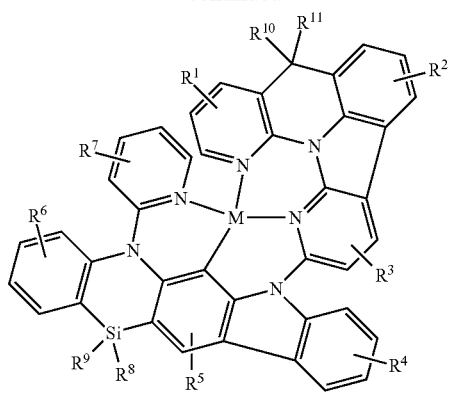
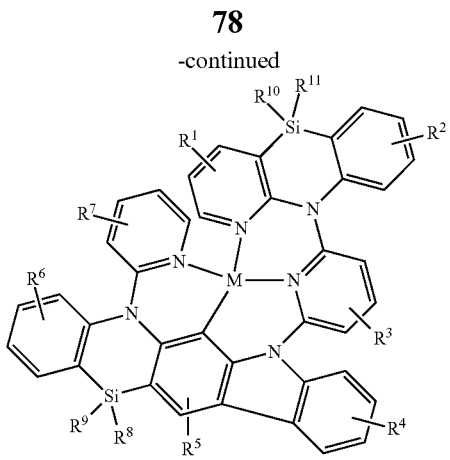
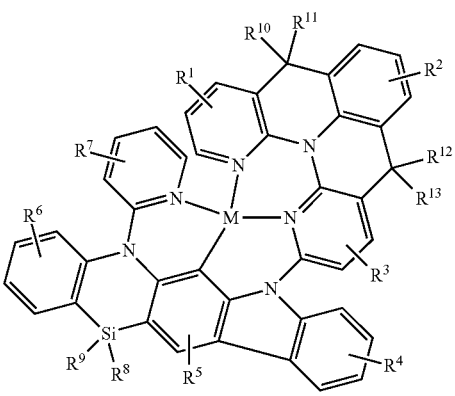
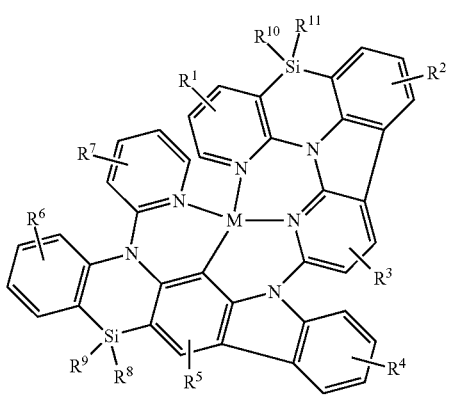
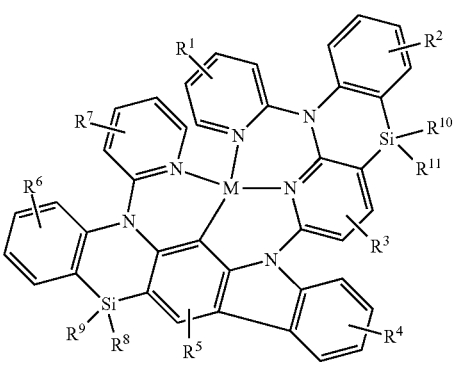
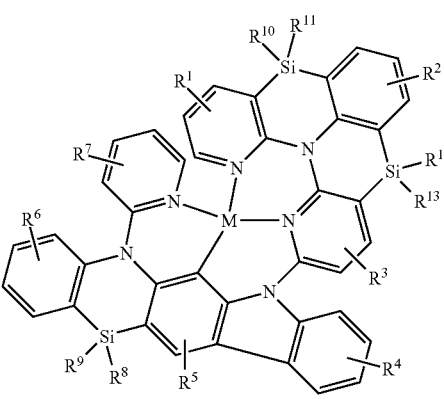
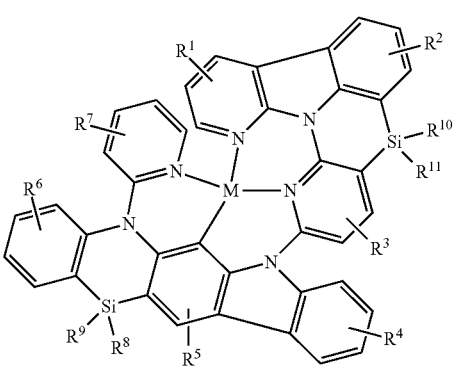
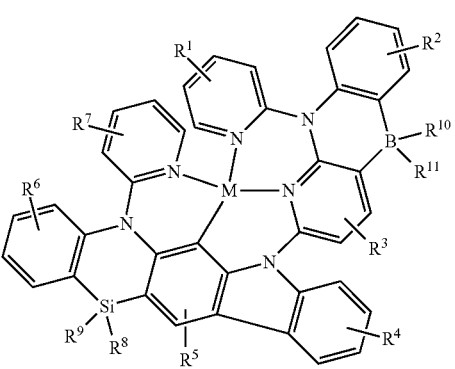

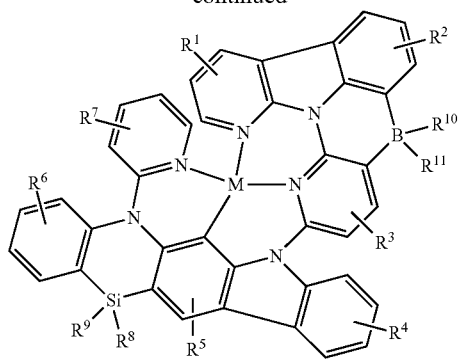
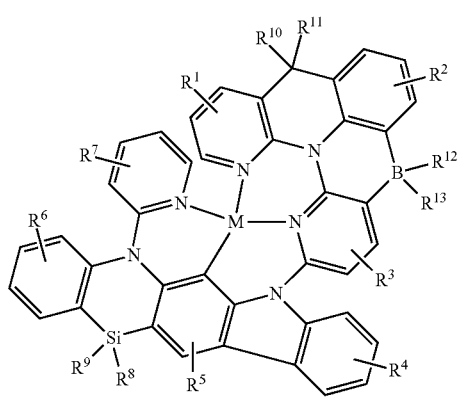
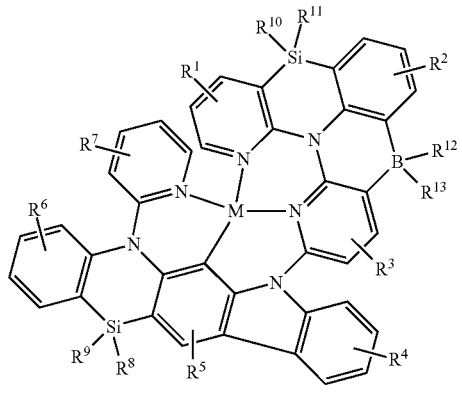
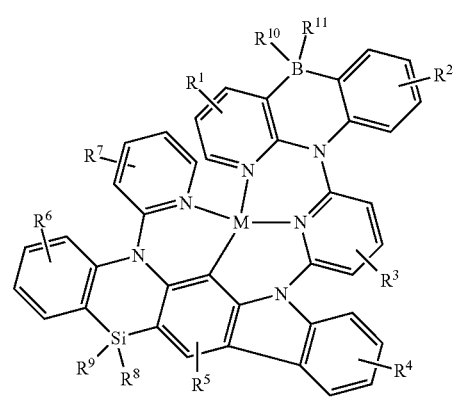
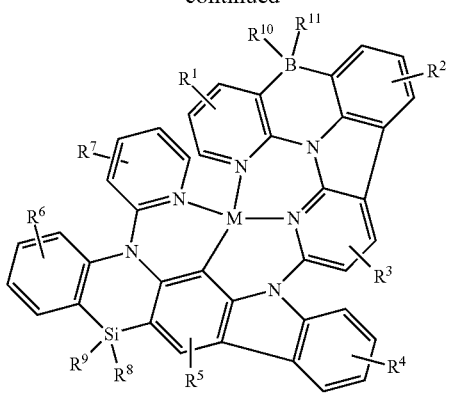
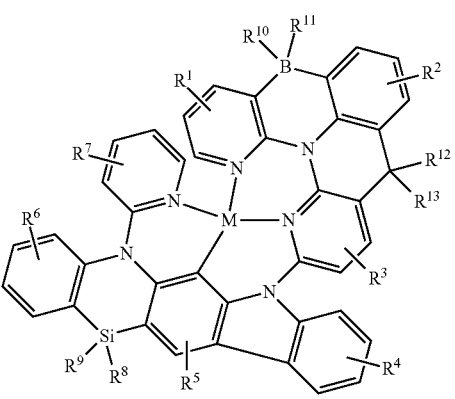
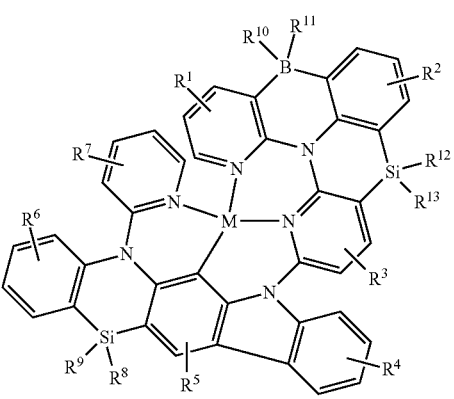
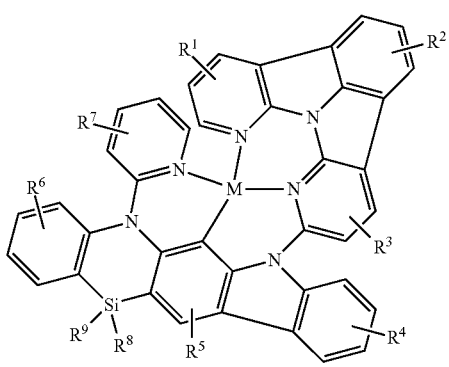

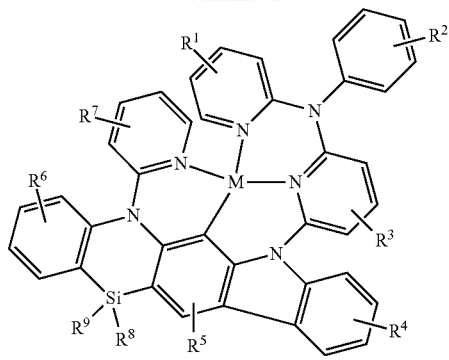
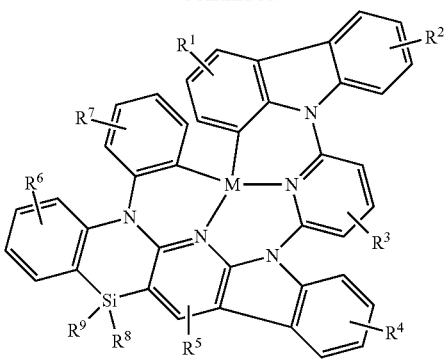
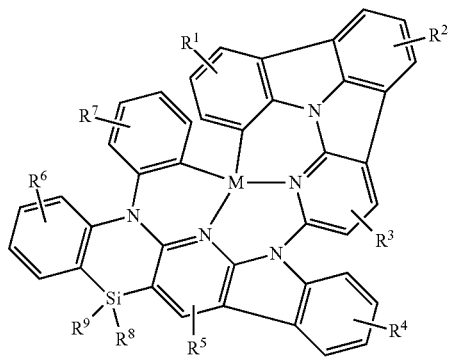
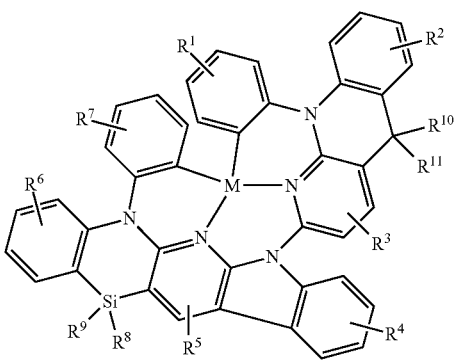
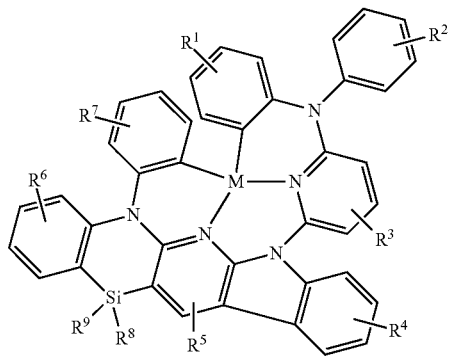
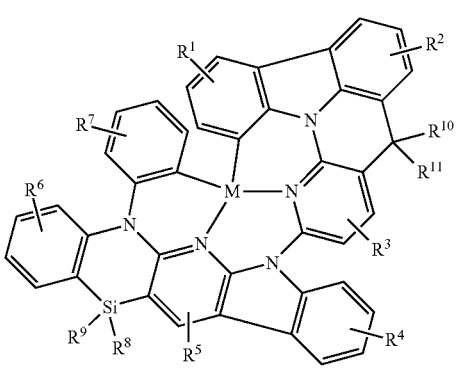

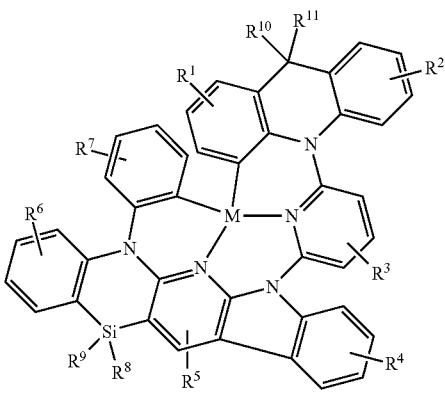

83
-continued
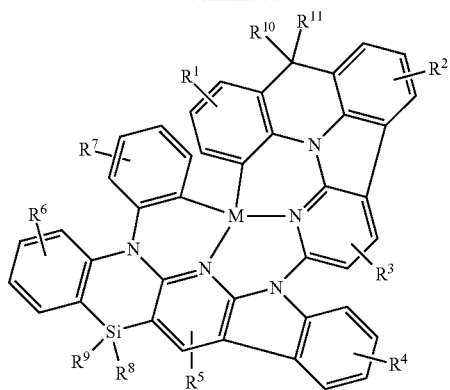
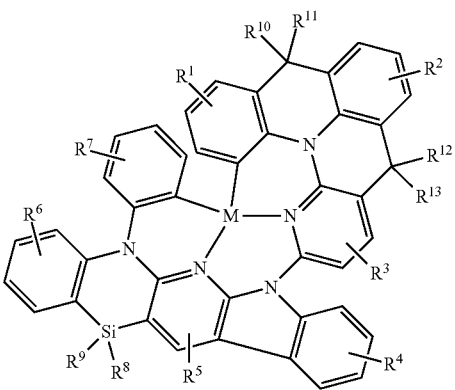
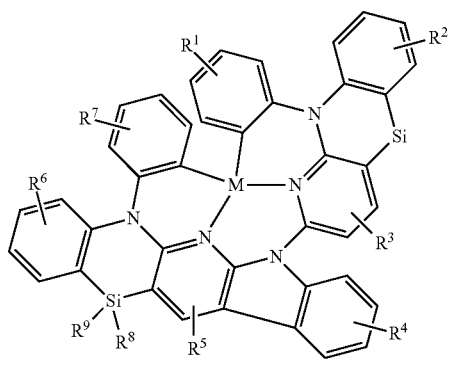
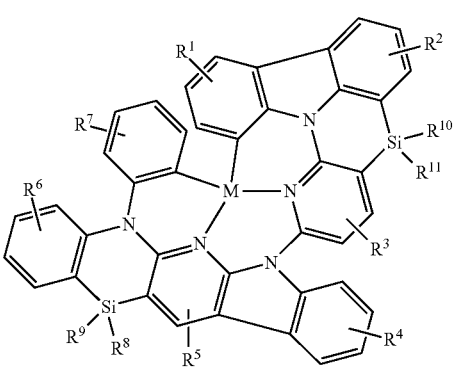
84
-continued
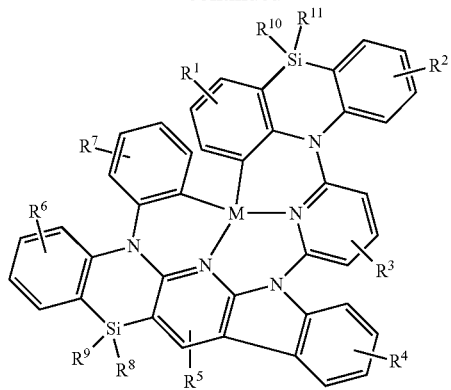
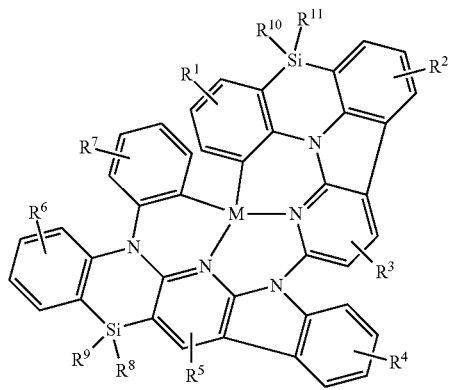
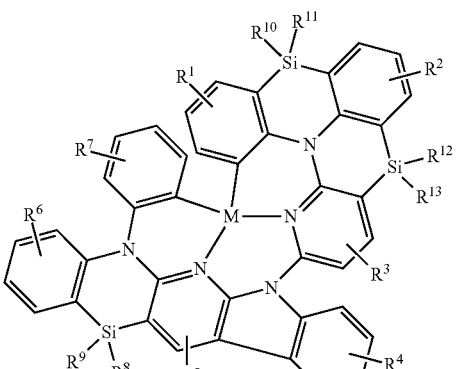
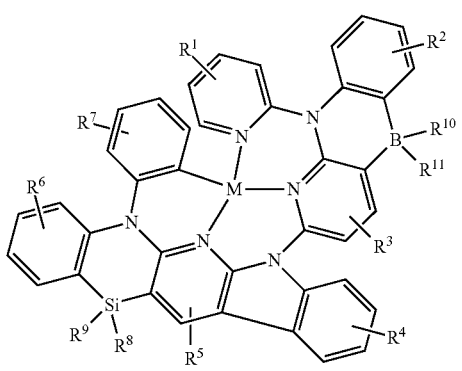

-continued
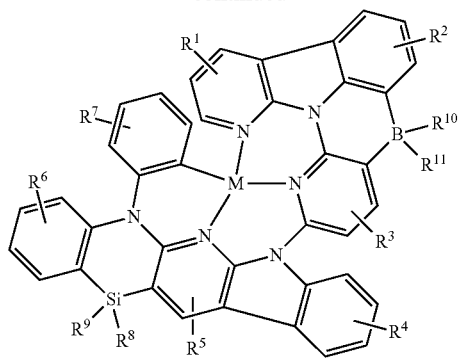
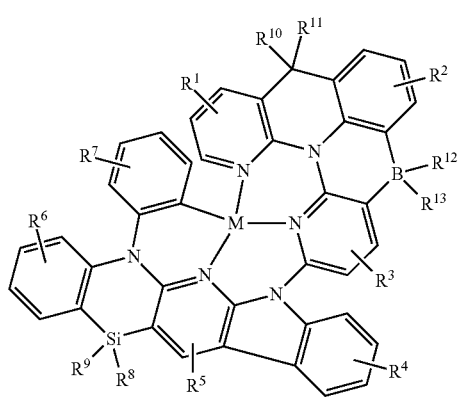
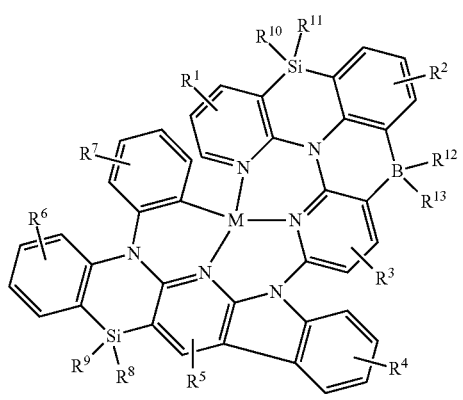
-continued
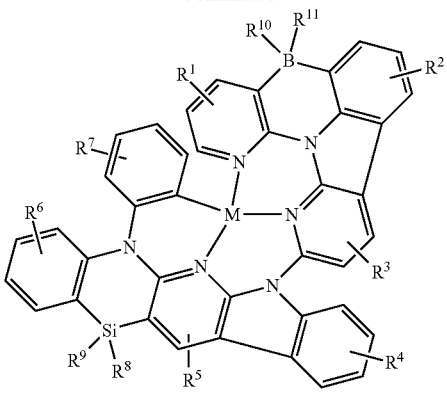
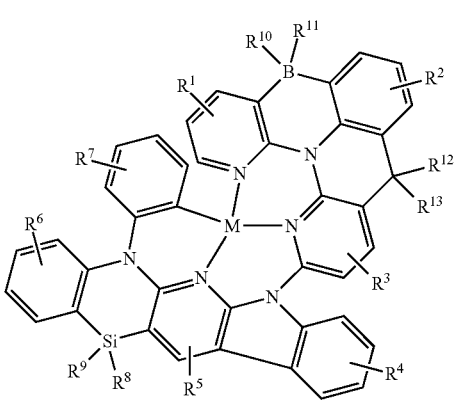
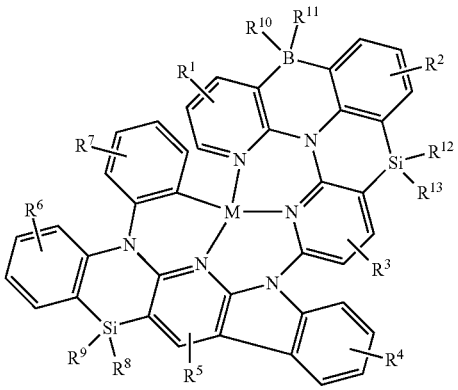
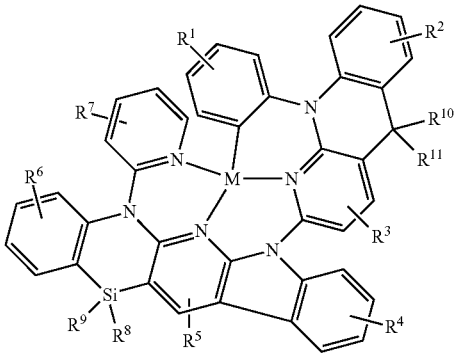

87
-continued
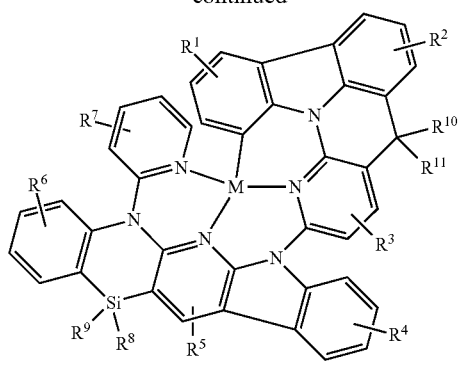
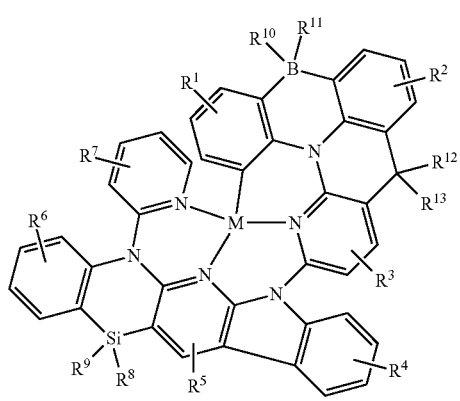
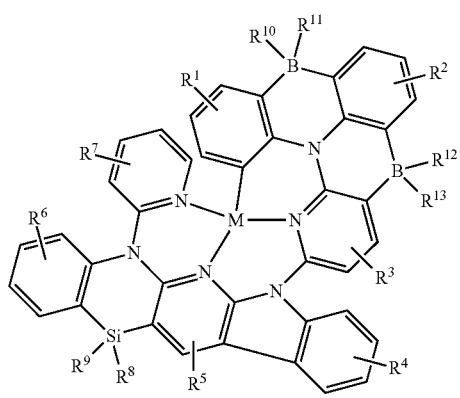
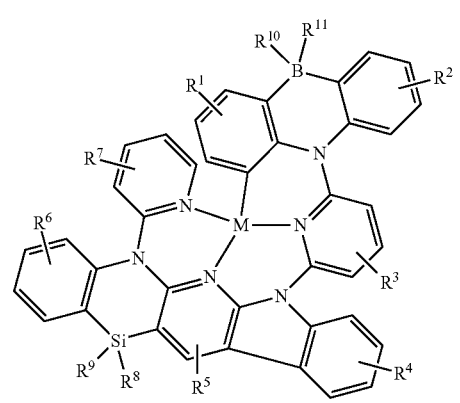
88
-continued
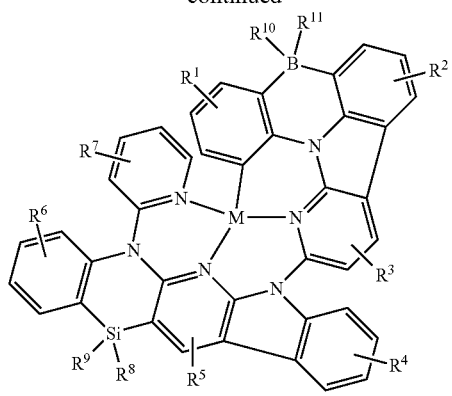
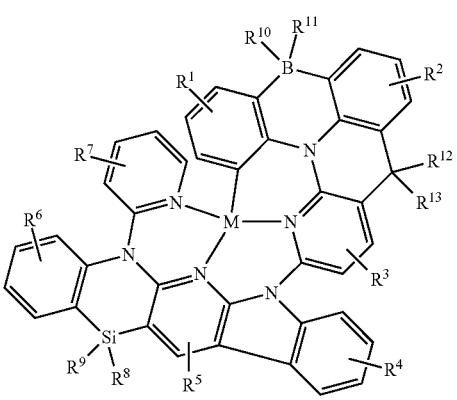
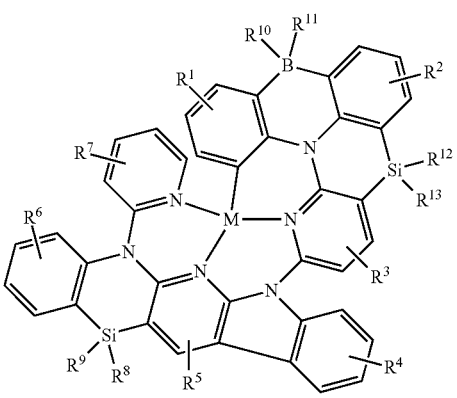
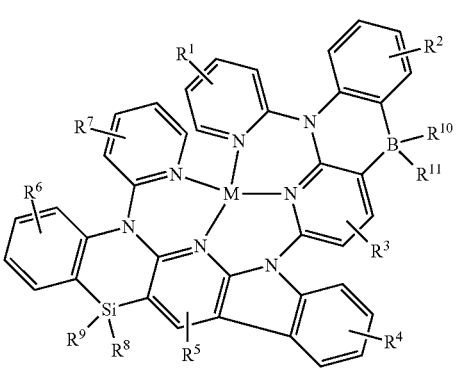

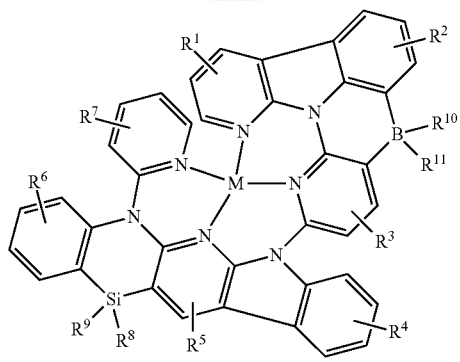
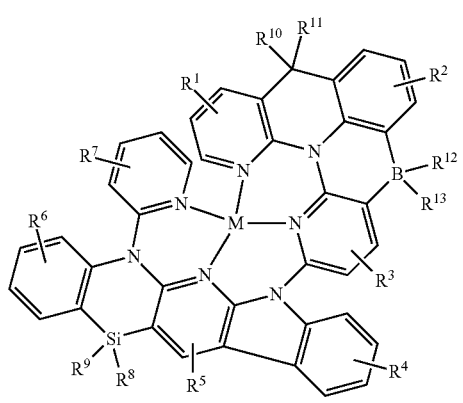
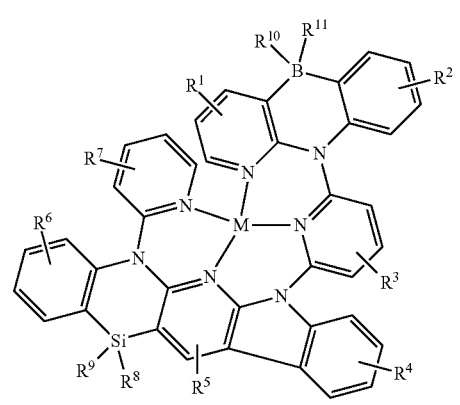
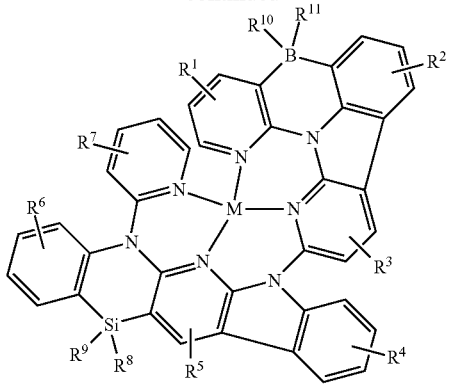
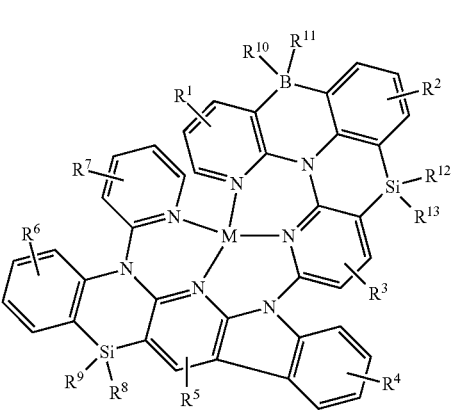
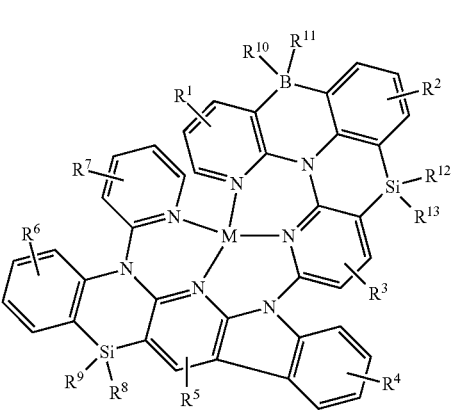
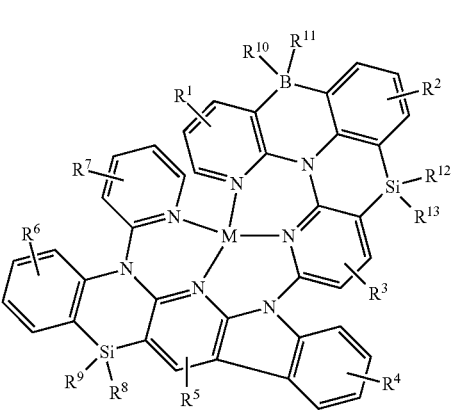

91
-continued
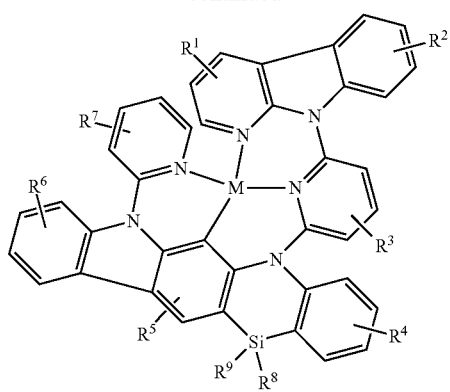
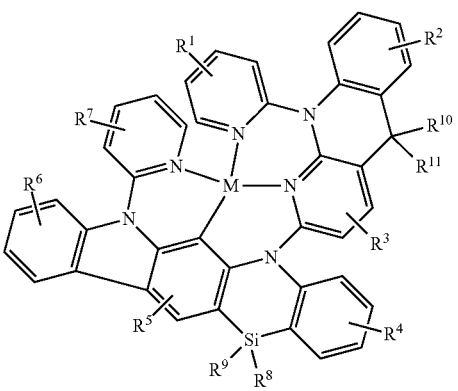
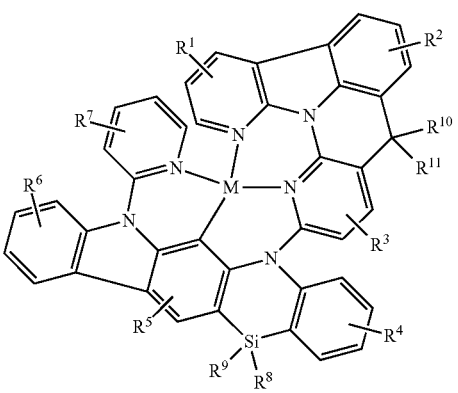
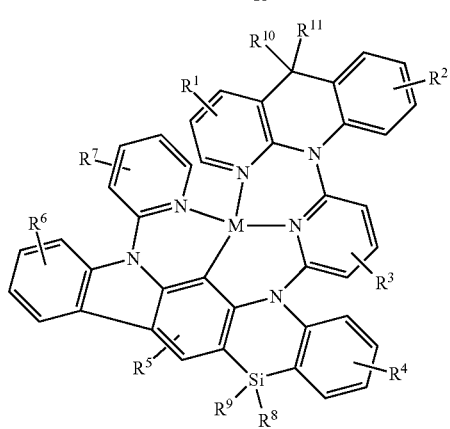
92
-continued
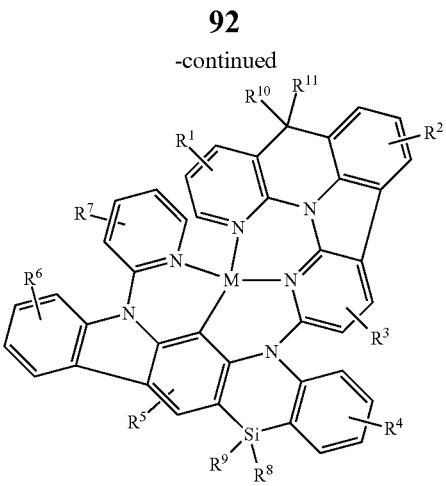
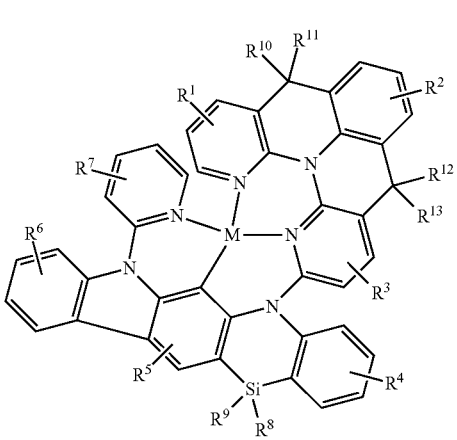
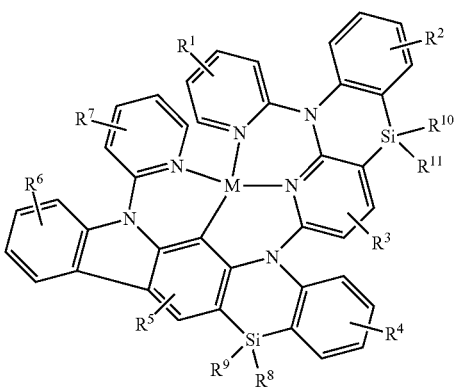
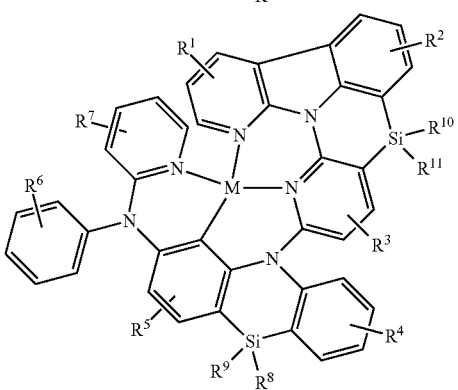

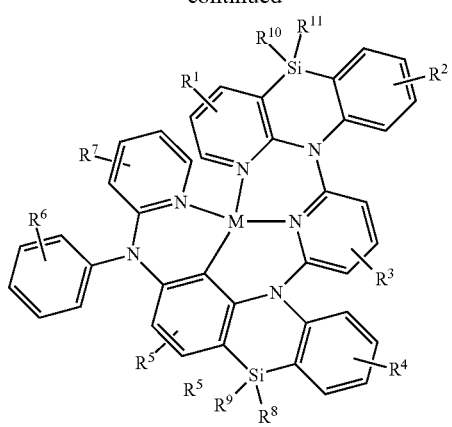
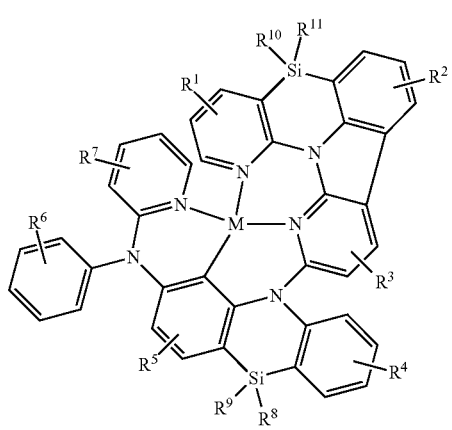
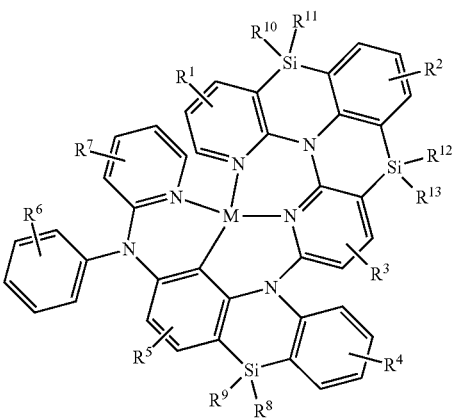
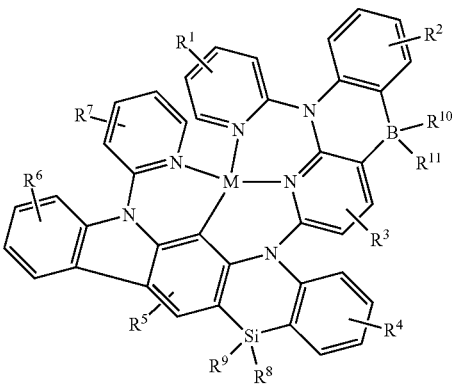
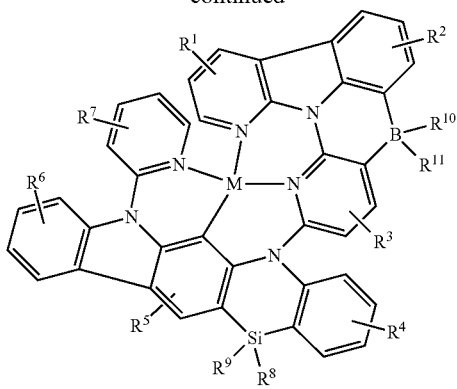
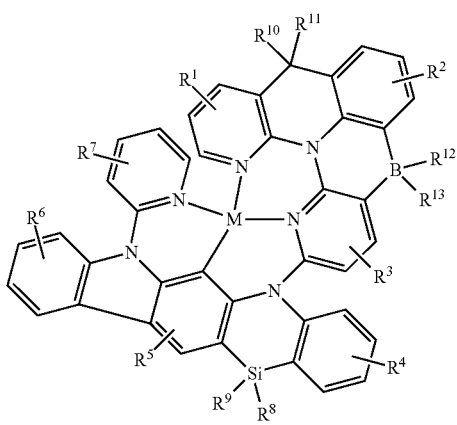
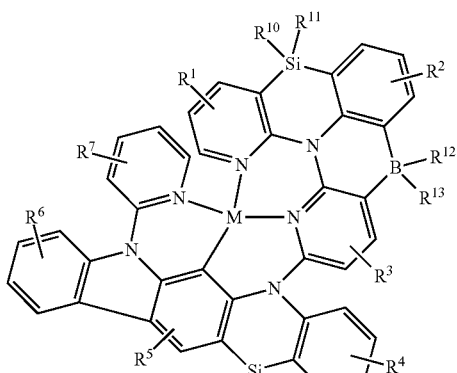
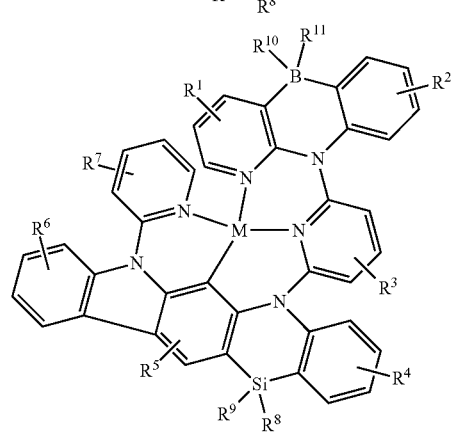

-continued
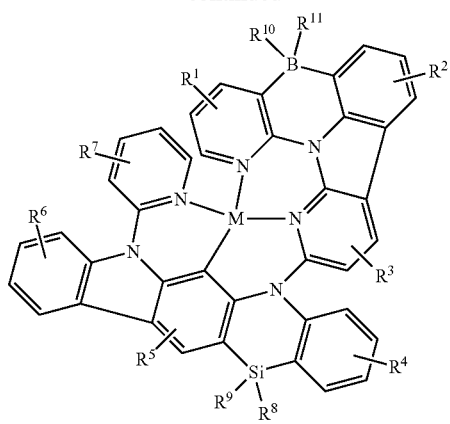
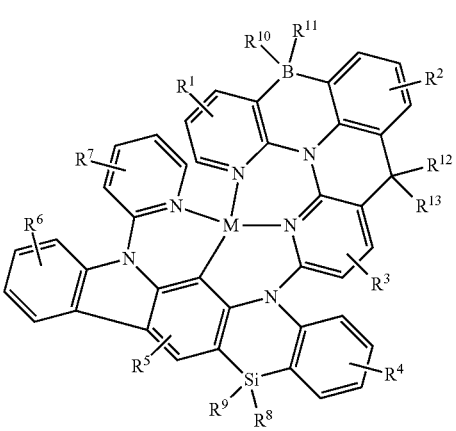
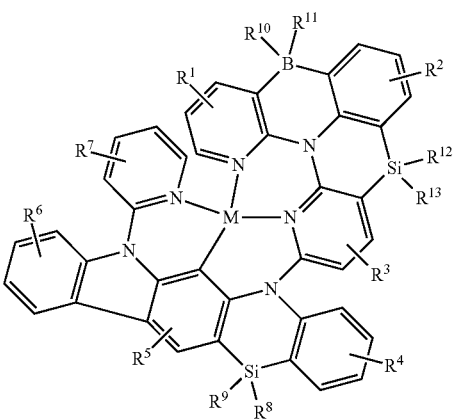
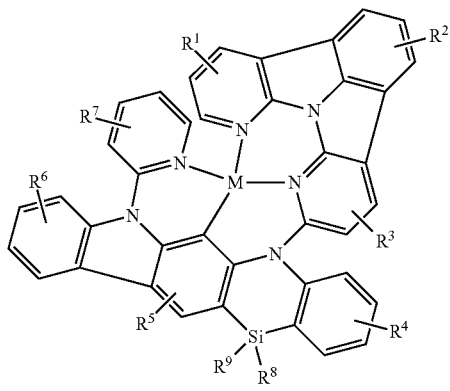
-continued
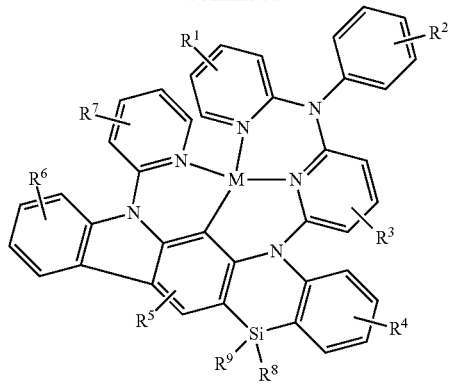
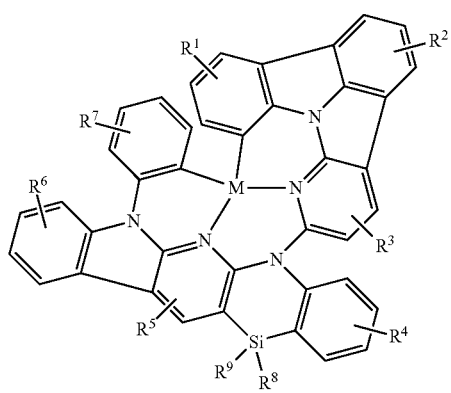
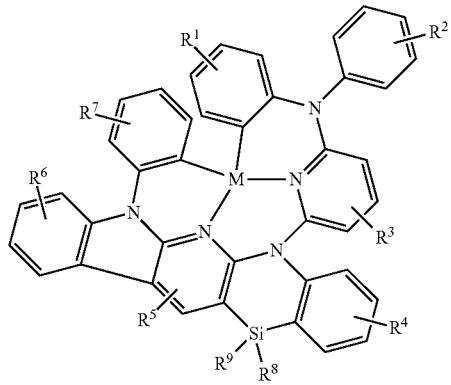
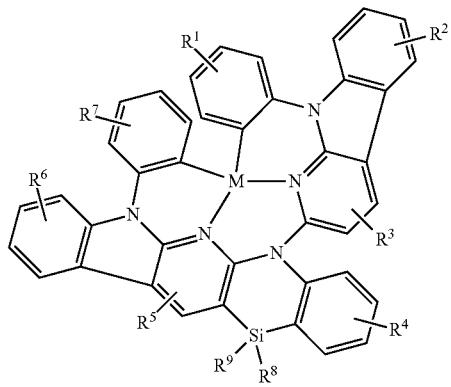

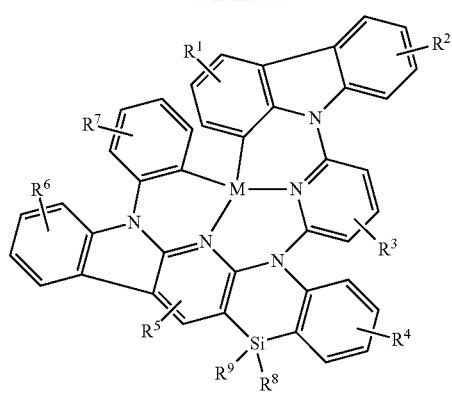
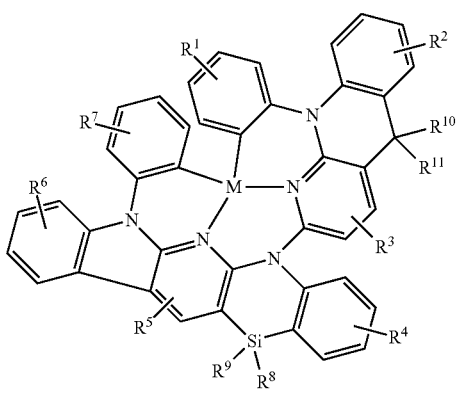
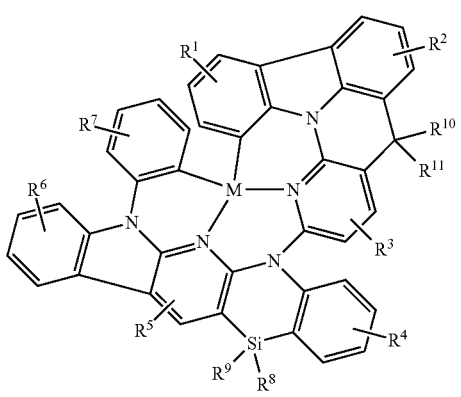
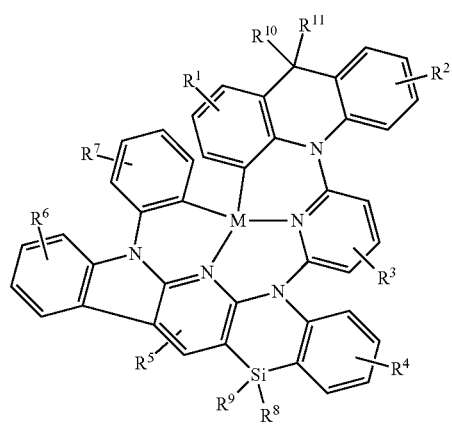
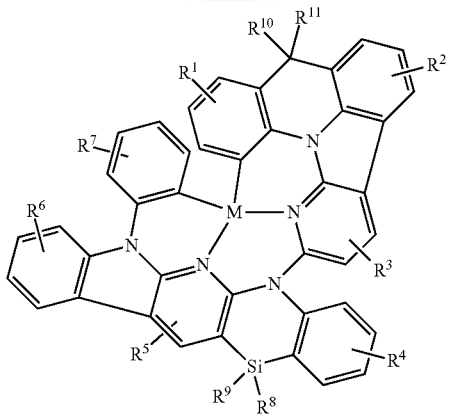
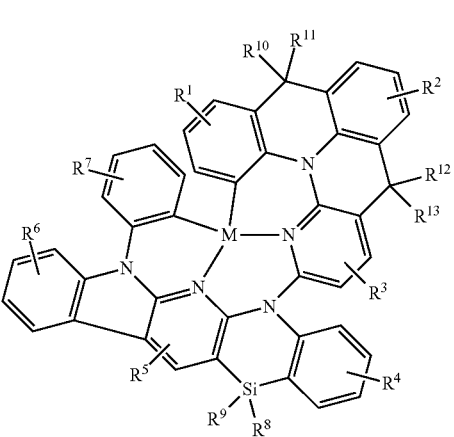
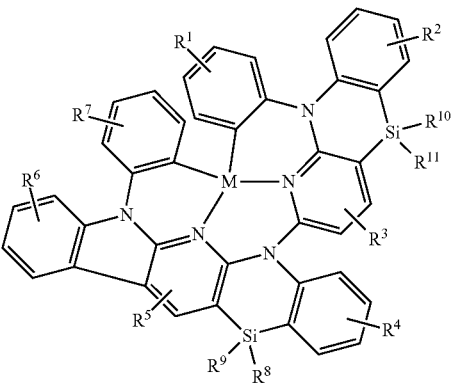
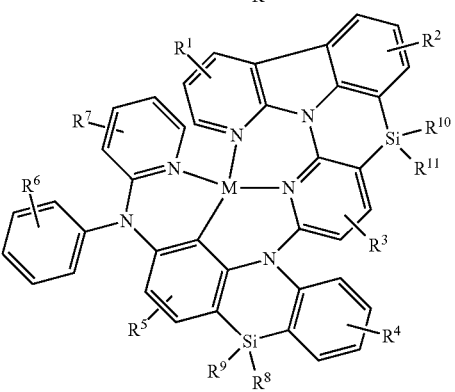

99
-continued
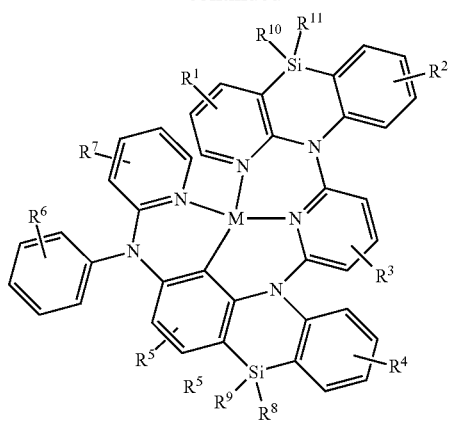
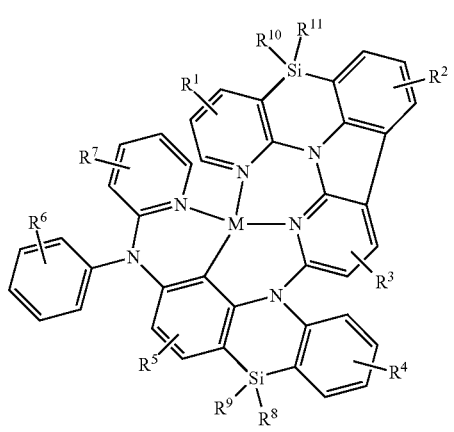
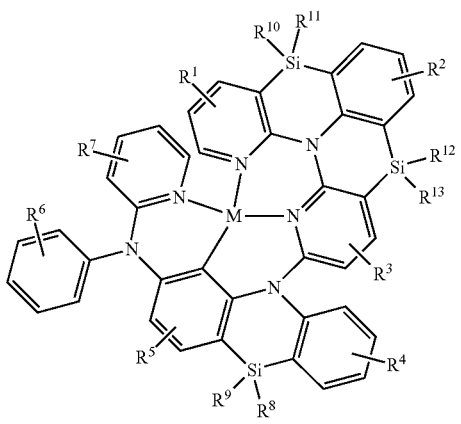
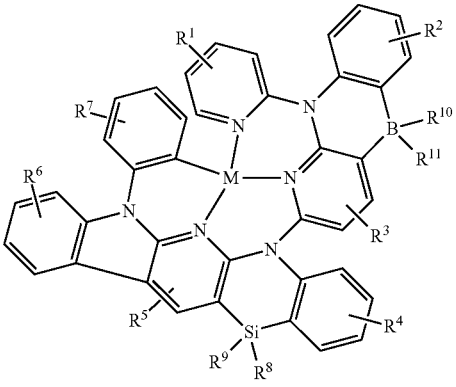
100
-continued
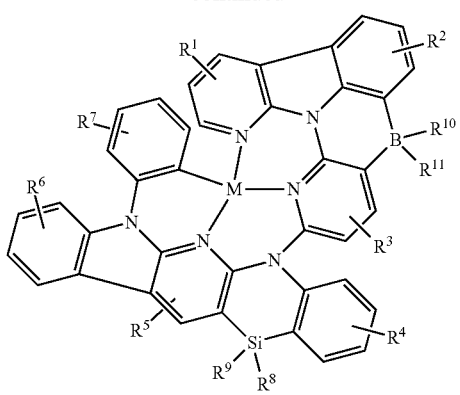
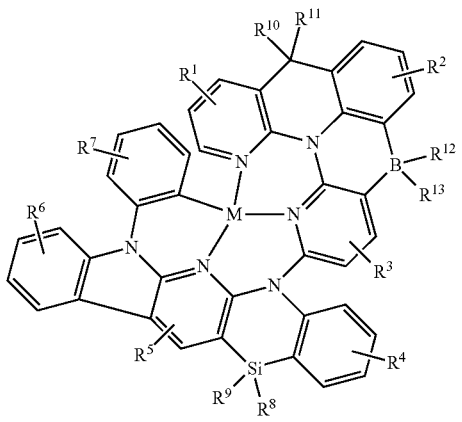
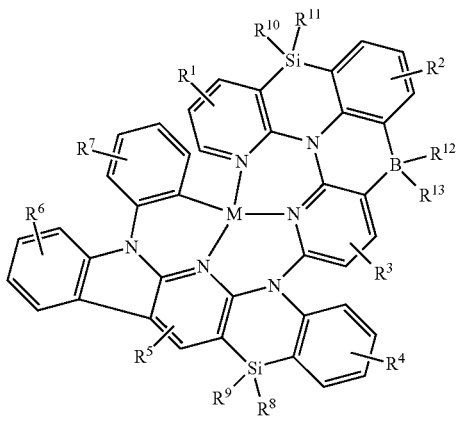
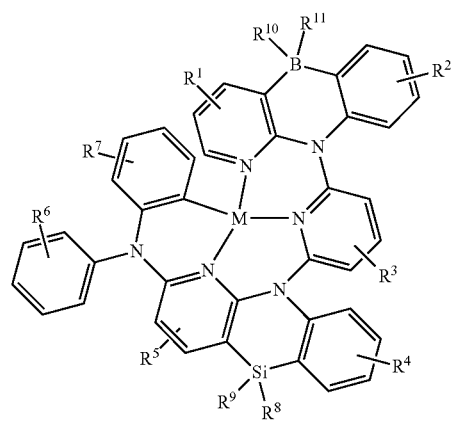

US 9,711,739 B2
101
-continued
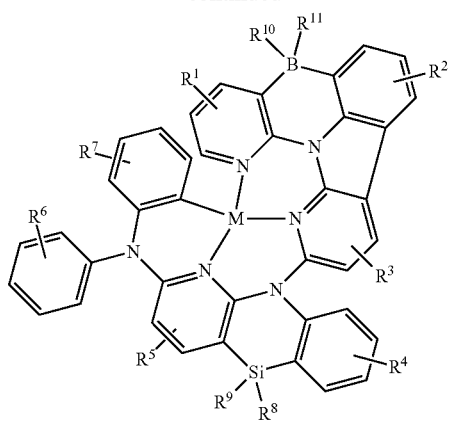
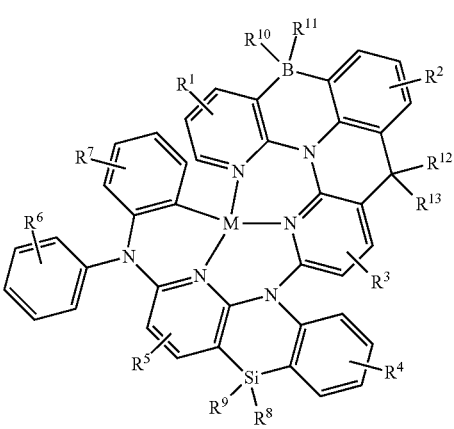
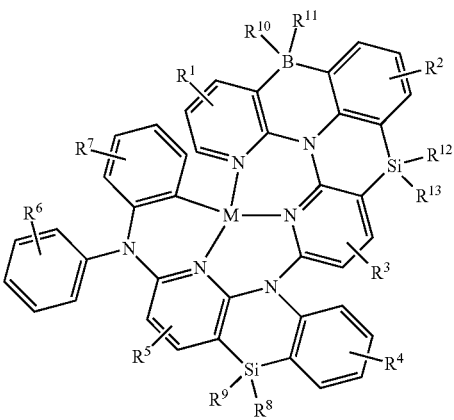
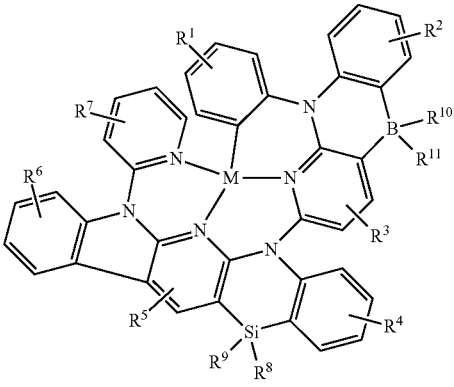
102
-continued
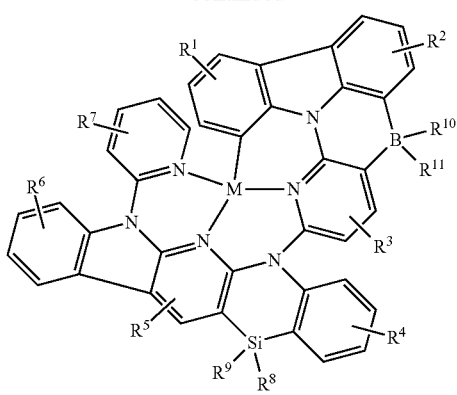
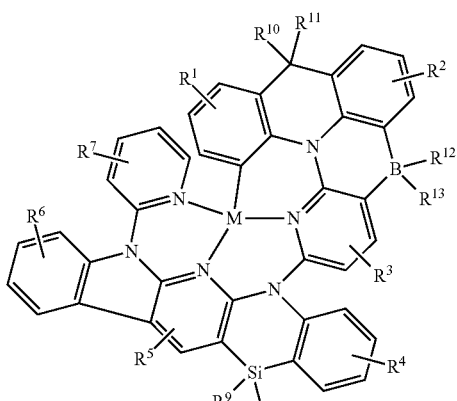
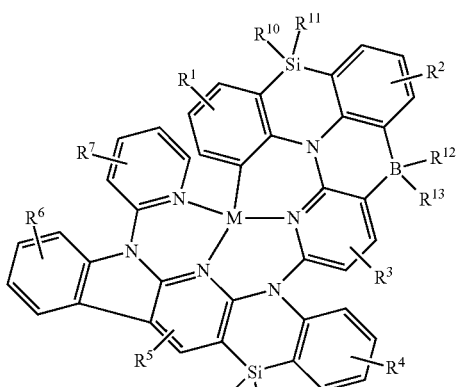
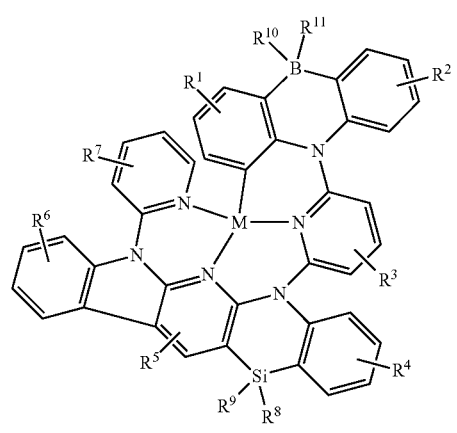

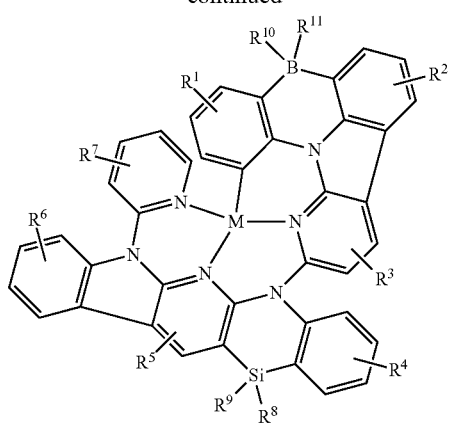
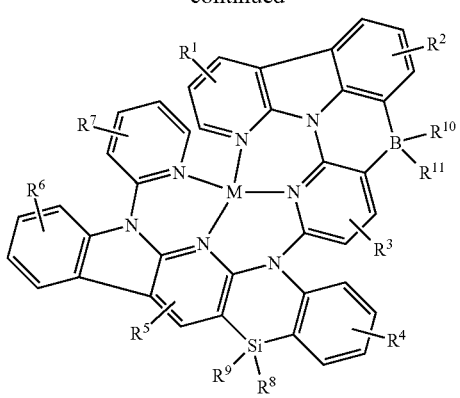
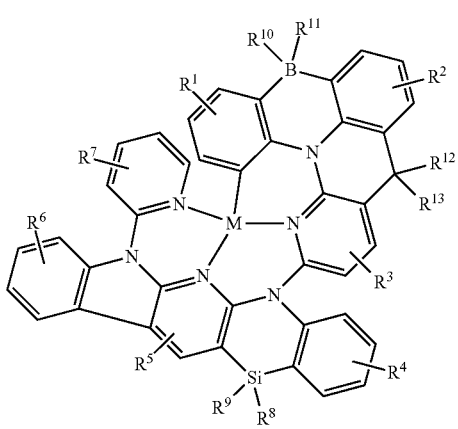
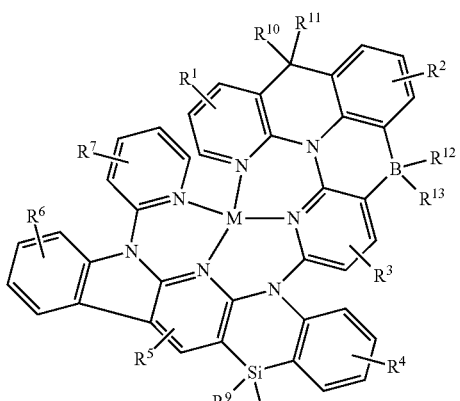
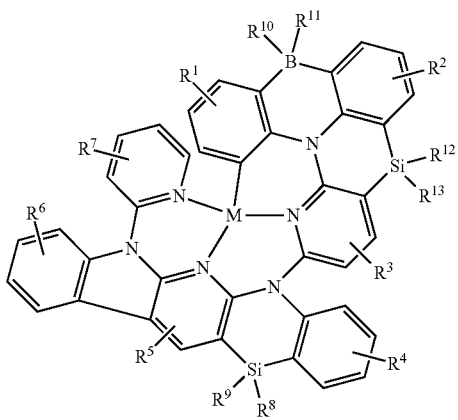
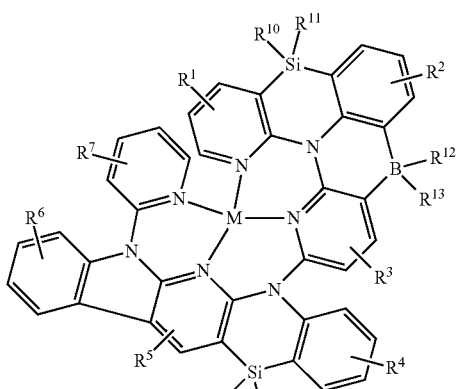
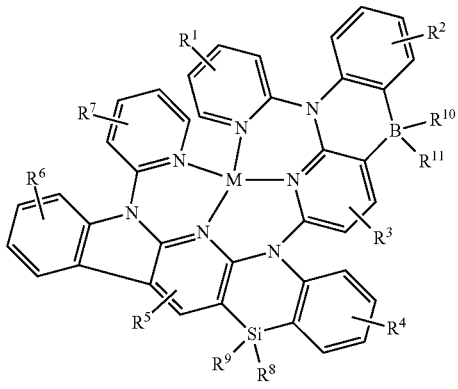
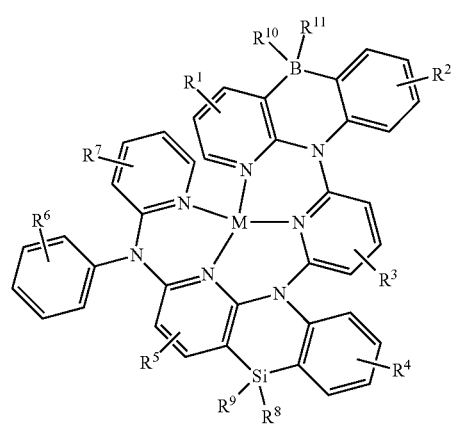

105
-continued
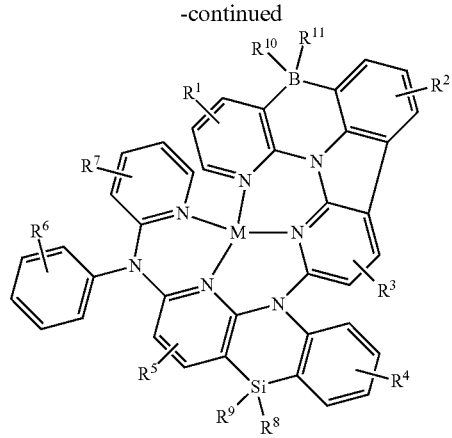
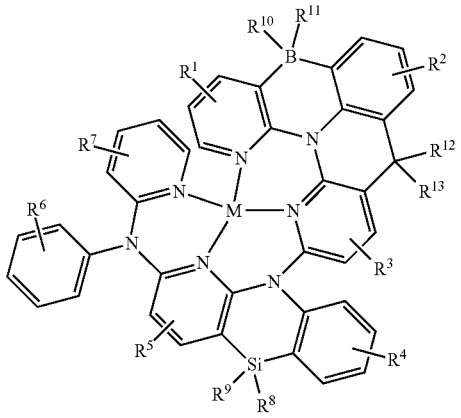
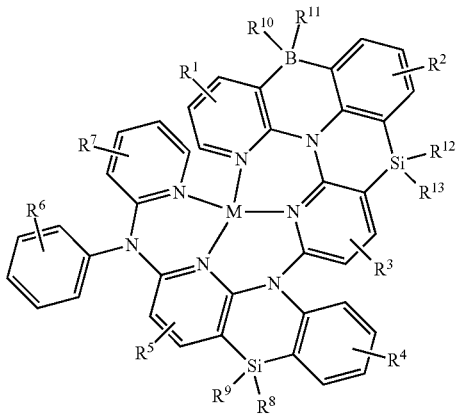
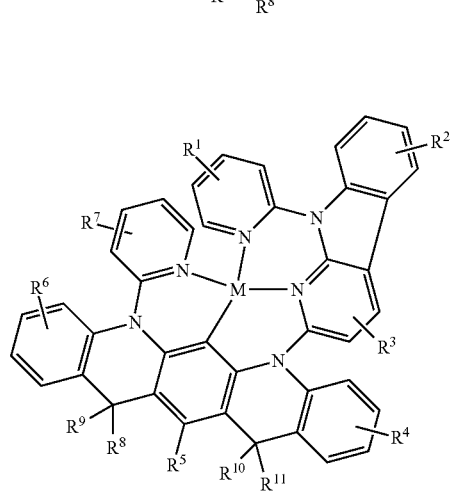
106
-continued
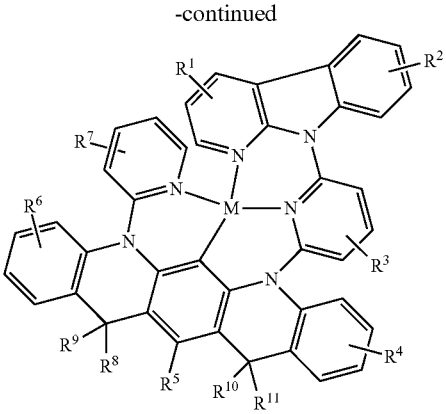
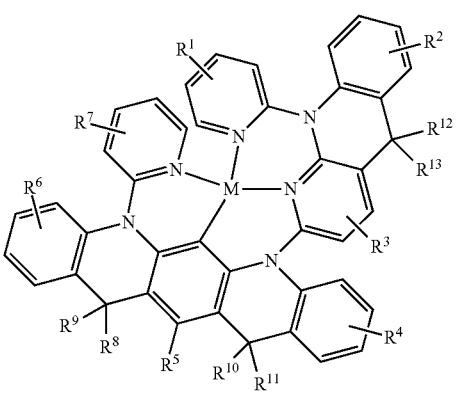
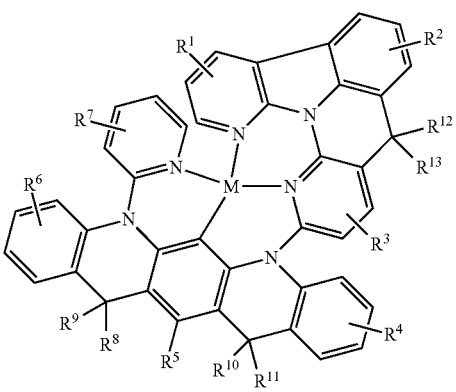
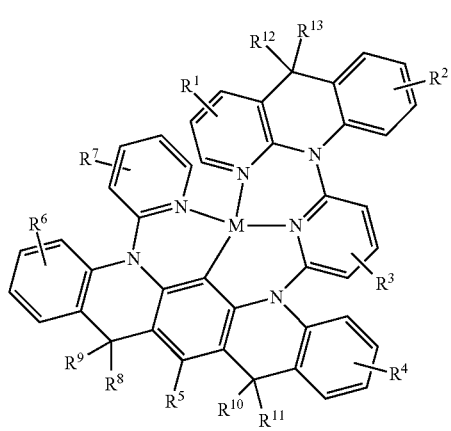

107
-continued
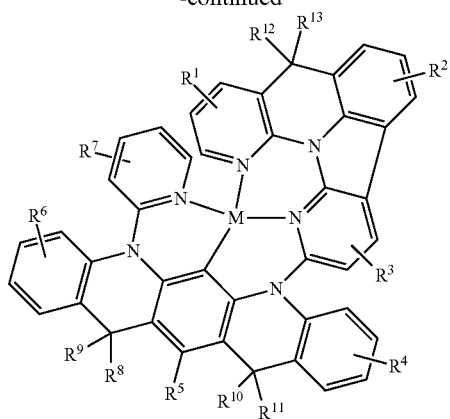
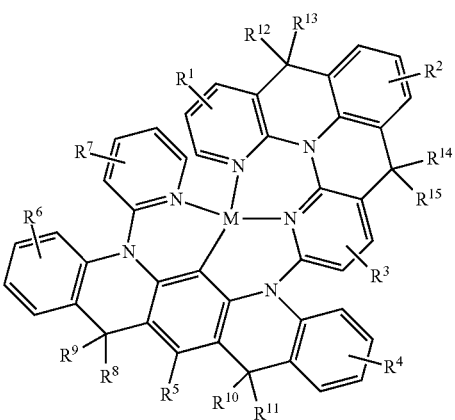
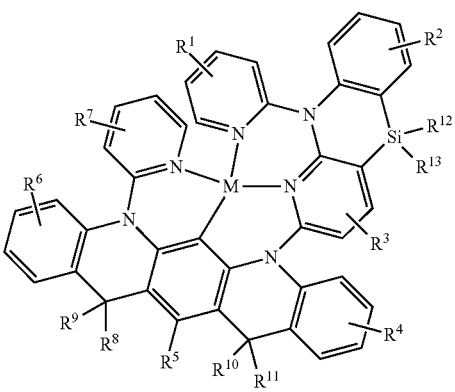
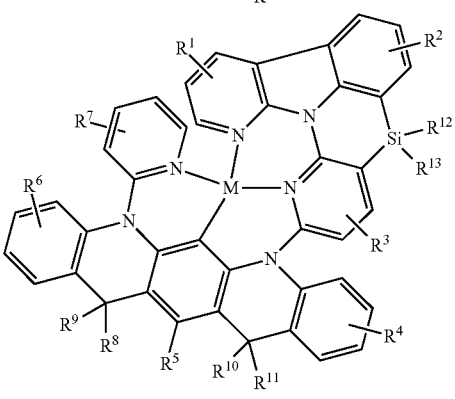
108
-continued
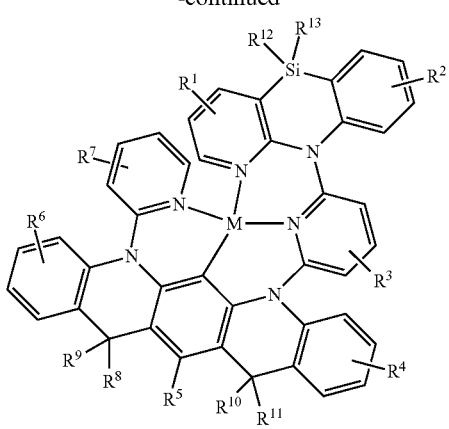
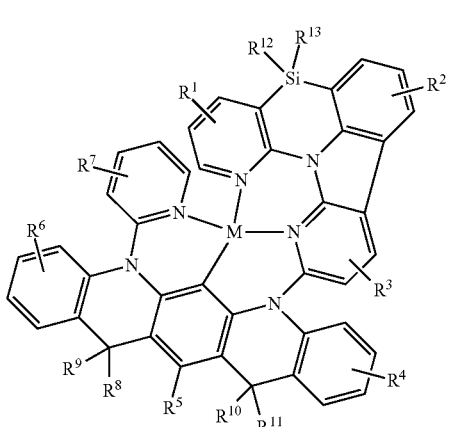
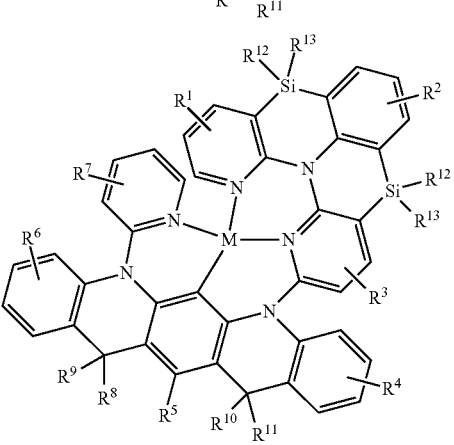
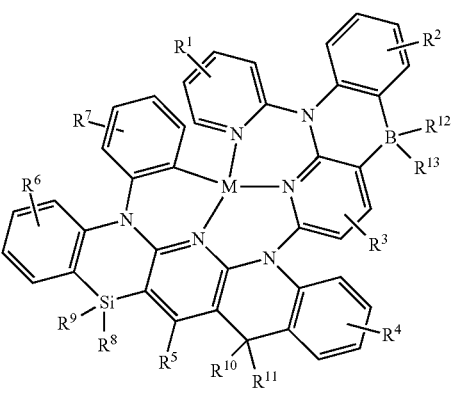

109
-continued
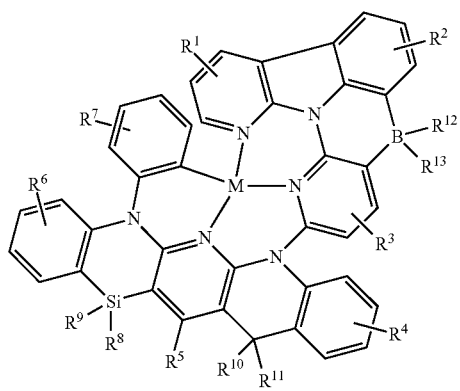
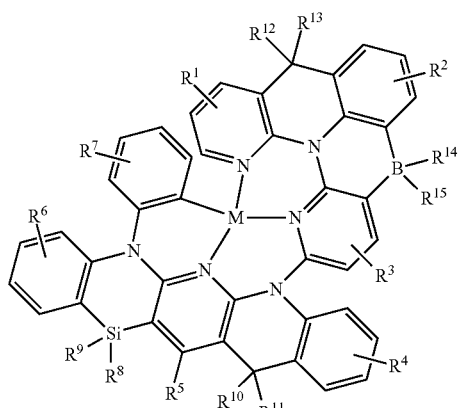
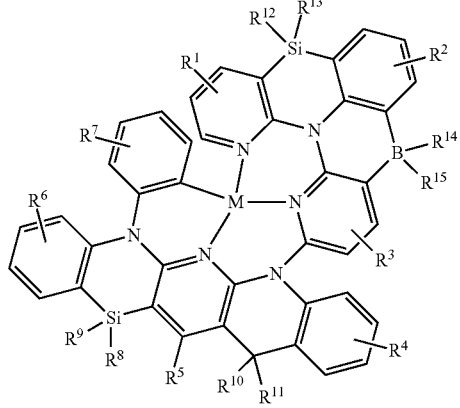
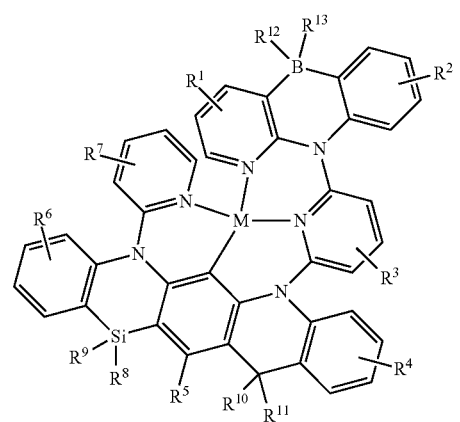
110
-continued
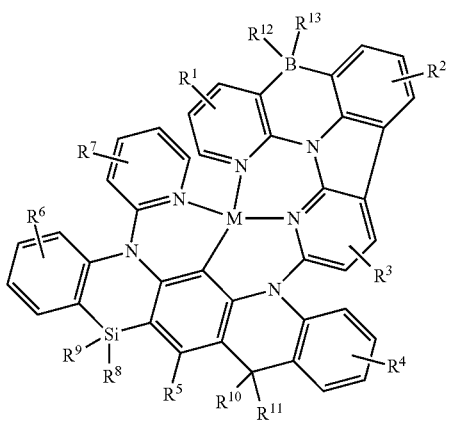
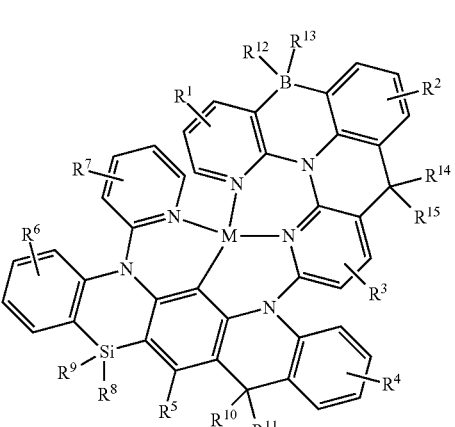
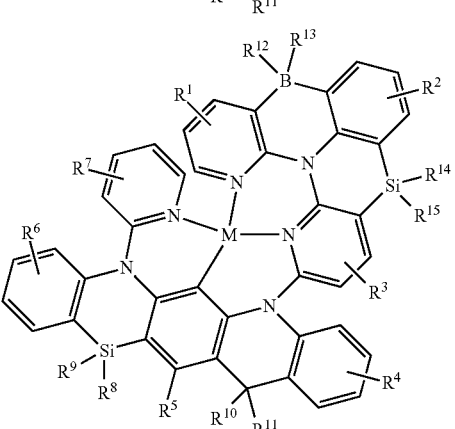
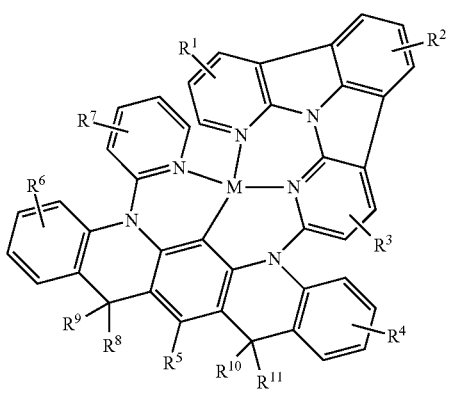

111
-continued
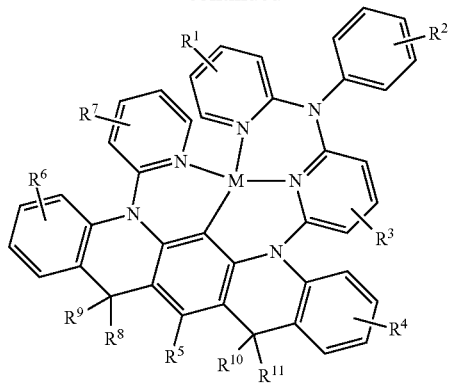
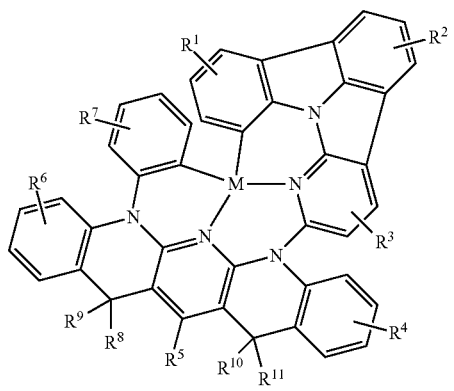
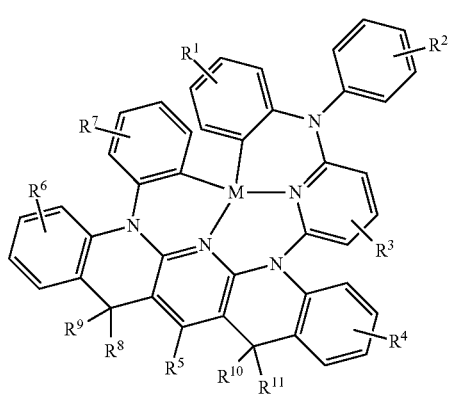
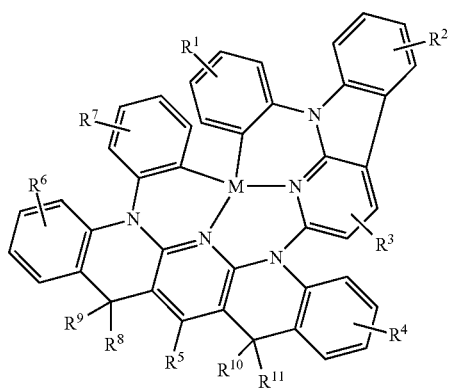
112
-continued
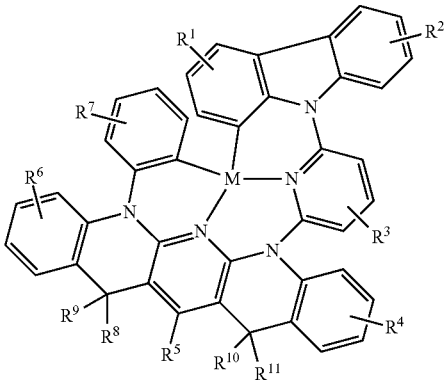
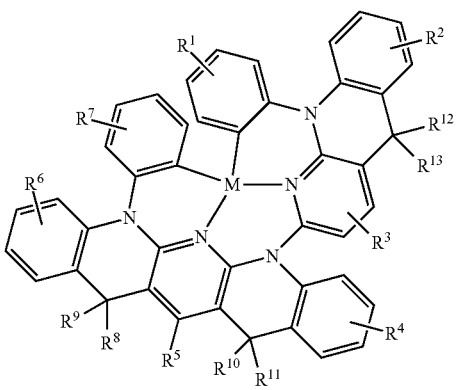
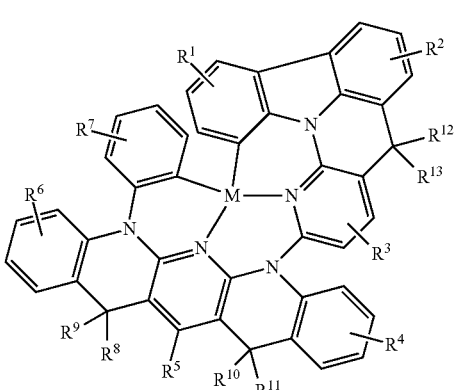
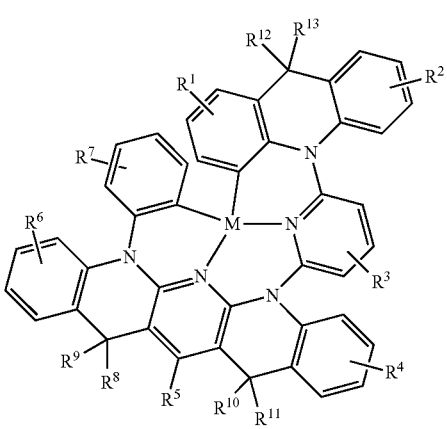

113
-continued
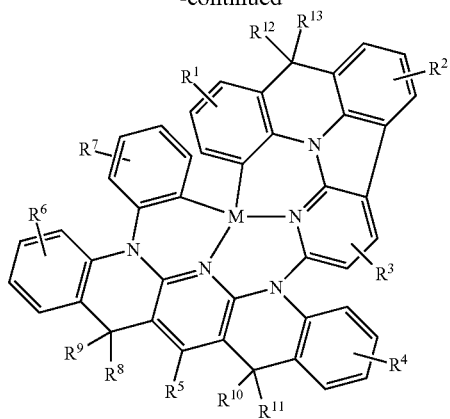
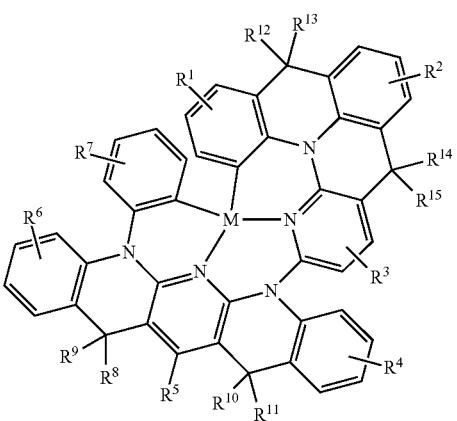
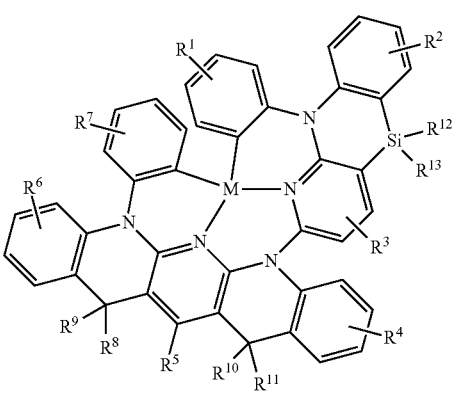
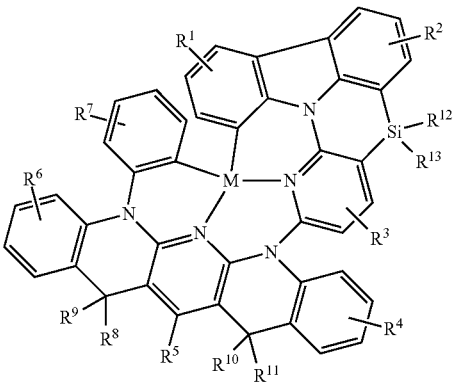
114
-continued
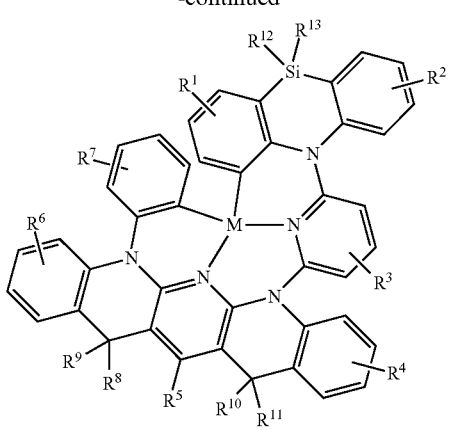
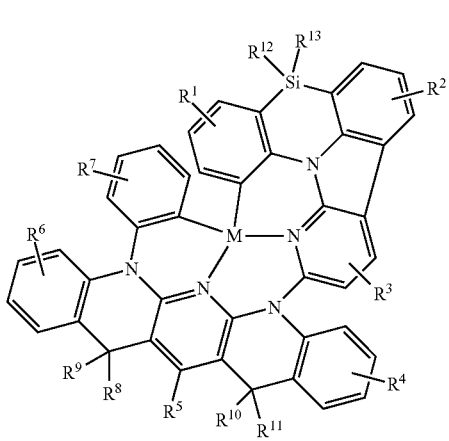
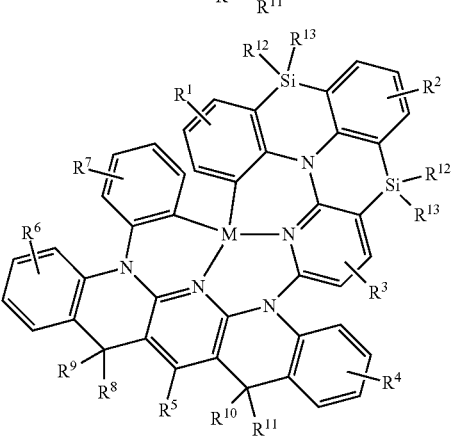
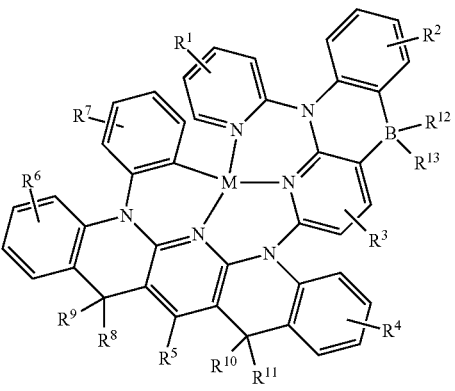

115
-continued
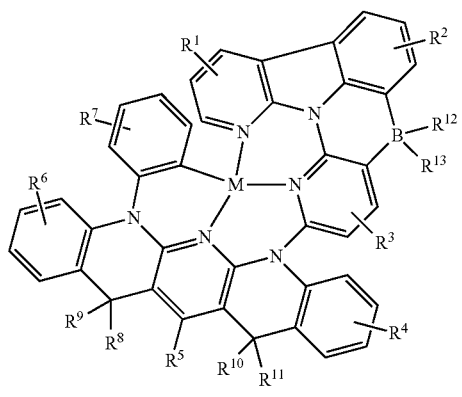
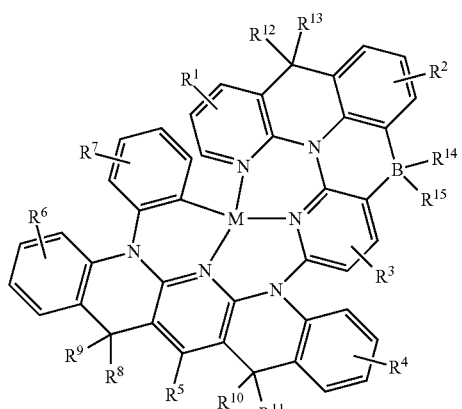
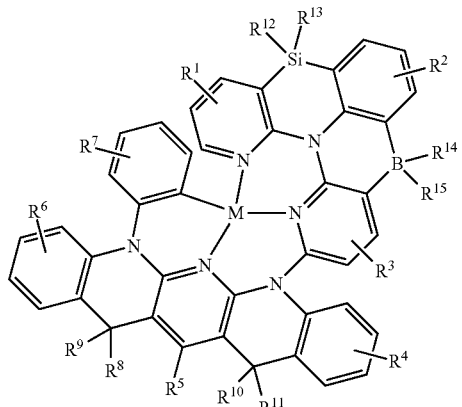
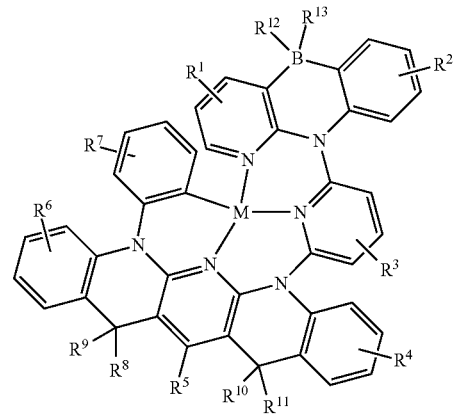
116
-continued
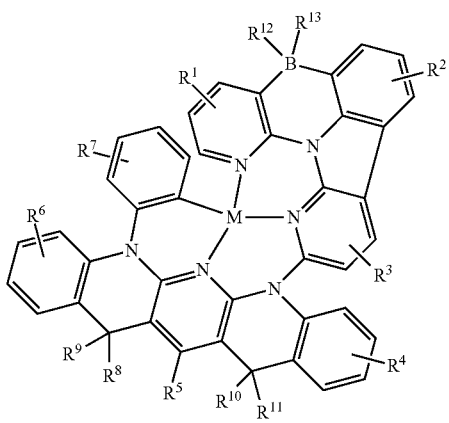
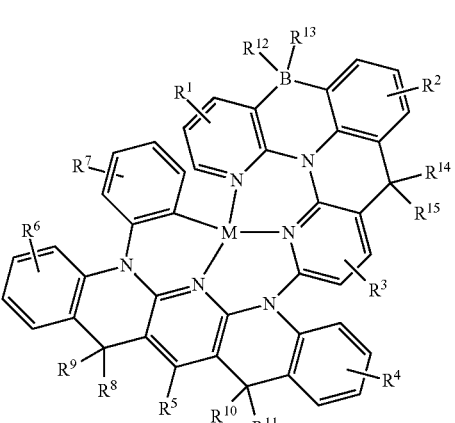
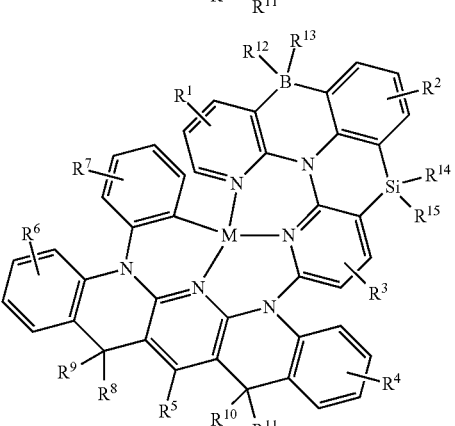
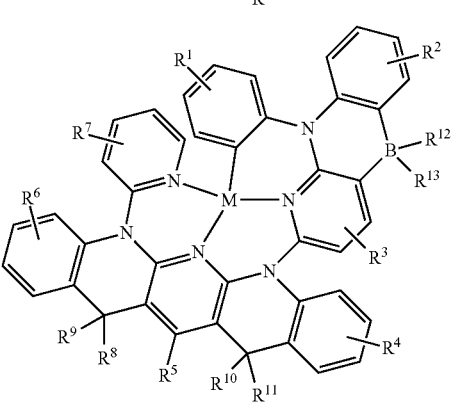

117
-continued
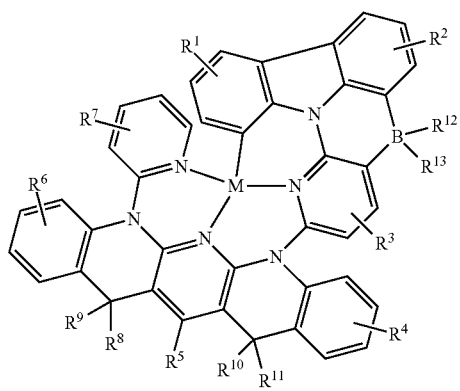
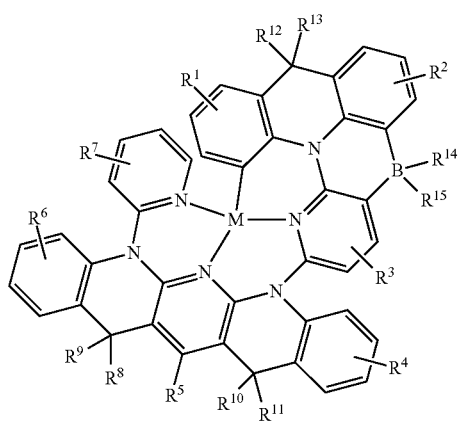
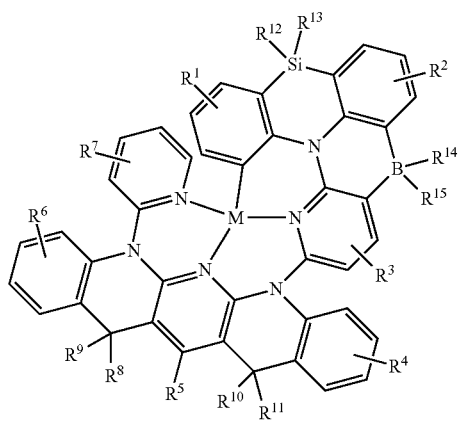
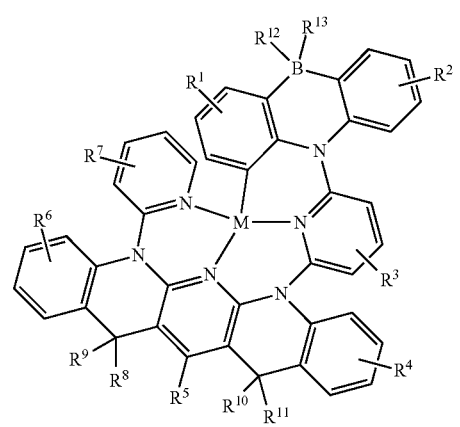
118
-continued
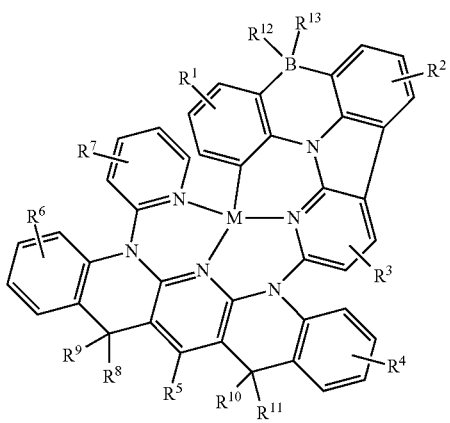
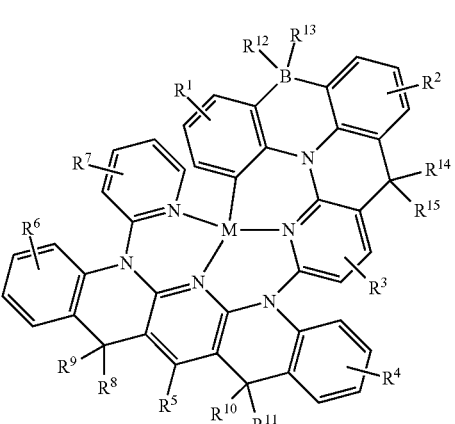
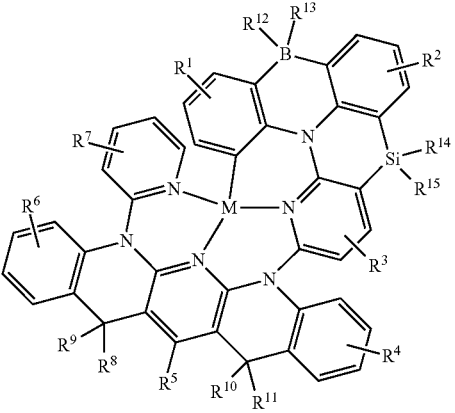
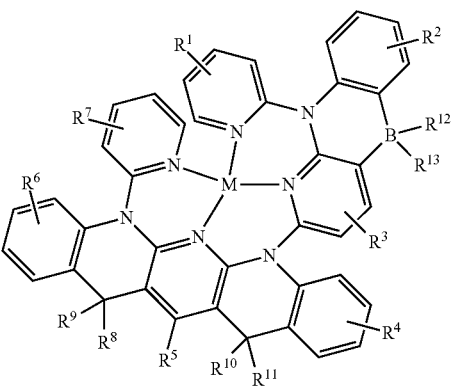

119
-continued
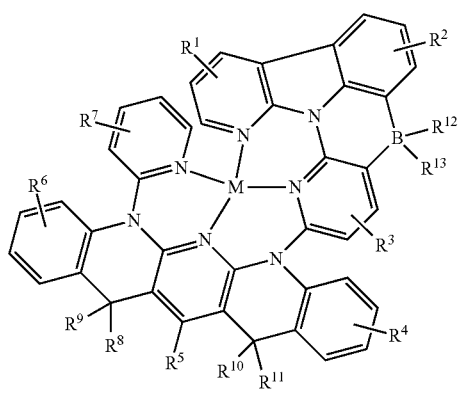
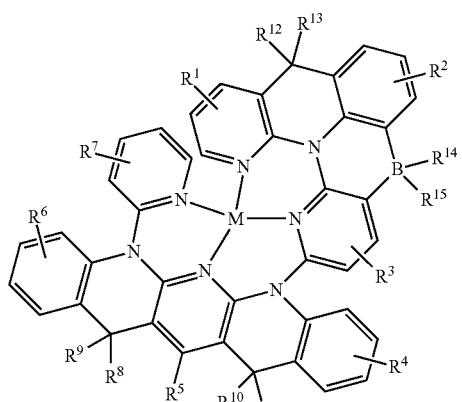
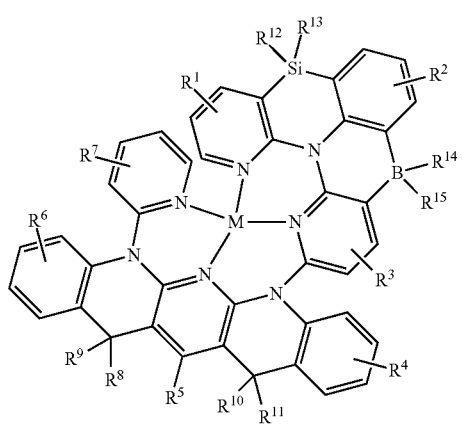
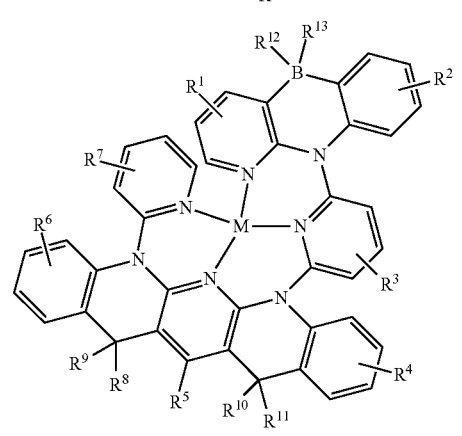
120
-continued
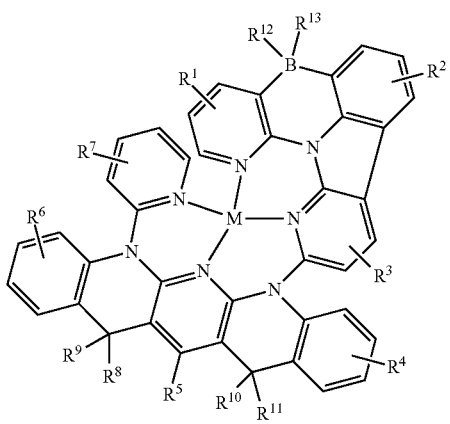
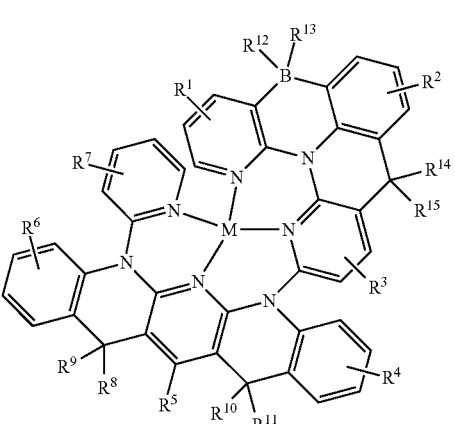
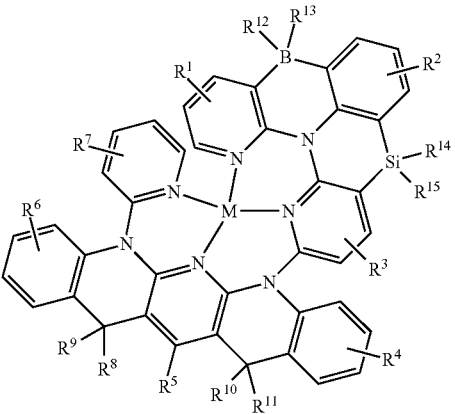
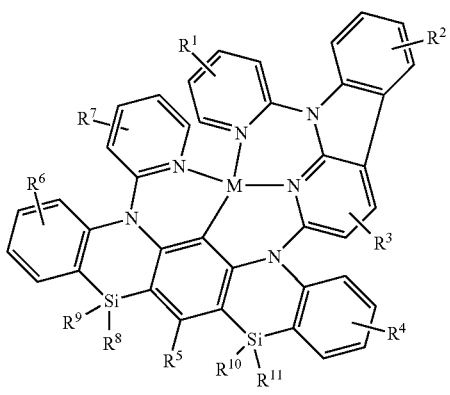

121
-continued
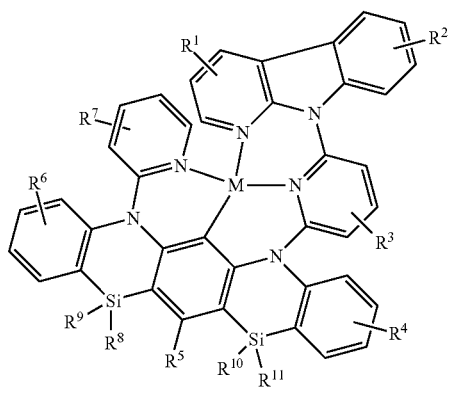
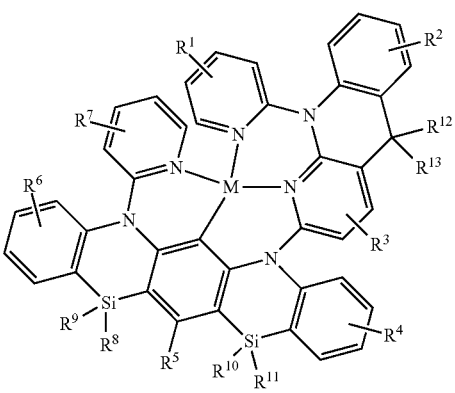
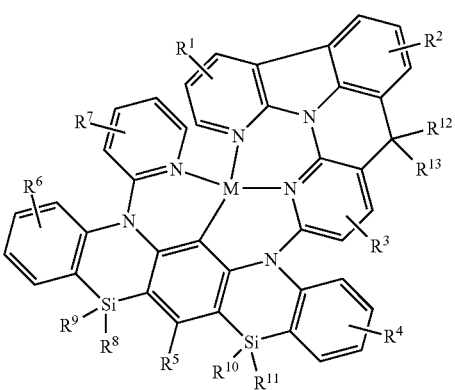
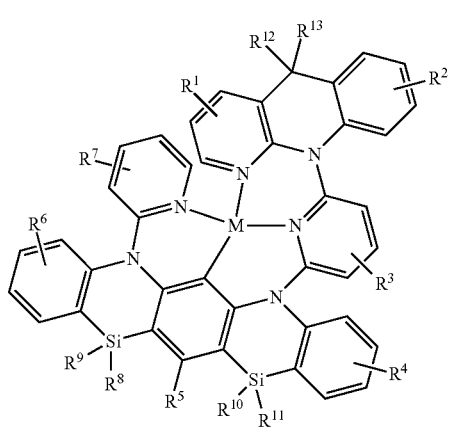
122
-continued
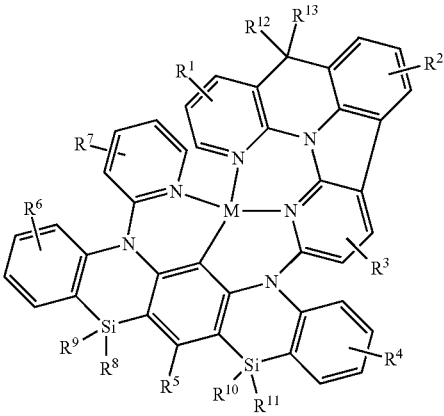
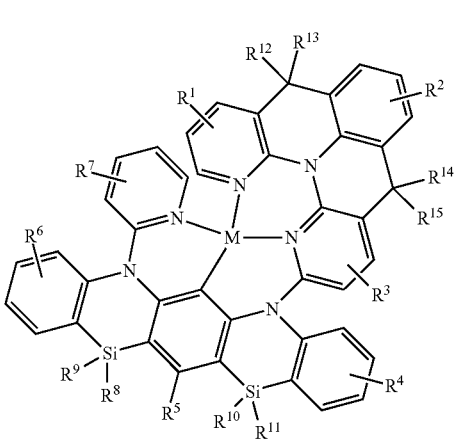
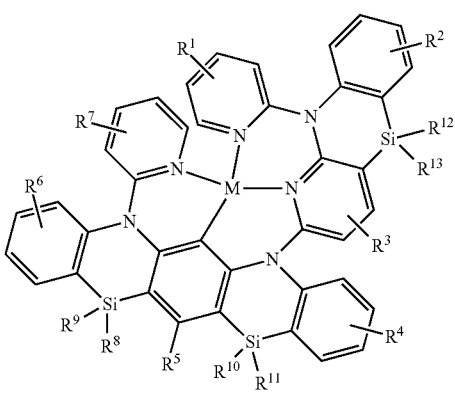
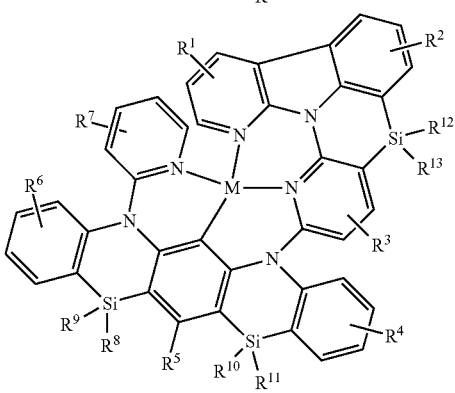

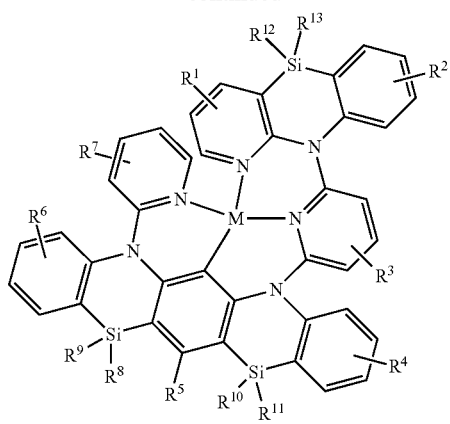
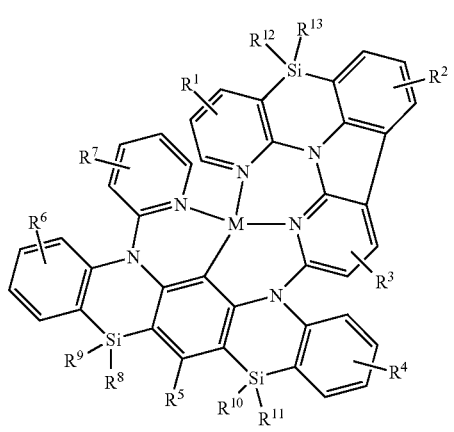
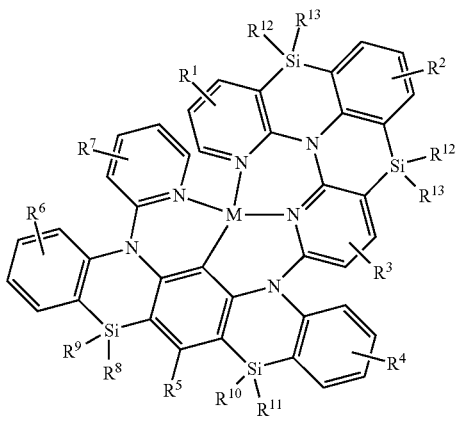
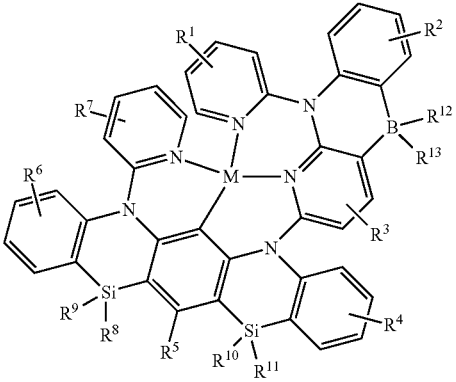
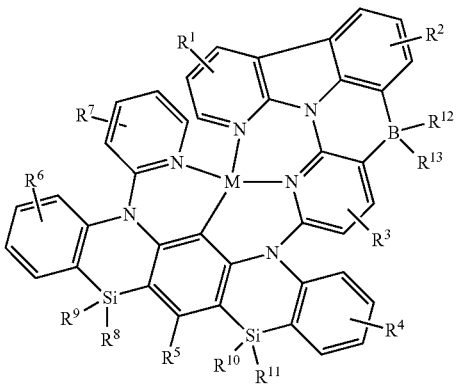
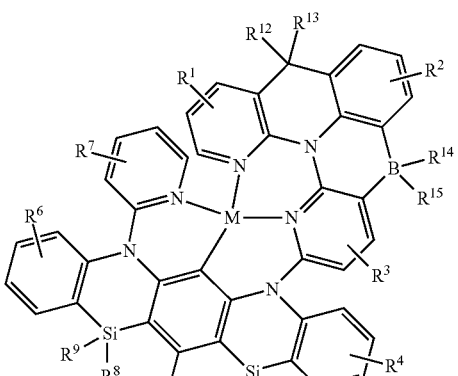
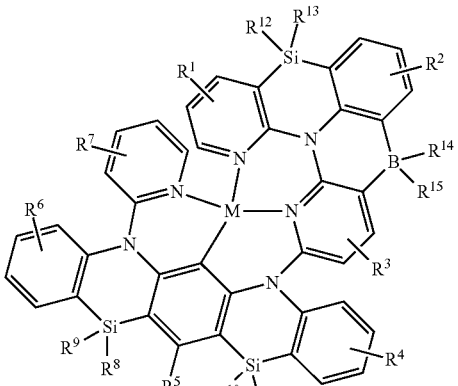
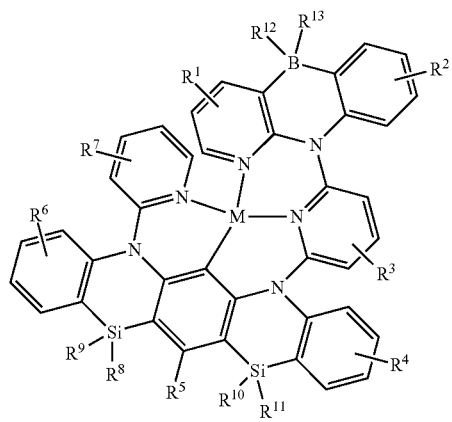

125
-continued
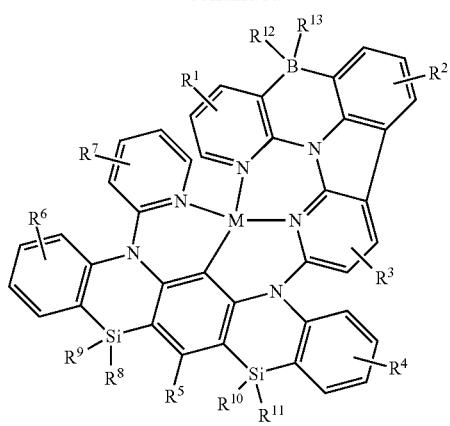
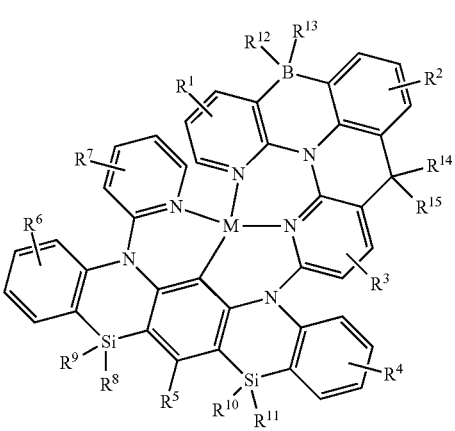
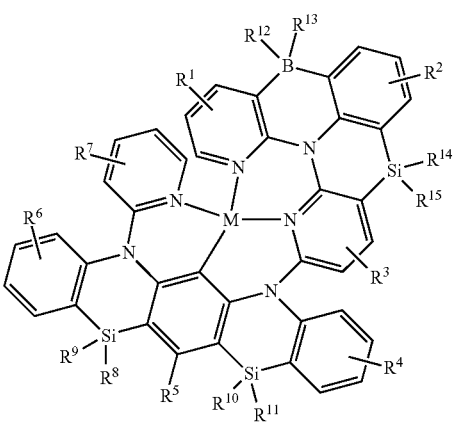
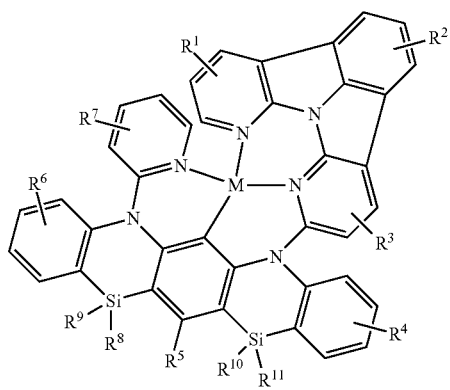
126
-continued
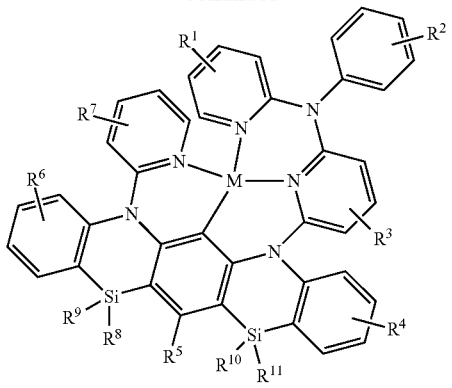
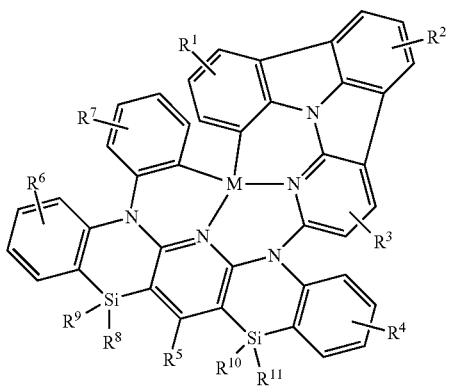
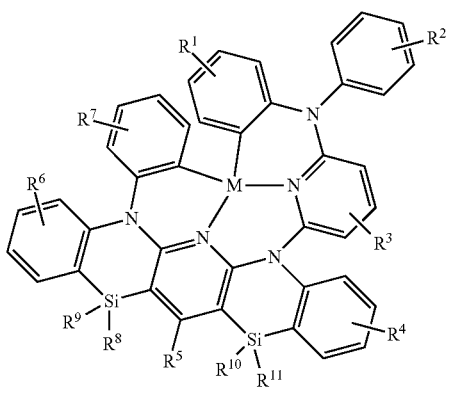
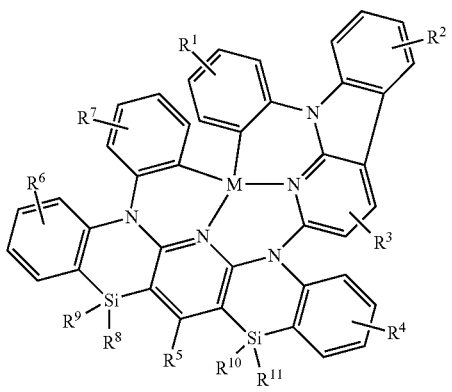

127
-continued
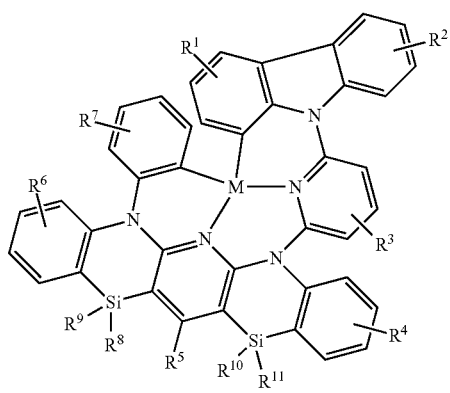
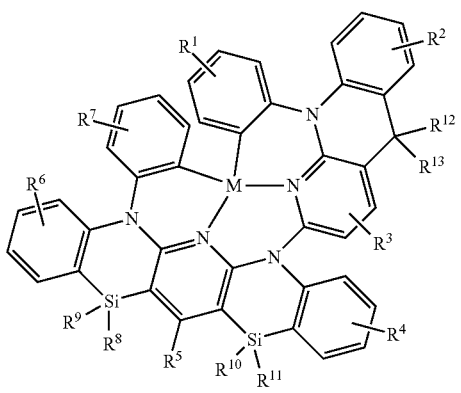
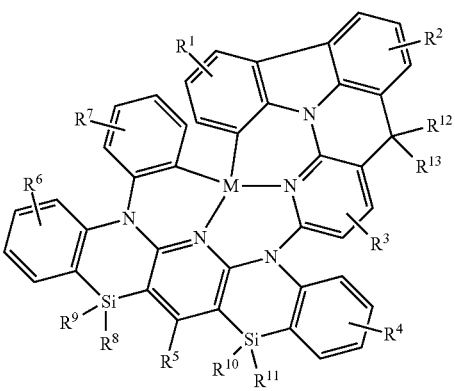
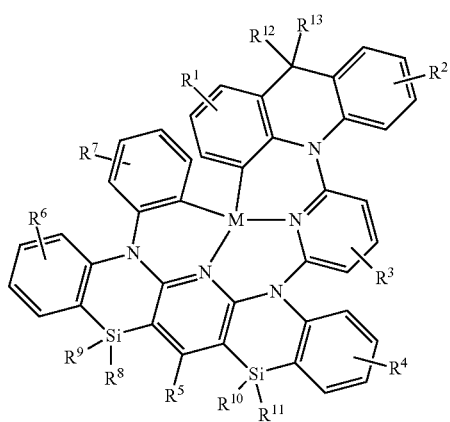
128
-continued
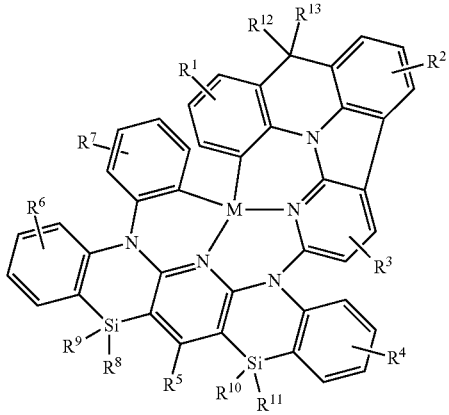
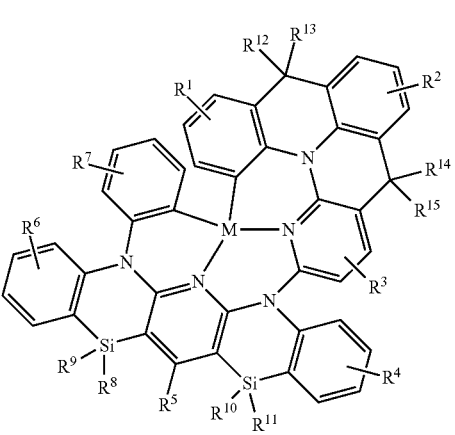
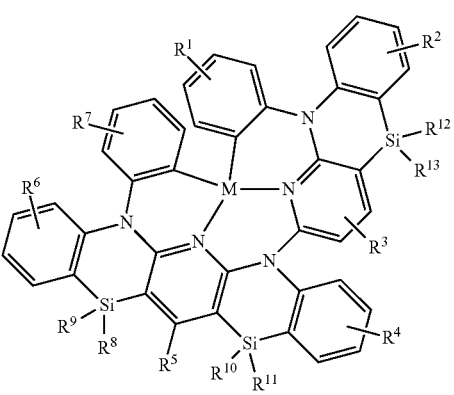
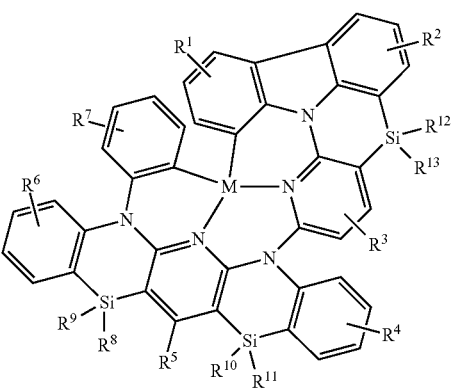

-continued
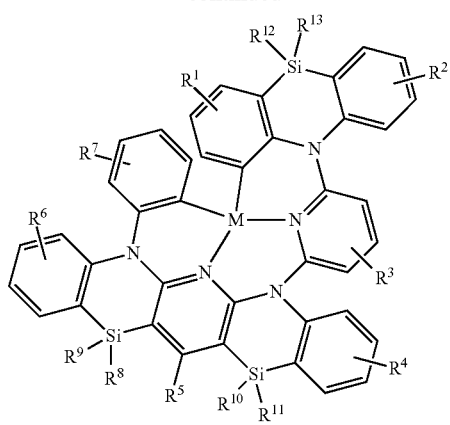
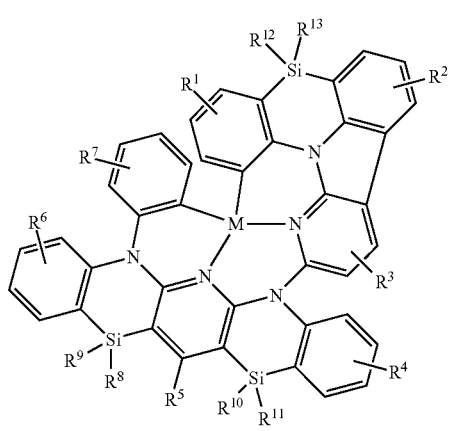
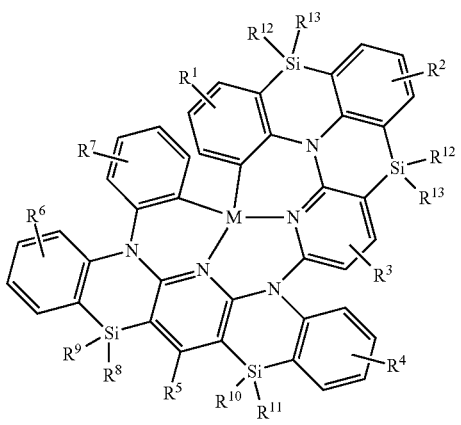
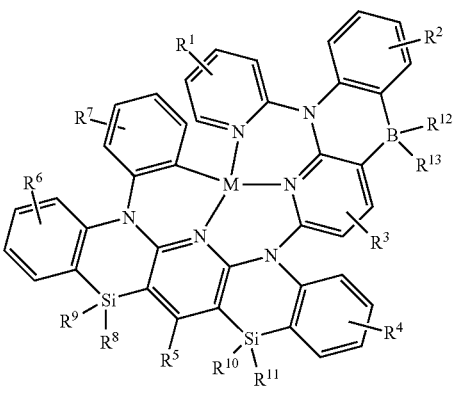
-continued
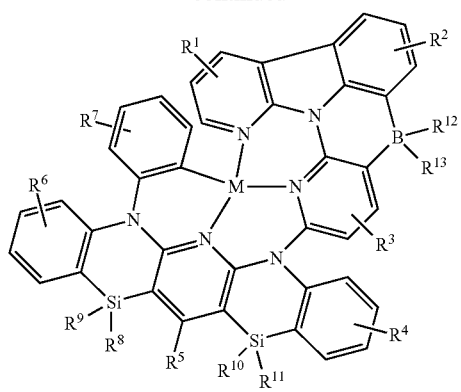
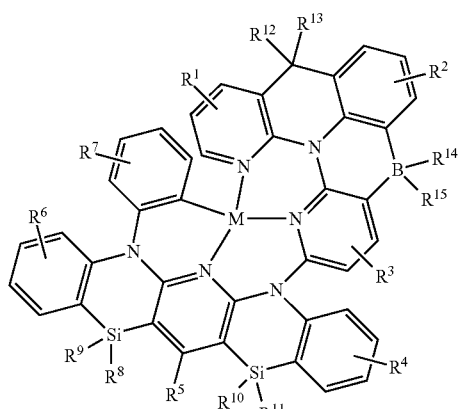
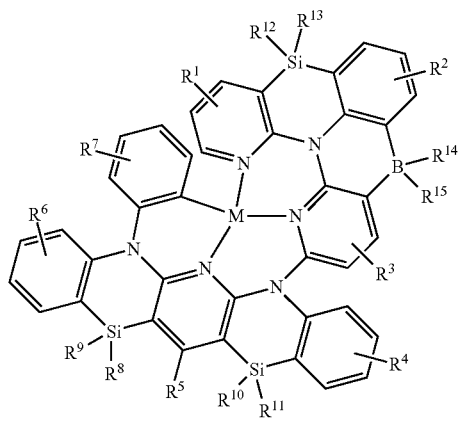
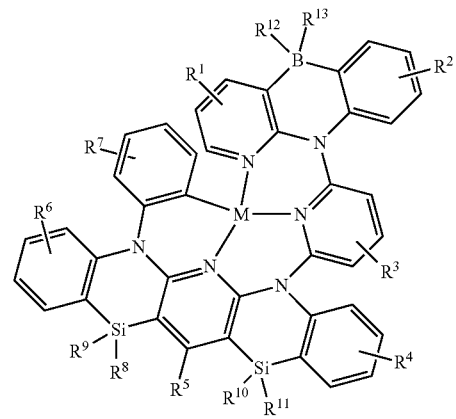

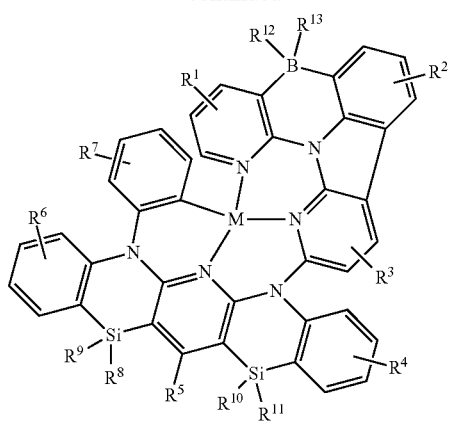
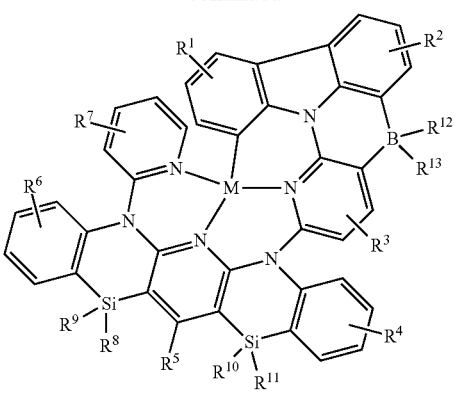
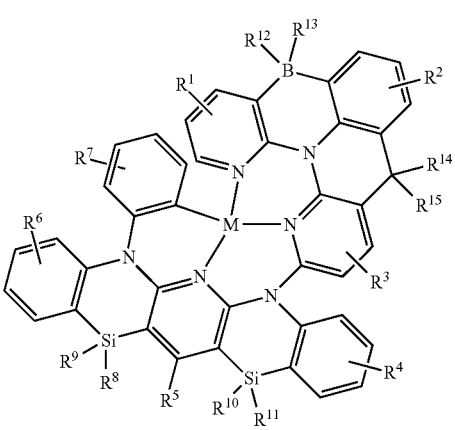
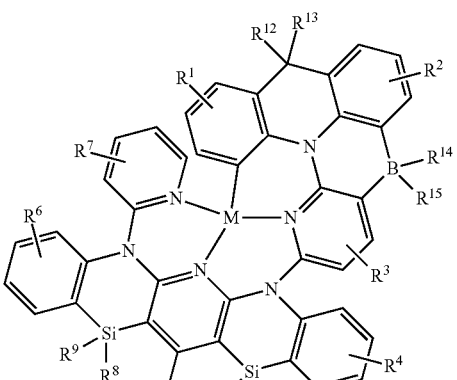
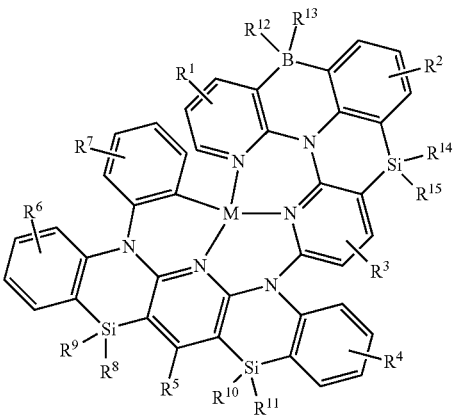
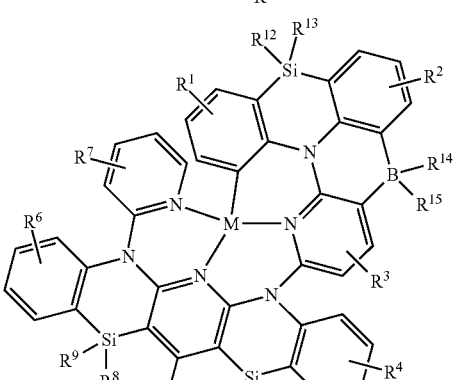
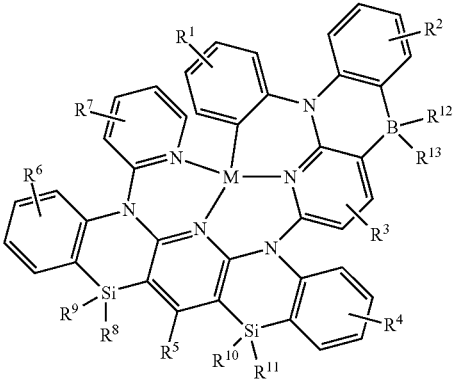
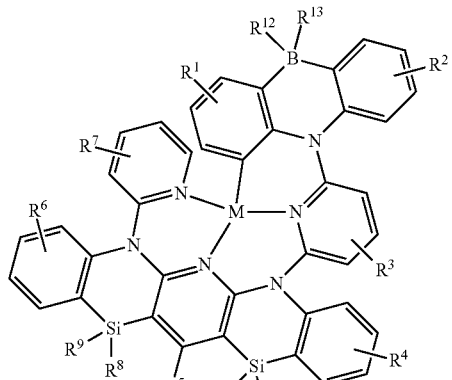

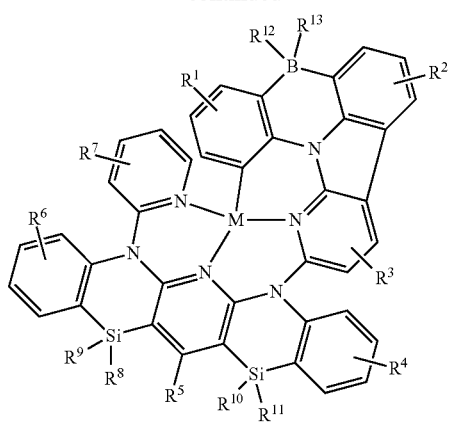
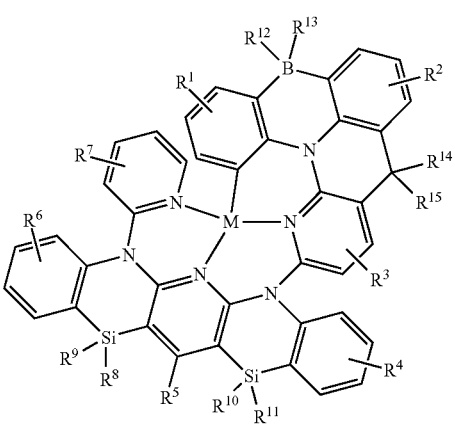
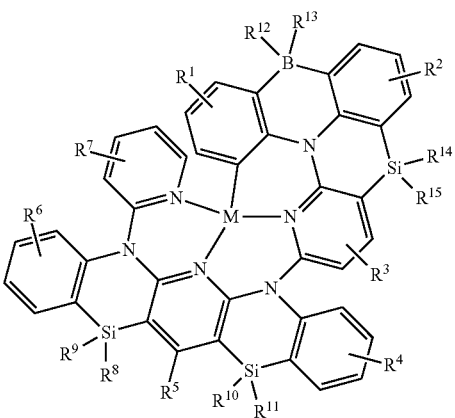
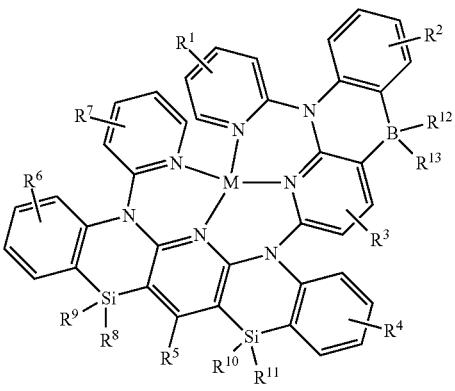
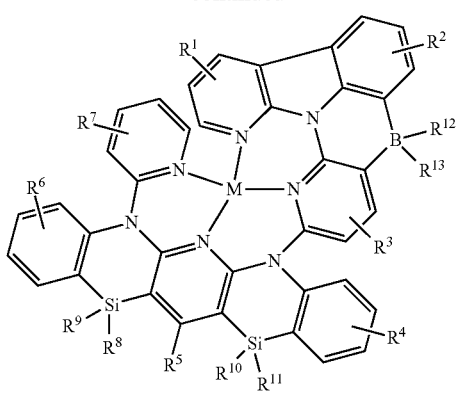
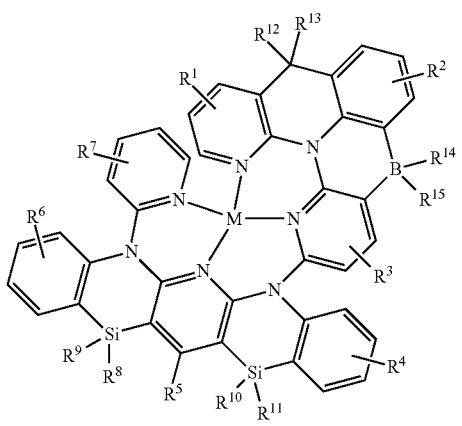
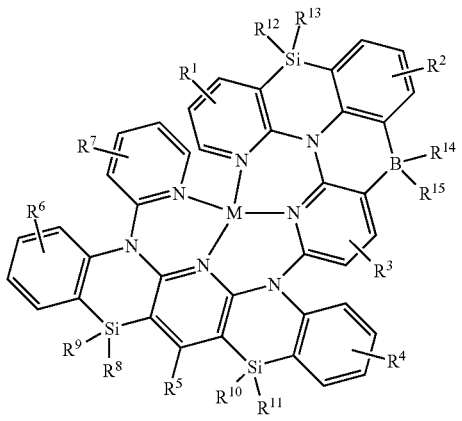
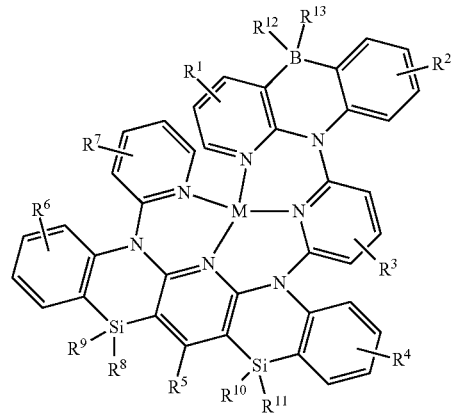

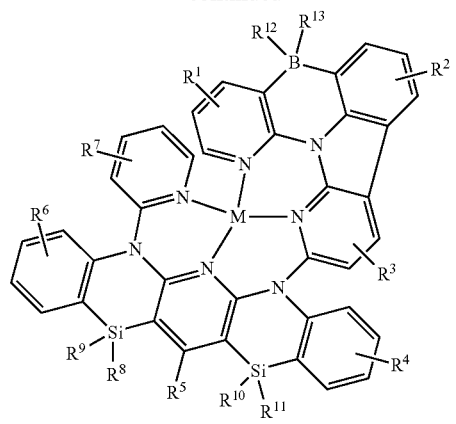
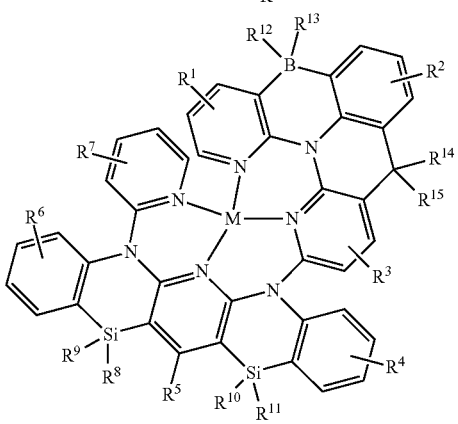
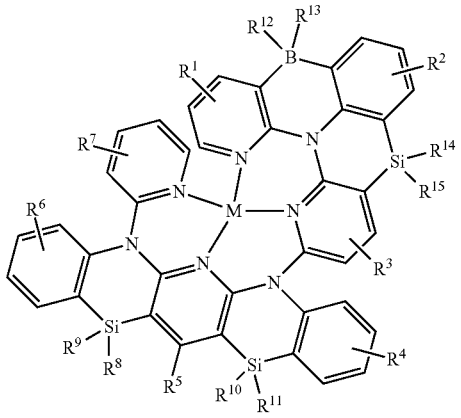
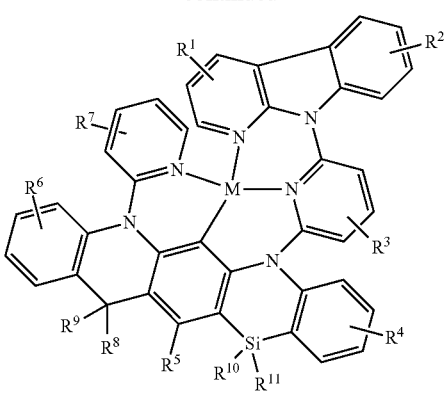
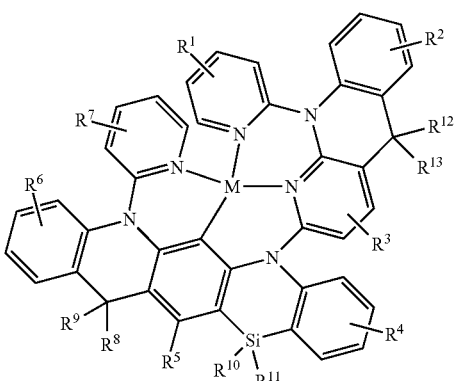
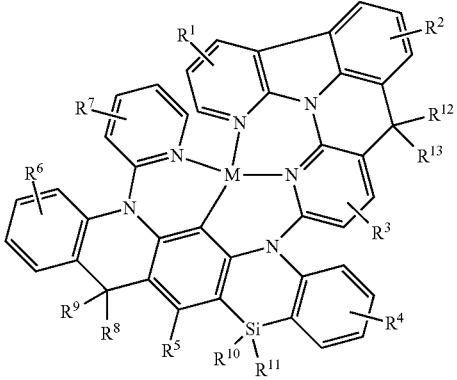
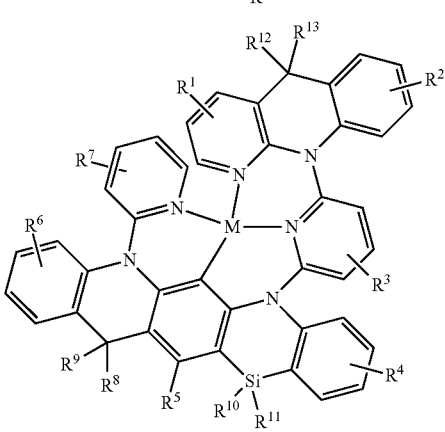

137
-continued
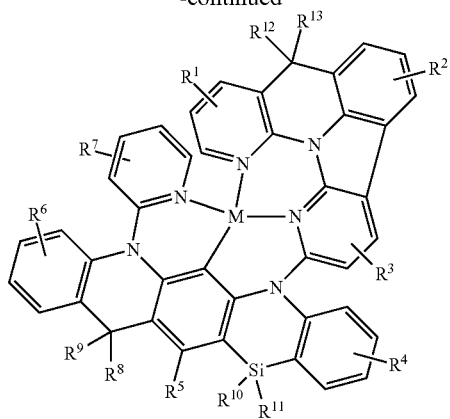
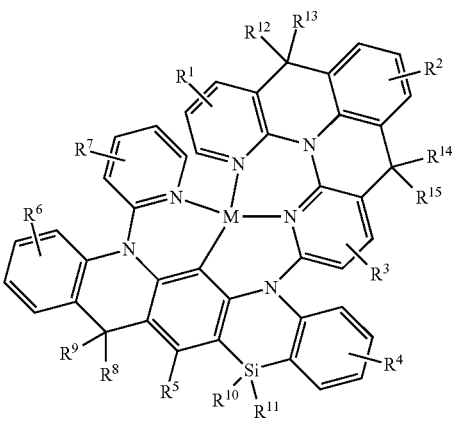
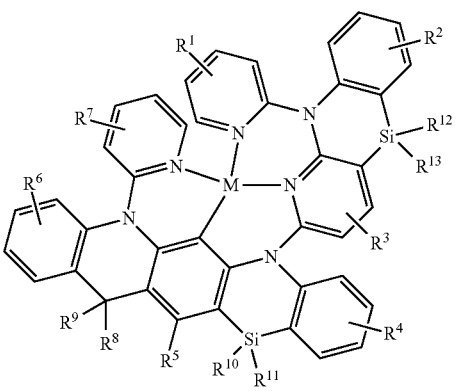
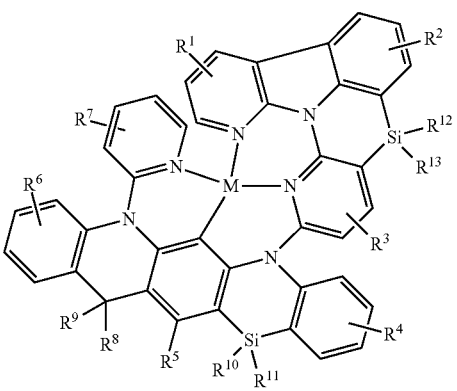
138
-continued
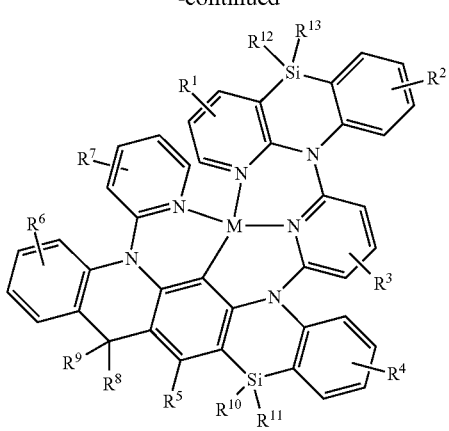
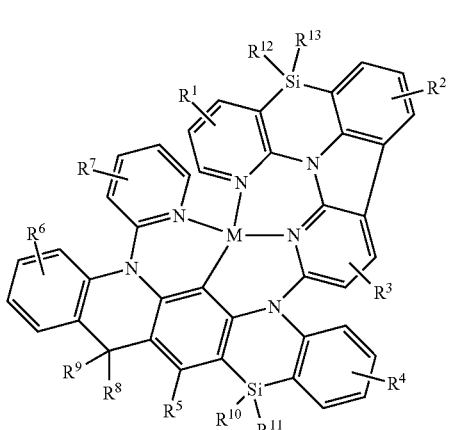
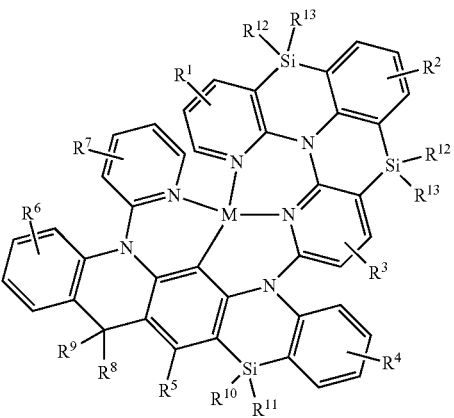
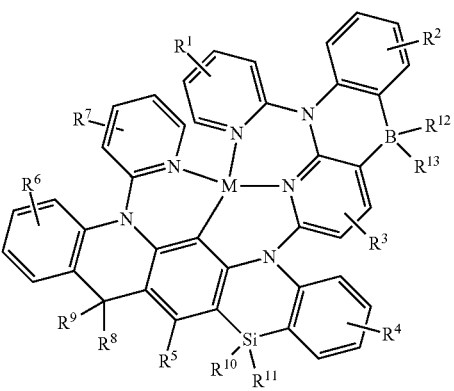

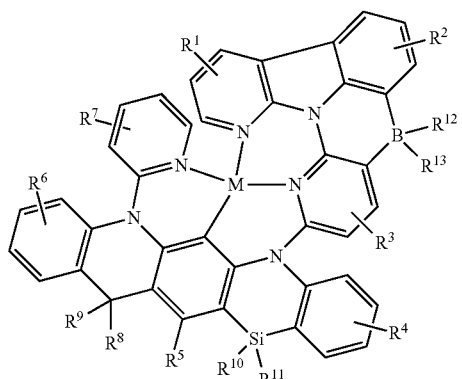
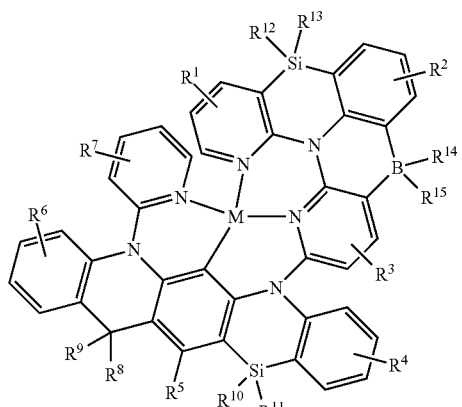
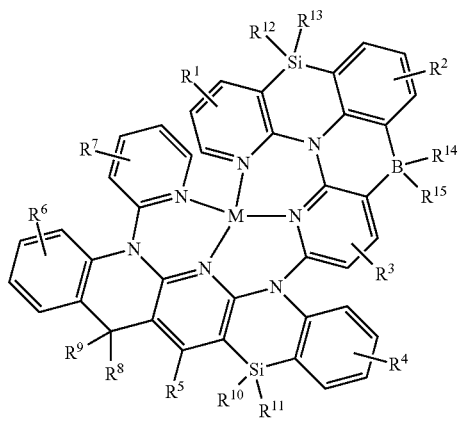
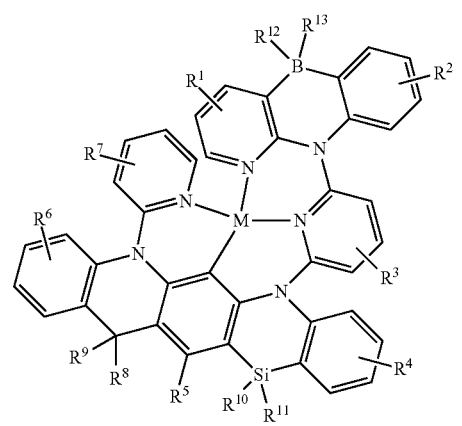
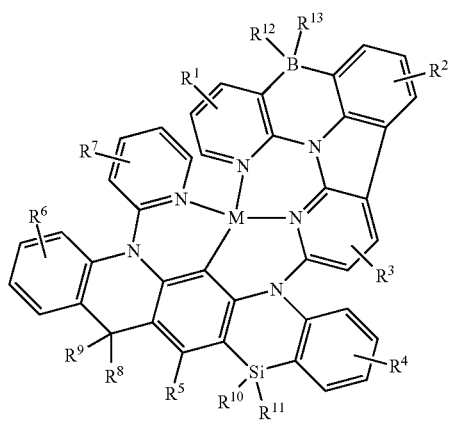
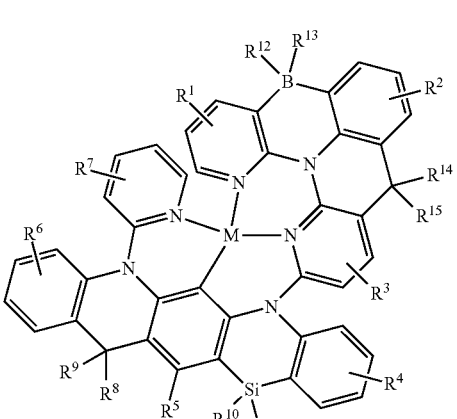
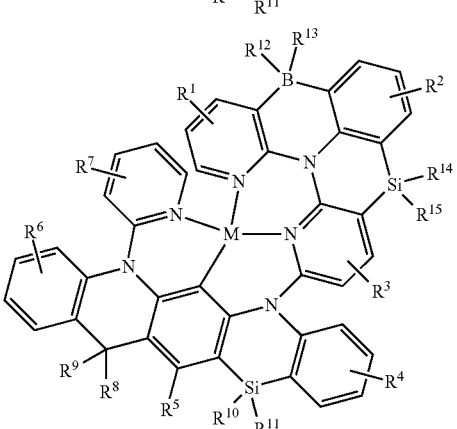
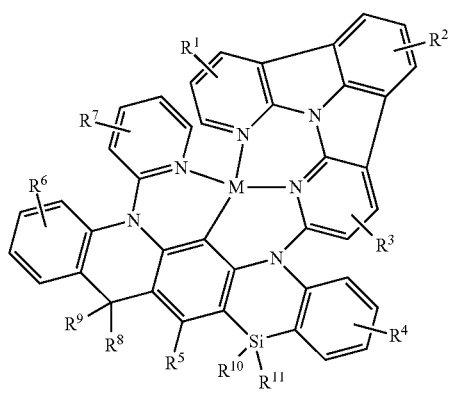

141
-continued
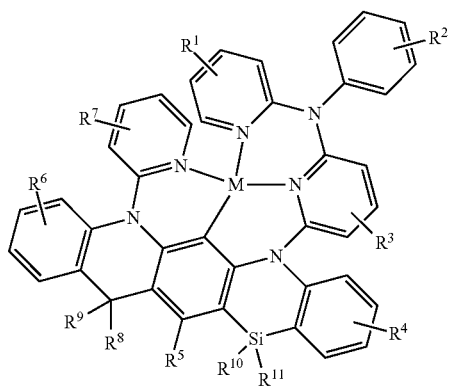
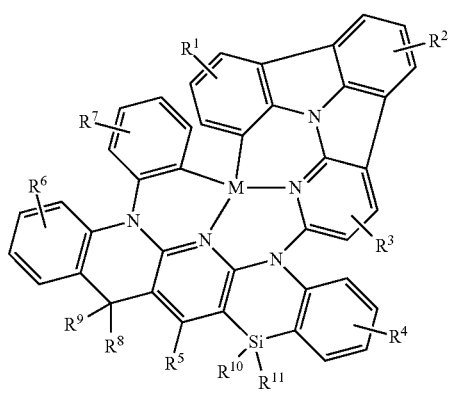
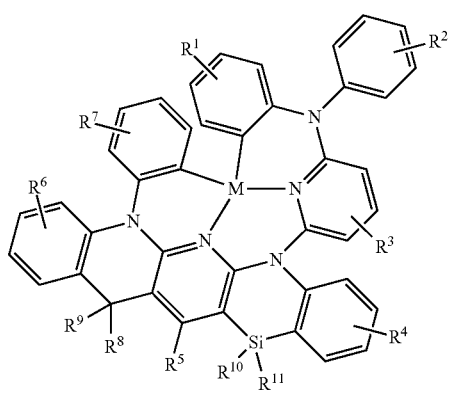
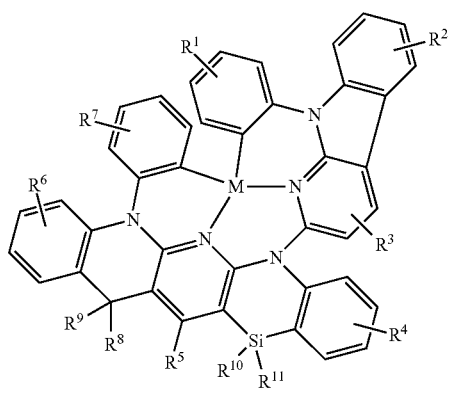
142
-continued
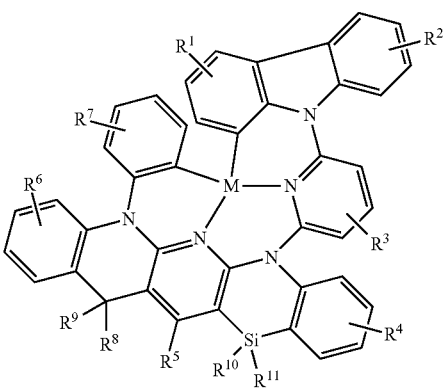
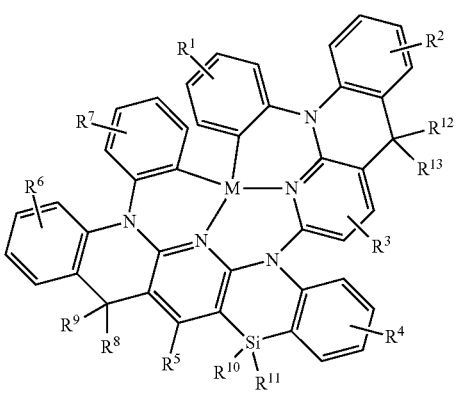
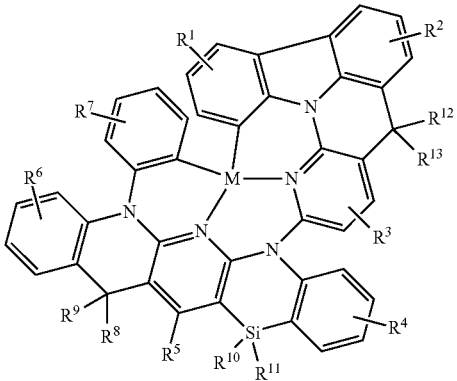
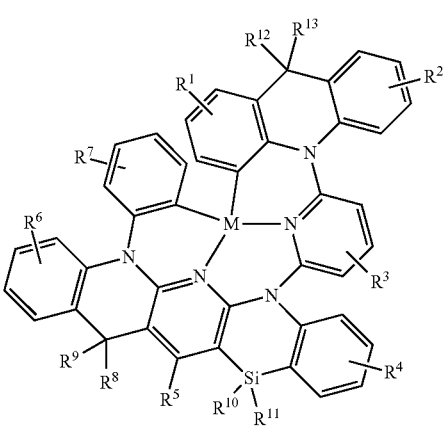

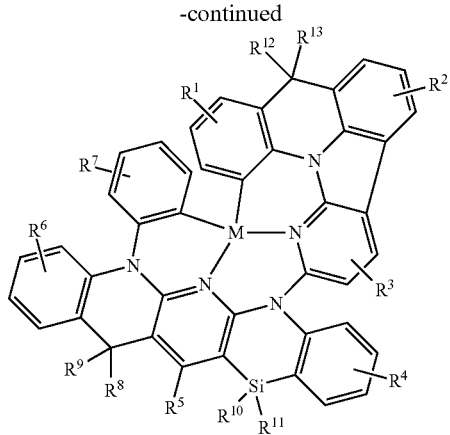
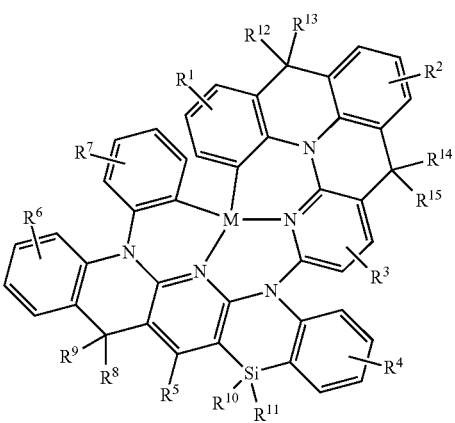
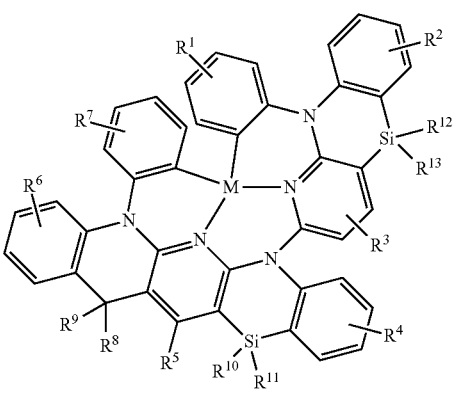
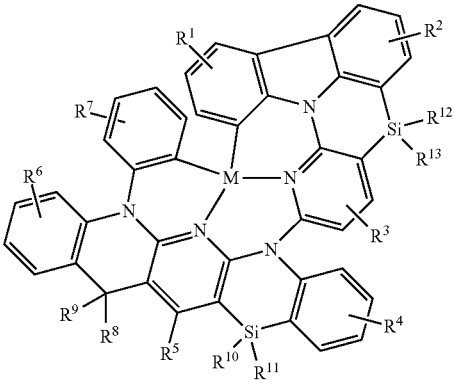
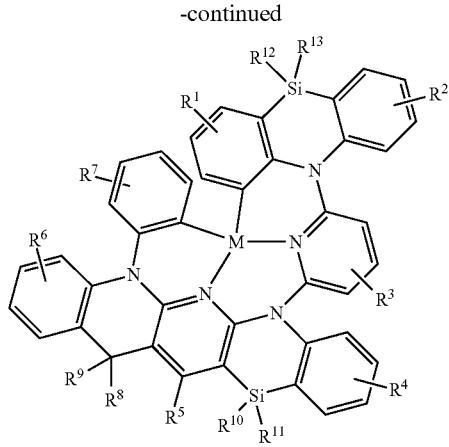
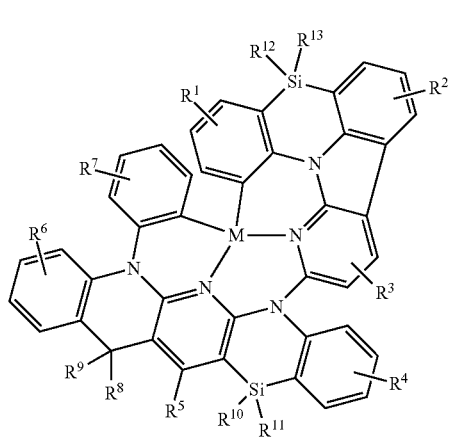
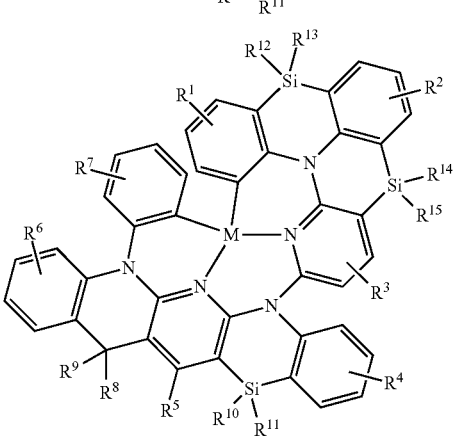
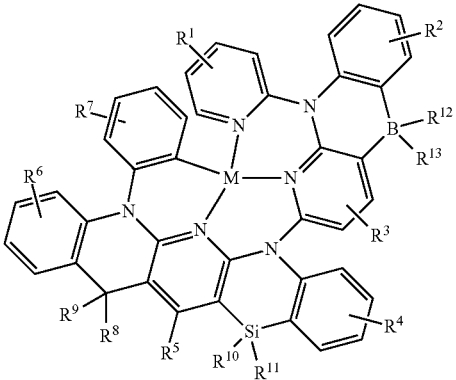

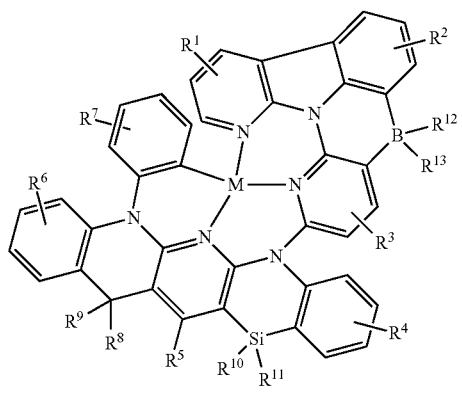
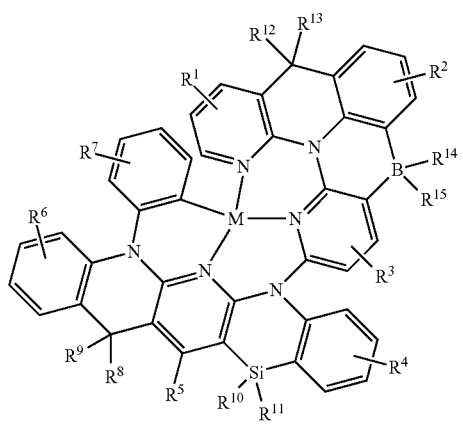
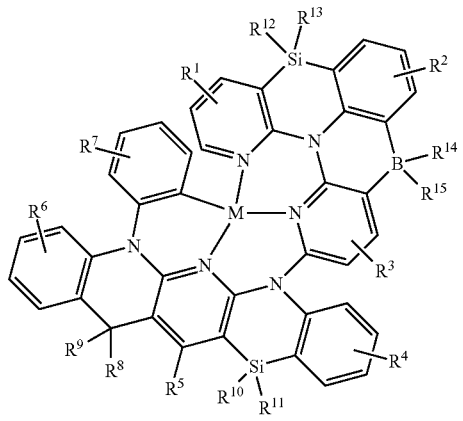
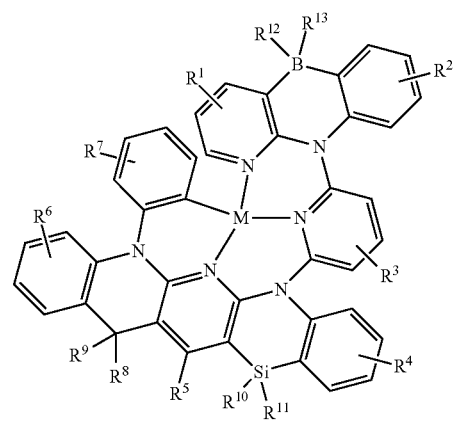
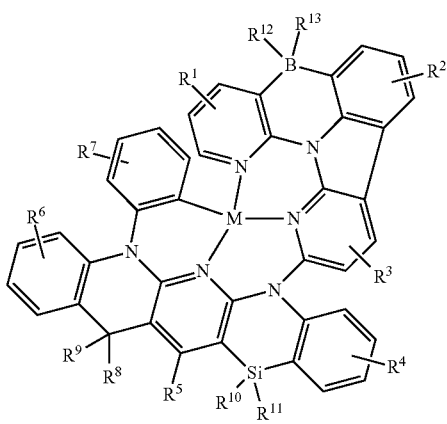
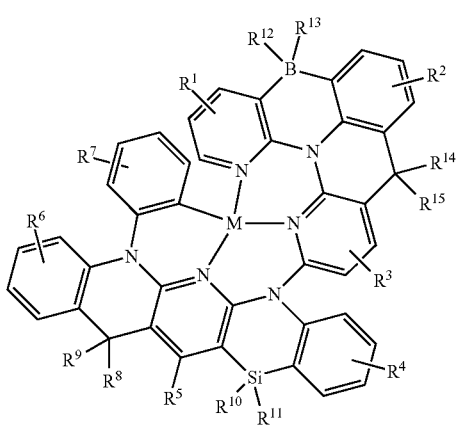
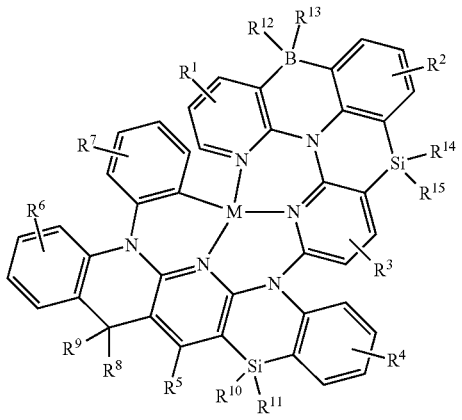
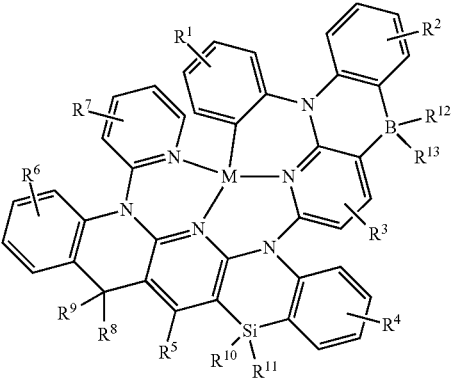

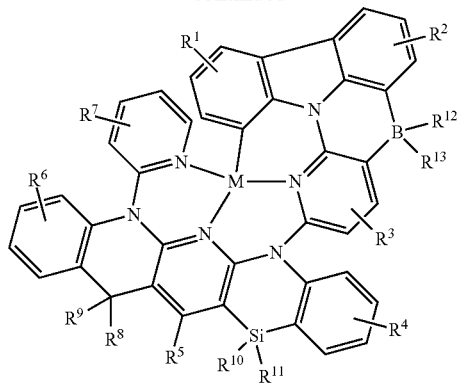
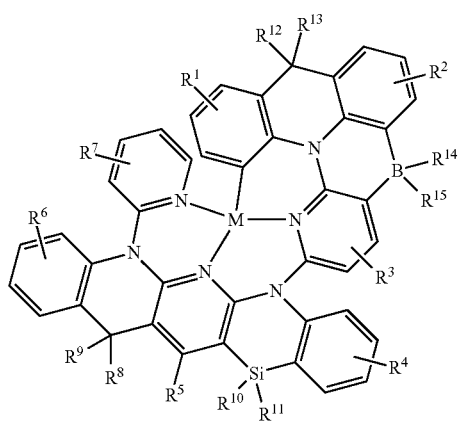
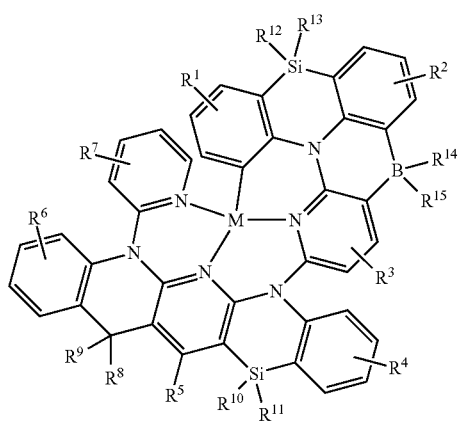
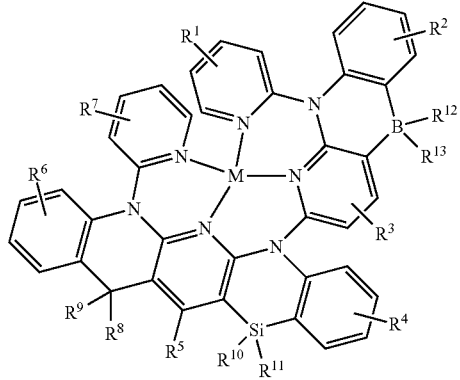
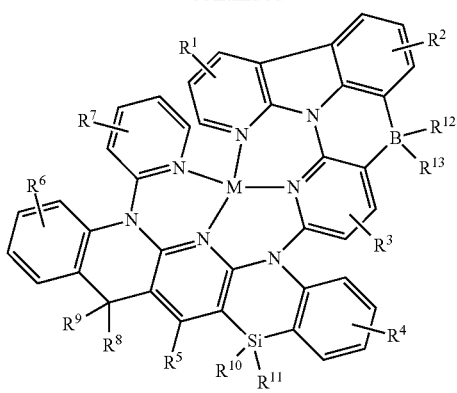
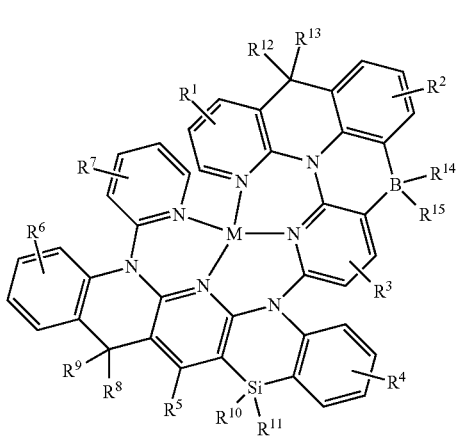
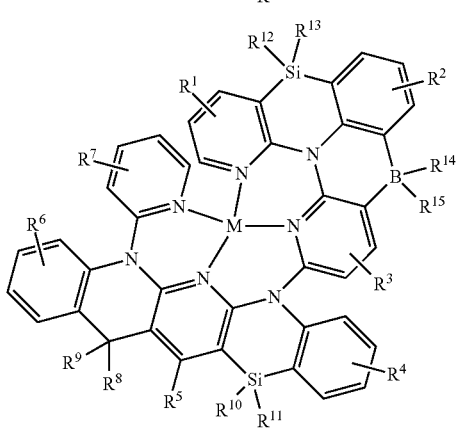
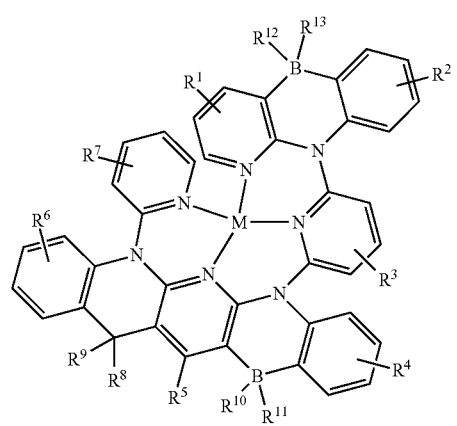

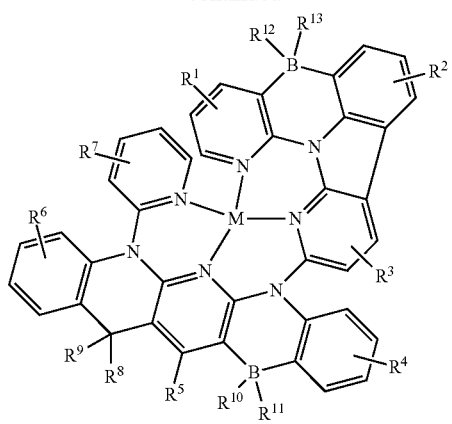
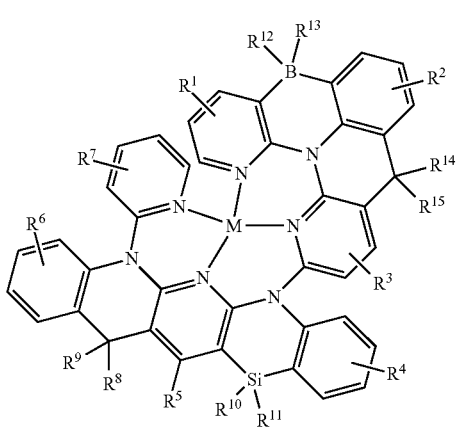
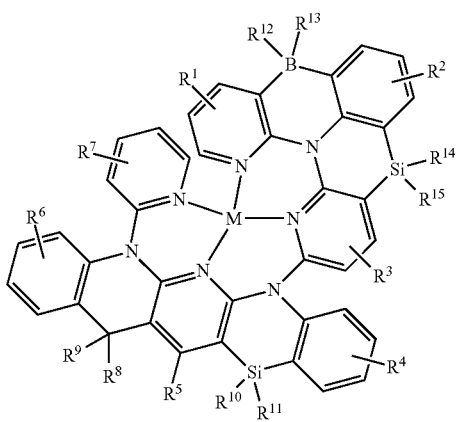
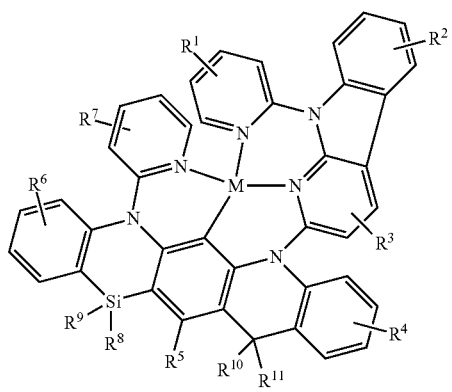
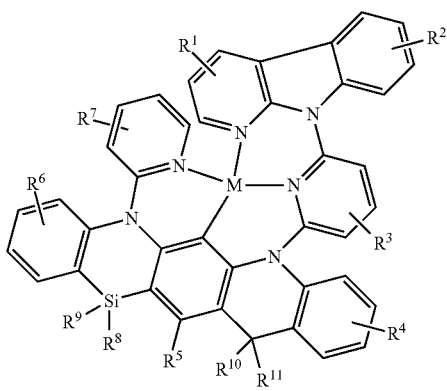
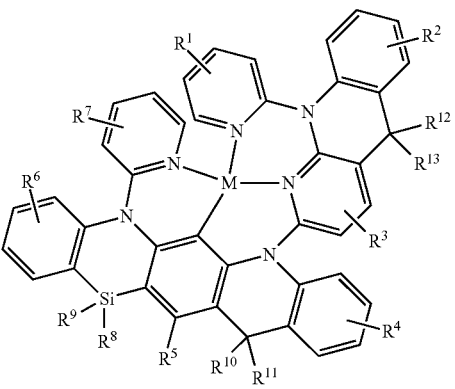
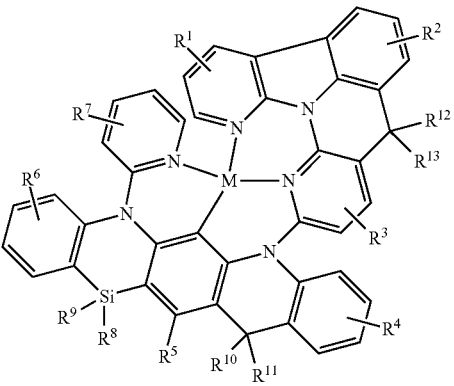
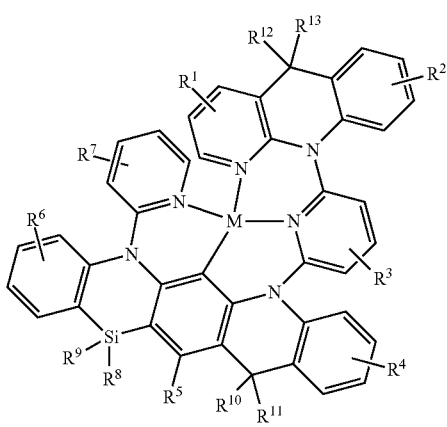

151
-continued
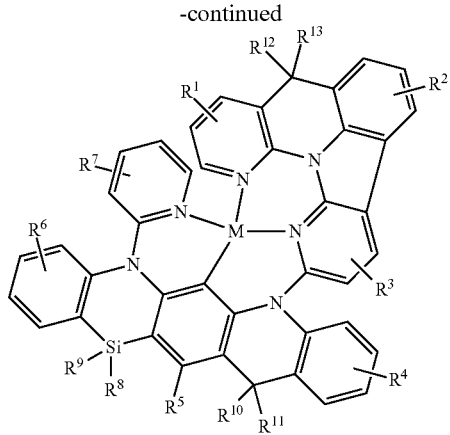
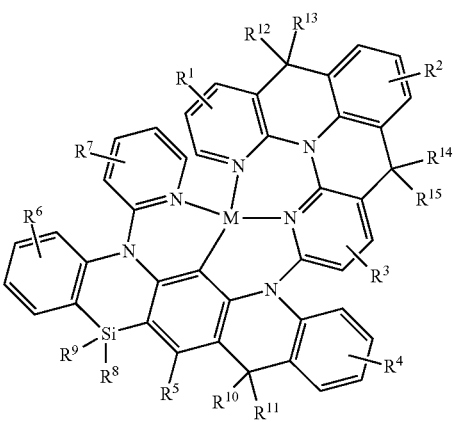
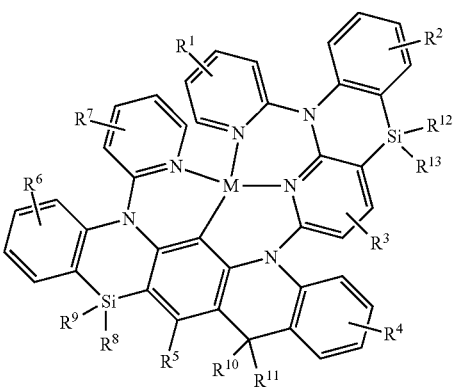
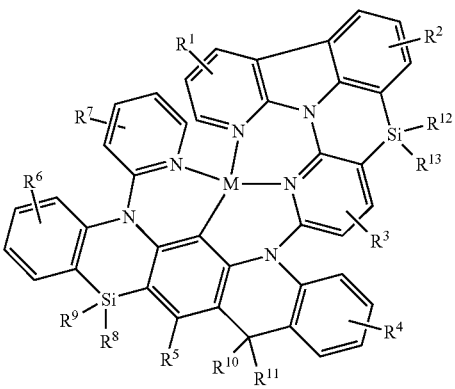
152
-continued
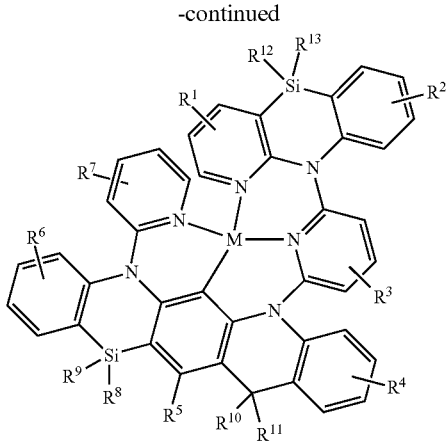
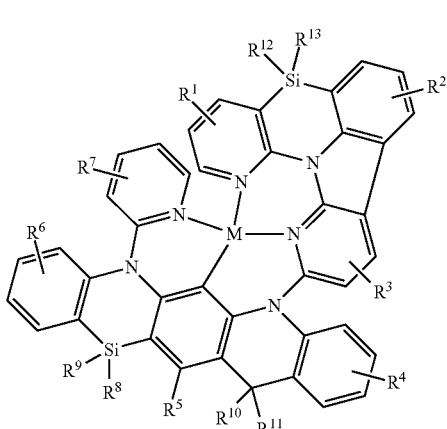
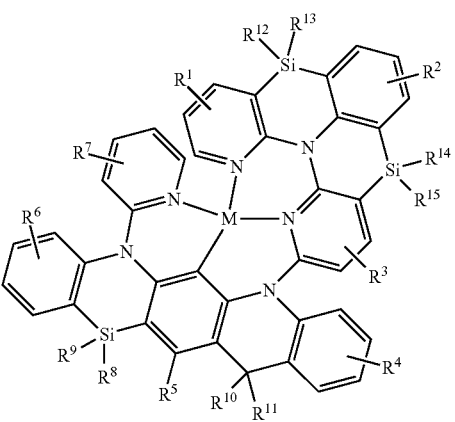
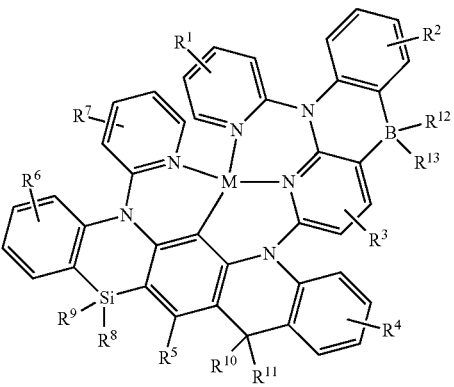

153
-continued

154
-continued

-continued
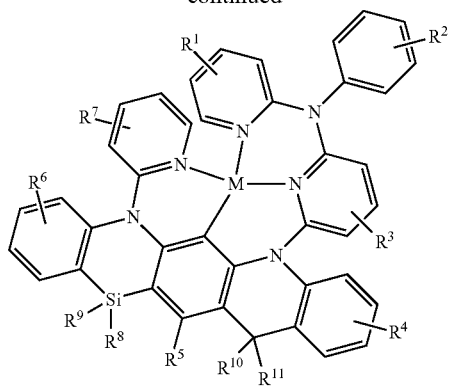
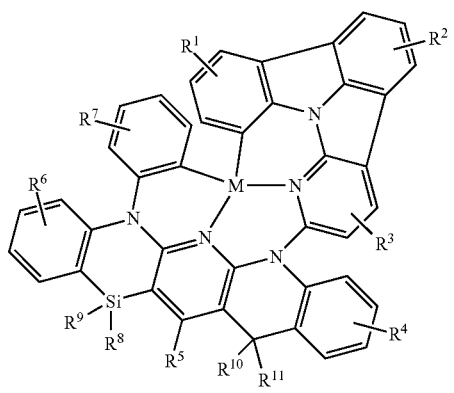
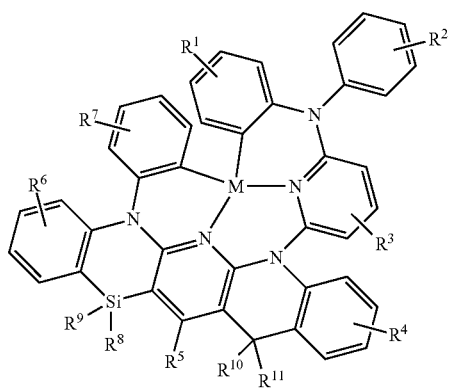
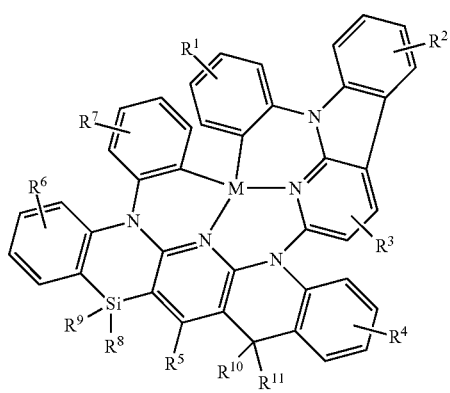
-continued
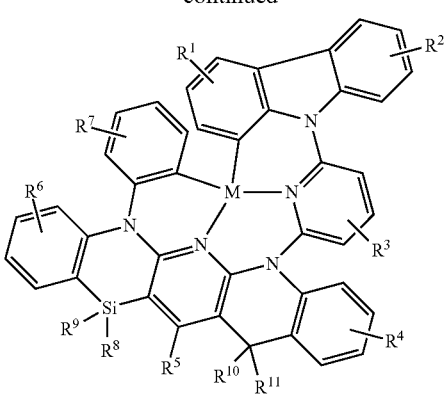
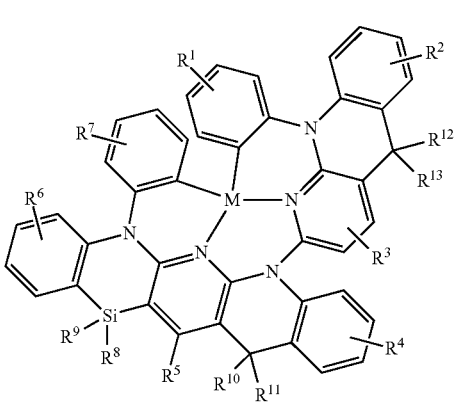
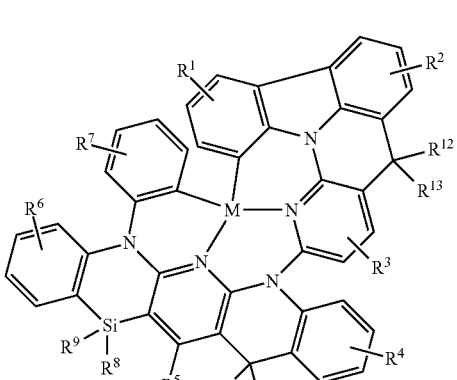
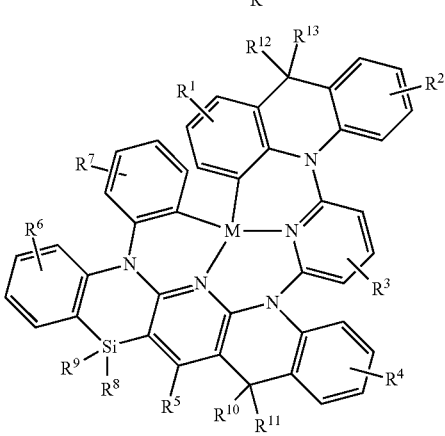

-continued
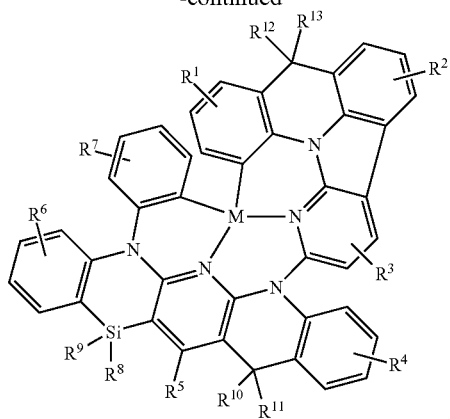
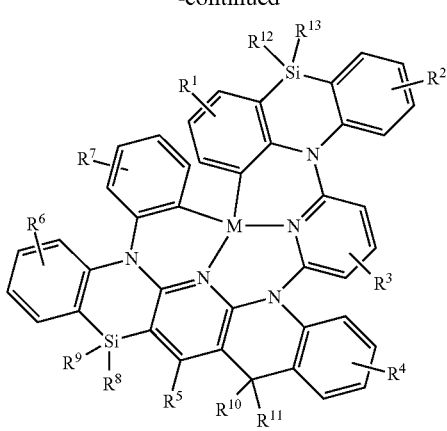
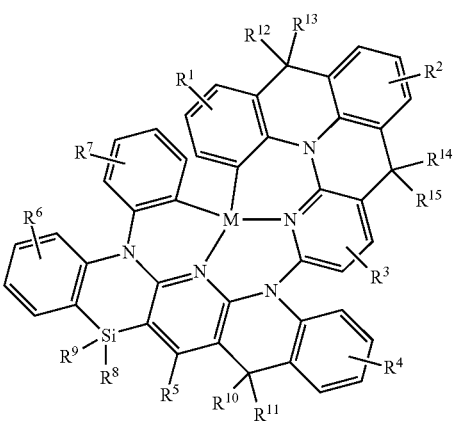
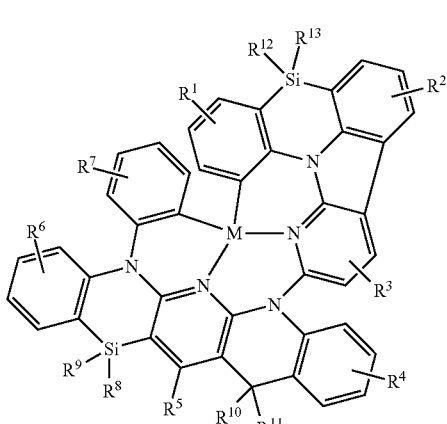
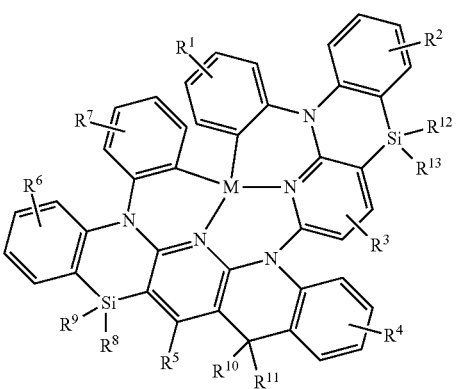
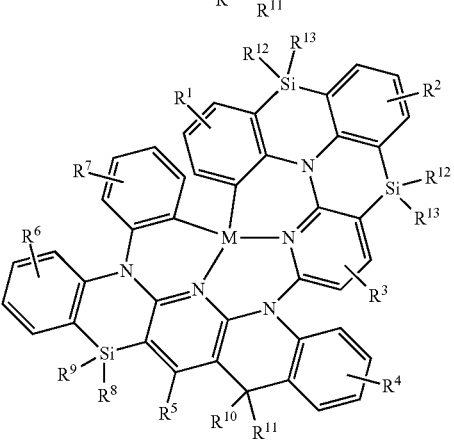
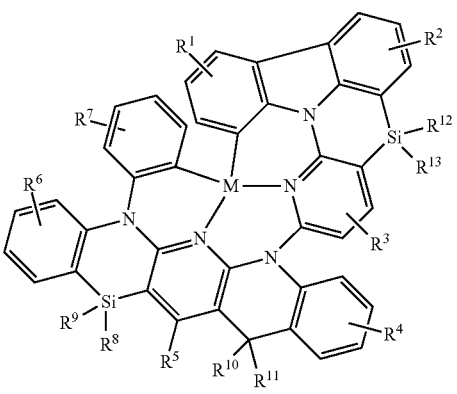
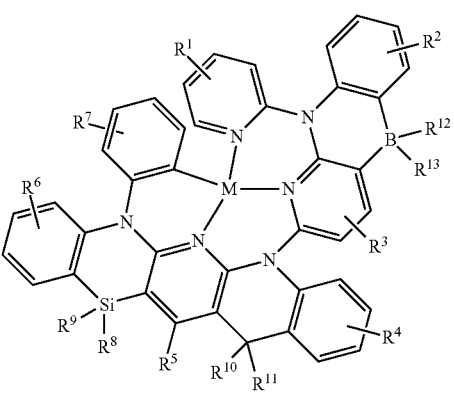

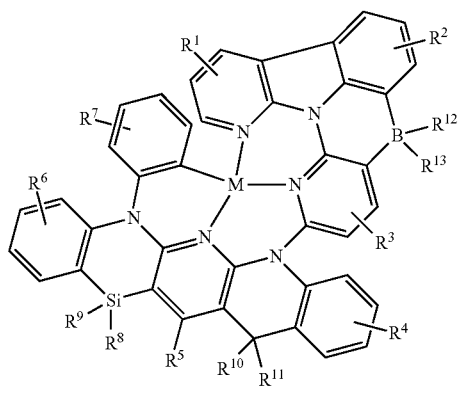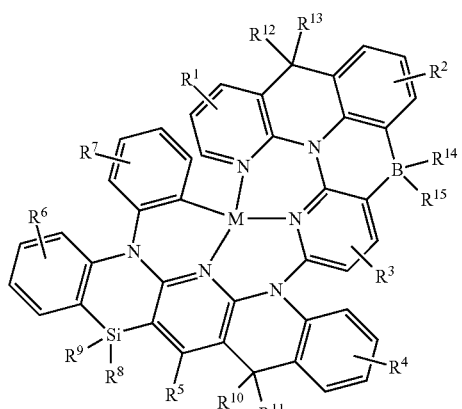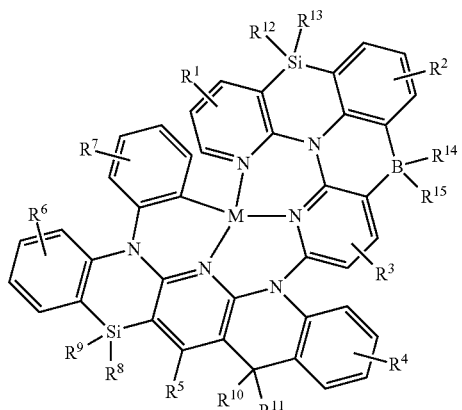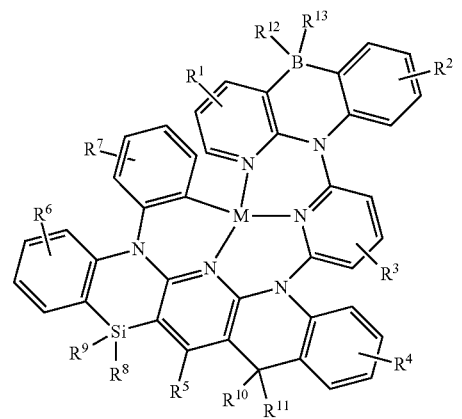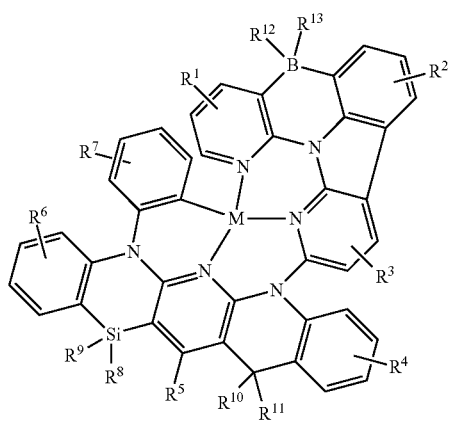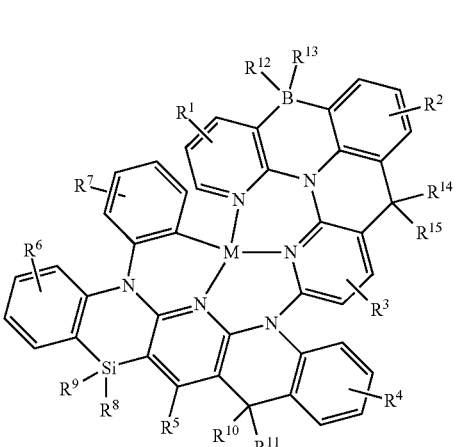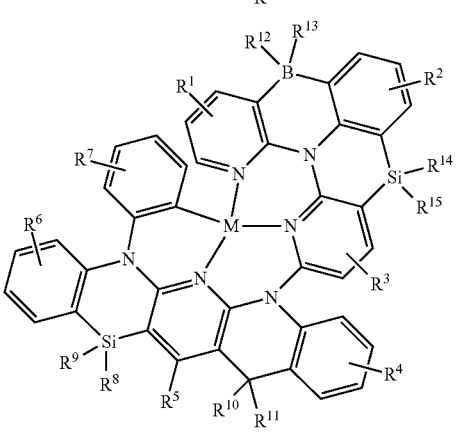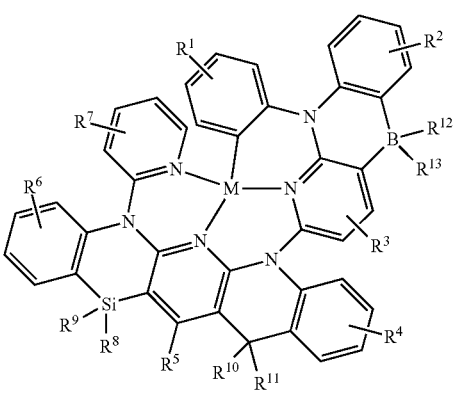

161
-continued
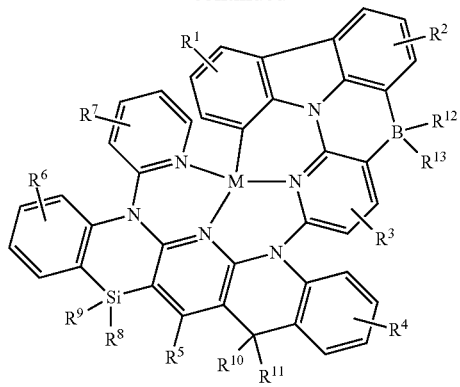
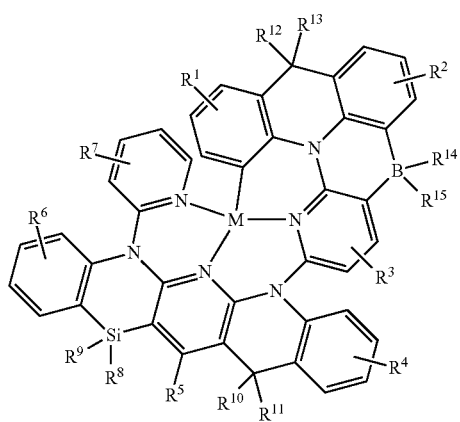
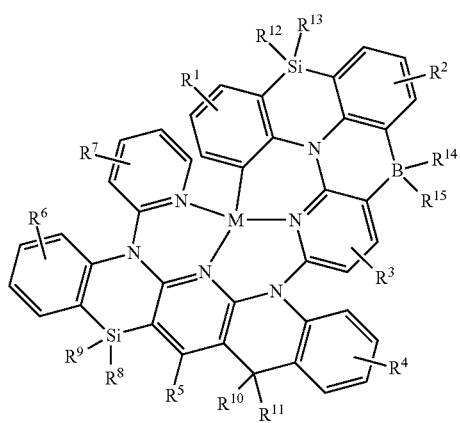
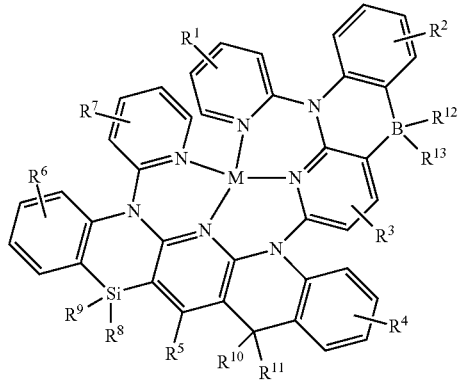
162
-continued
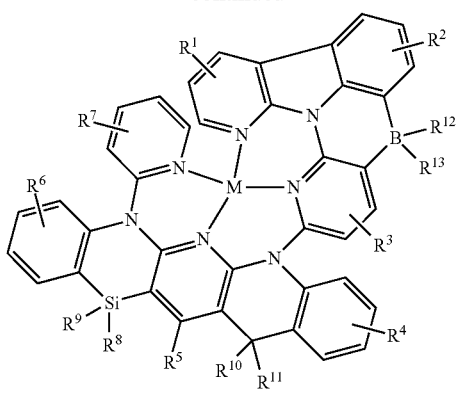
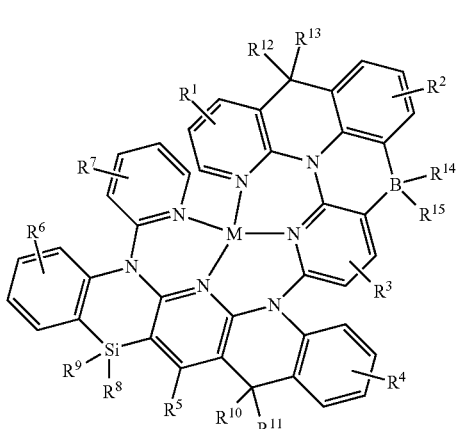
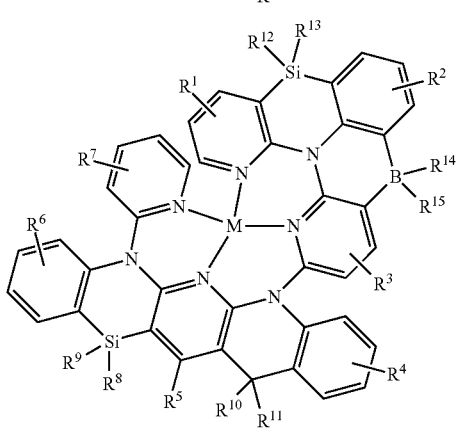
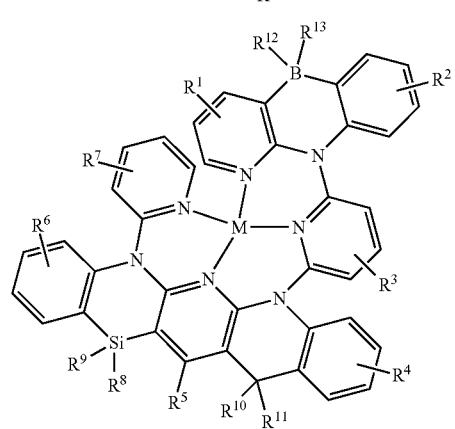

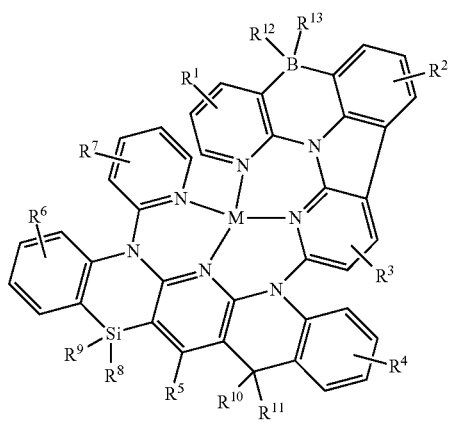

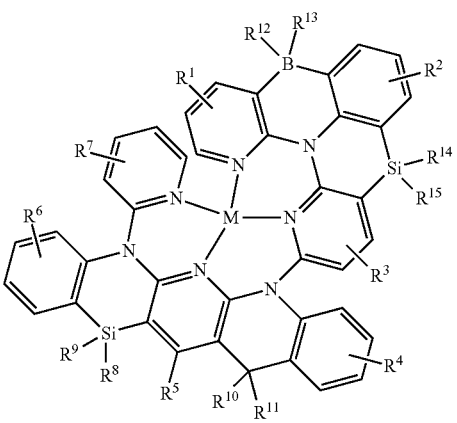
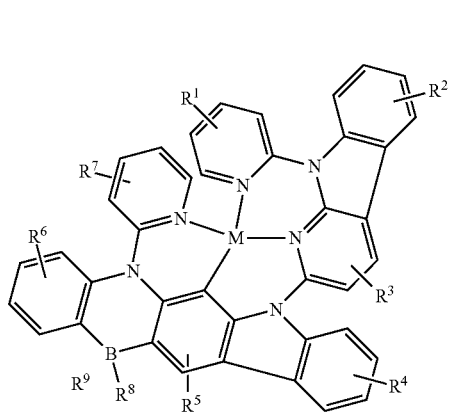
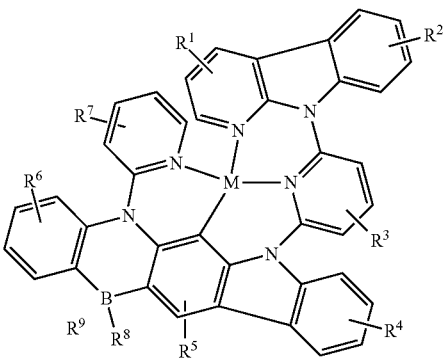
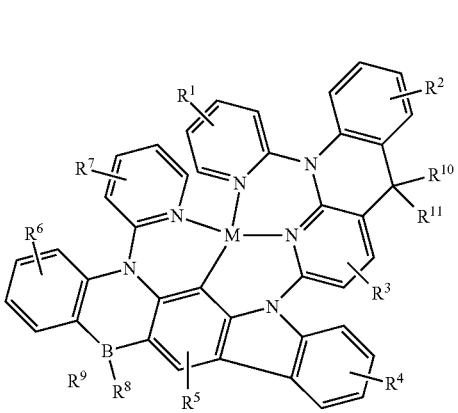
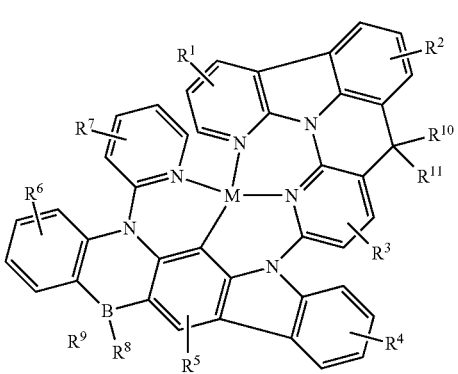
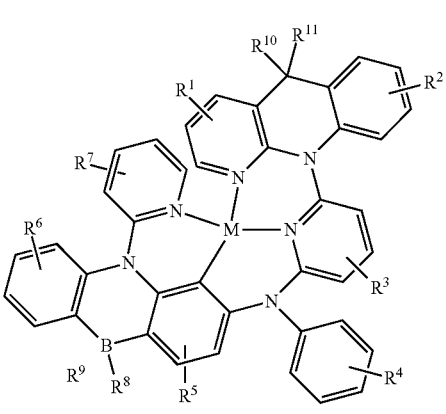

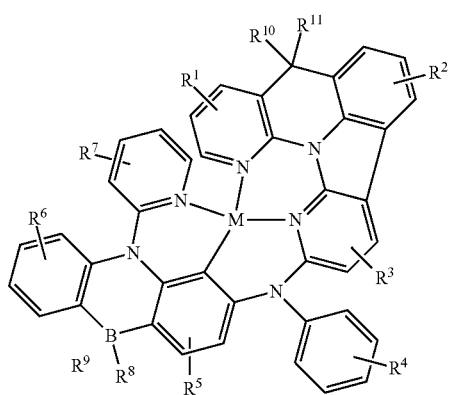
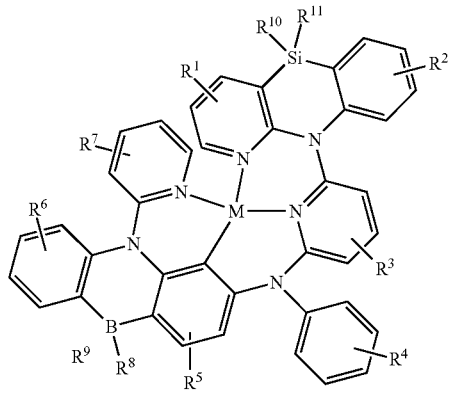
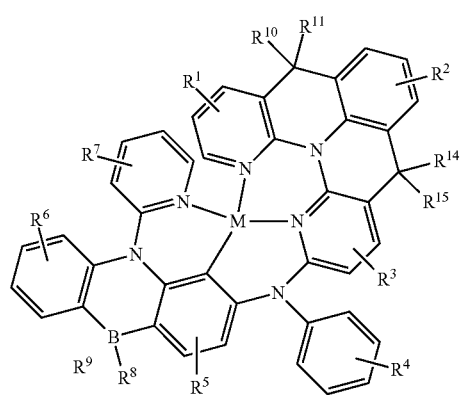
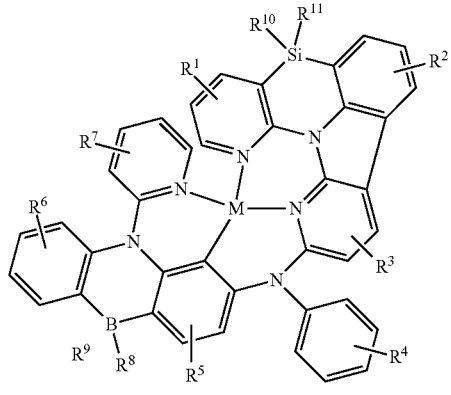
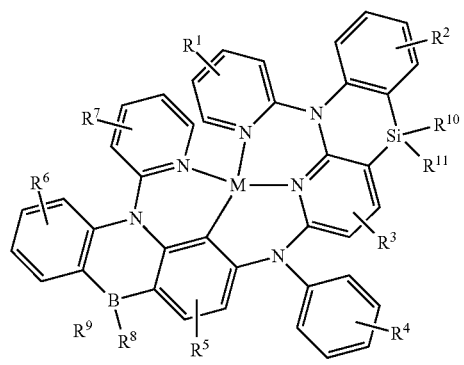
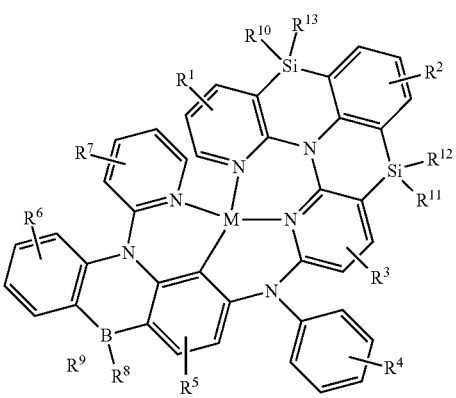
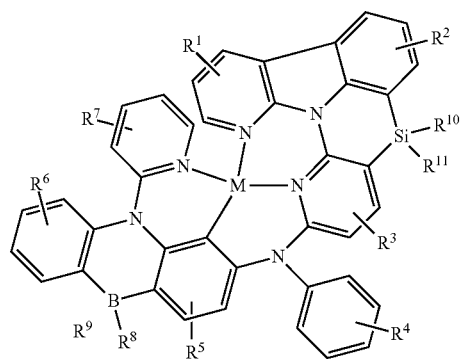
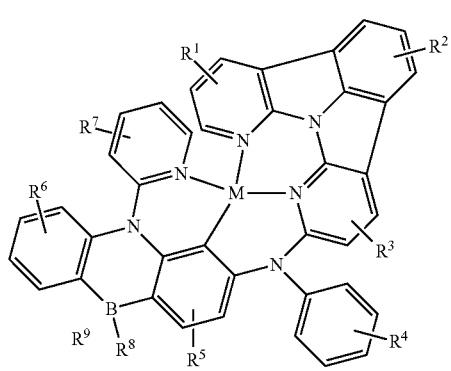

167
-continued
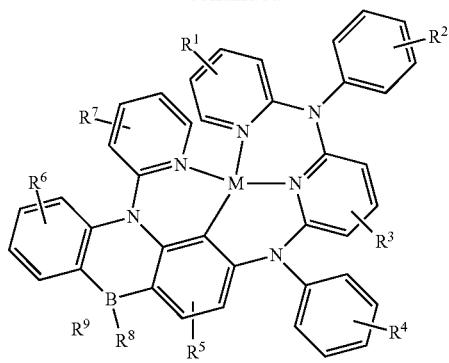
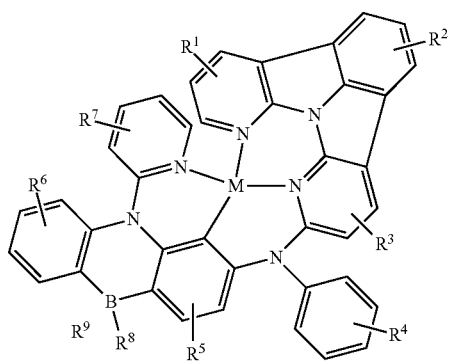
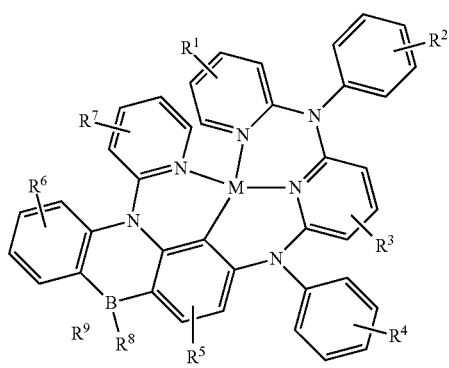
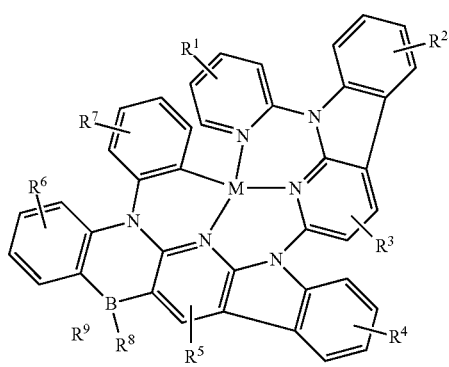
168
-continued
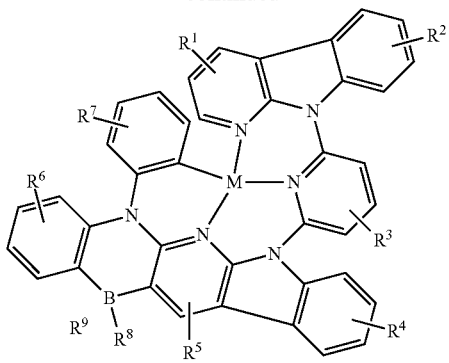
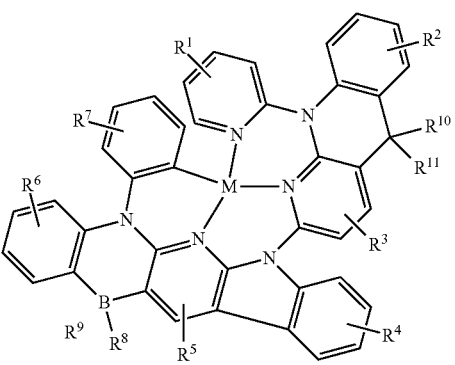
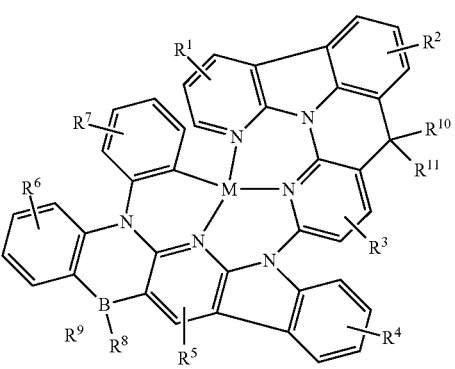
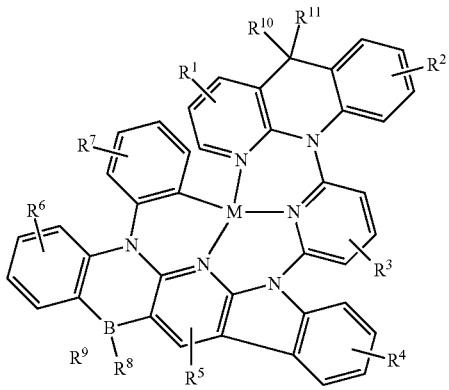

-continued
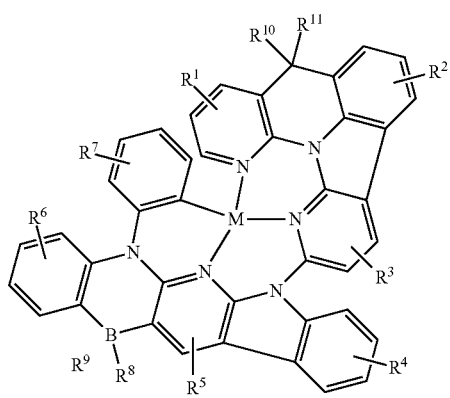
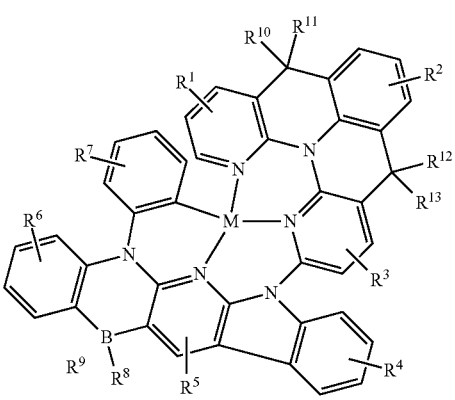
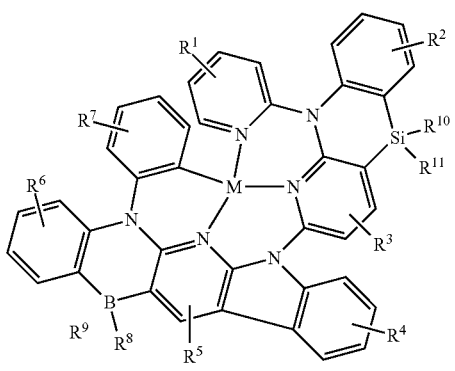
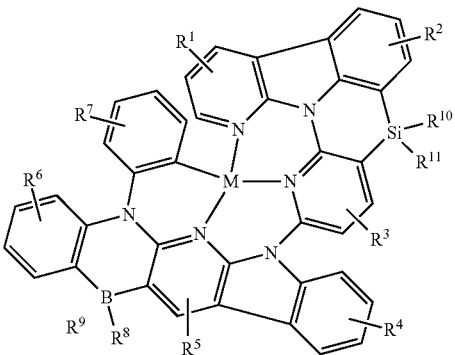
-continued
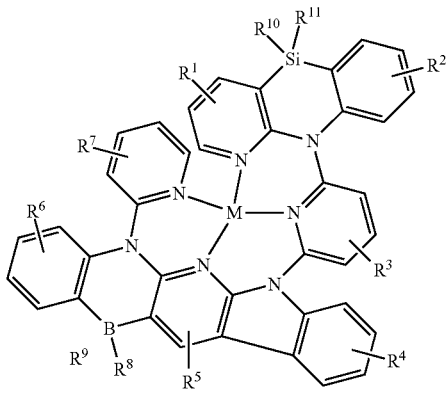
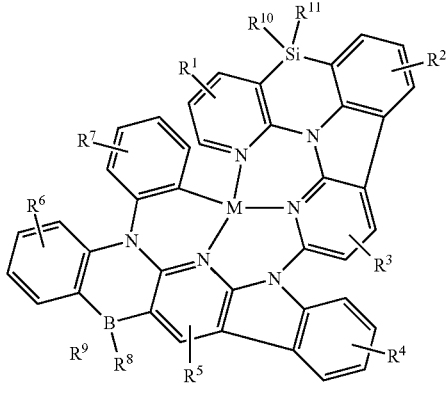
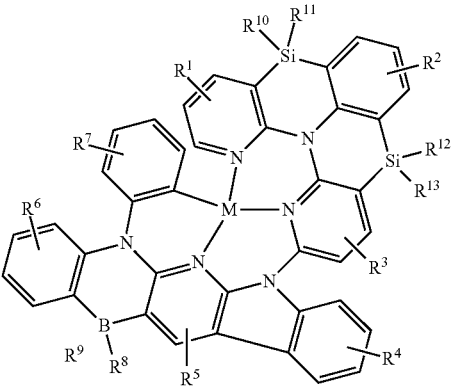
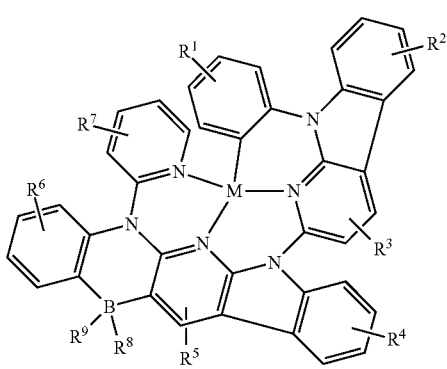

171
-continued
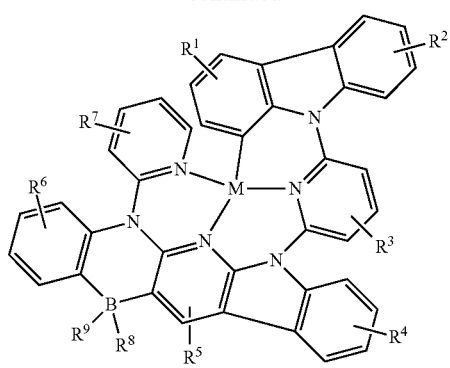
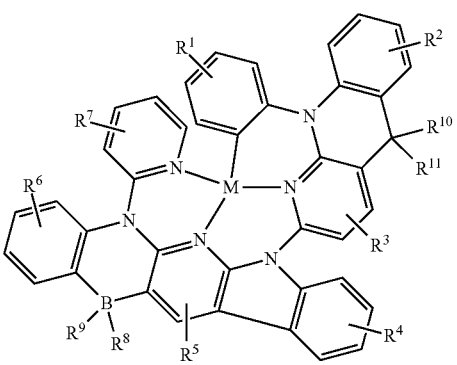
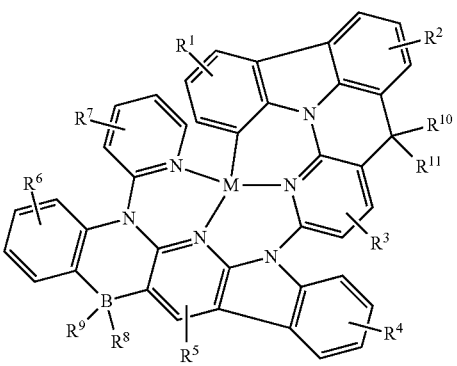
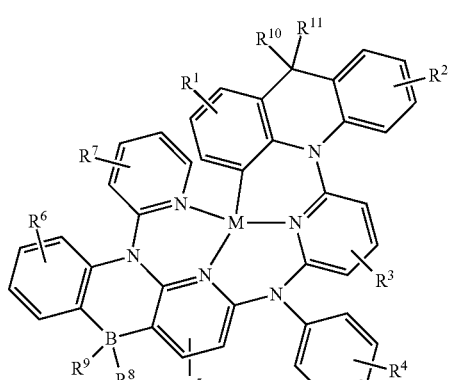
172
-continued
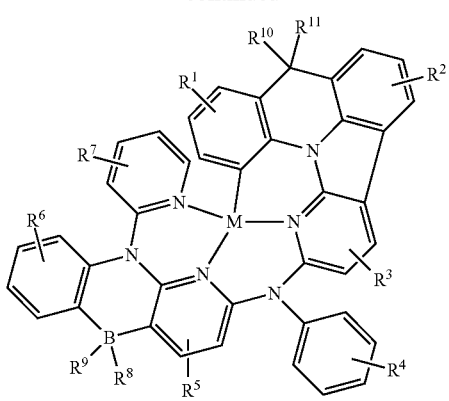
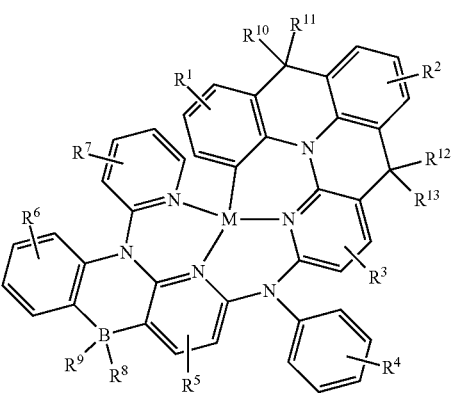
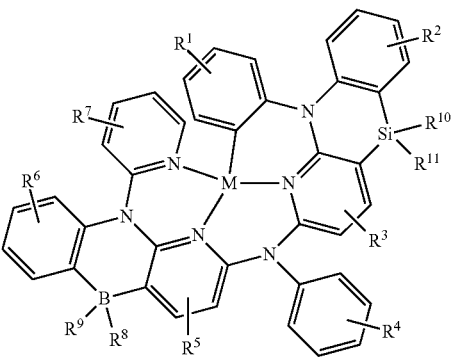
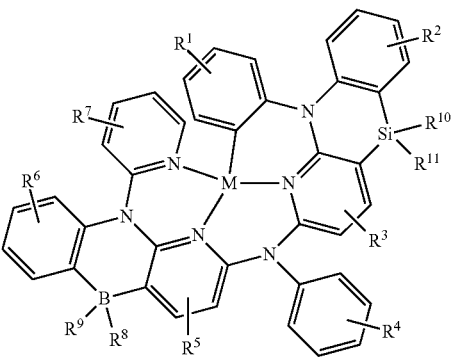

173
-continued
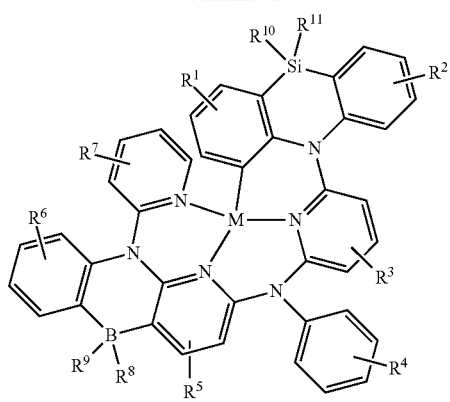
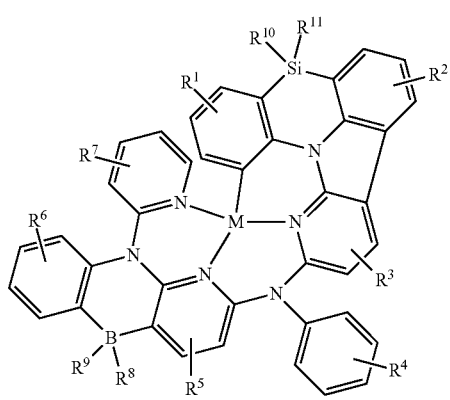
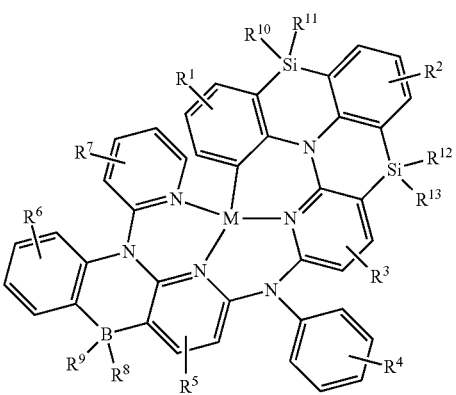
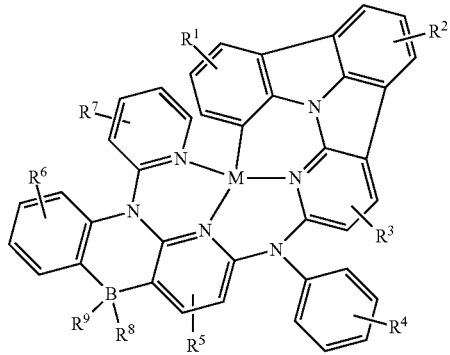
174
-continued
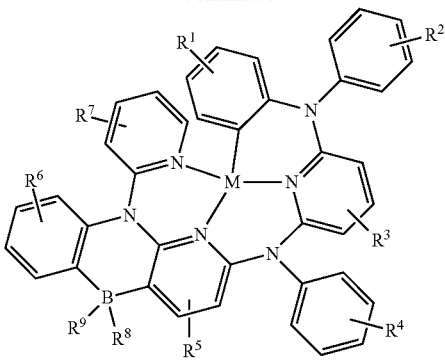
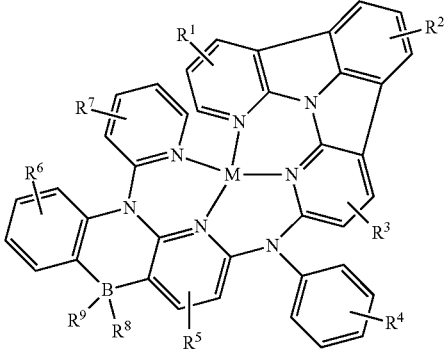
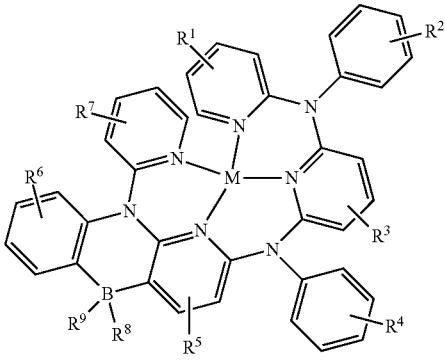
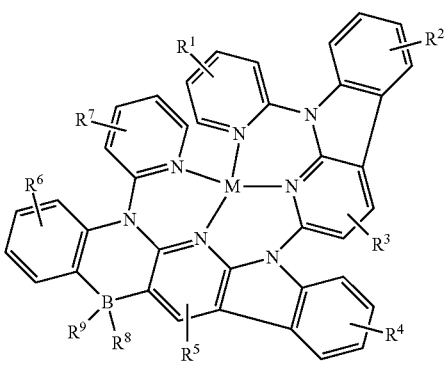

175
-continued
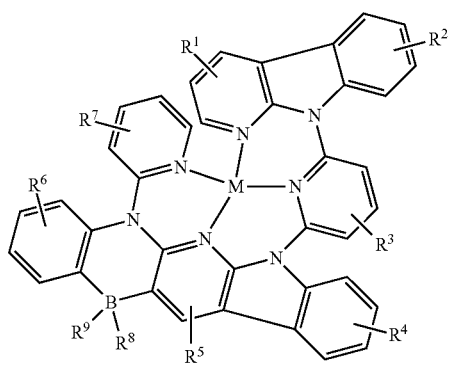
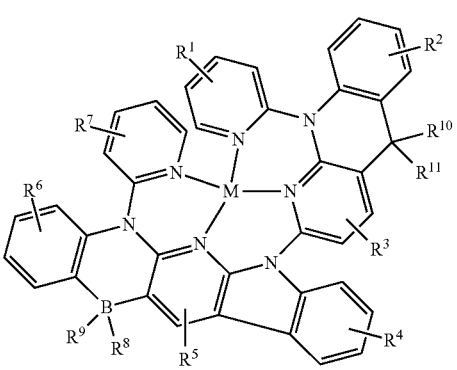
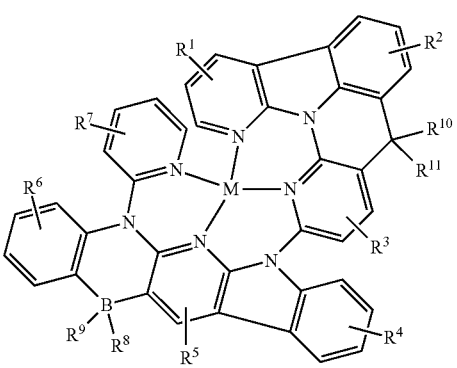
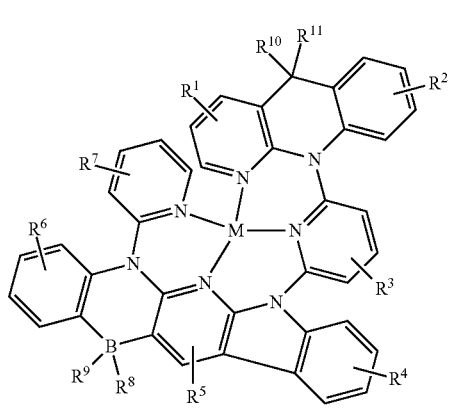
176
-continued
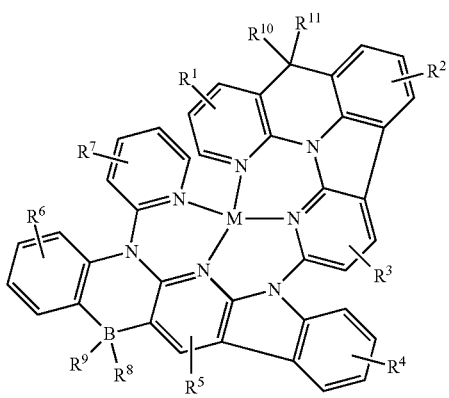
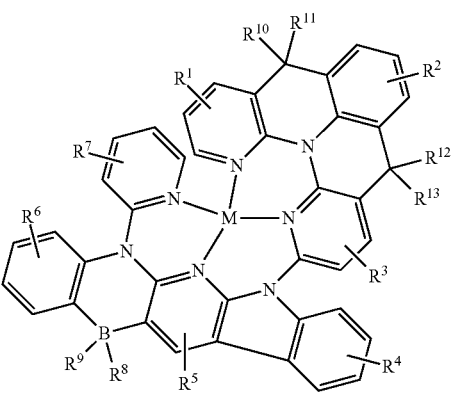
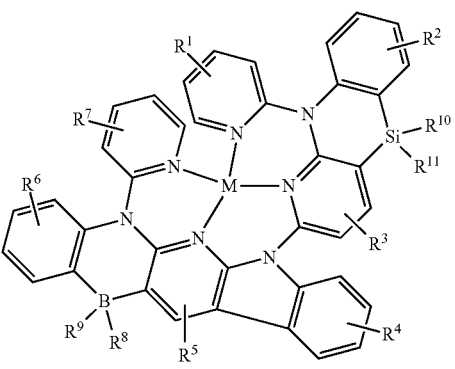
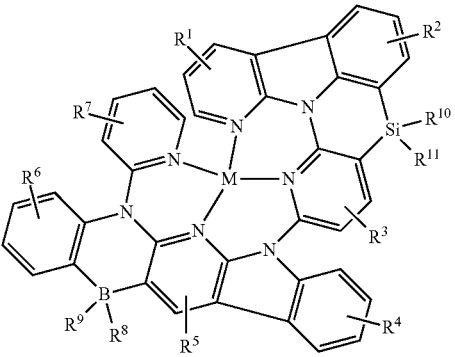

177
-continued
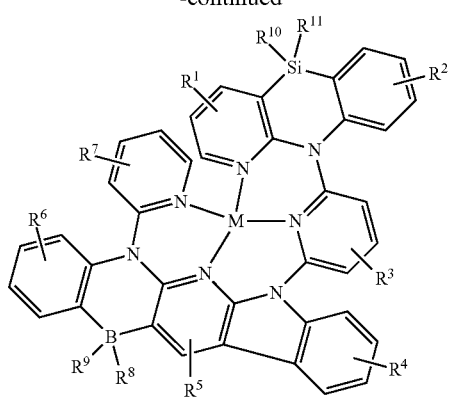
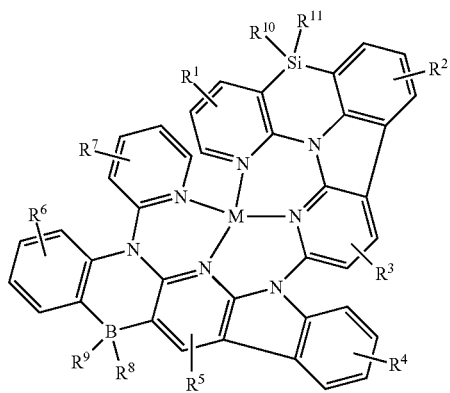
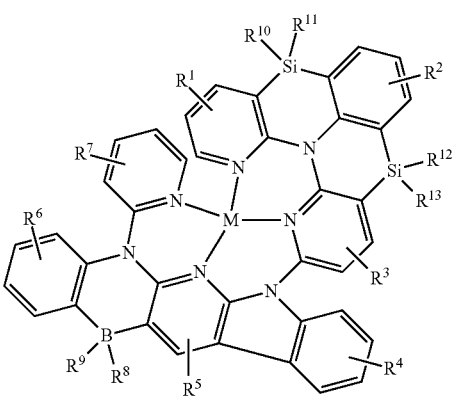
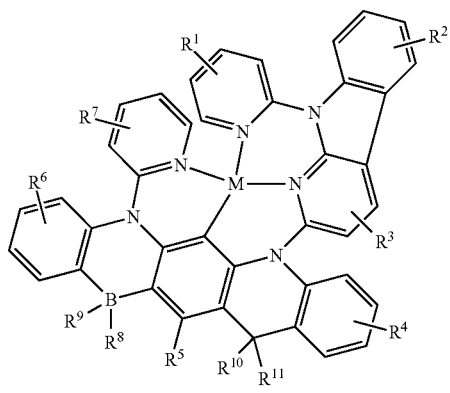
178
-continued
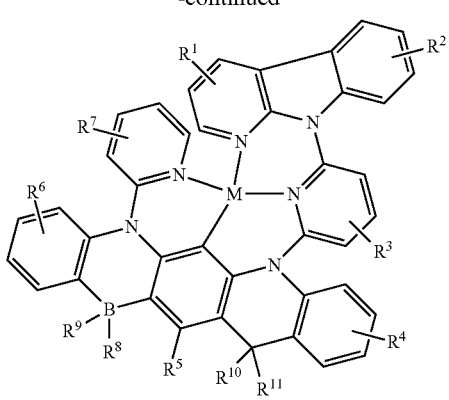
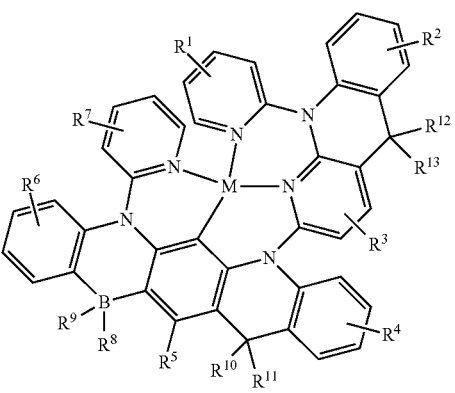
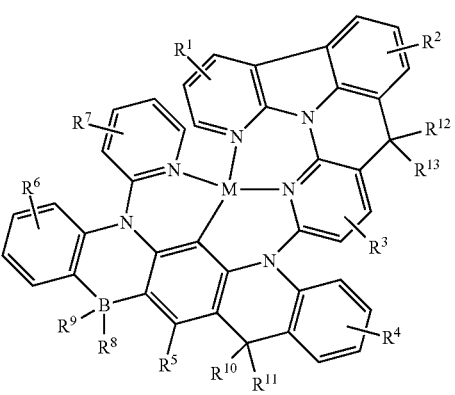
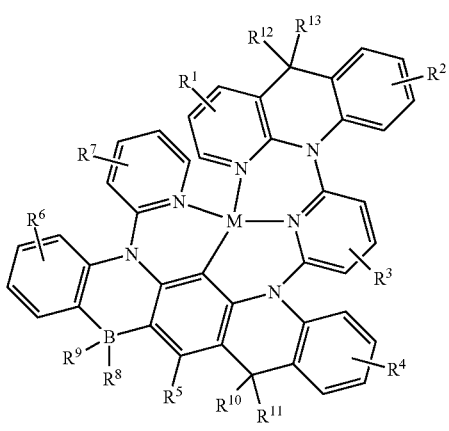

179
-continued
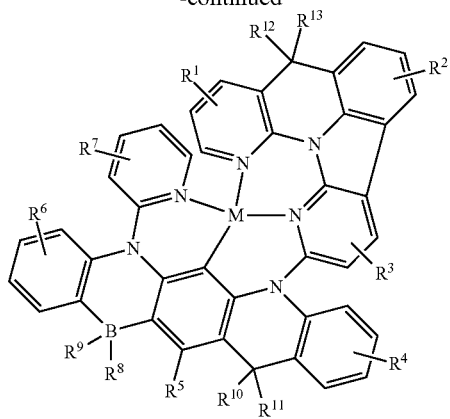
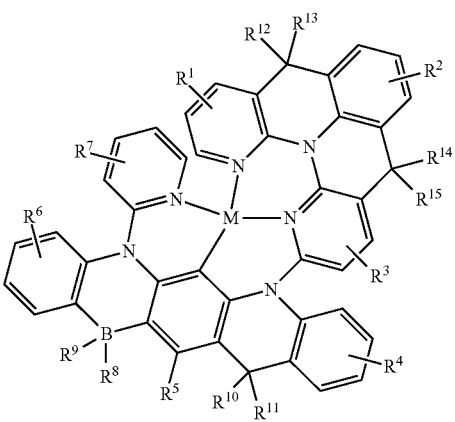
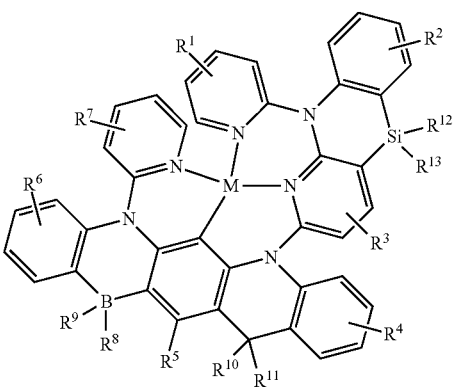
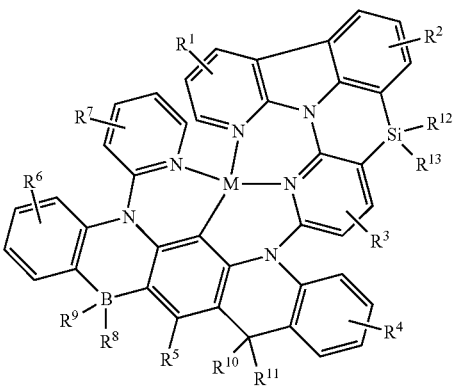
180
-continued
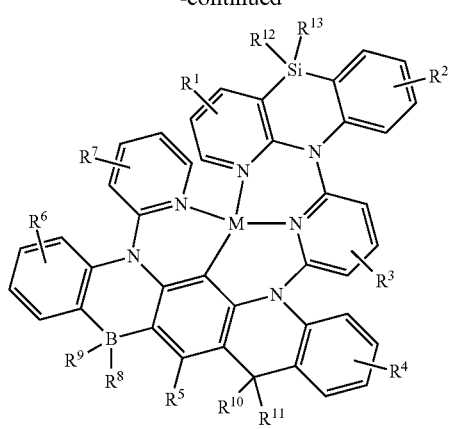
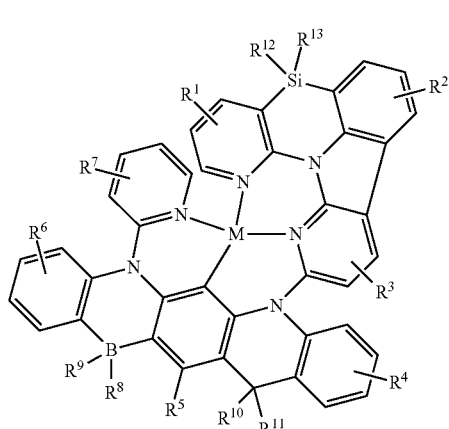
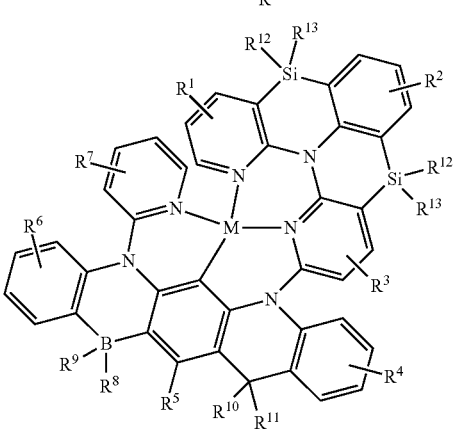
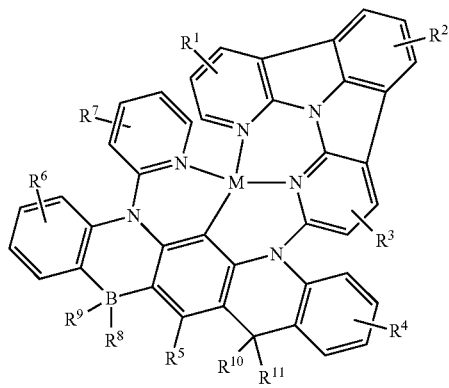

-continued
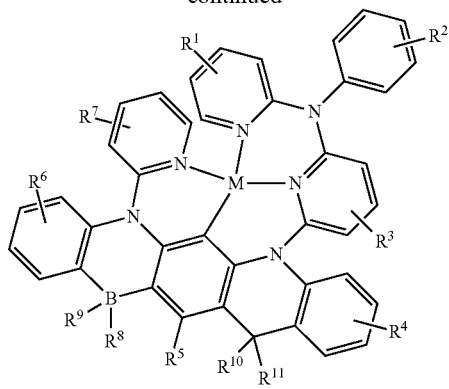
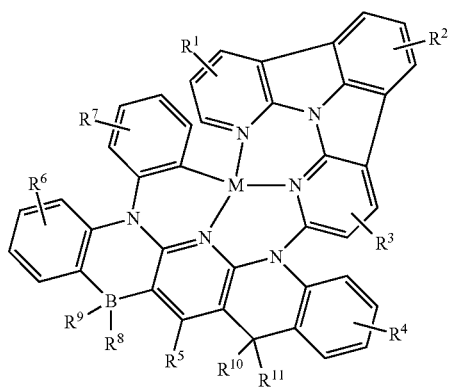
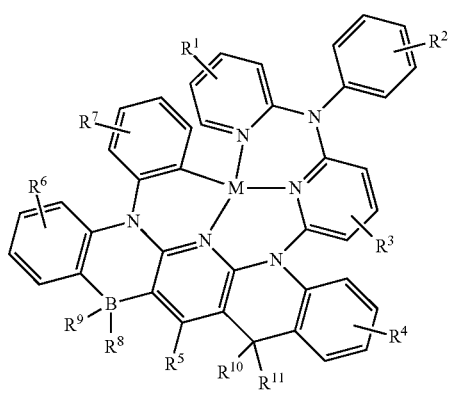
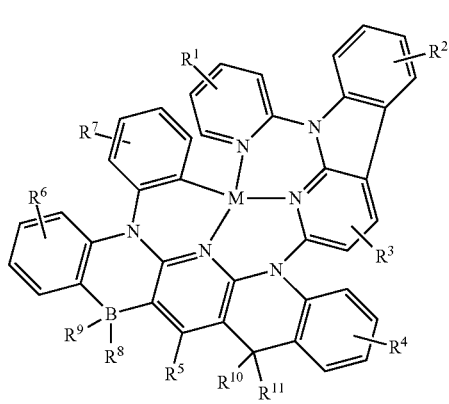
-continued
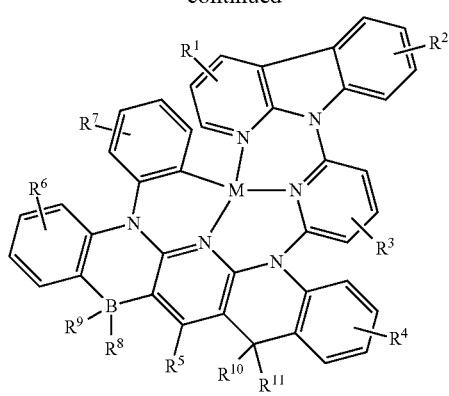
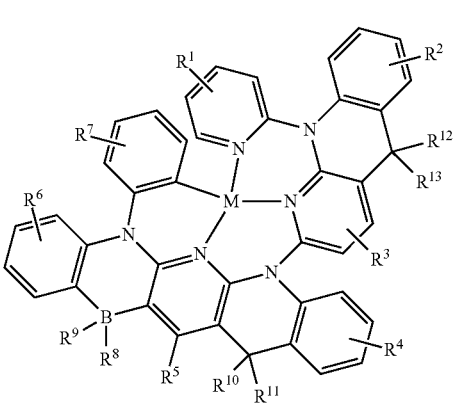
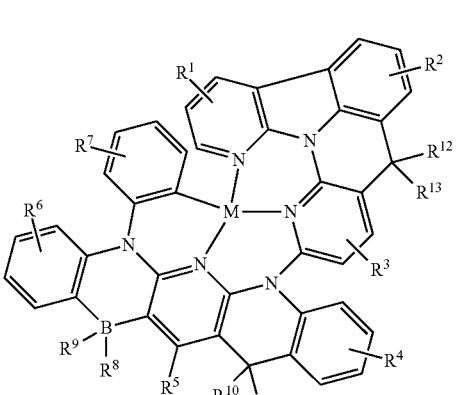
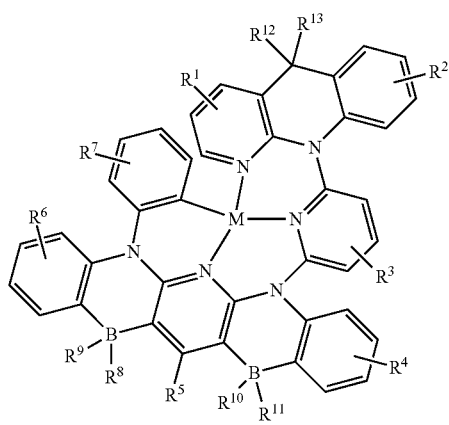

-continued
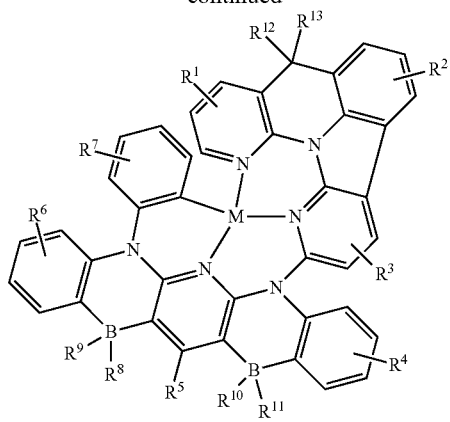
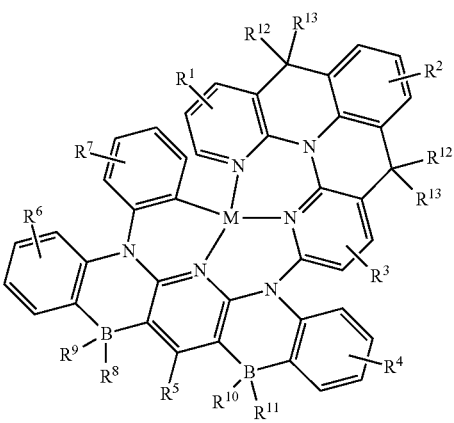
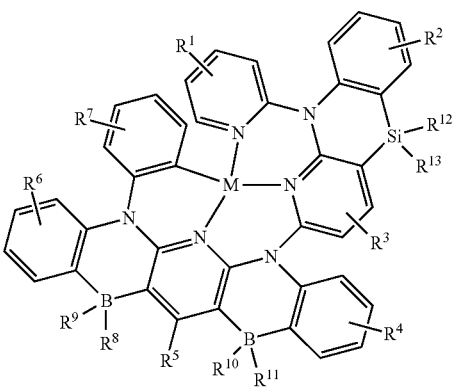
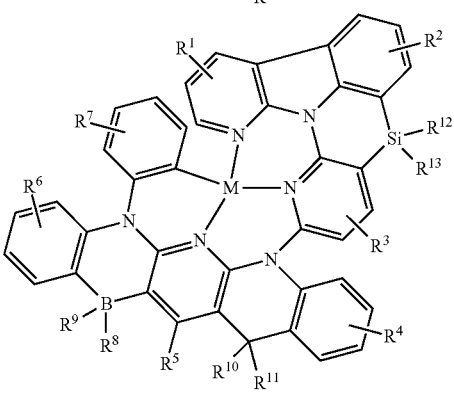
-continued
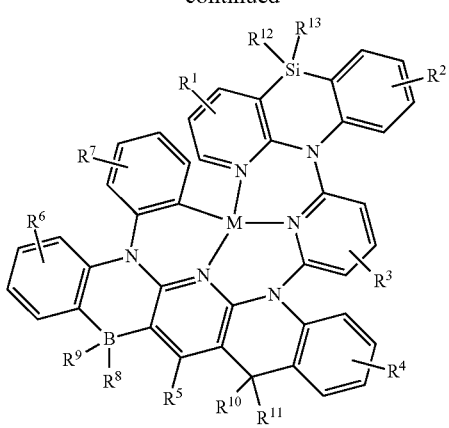
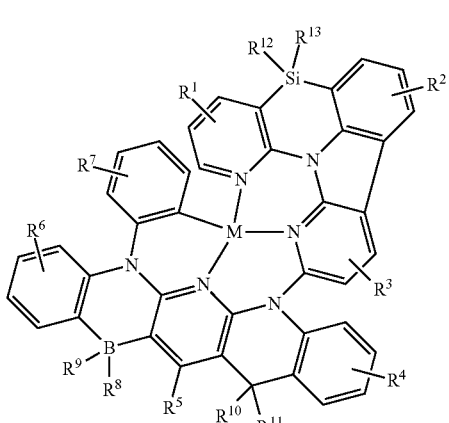
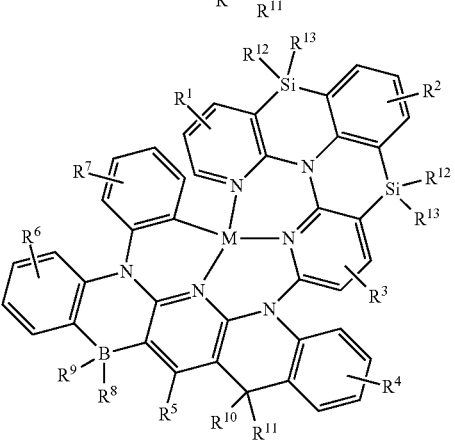
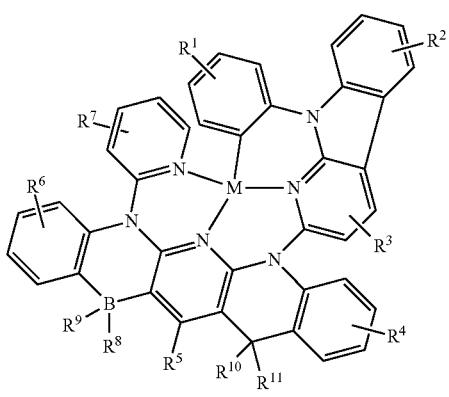

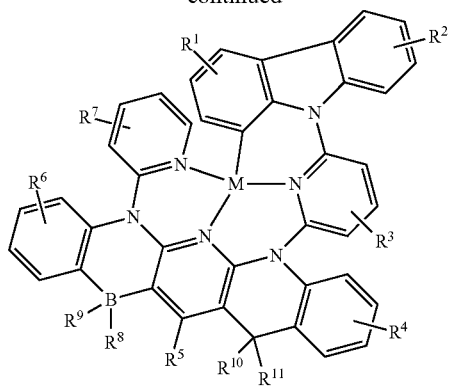
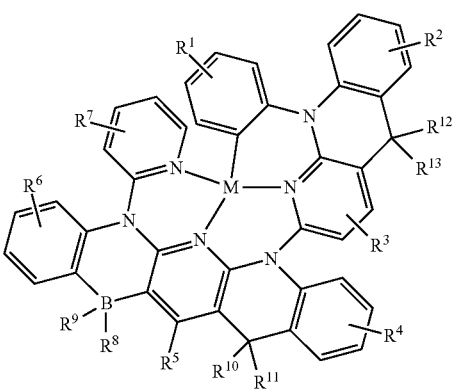
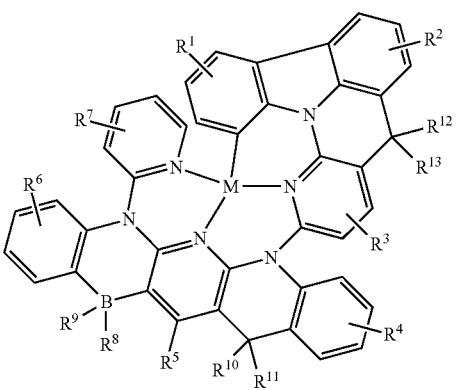
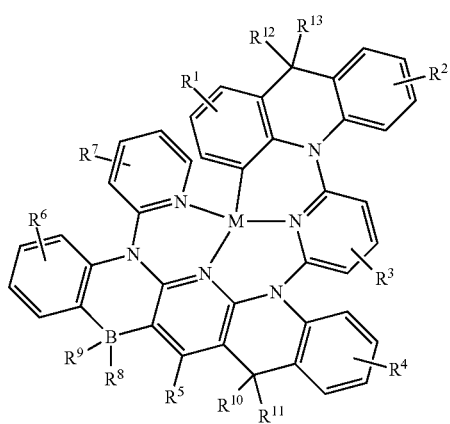
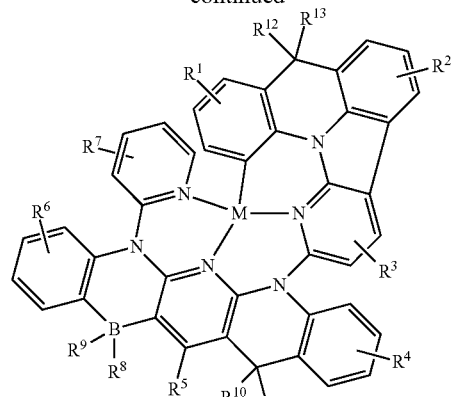
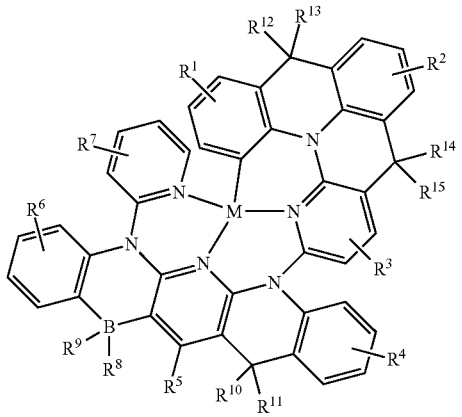
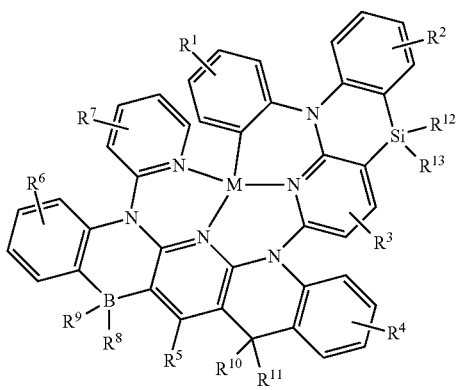
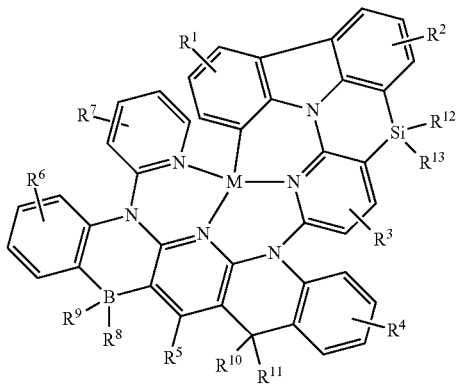

187
-continued
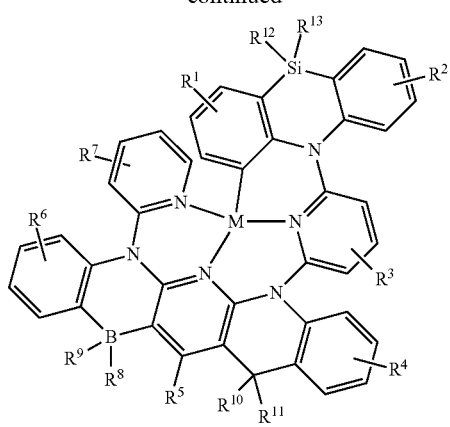
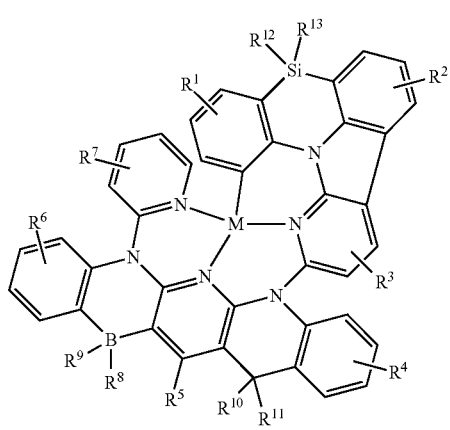
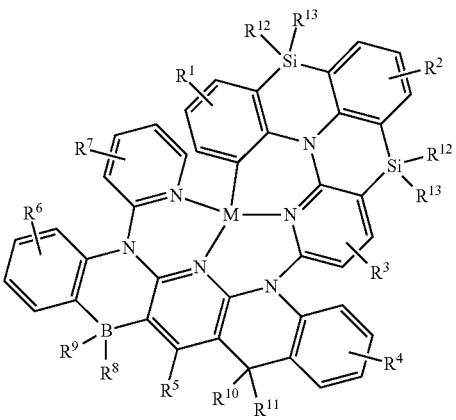
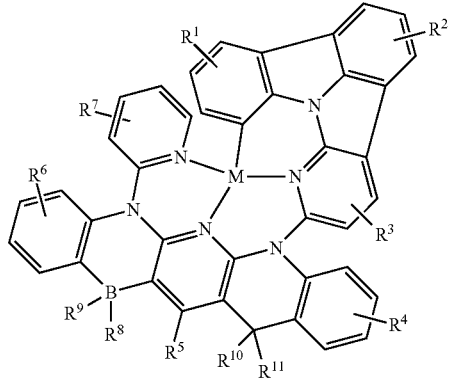
188
-continued
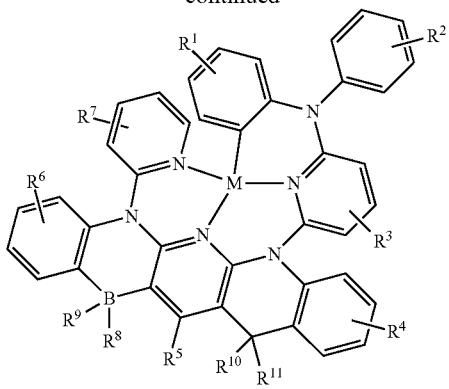
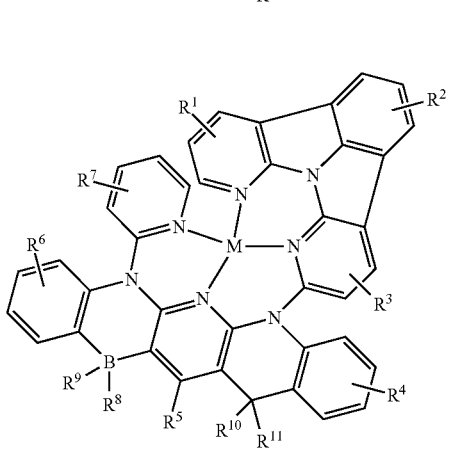
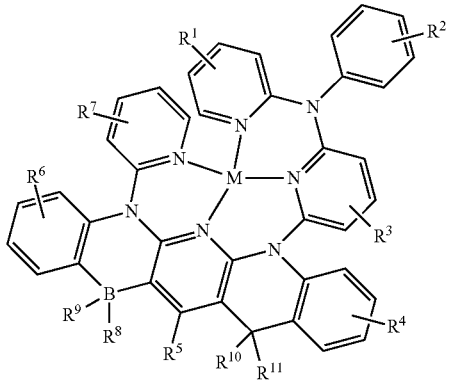
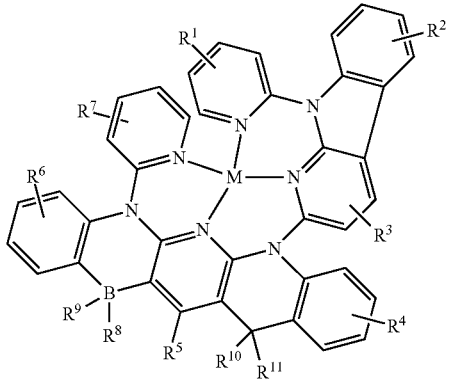

189
-continued
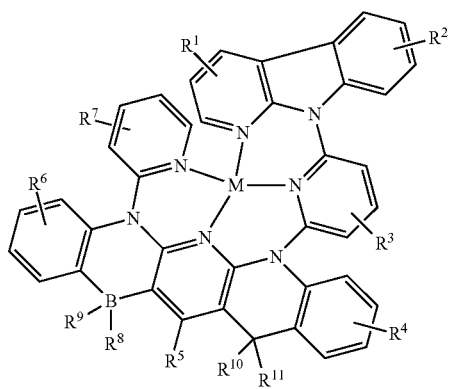
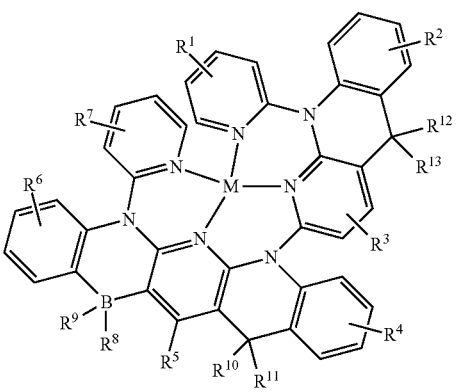
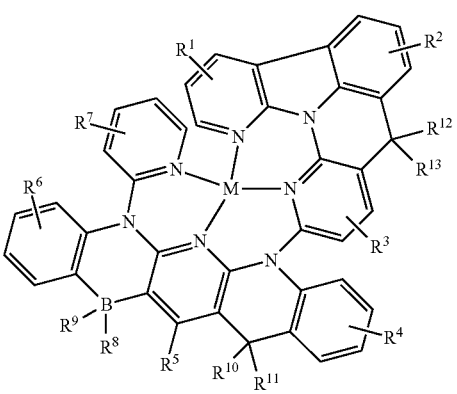
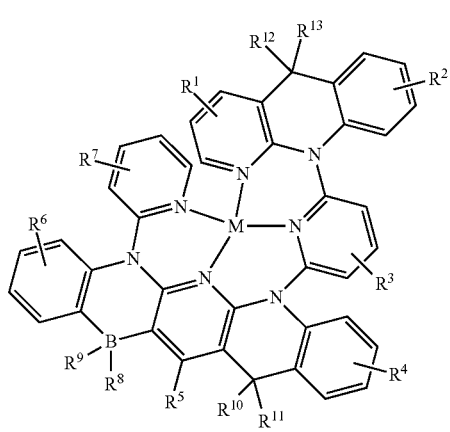
190
-continued
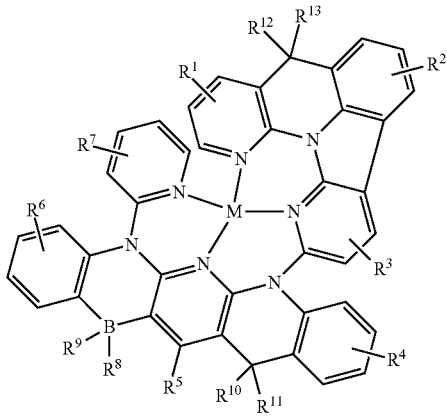
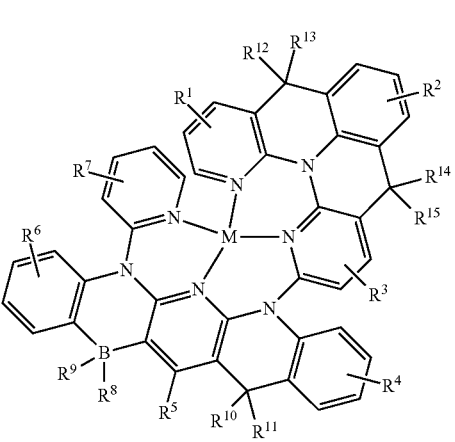
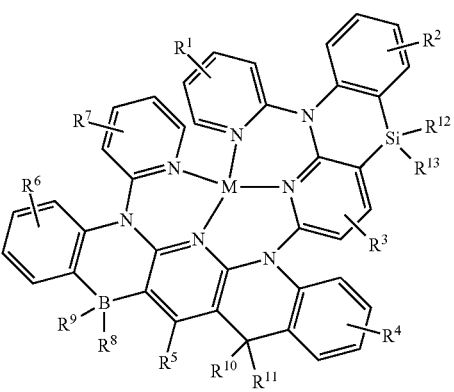
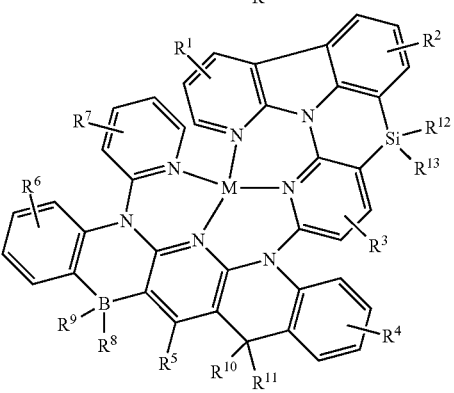

191
-continued
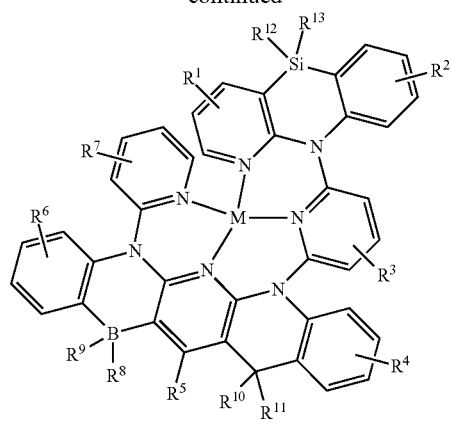
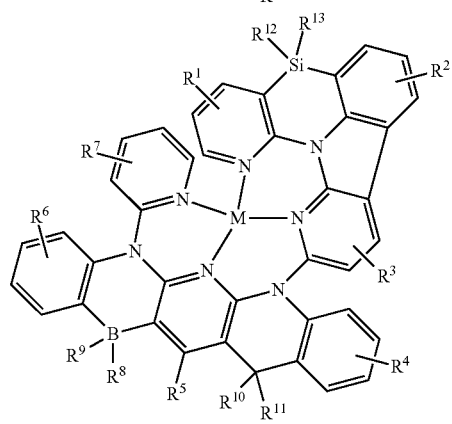
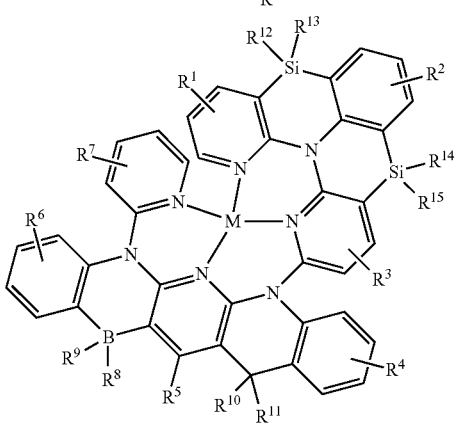
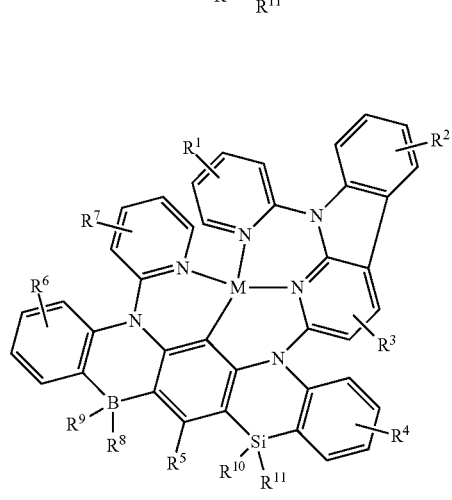
192
-continued
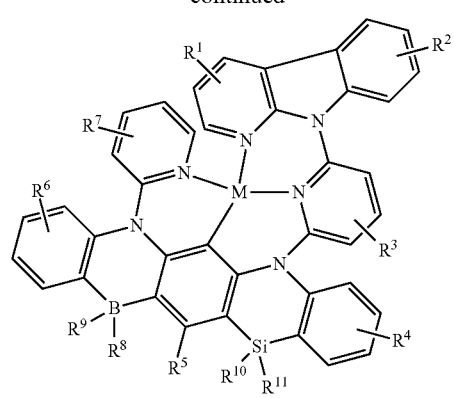
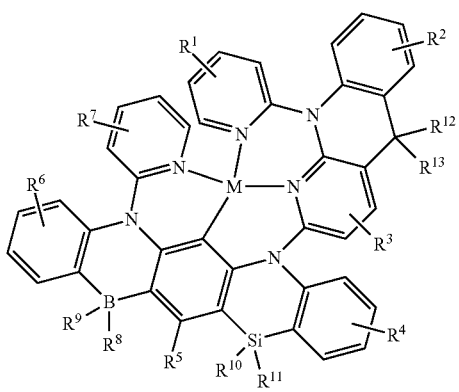
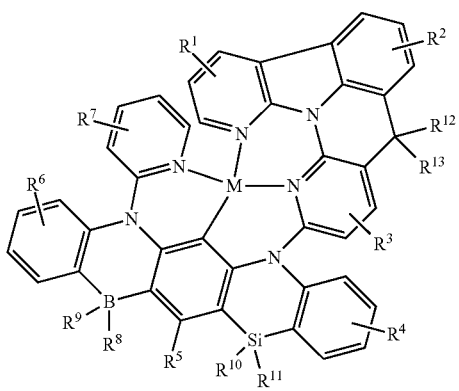
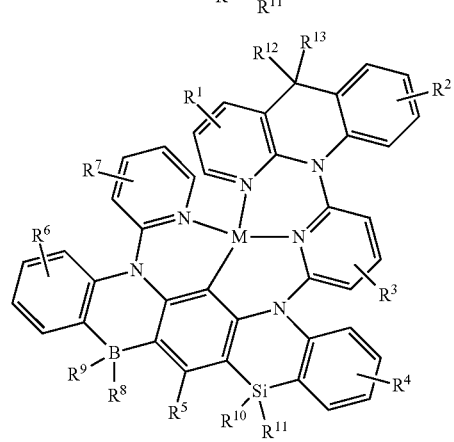

193
-continued
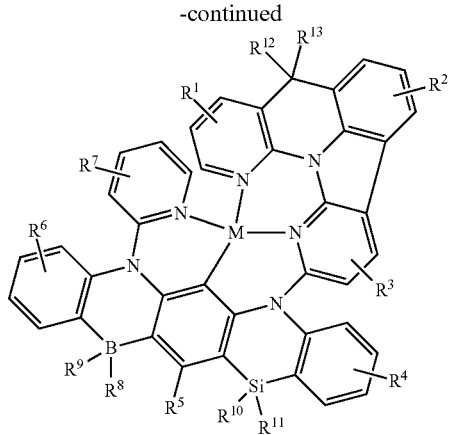
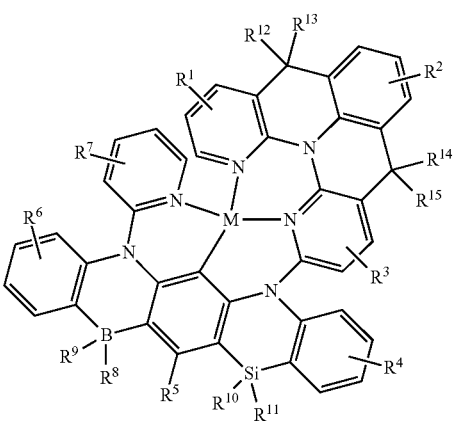
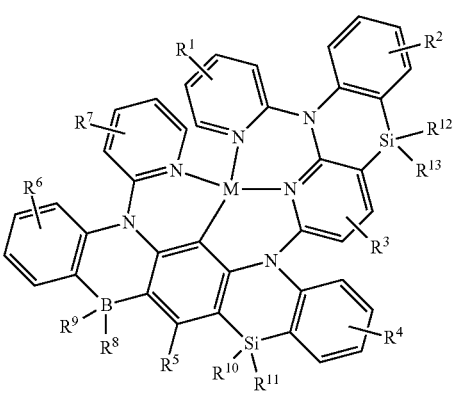
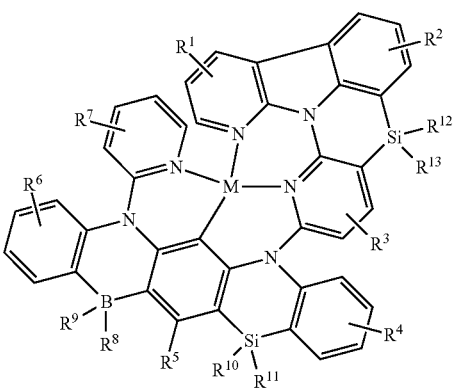
194
-continued
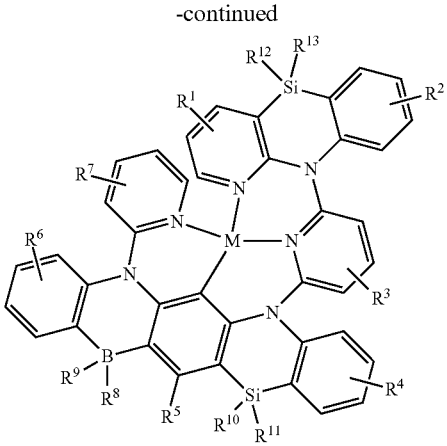
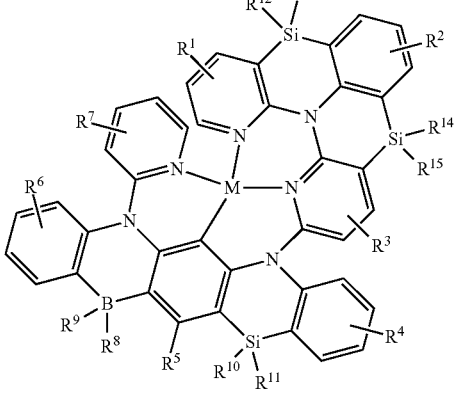
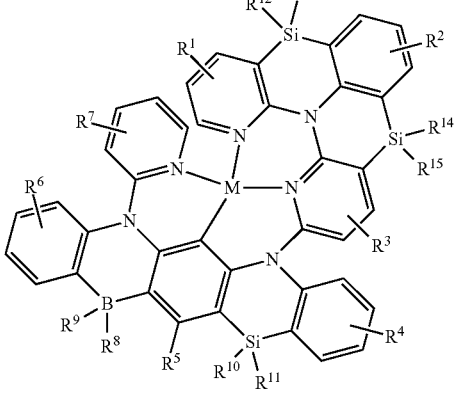
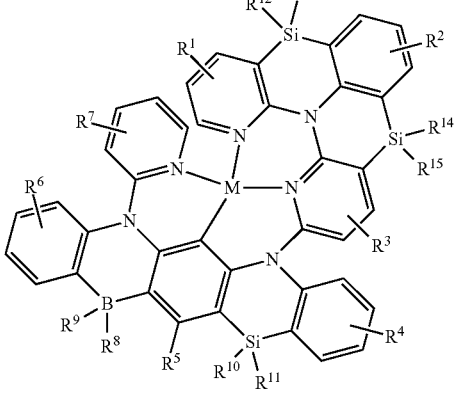

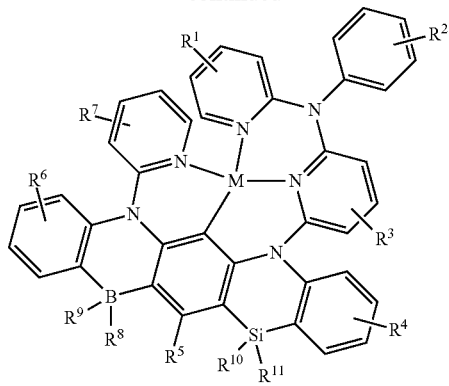
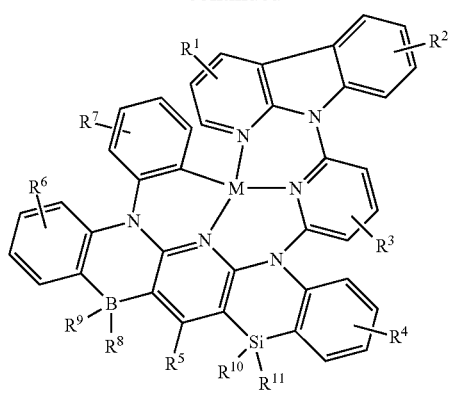
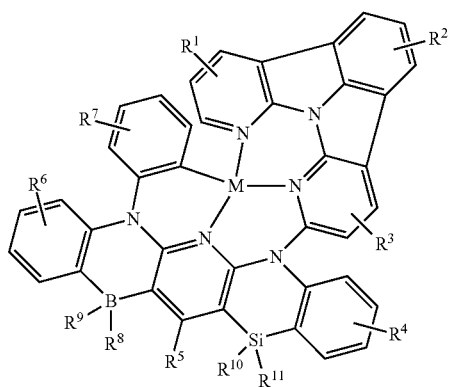
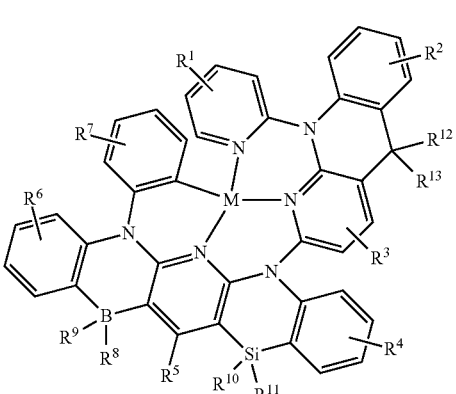
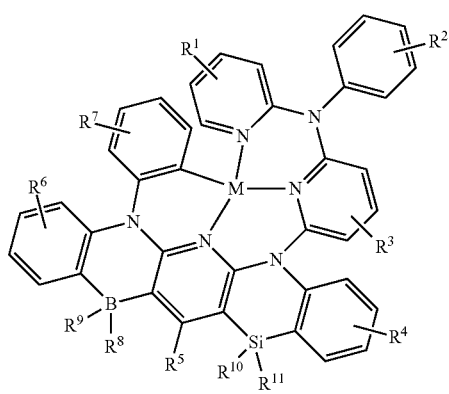
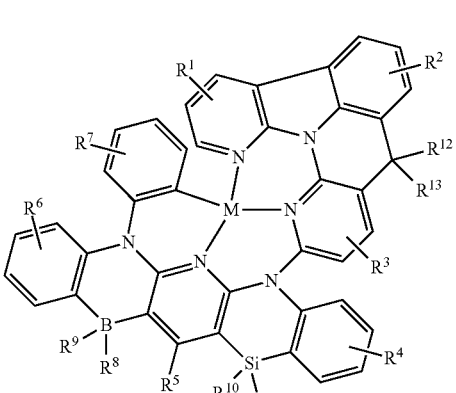
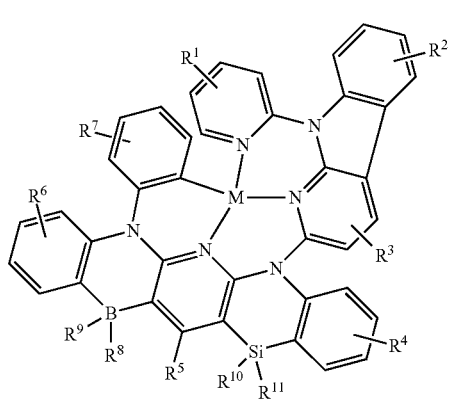
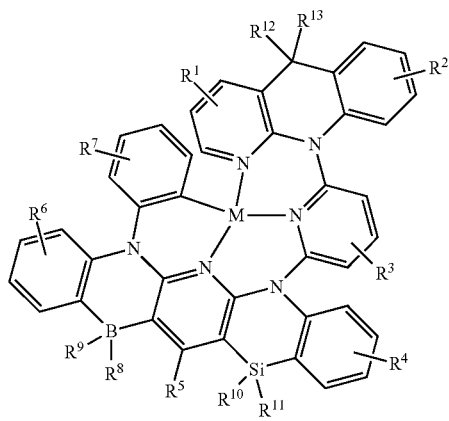

197
-continued
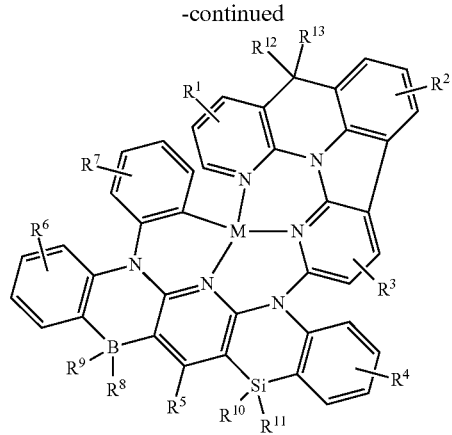
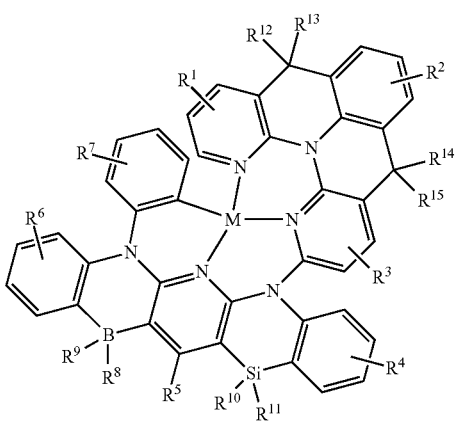
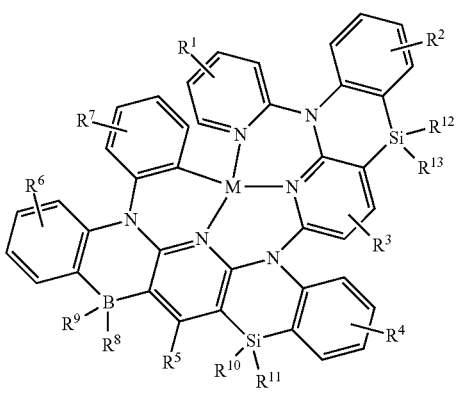
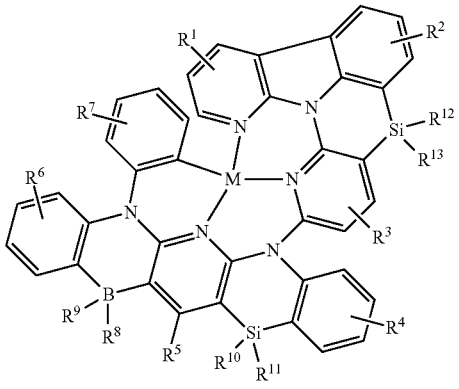
198
-continued
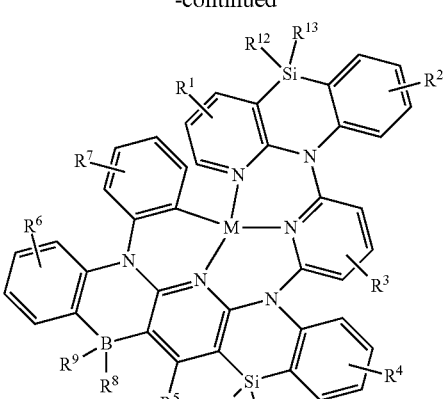
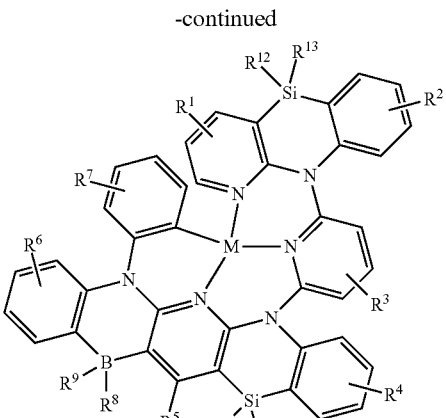
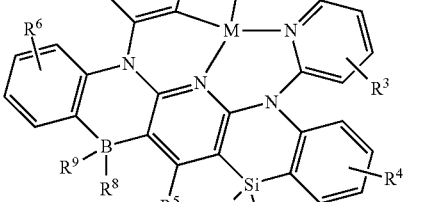
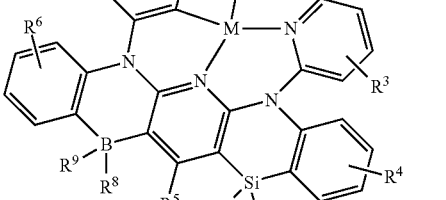

199
-continued
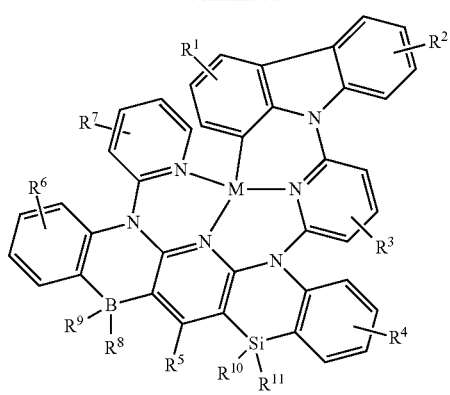
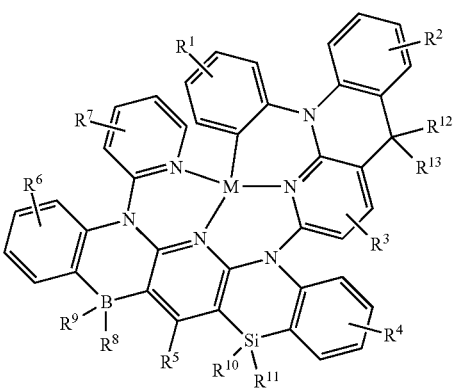
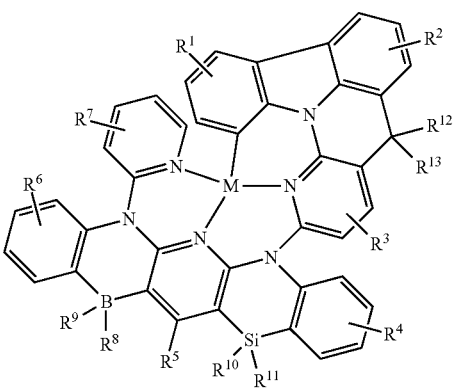
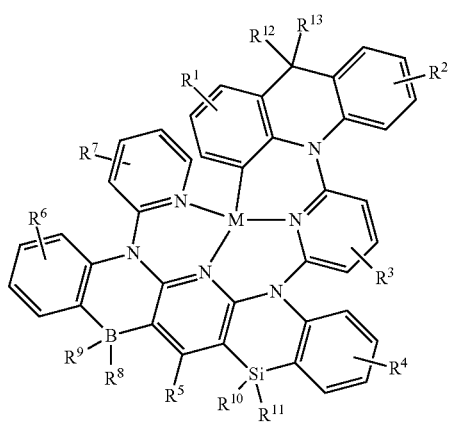
200
-continued
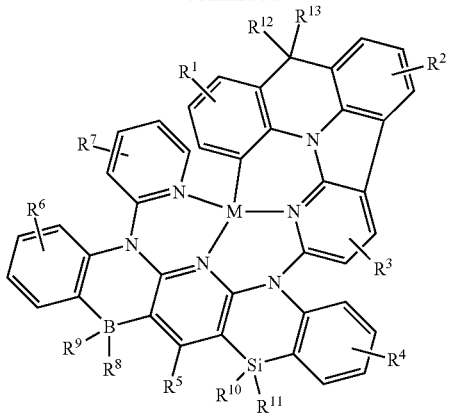
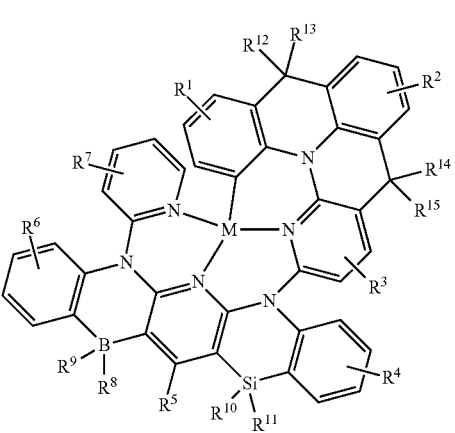
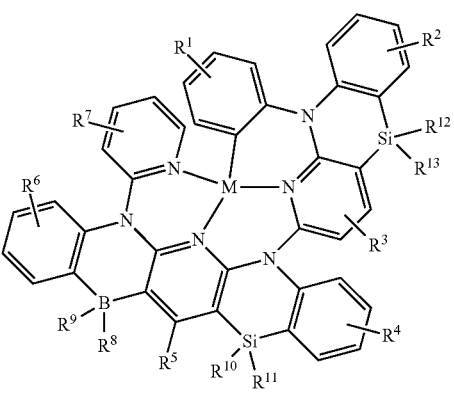
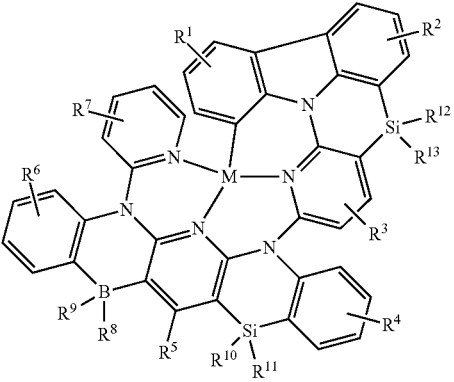

201
-continued
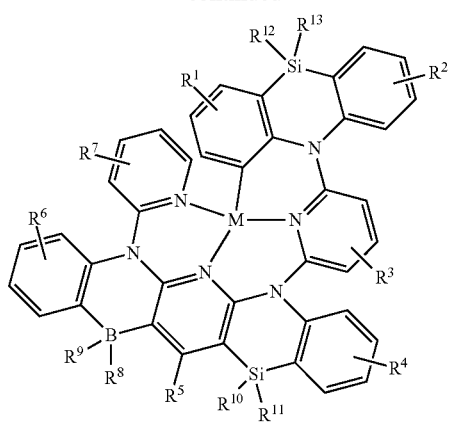
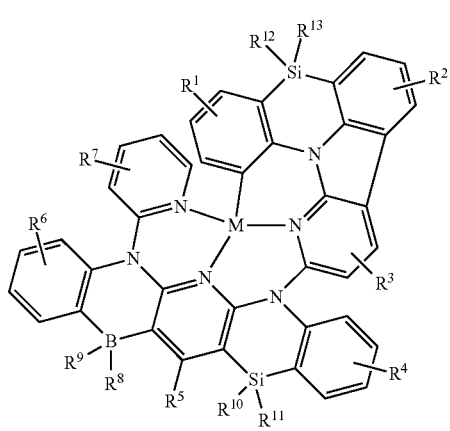
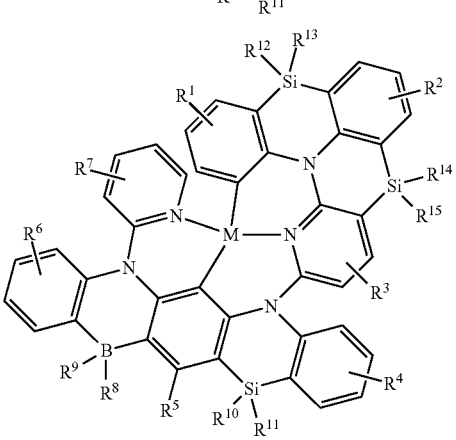
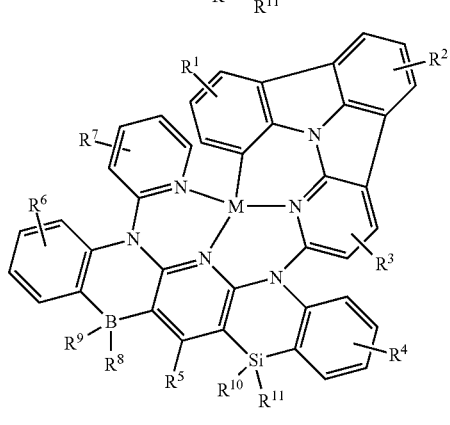
202
-continued
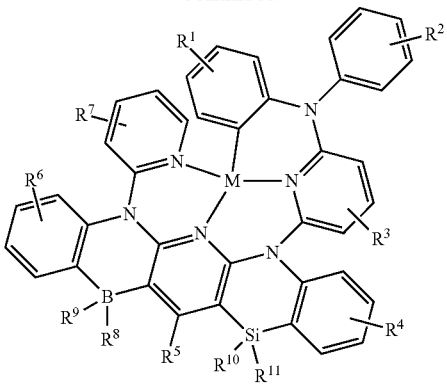
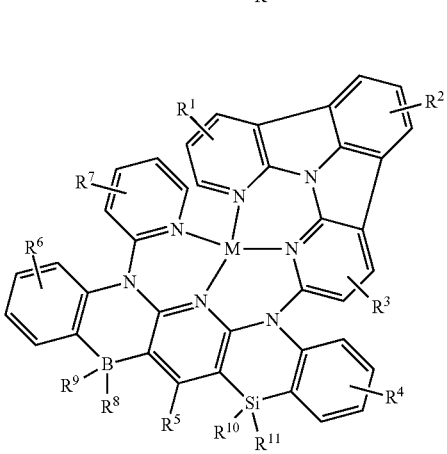
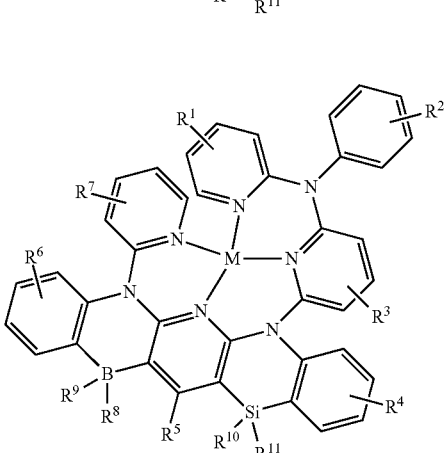
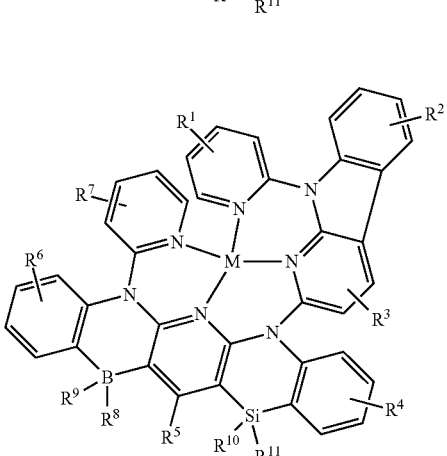

203
-continued
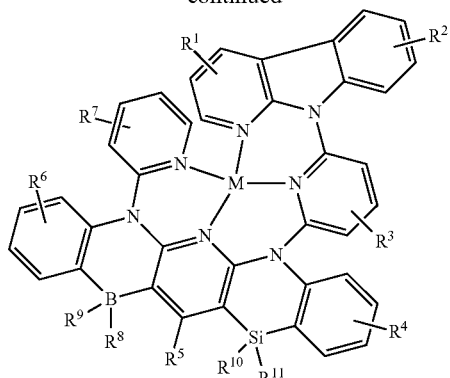
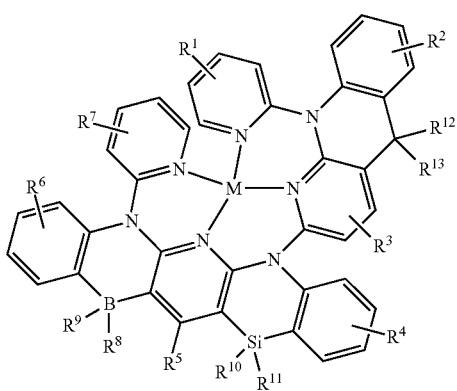
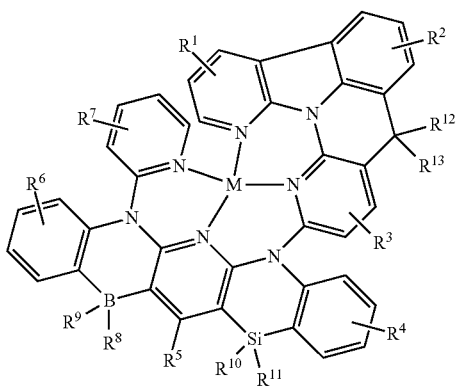
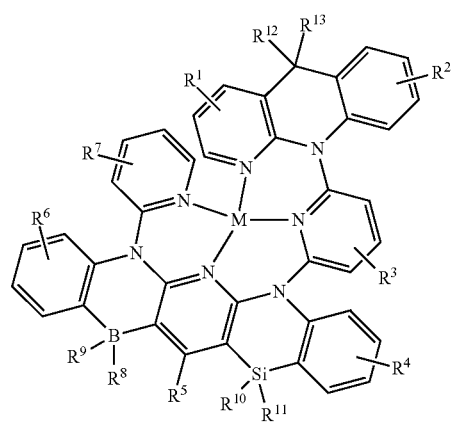
204
-continued
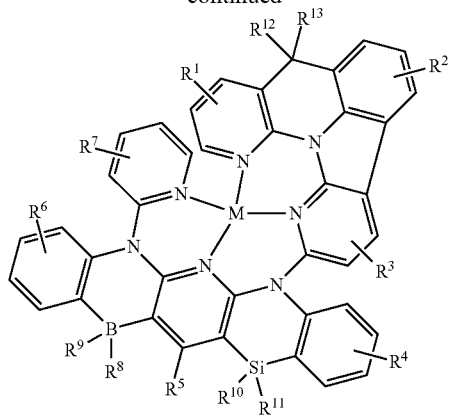
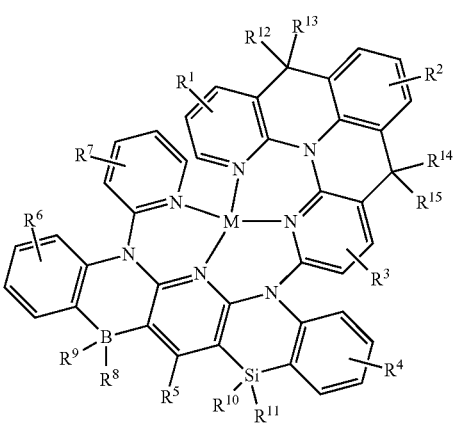
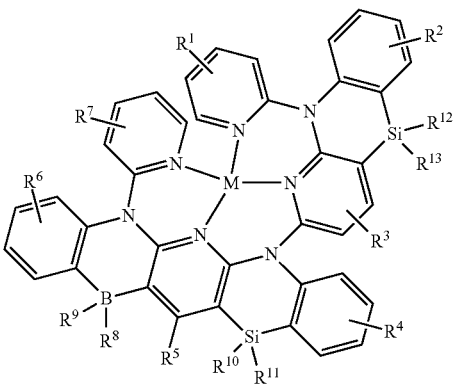
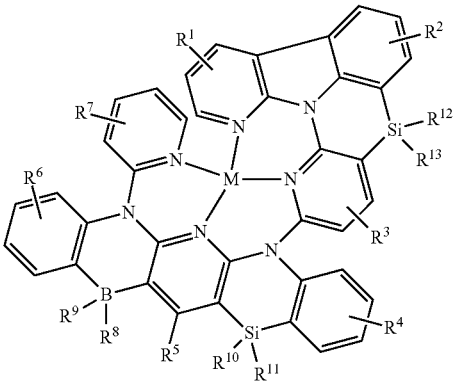

205
-continued
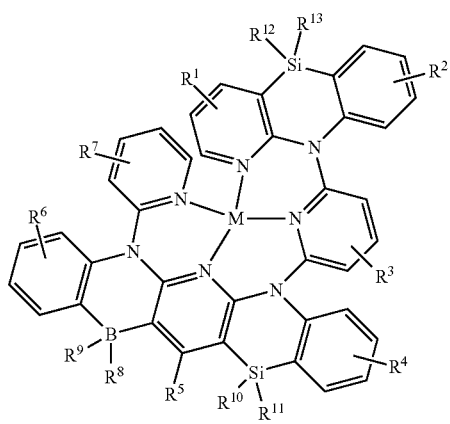
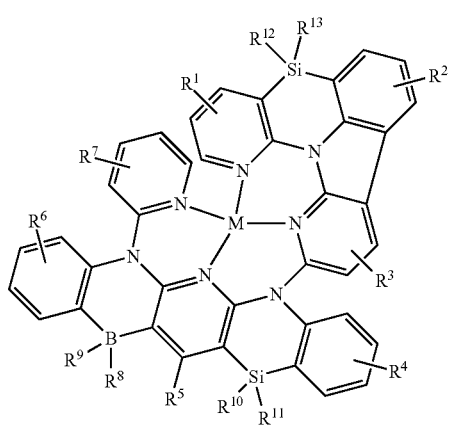
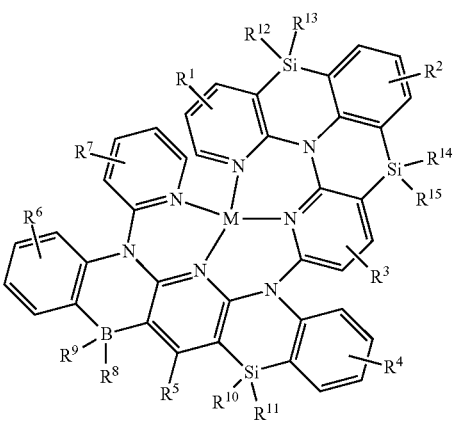
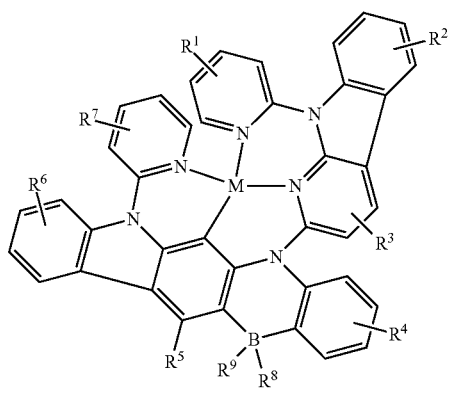
206
-continued
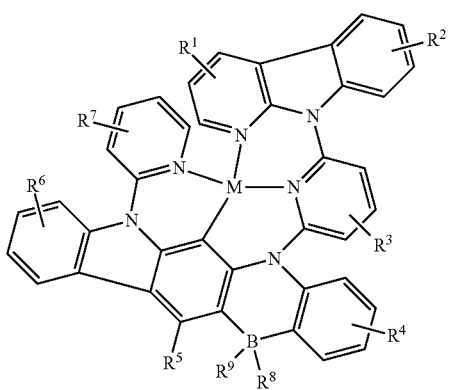
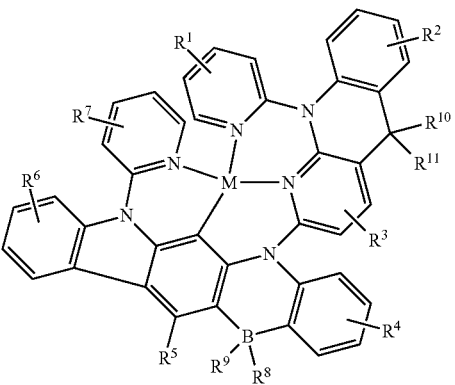
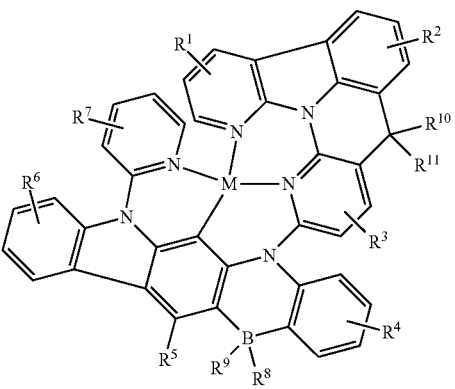
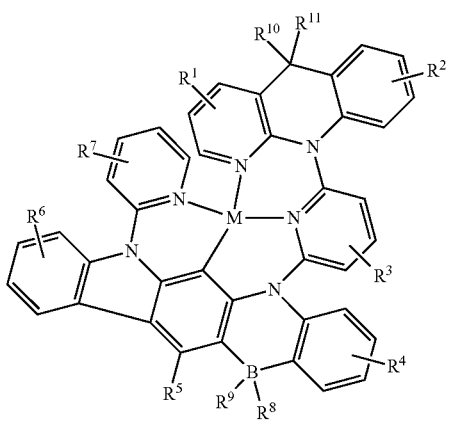

207
-continued
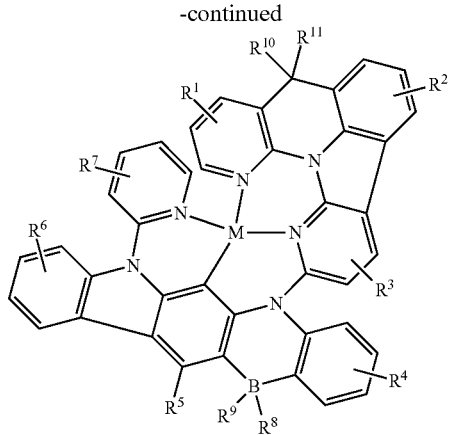
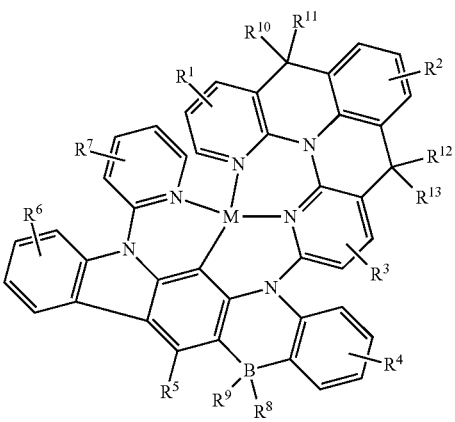
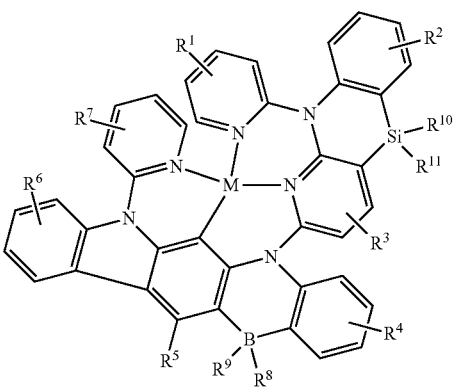
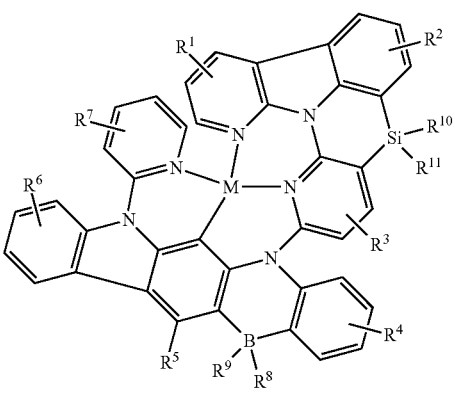
208
-continued
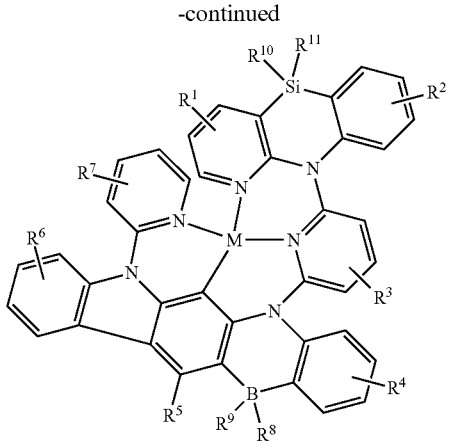
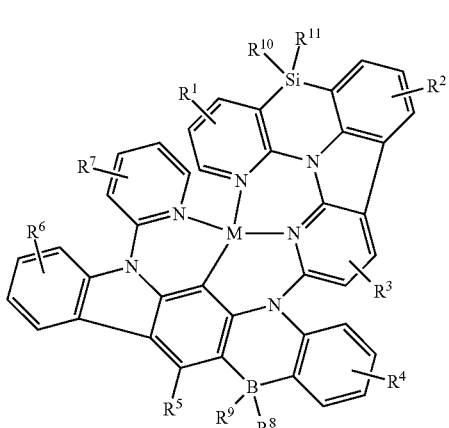
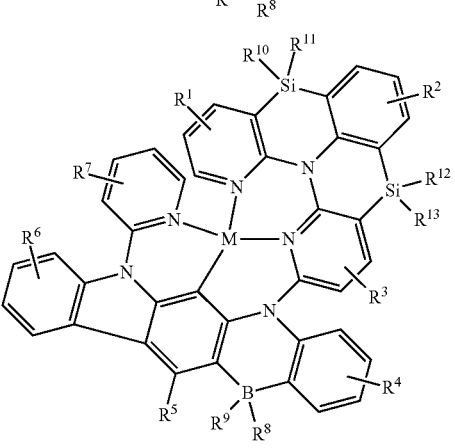
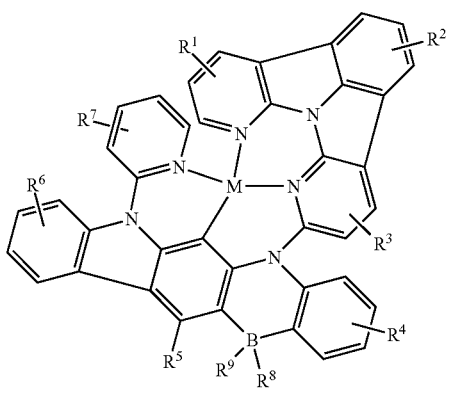

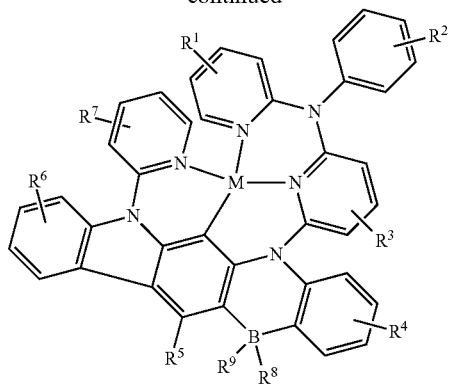
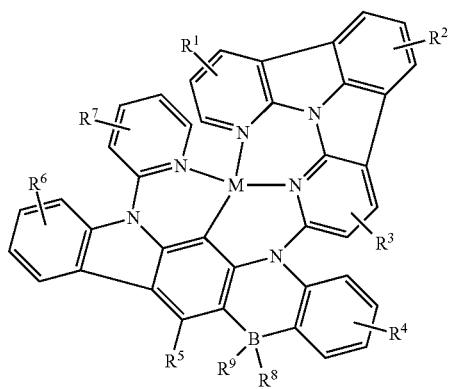
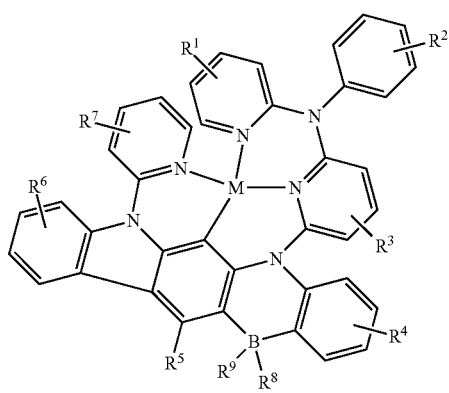
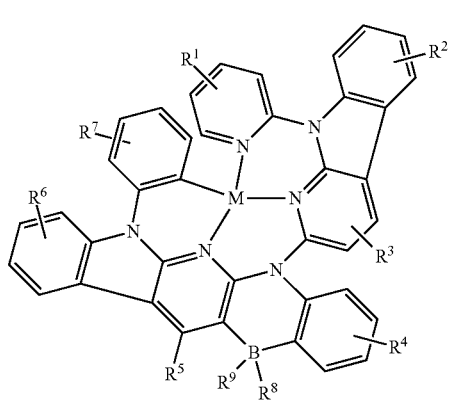
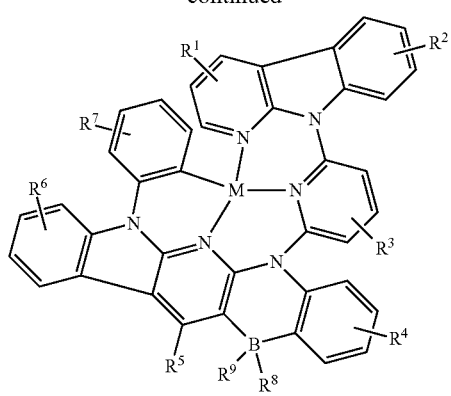
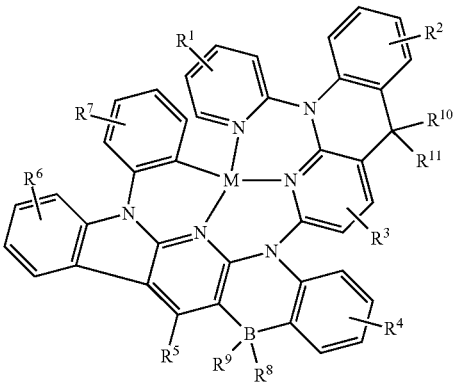
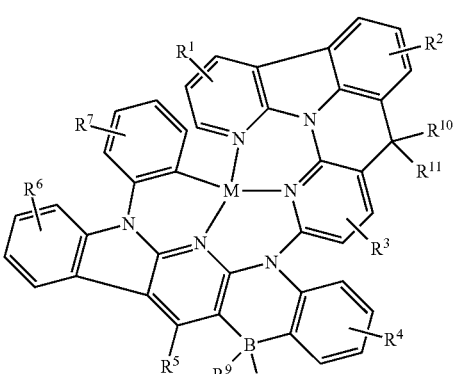
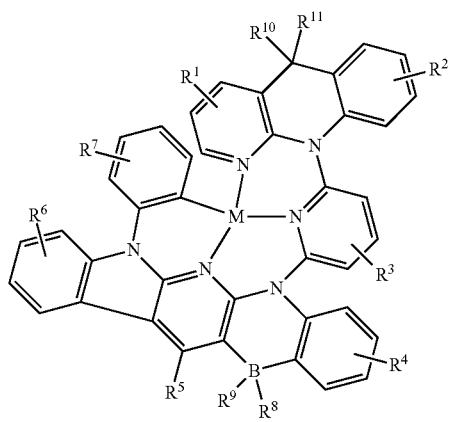

211
-continued
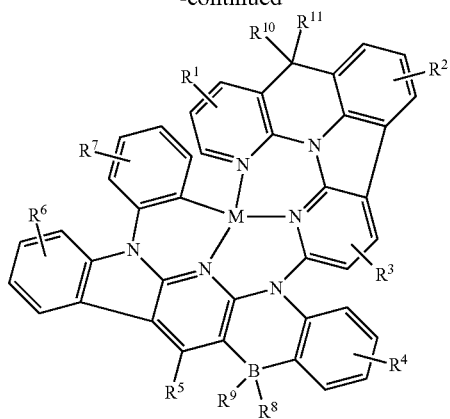
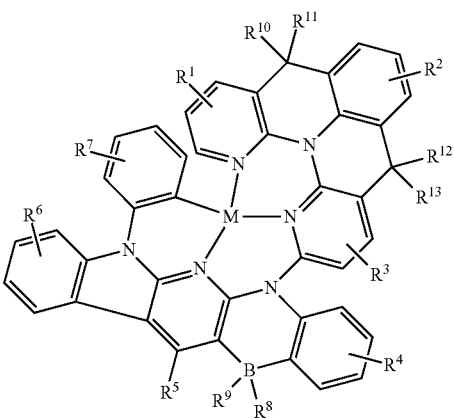
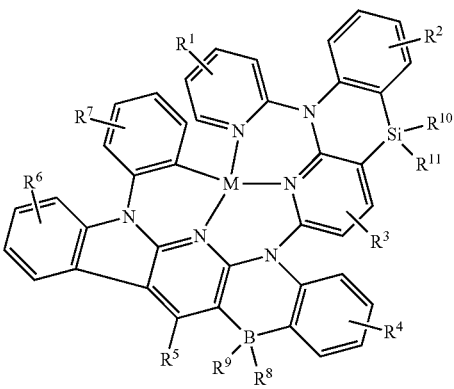
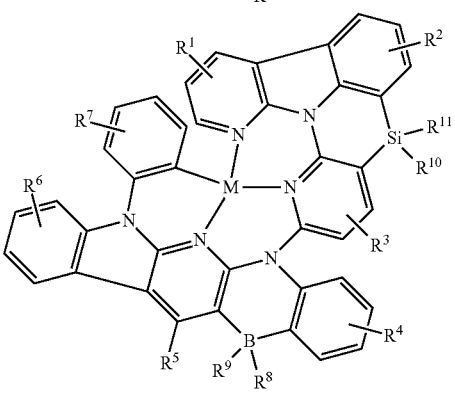
212
-continued
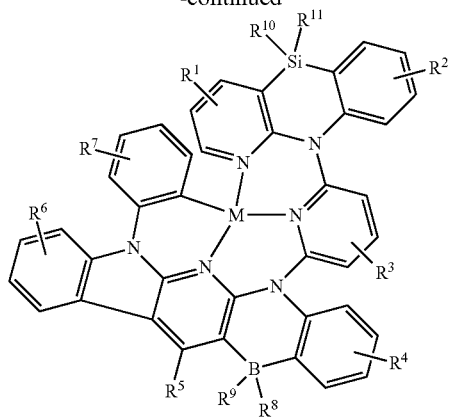
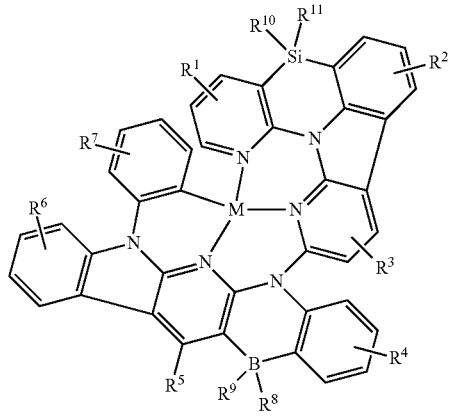
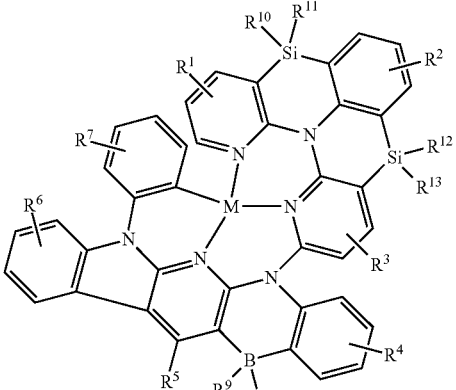
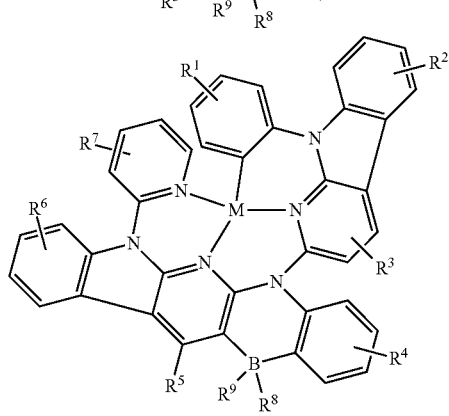

213
-continued
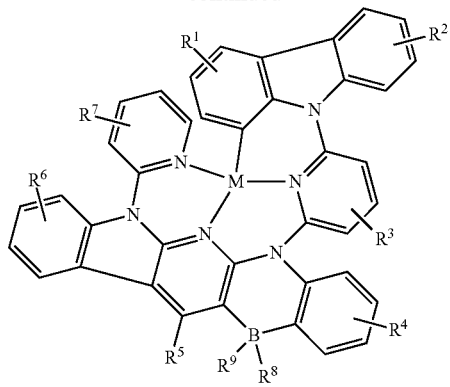
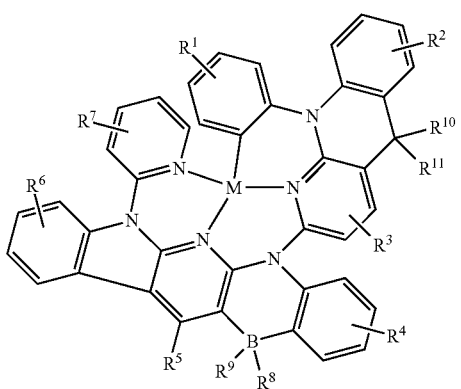
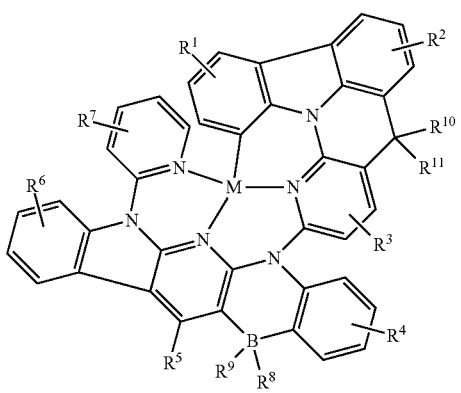
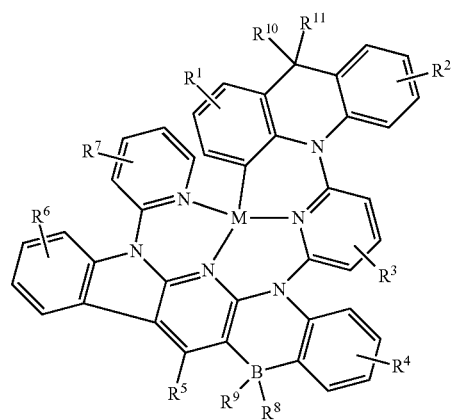
214
-continued
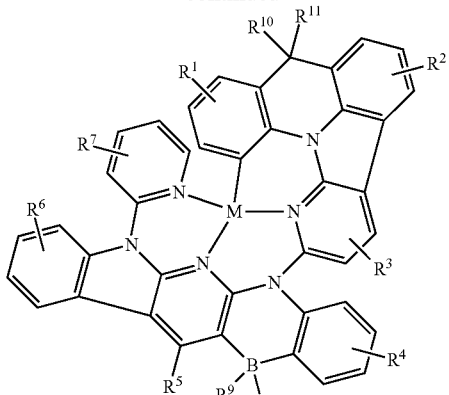
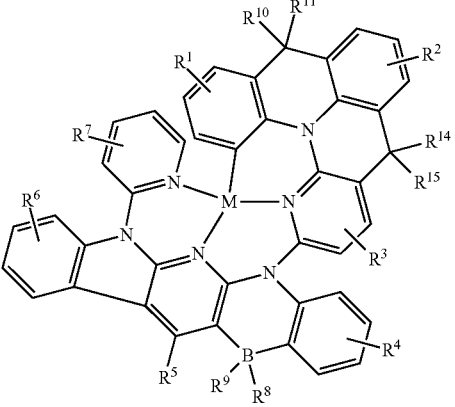
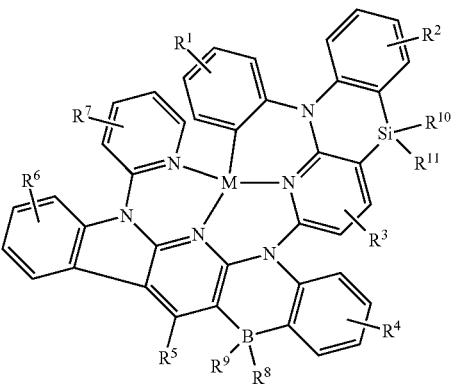
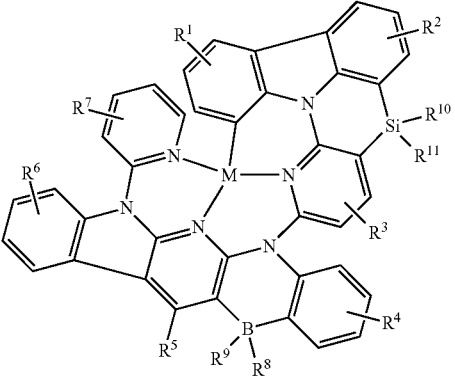

215
-continued
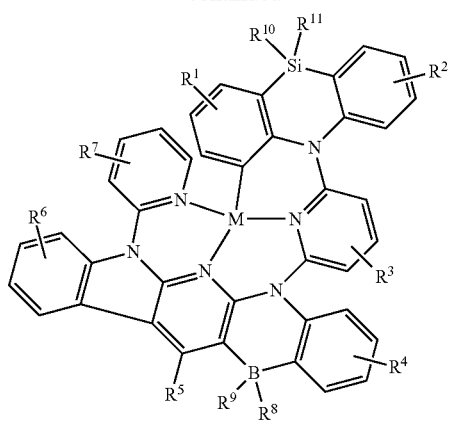
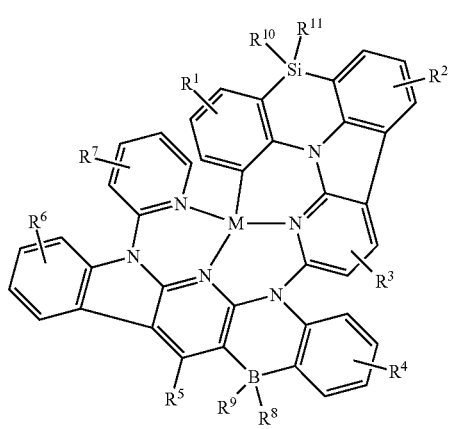
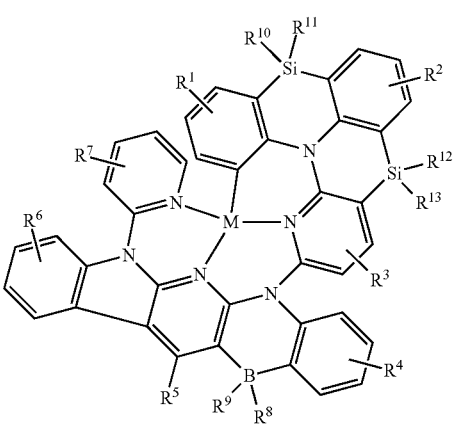
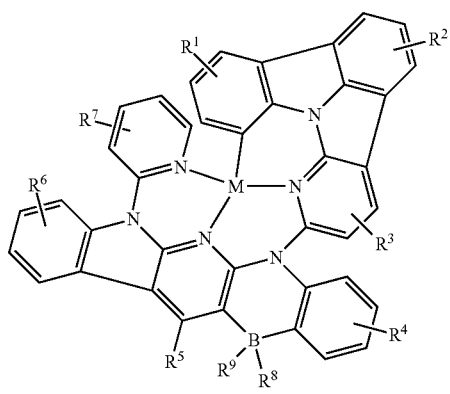
216
-continued
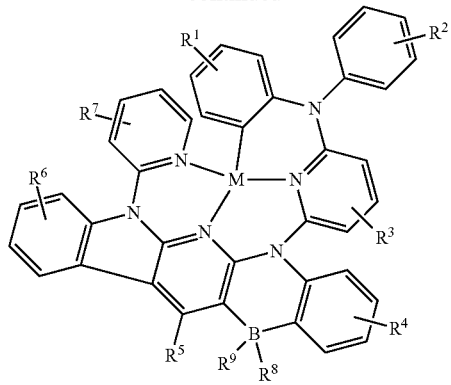
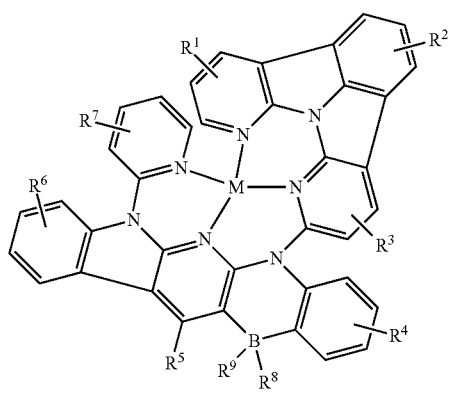
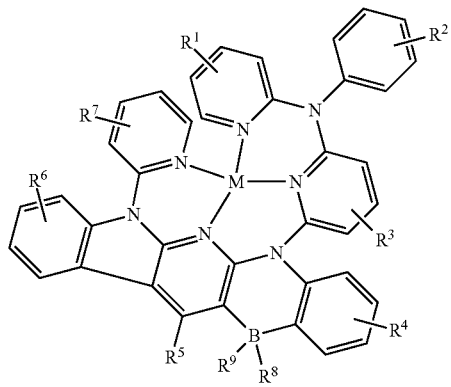
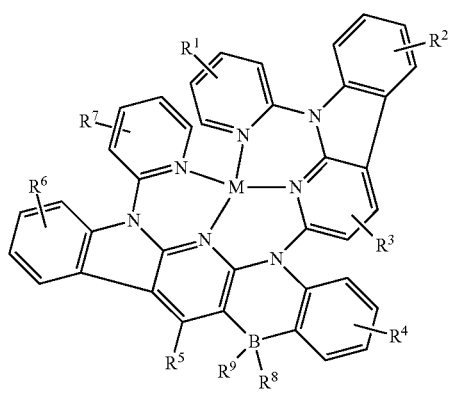

217
-continued
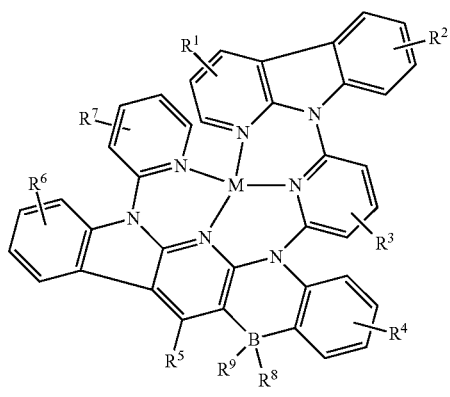
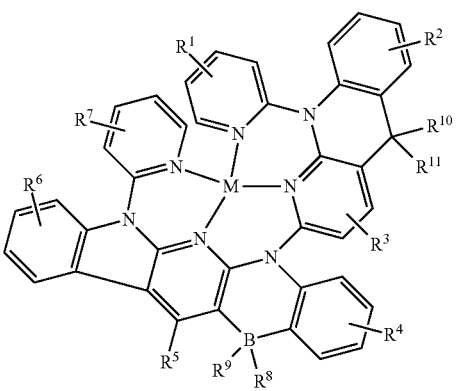
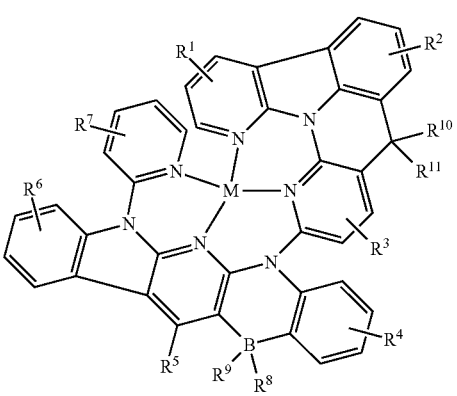
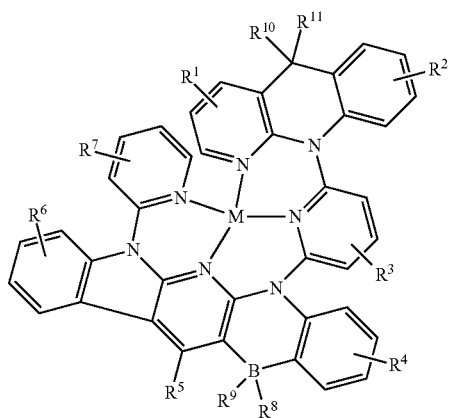
218
-continued
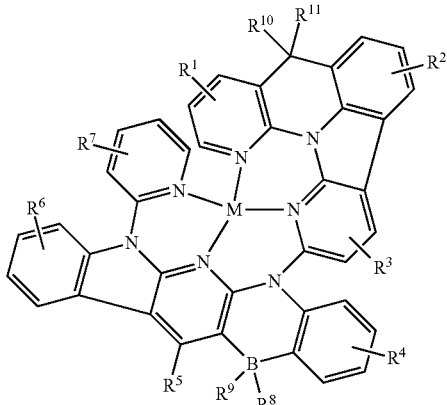
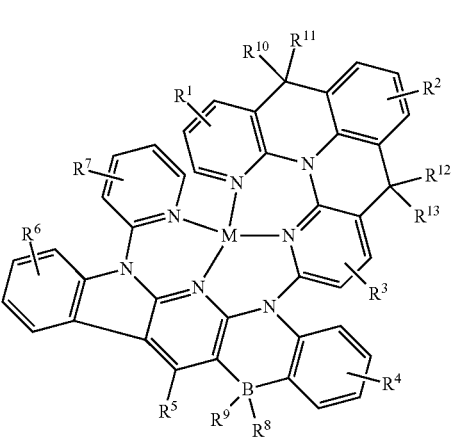
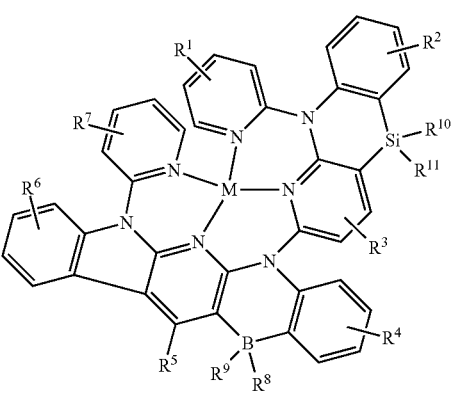
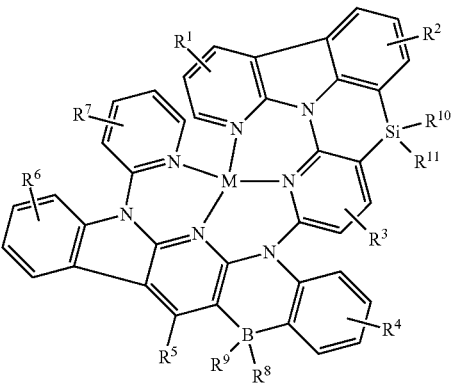

219
-continued
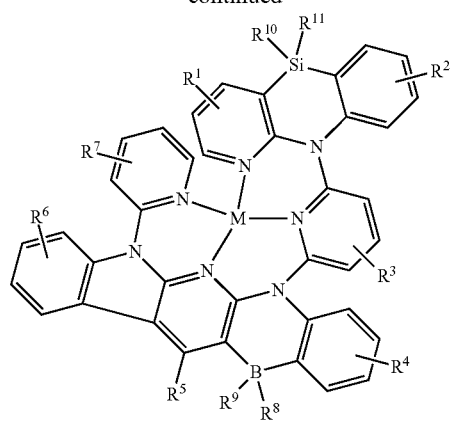
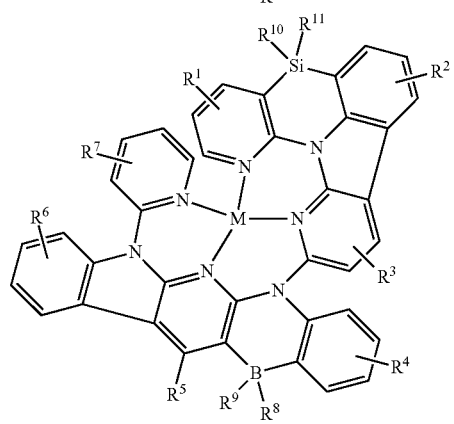
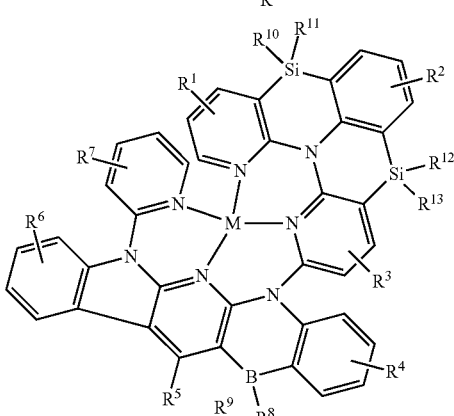
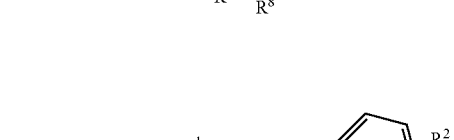
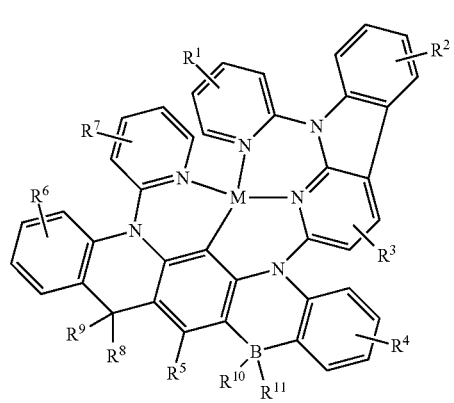
220
-continued
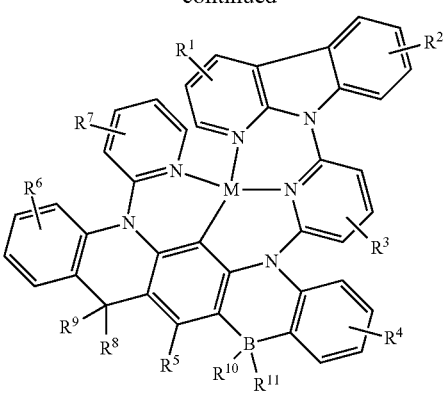
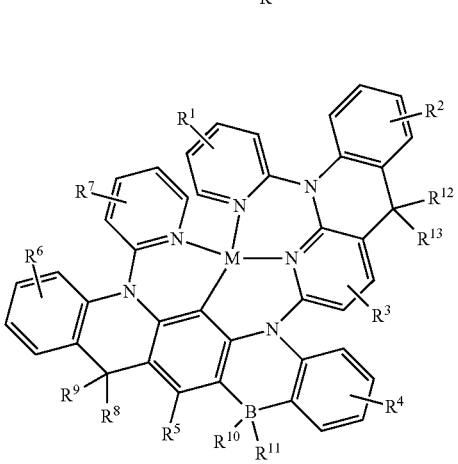
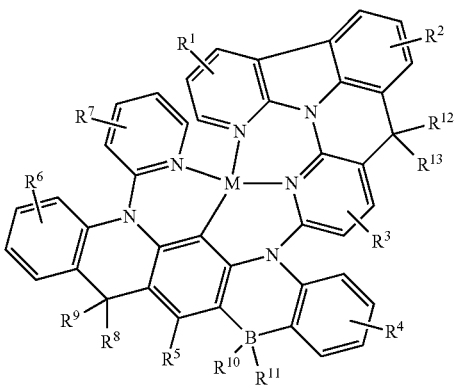
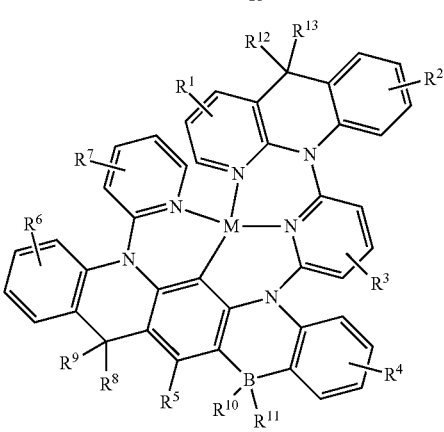

221
-continued
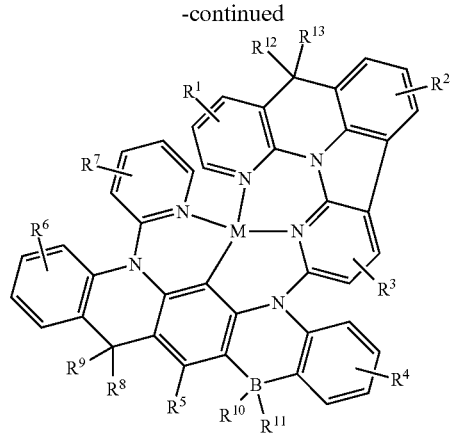
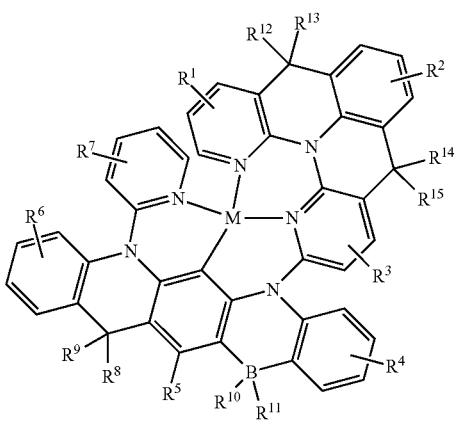
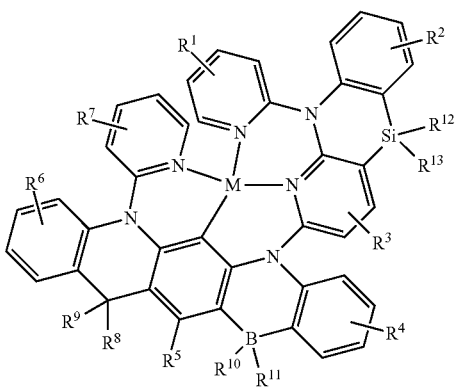
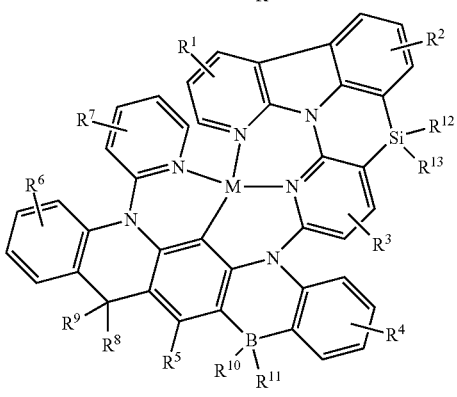
222
-continued
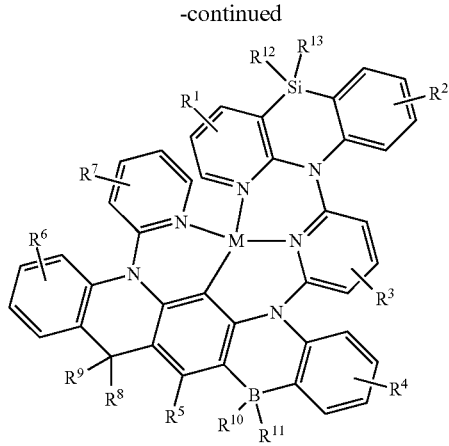
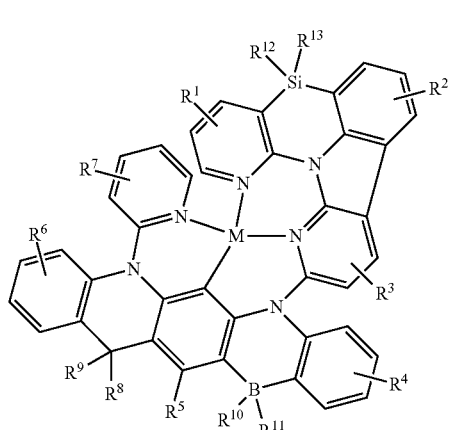
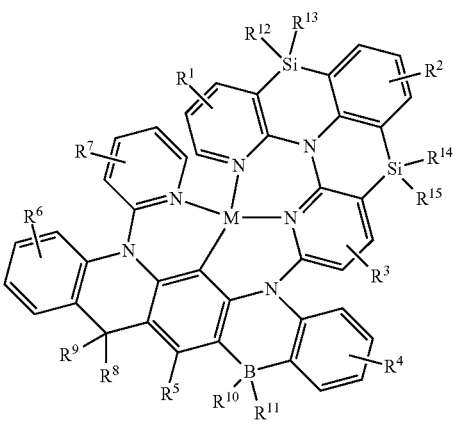
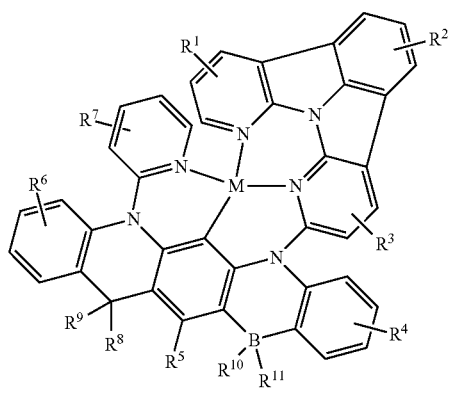

223
-continued
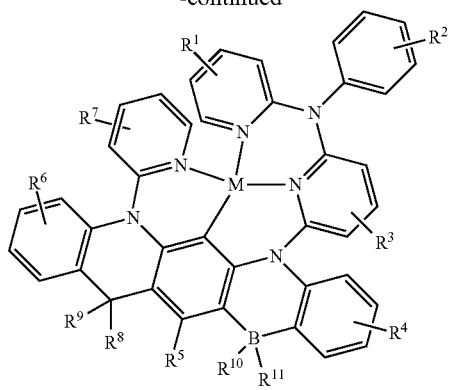
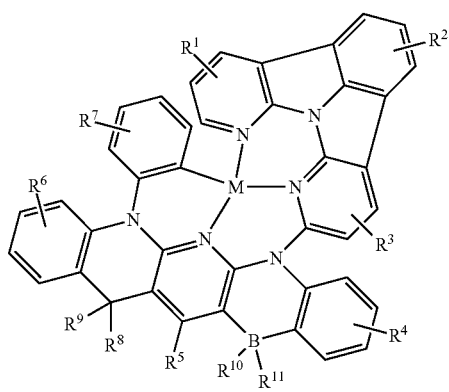
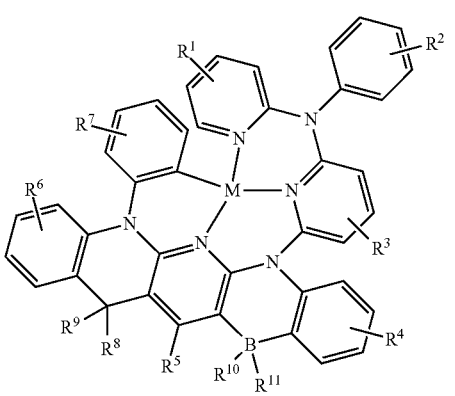
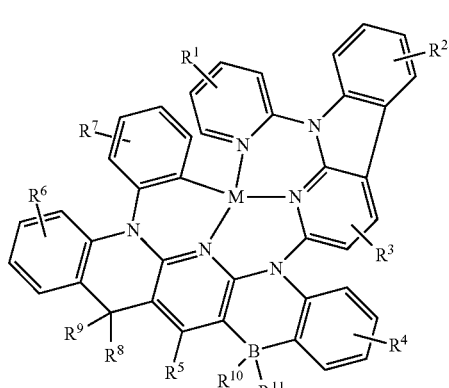
224
-continued
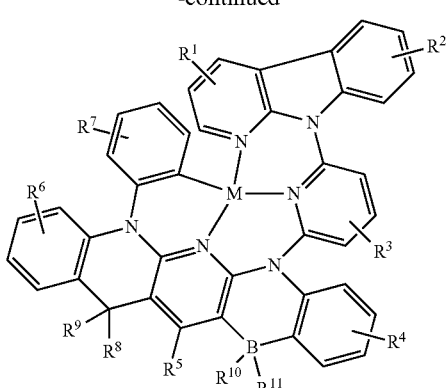
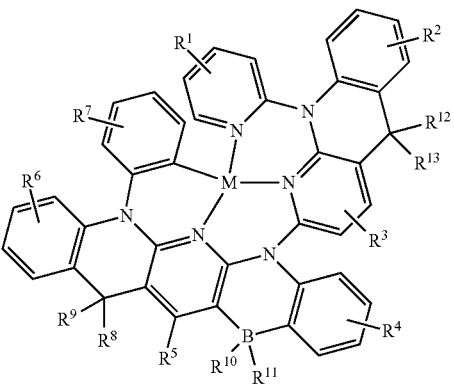
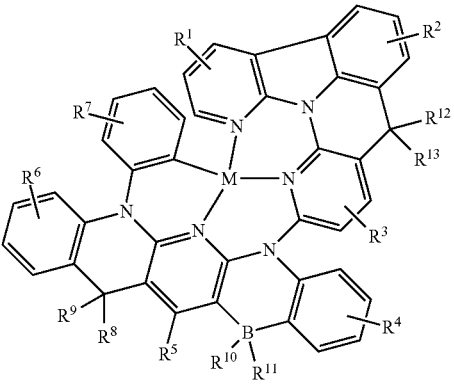
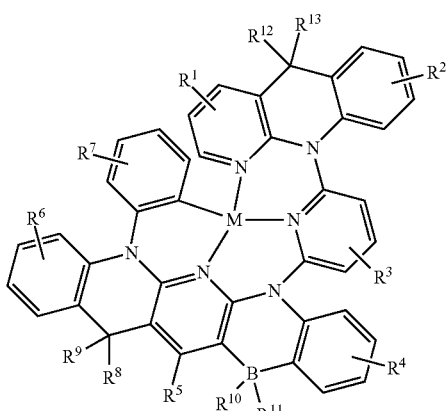

225
-continued
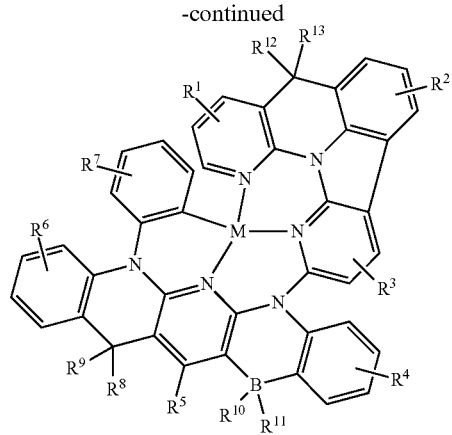
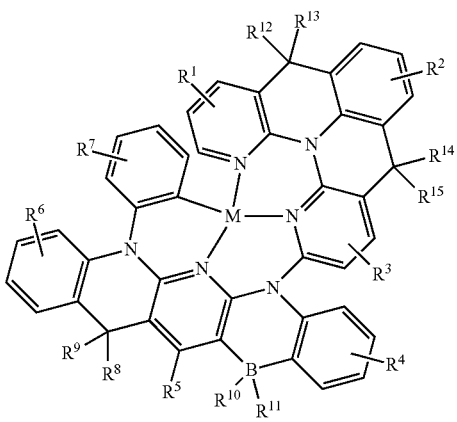
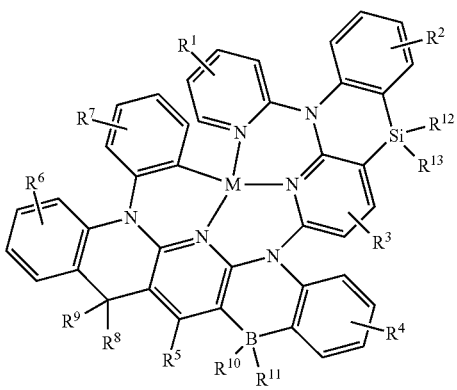
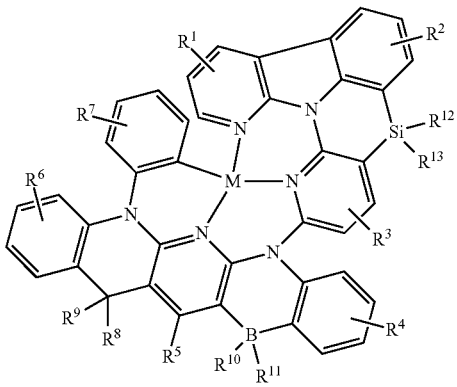
226
-continued
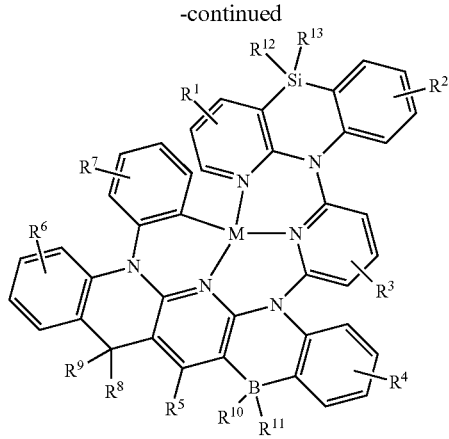
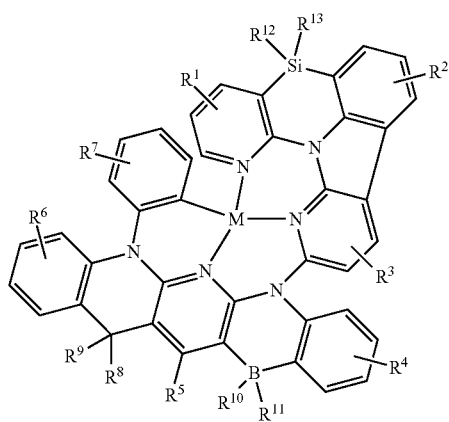
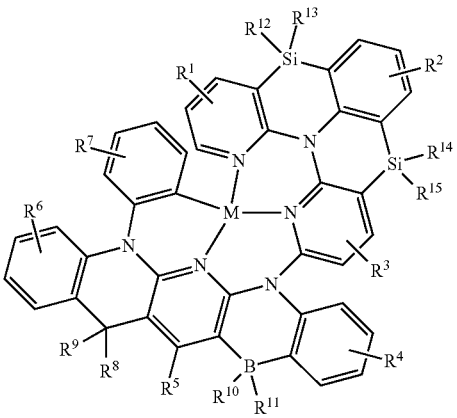
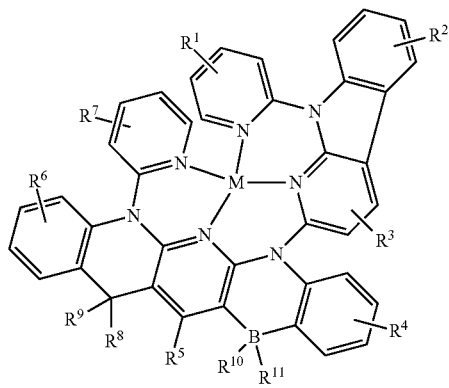

227
-continued
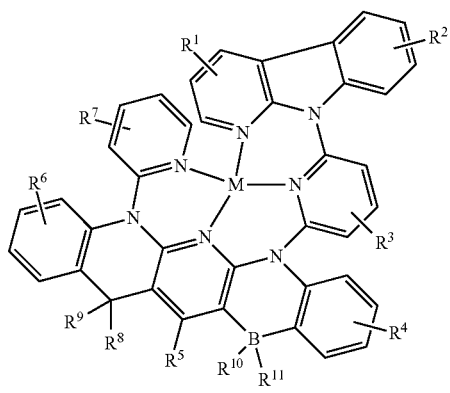
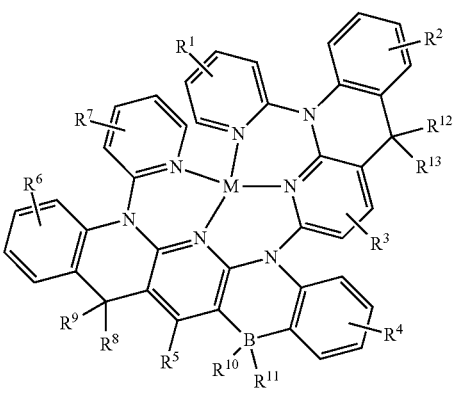
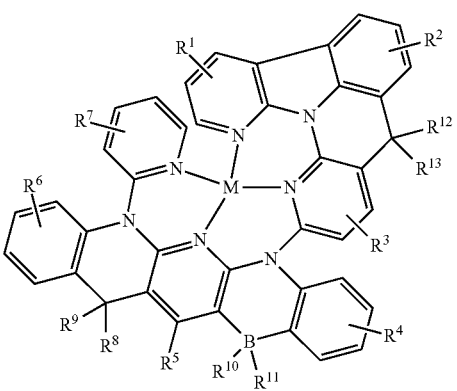
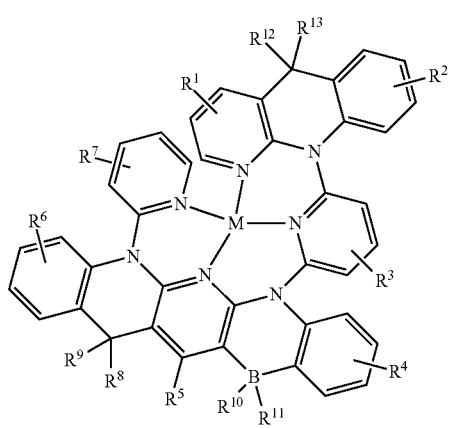
228
-continued
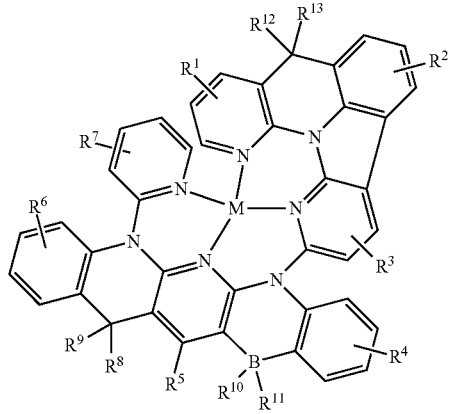
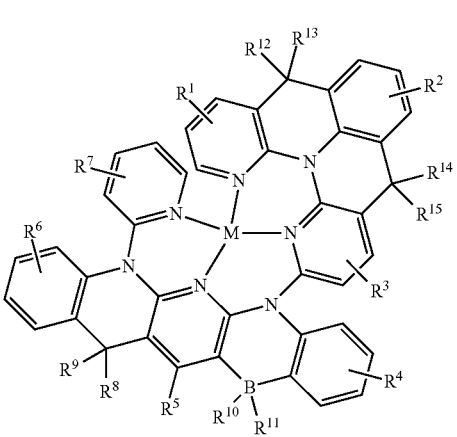
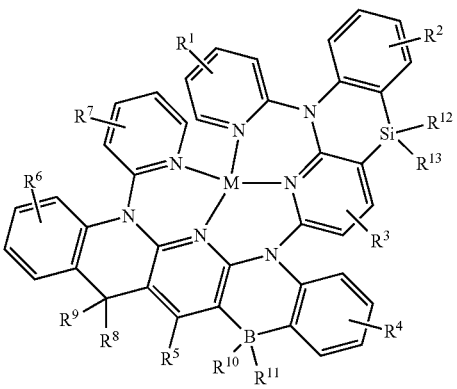
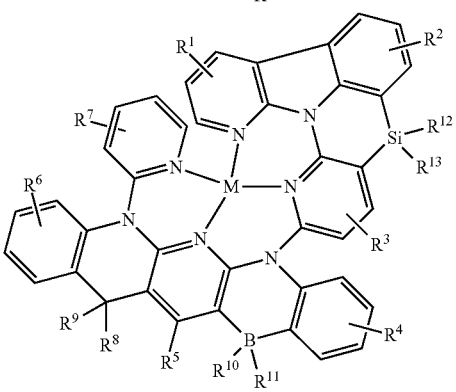

229
-continued
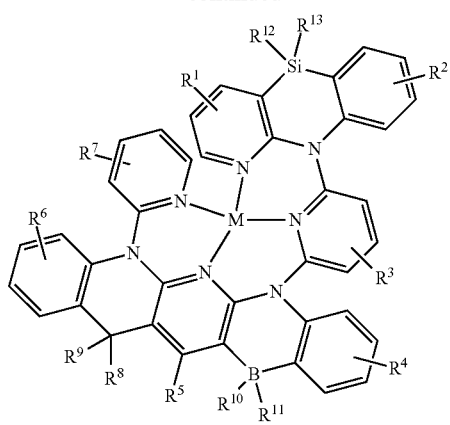
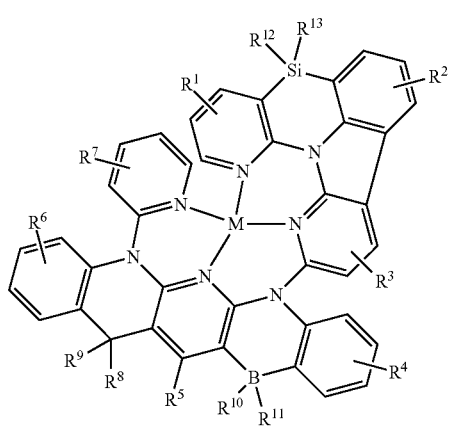
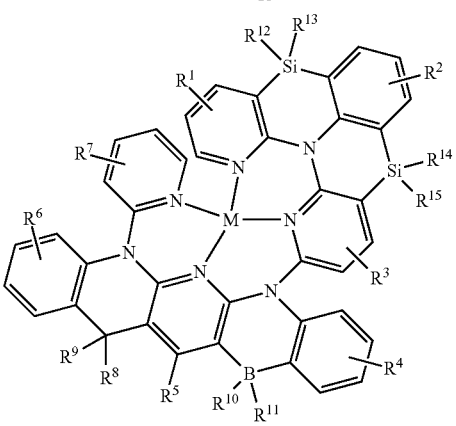
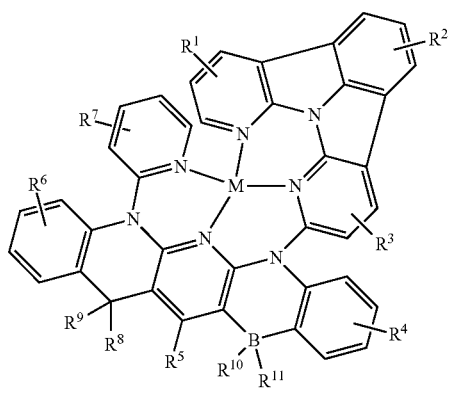
230
-continued
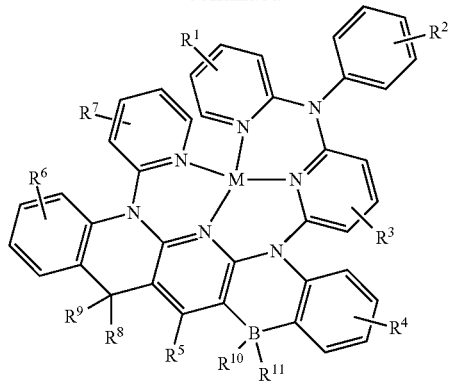
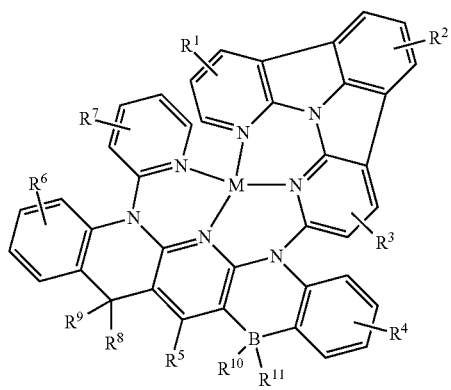
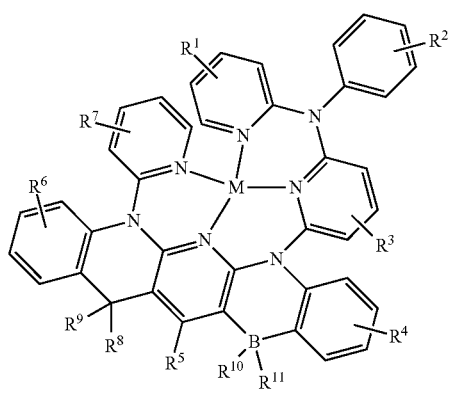
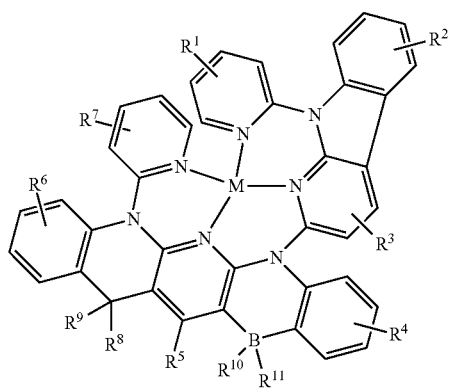

231
-continued
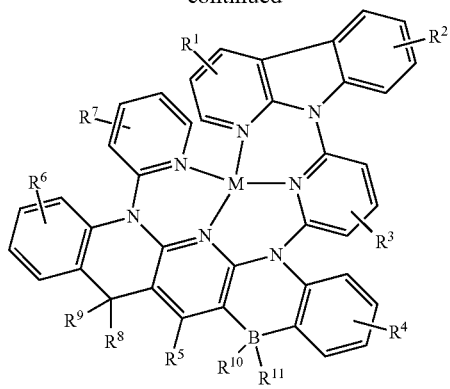
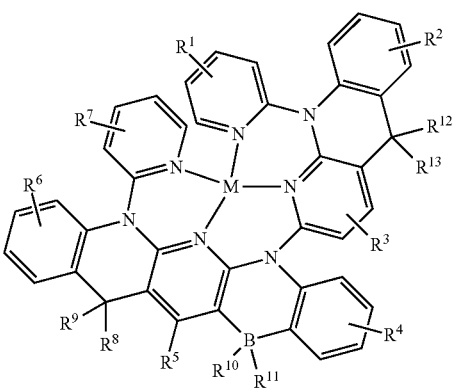
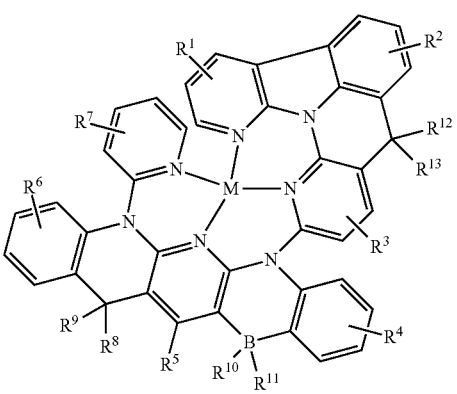
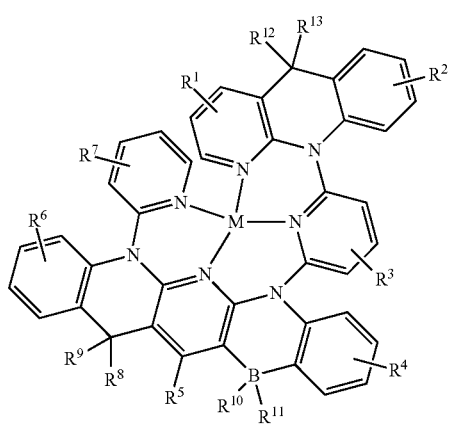
232
-continued
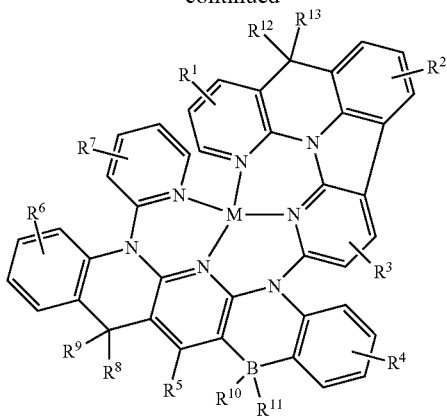
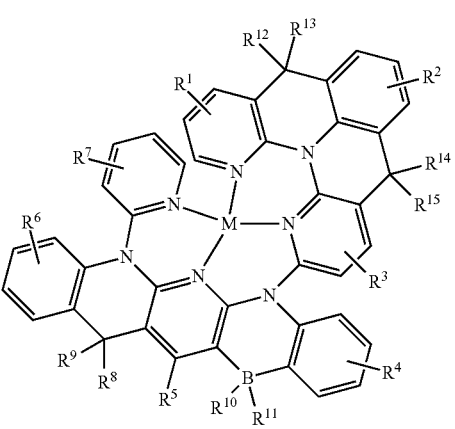
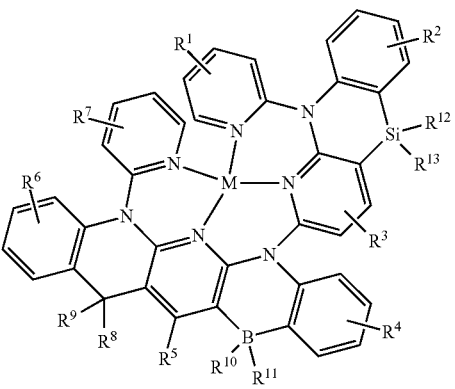
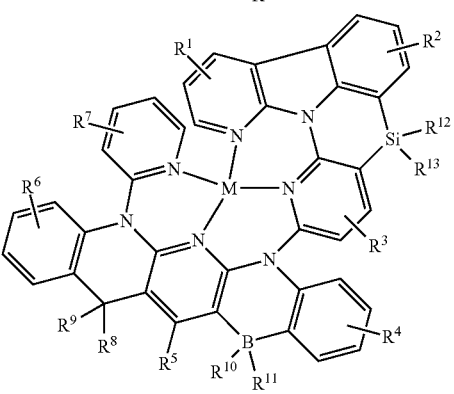

233
-continued
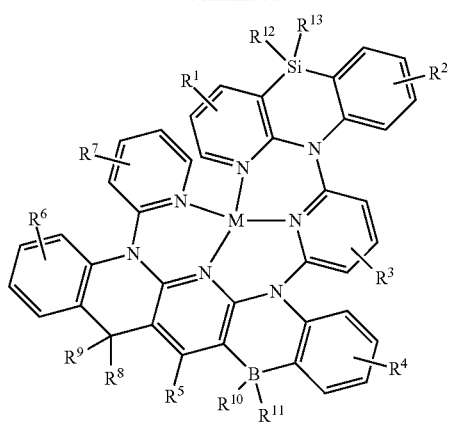
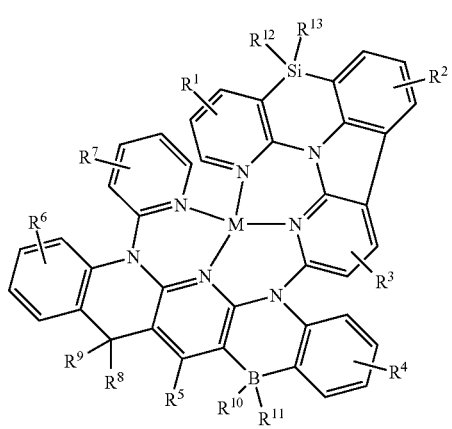
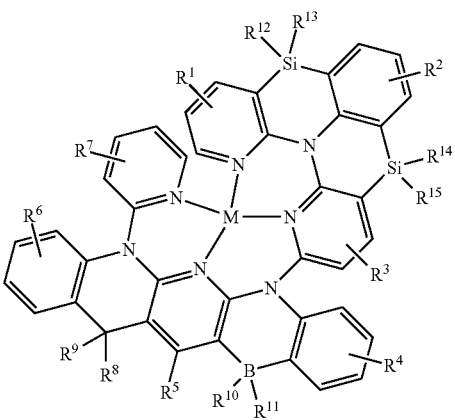
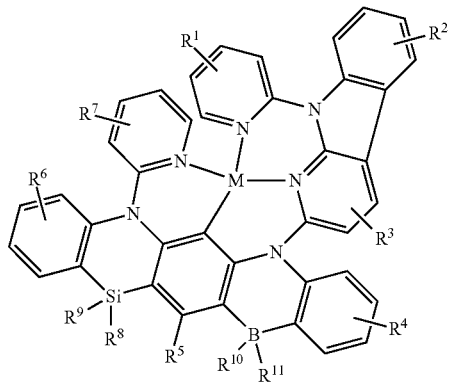
234
-continued
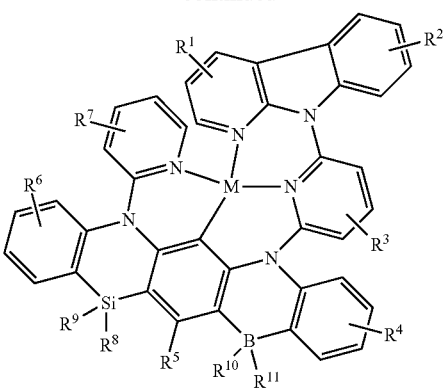
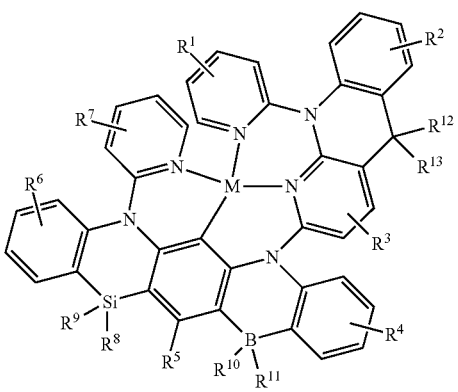
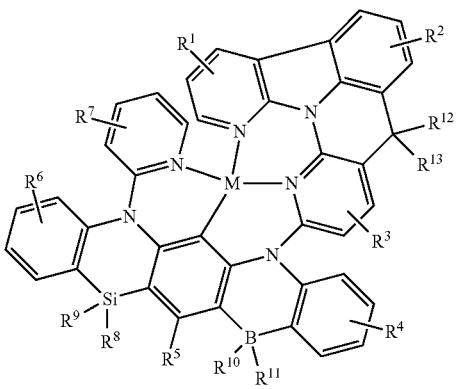
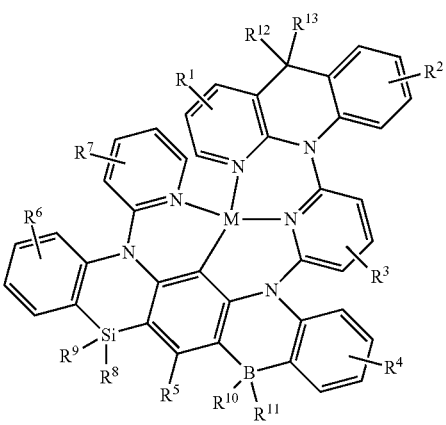

-continued
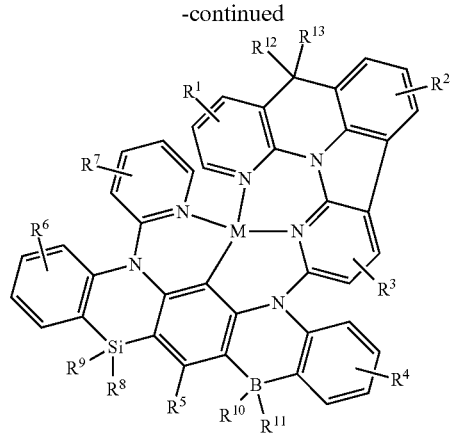
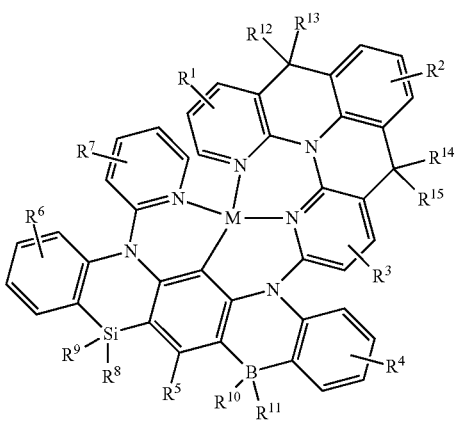
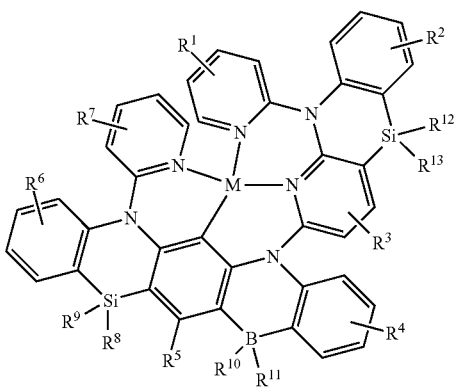
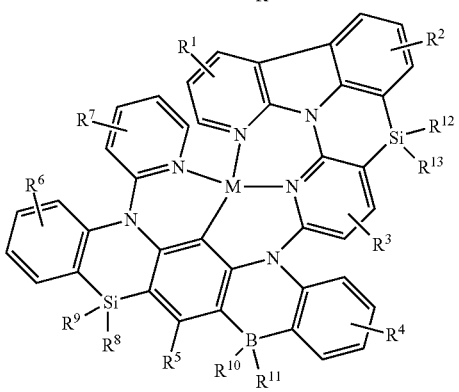
-continued
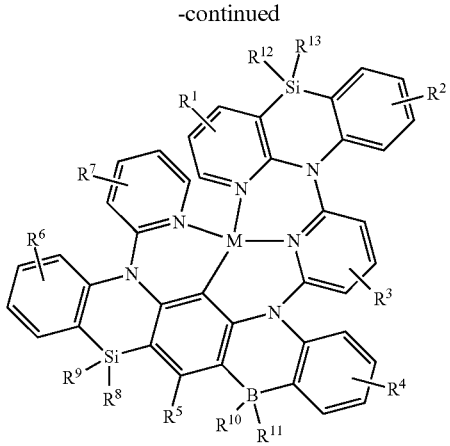
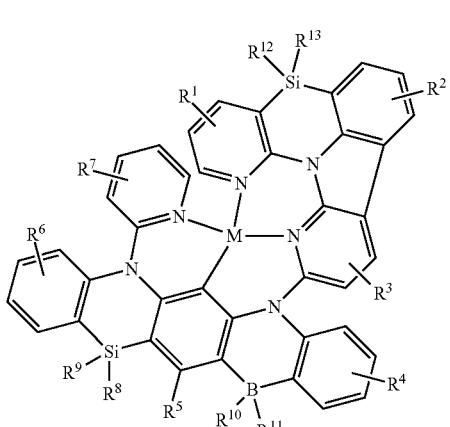
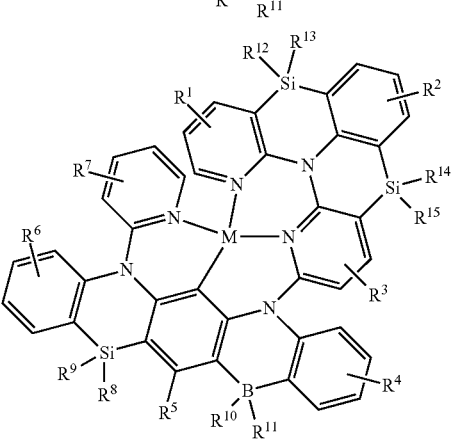
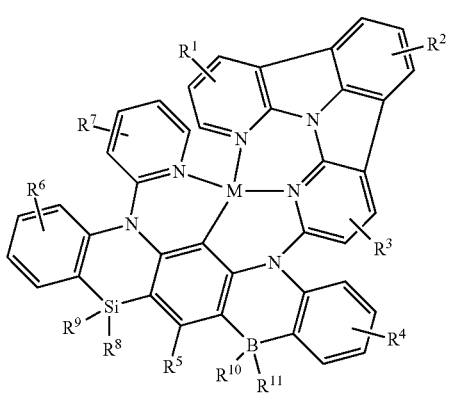

237
-continued
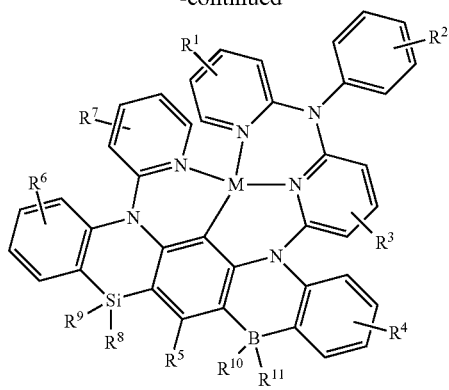
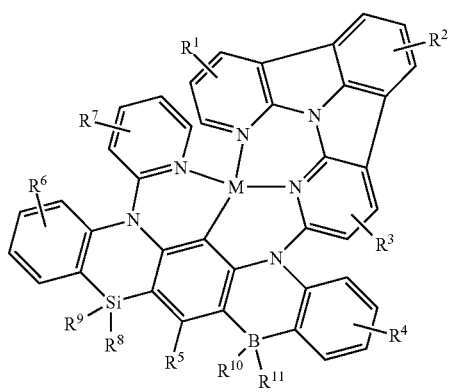
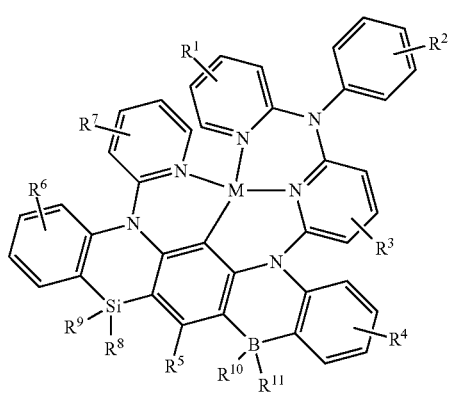
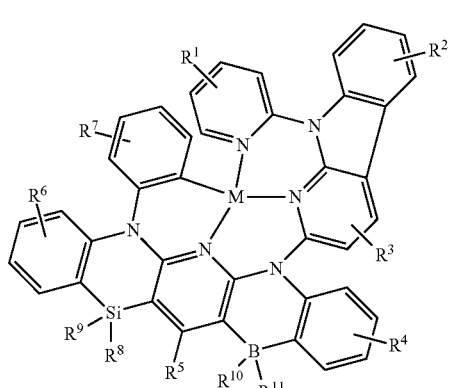
238
-continued
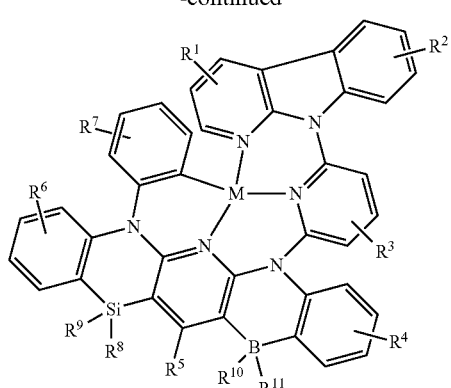
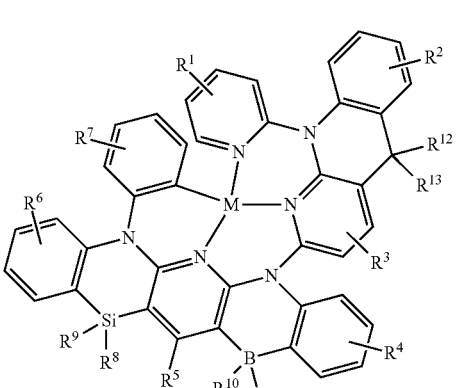
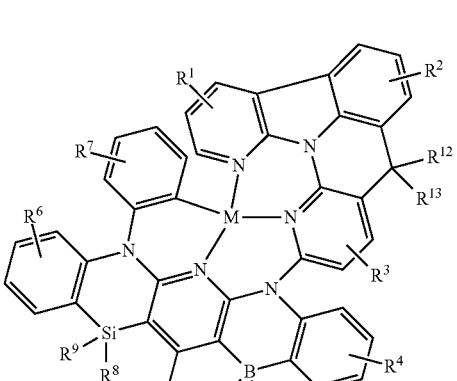
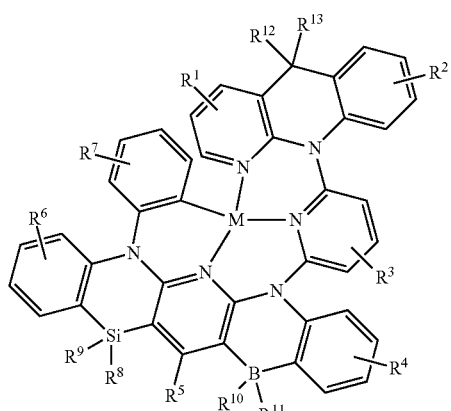

-continued
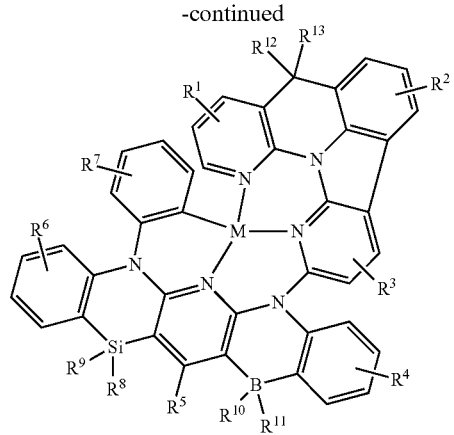
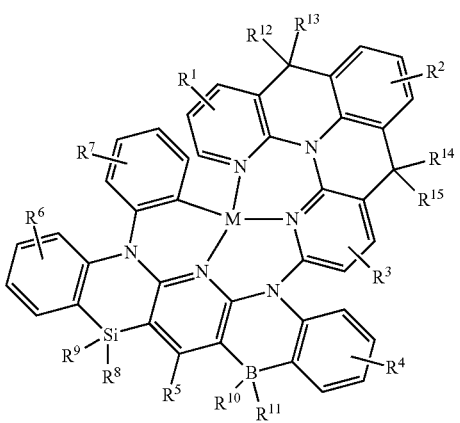
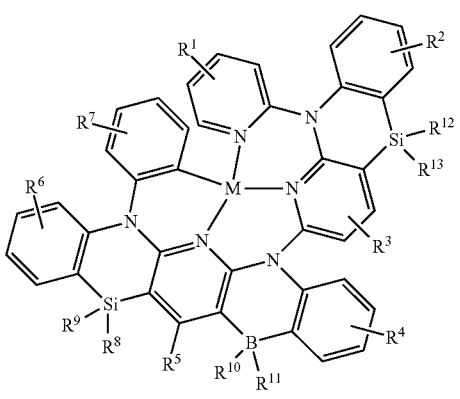
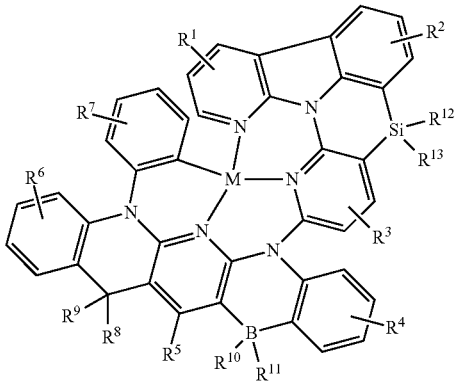
-continued
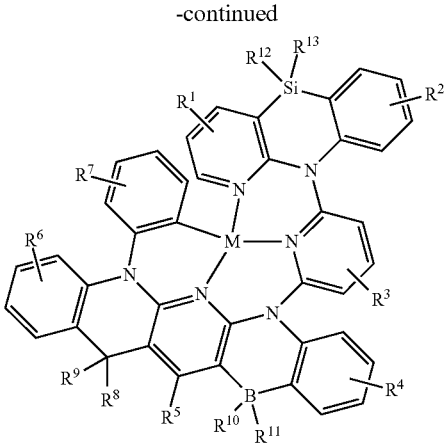
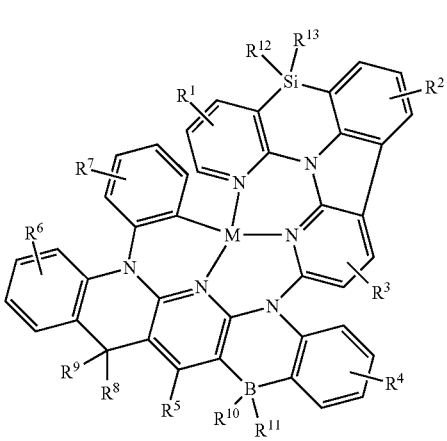
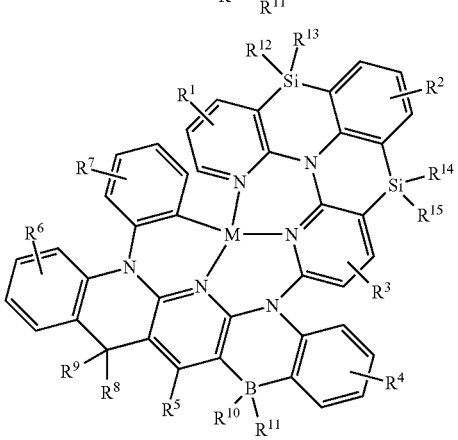
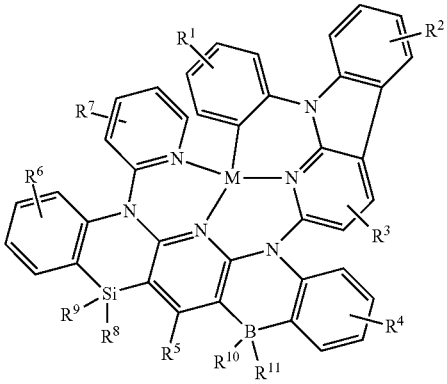

-continued
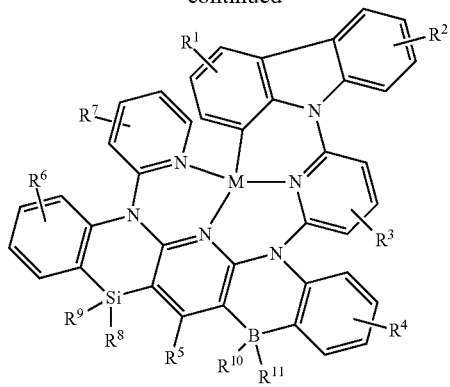
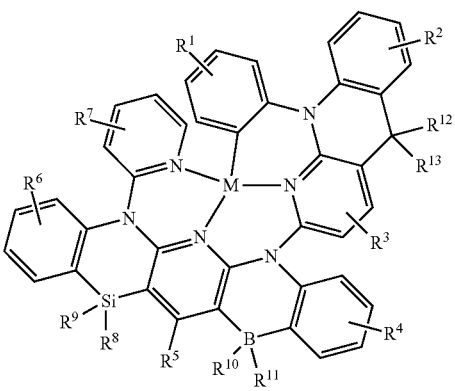
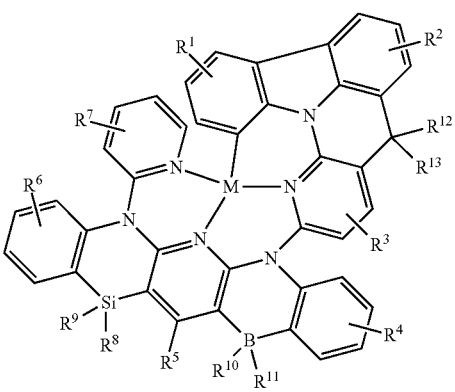
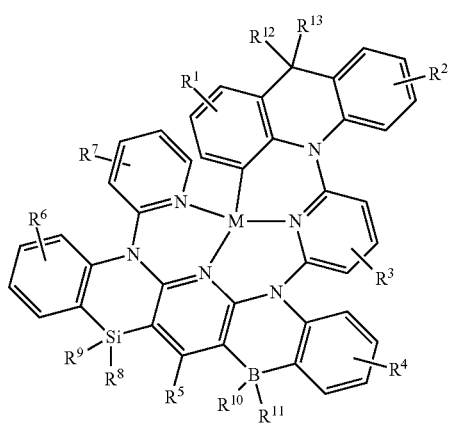
-continued
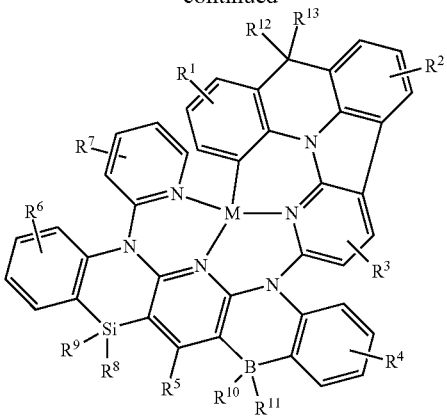
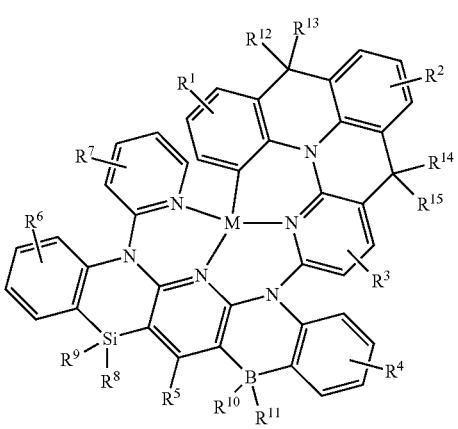
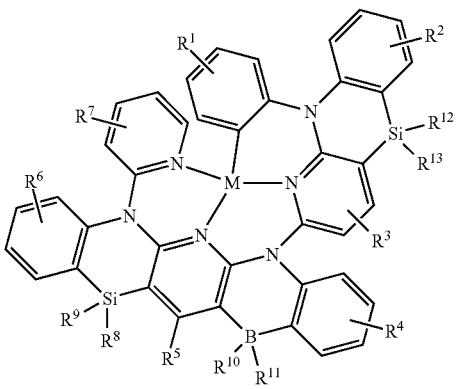
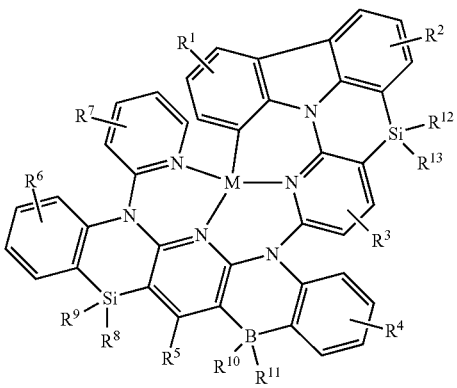

243
-continued
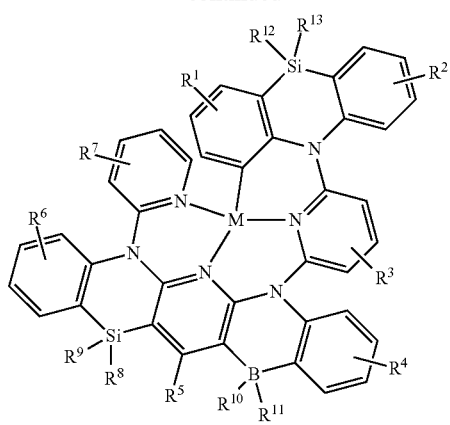
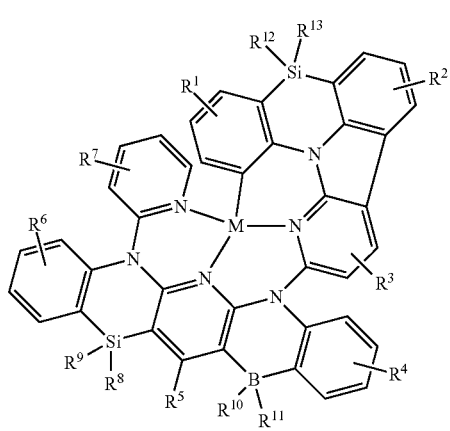
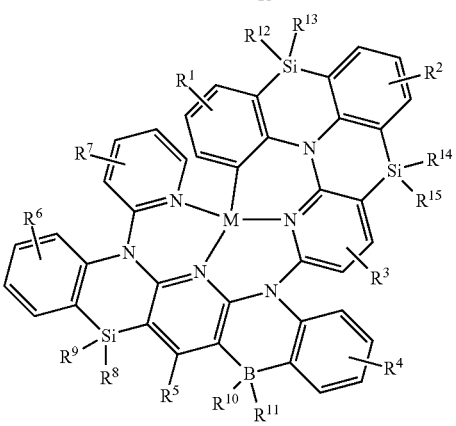
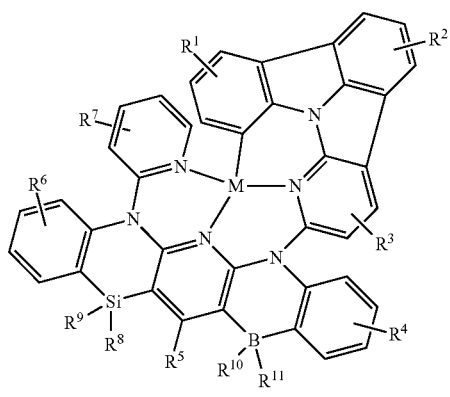
244
-continued
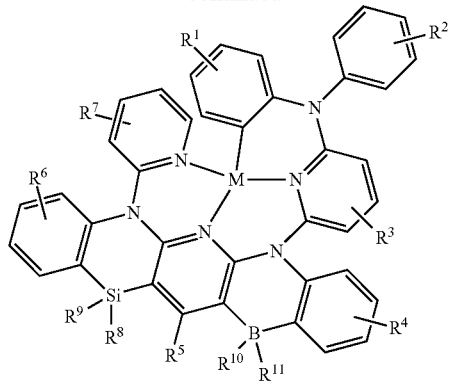
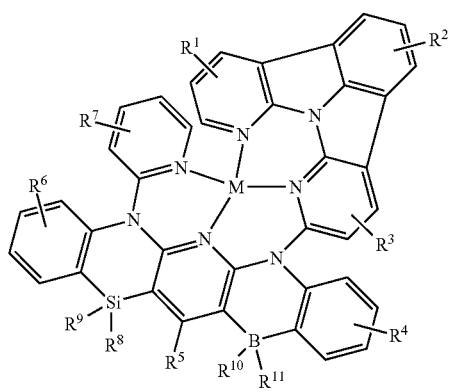
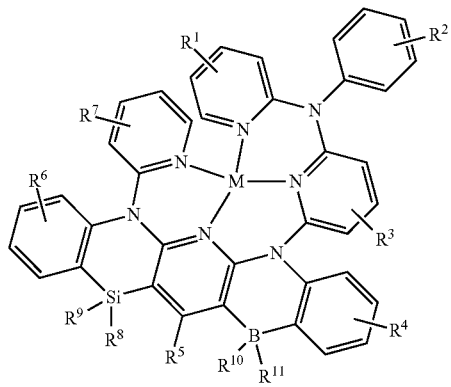
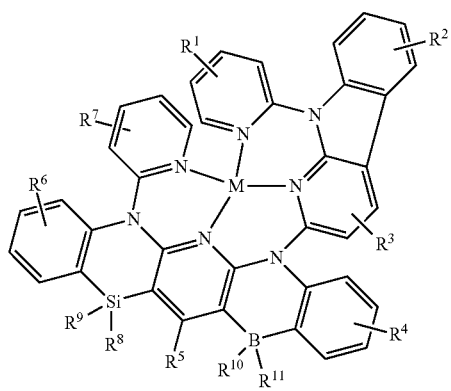

245
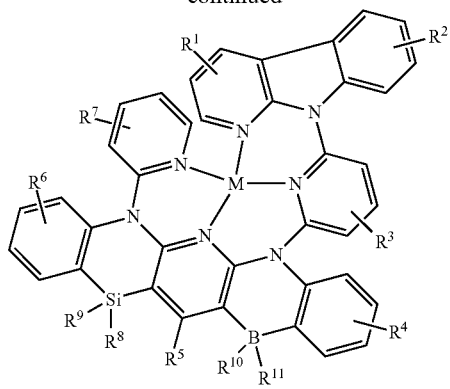
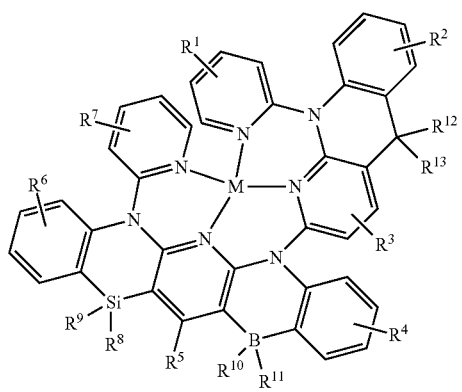
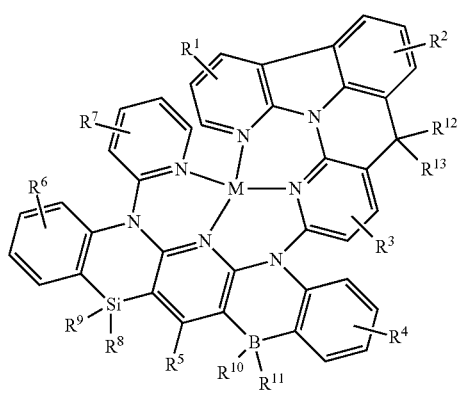
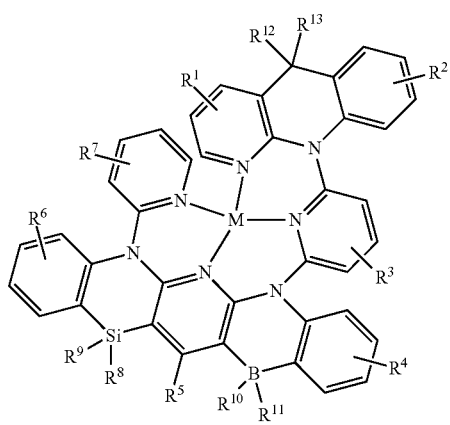
246
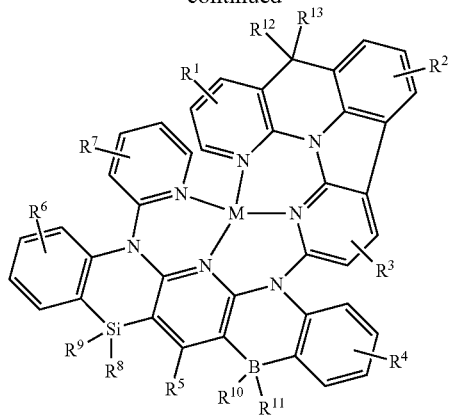
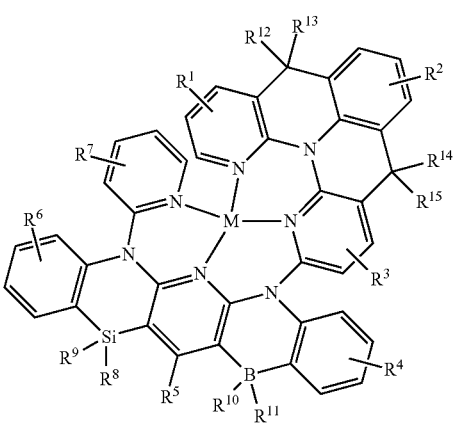
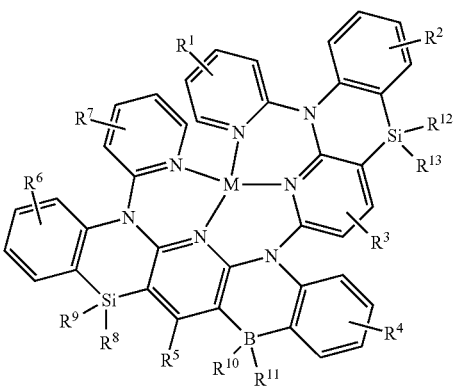
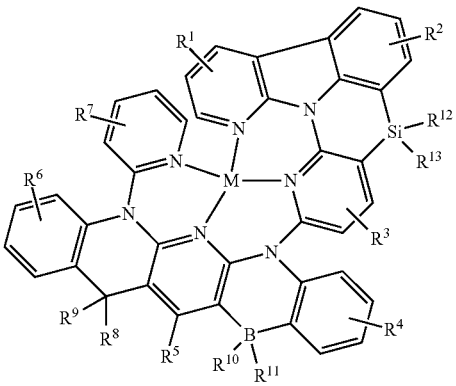

247
-continued
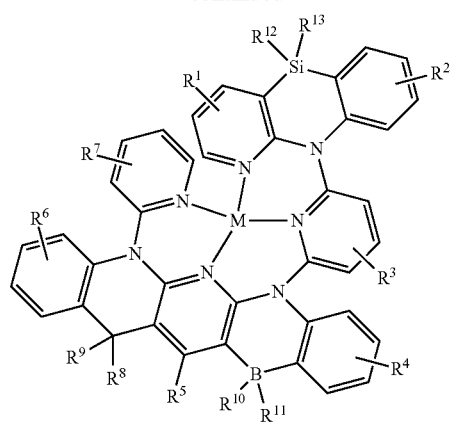
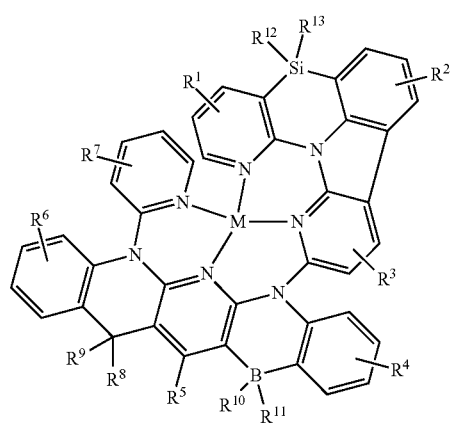
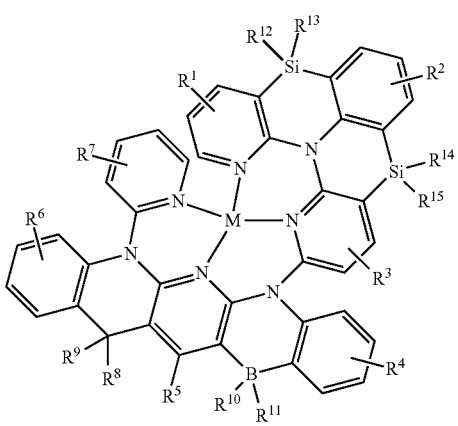
Further implementations of Formula I include the structures below, in which M=Au(III).
248
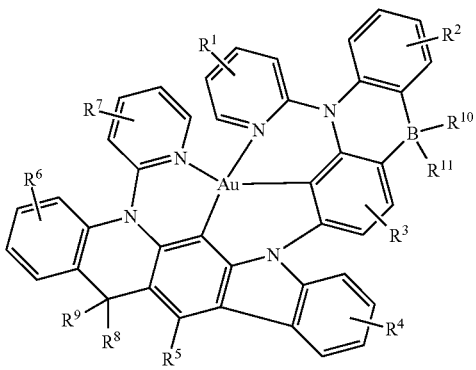
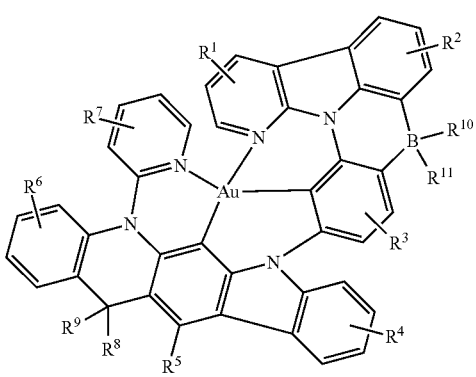
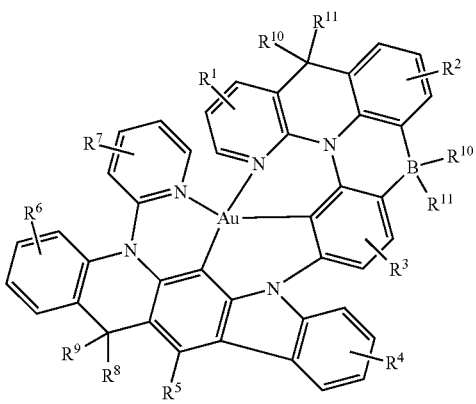
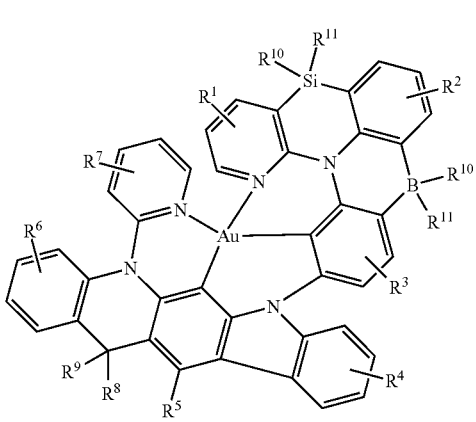

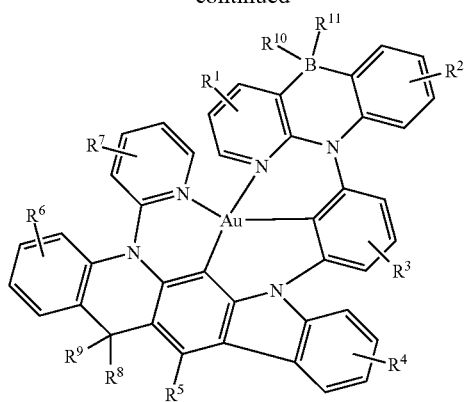
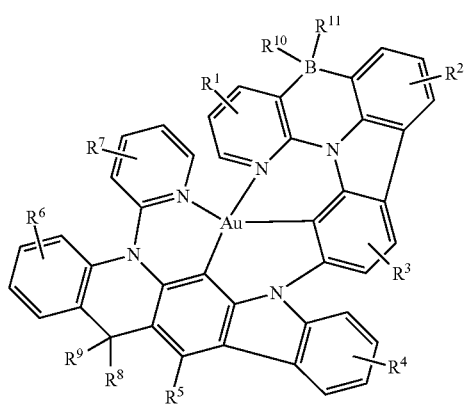
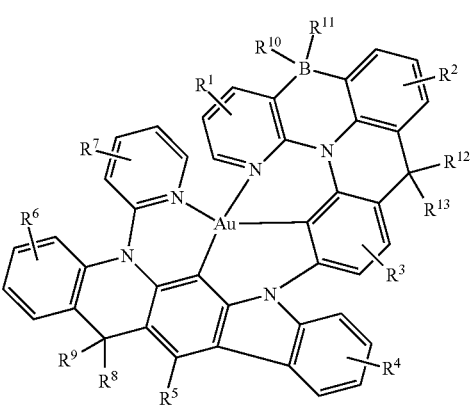
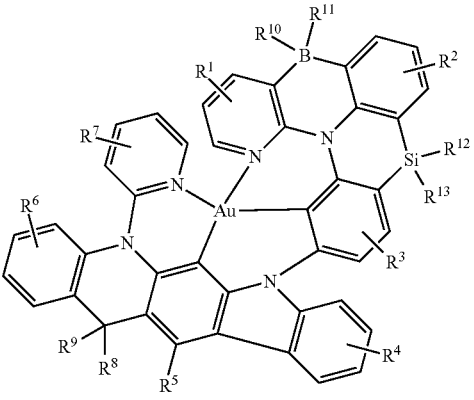
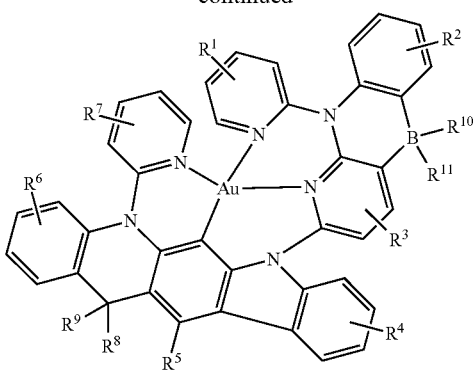
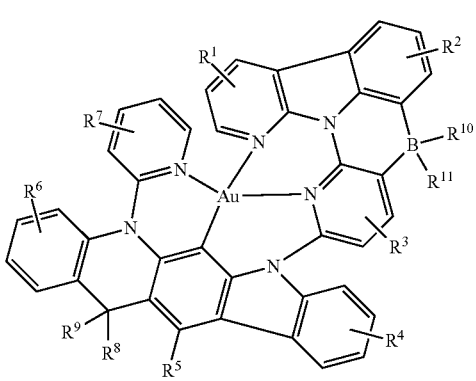
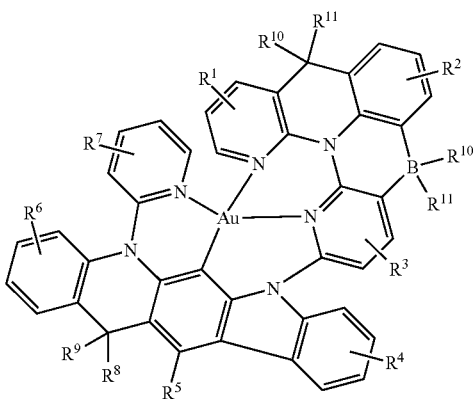
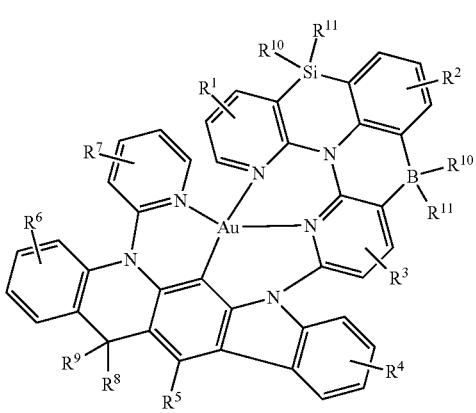

-continued
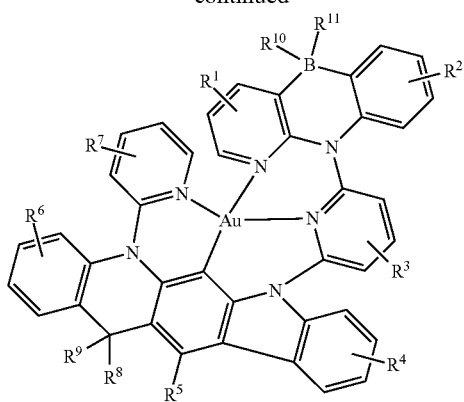
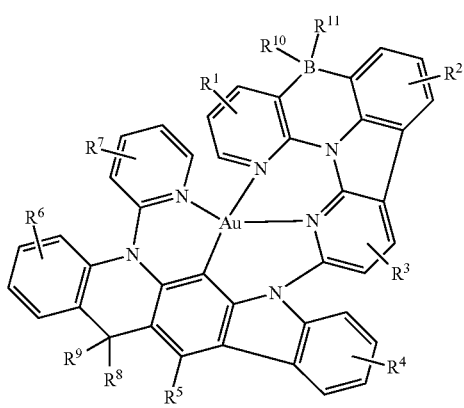
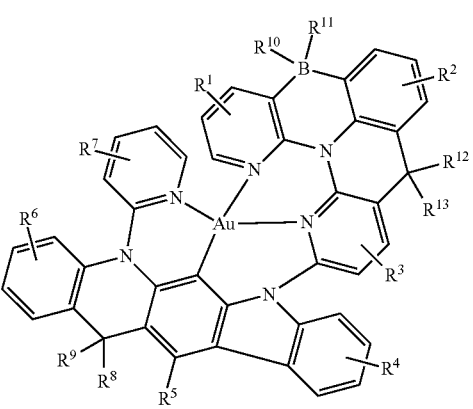
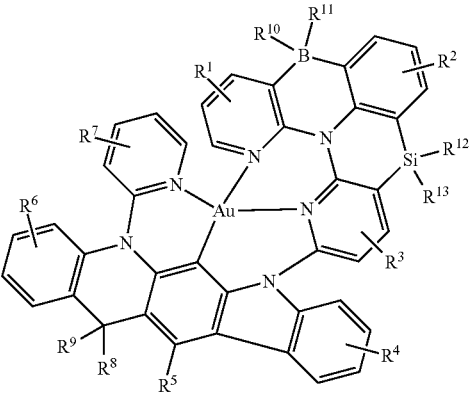
-continued
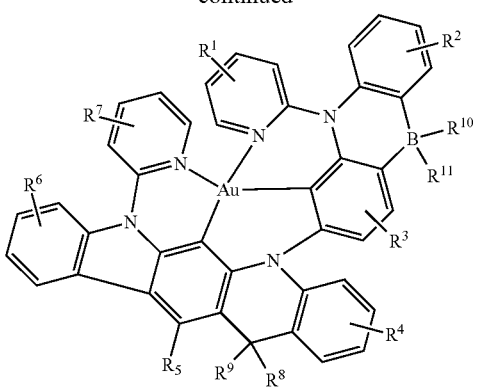
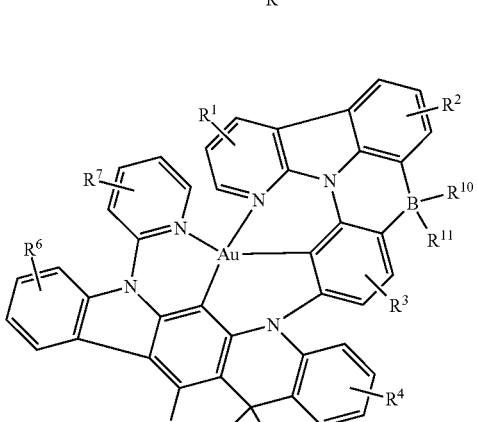
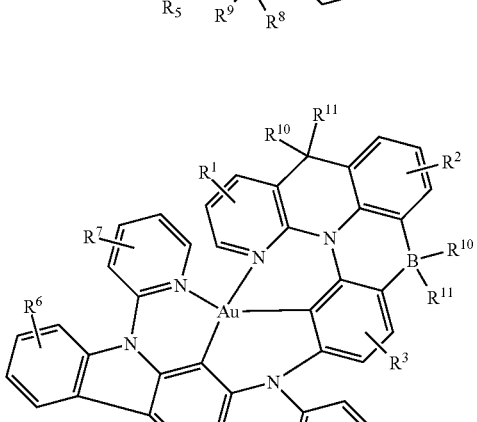
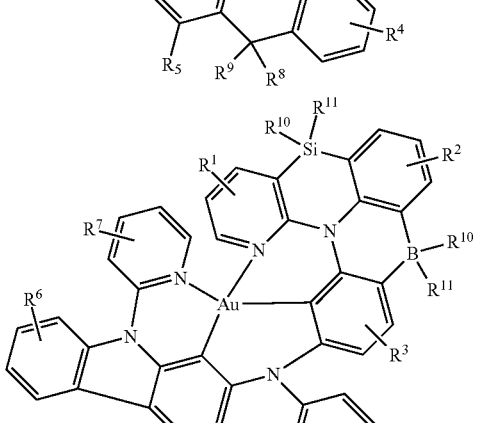

253
-continued
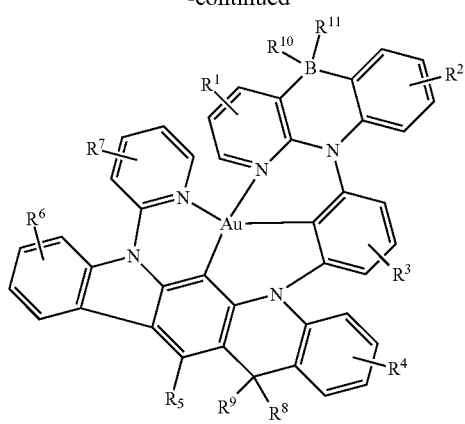
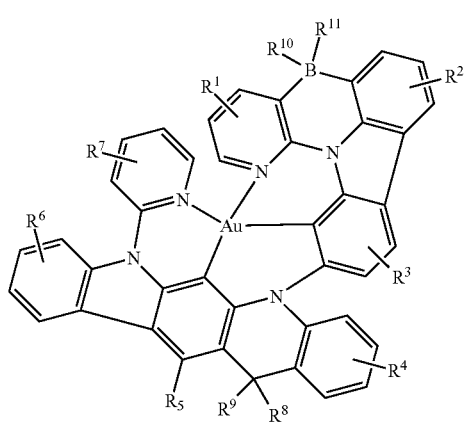
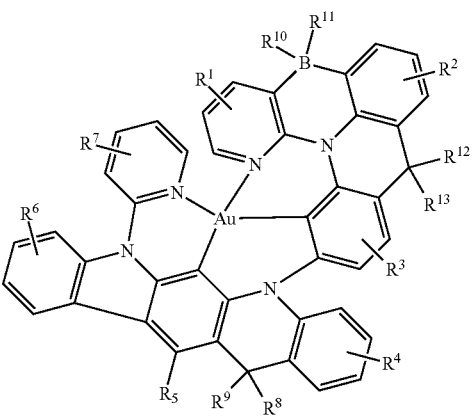
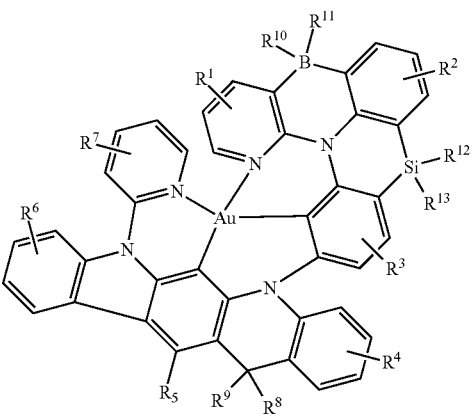
254
-continued
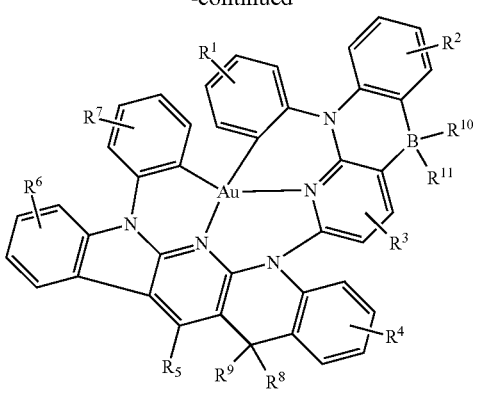
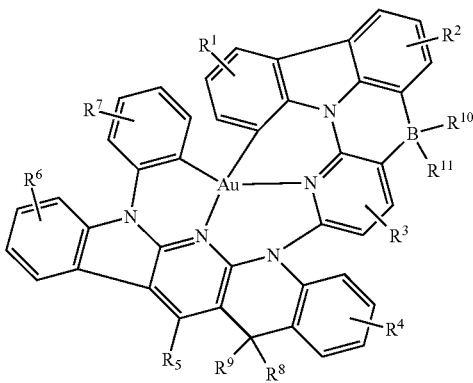
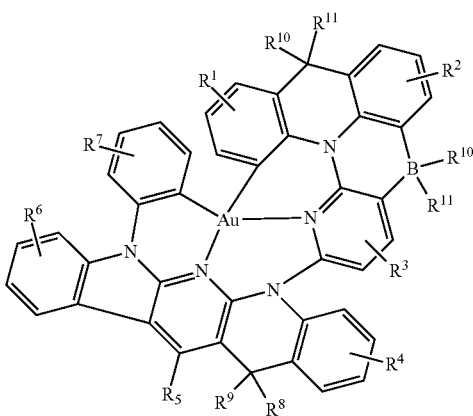
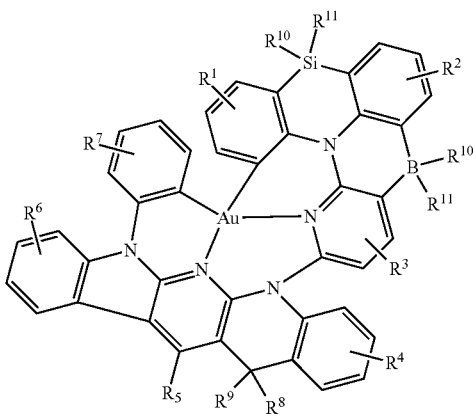

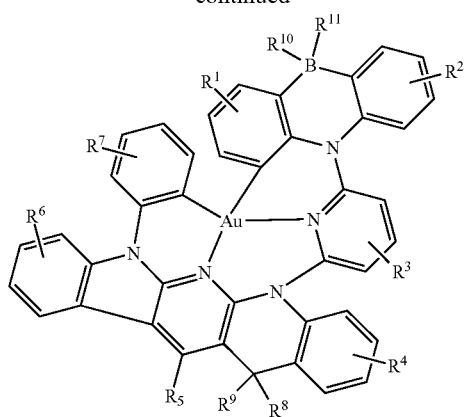
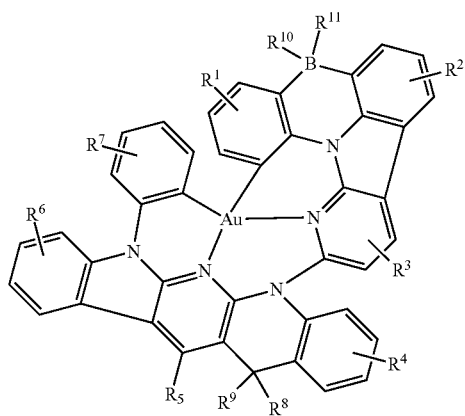
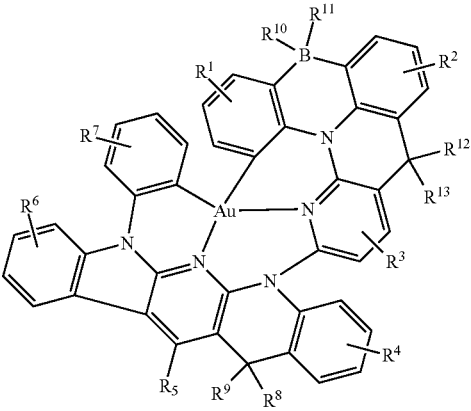
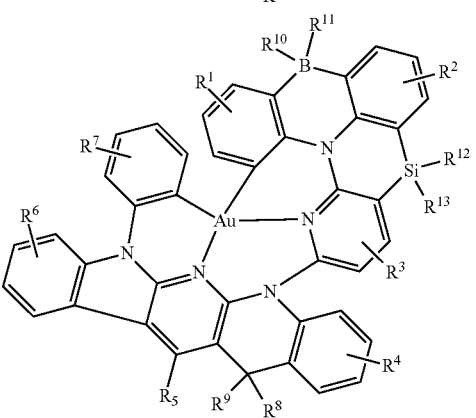
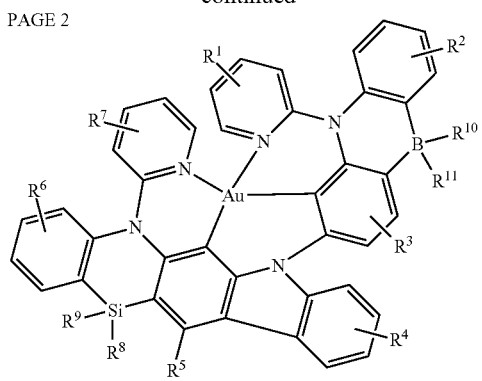
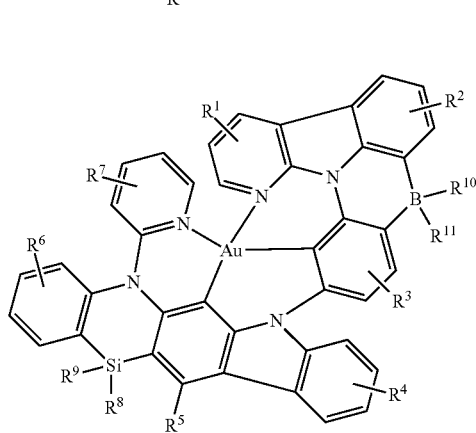
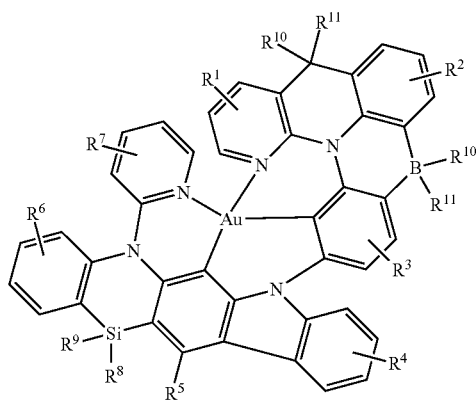
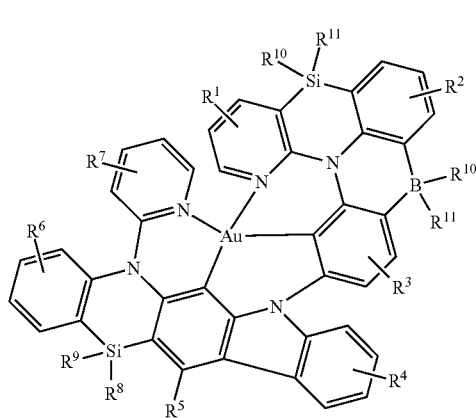

257
-continued
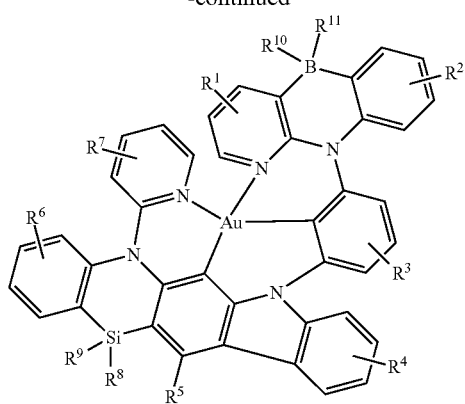
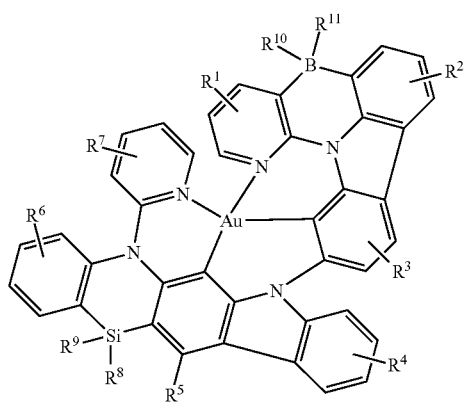
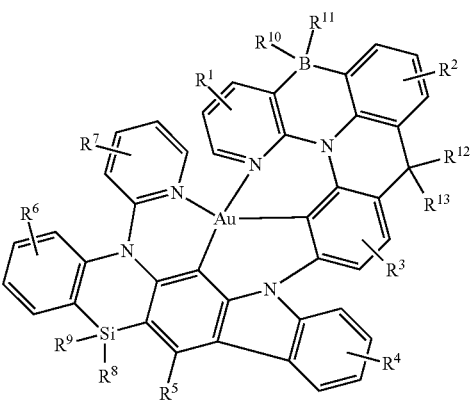
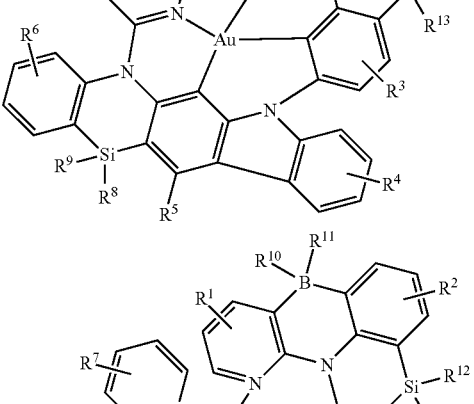
258
-continued
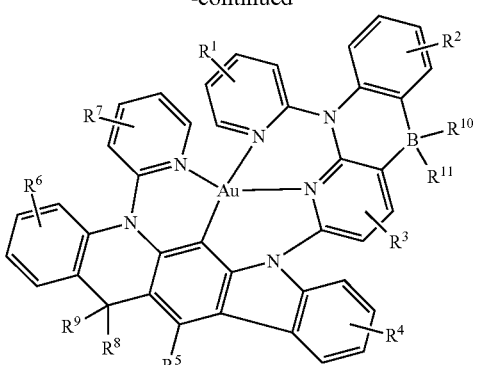
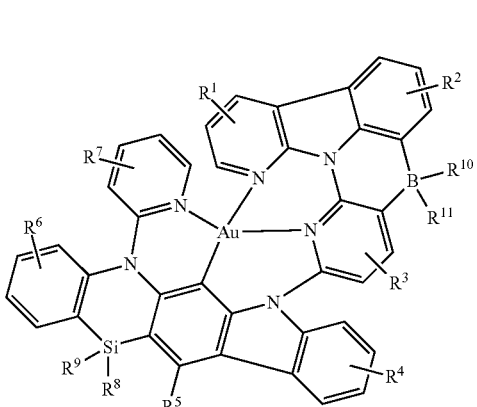
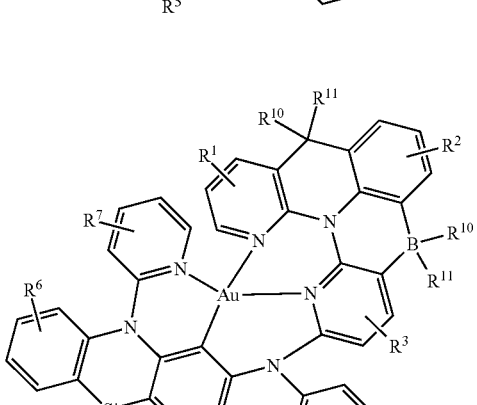
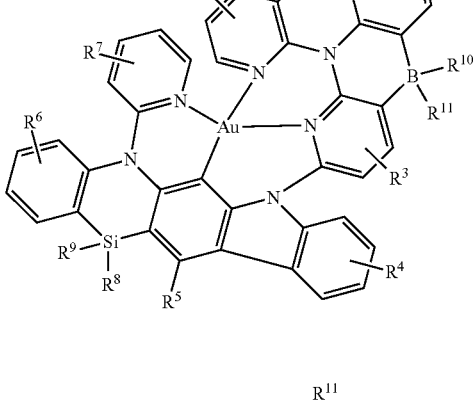
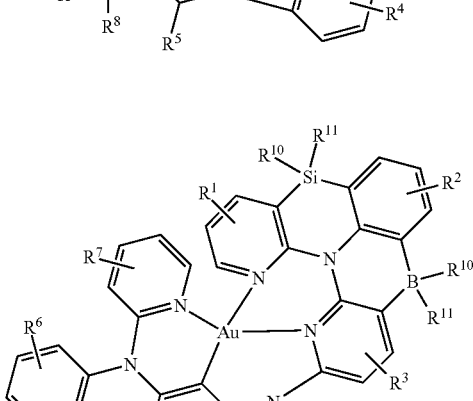
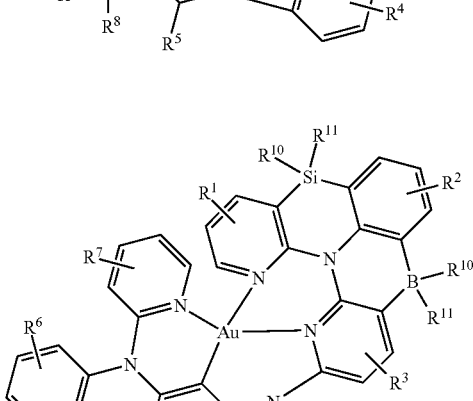

259
-continued
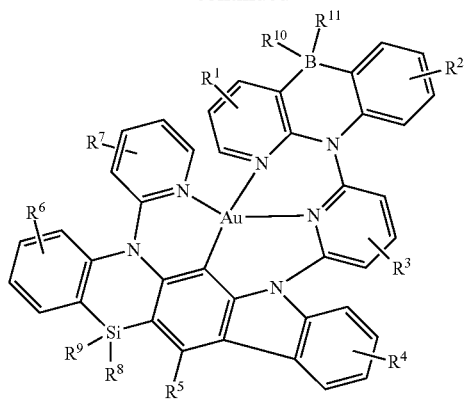
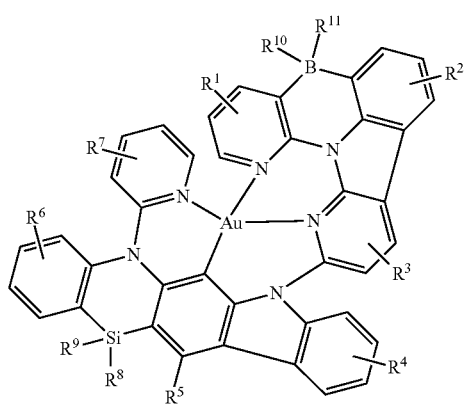
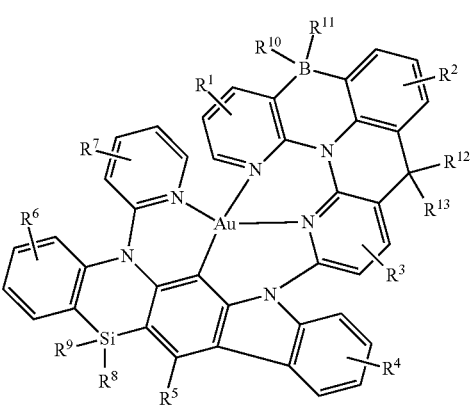
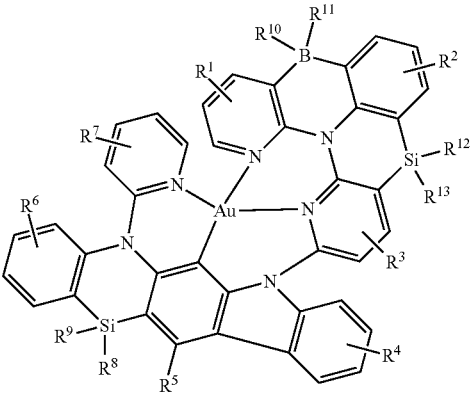
260
-continued
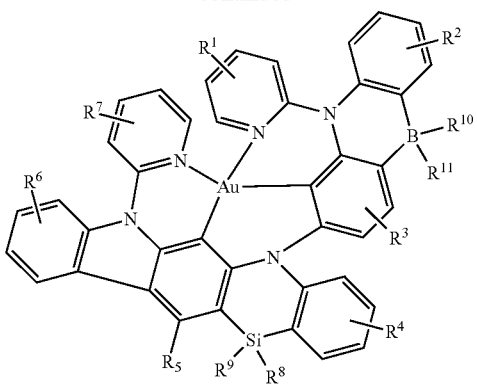
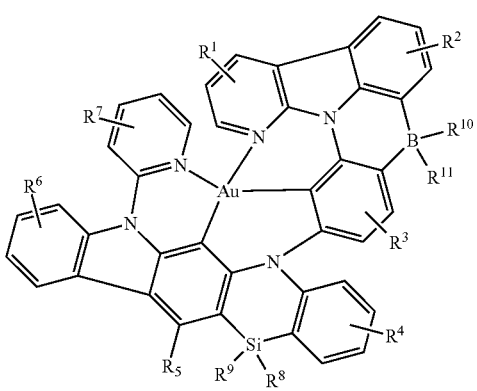
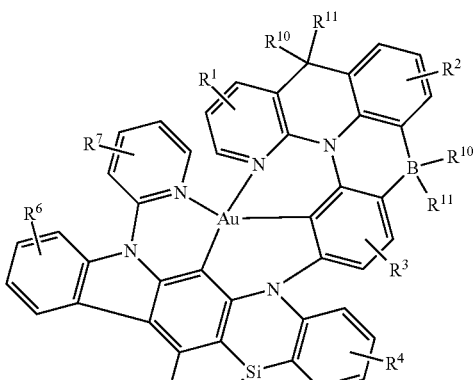
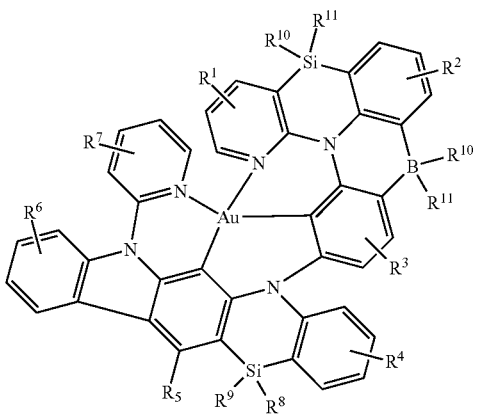

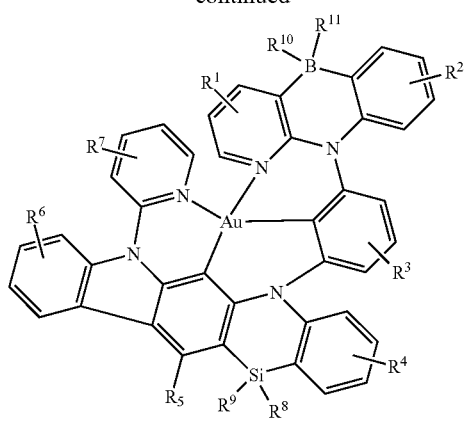
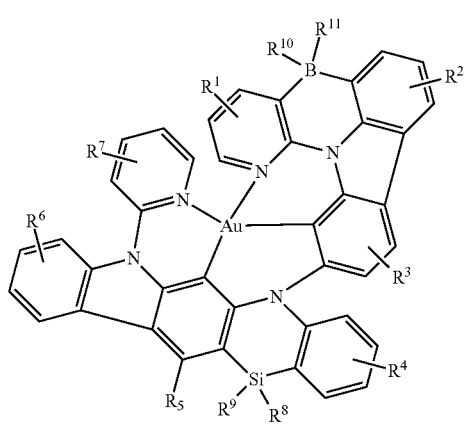
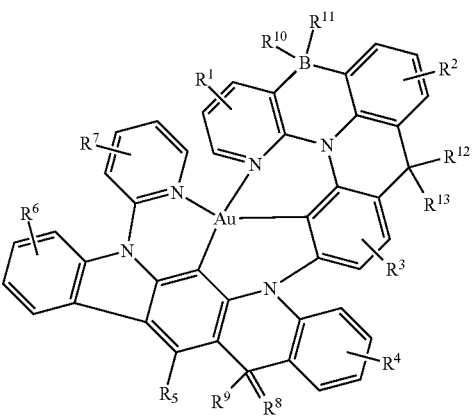
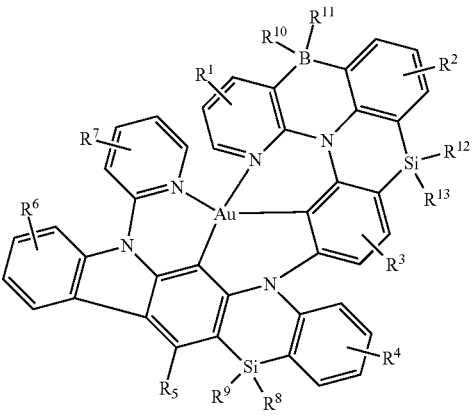
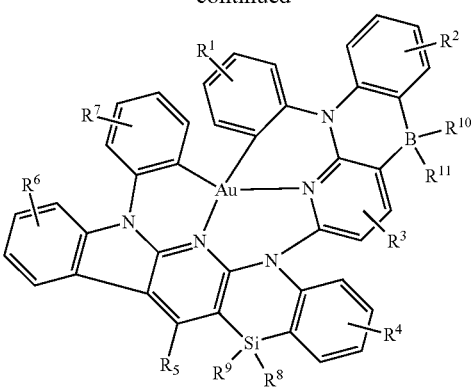
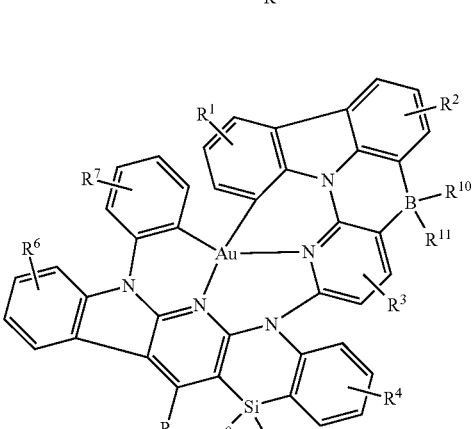
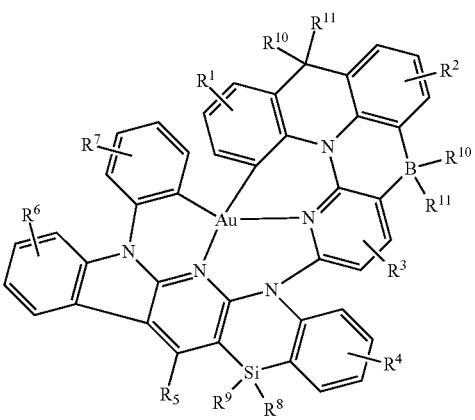
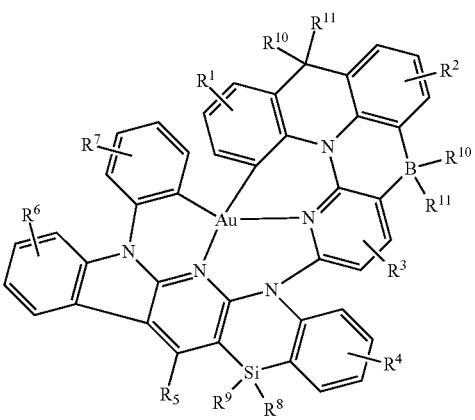

263
-continued
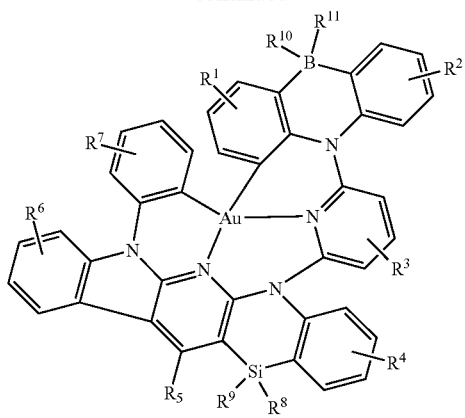
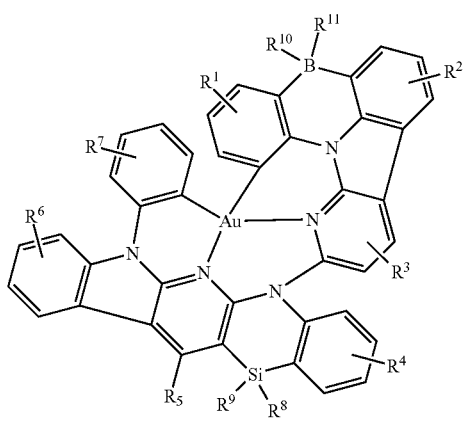
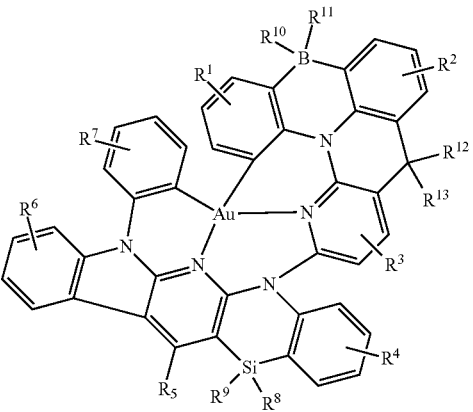
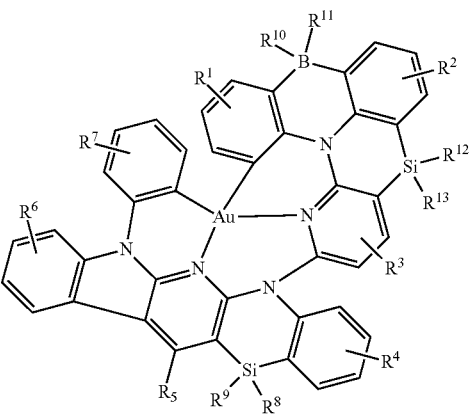
264
-continued
PAGE 3
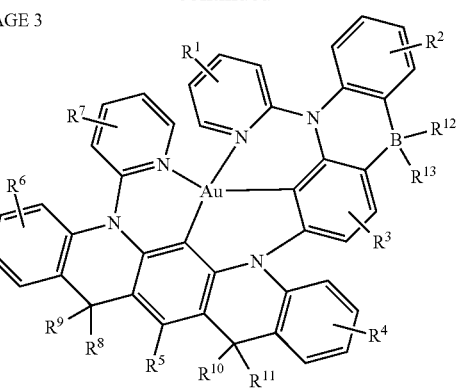
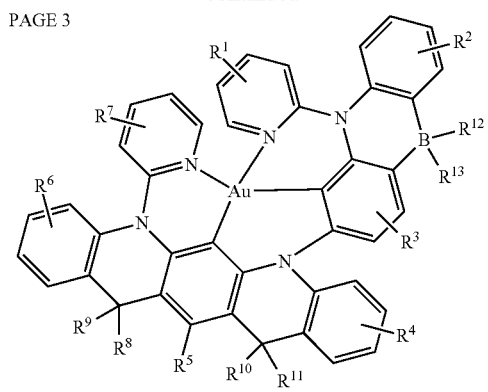
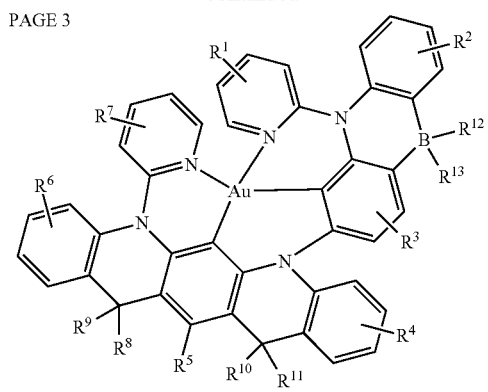
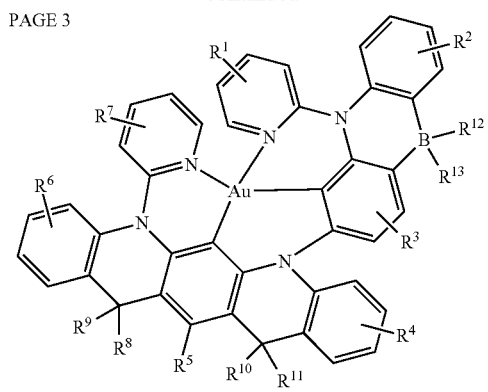

265
-continued
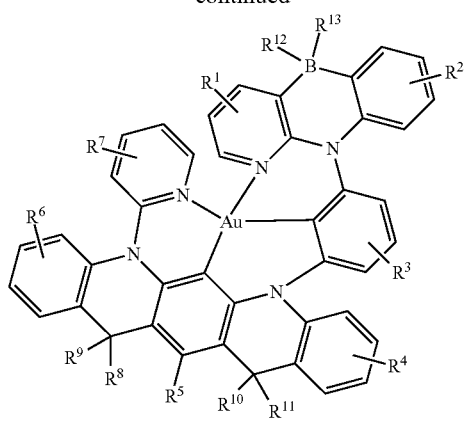
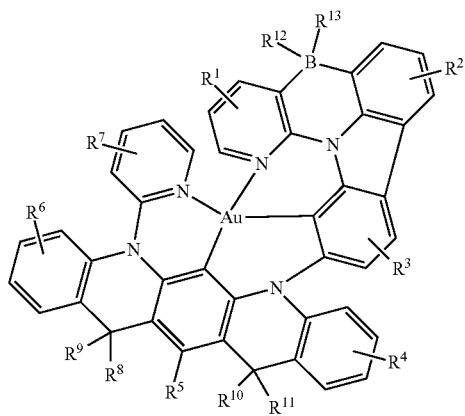
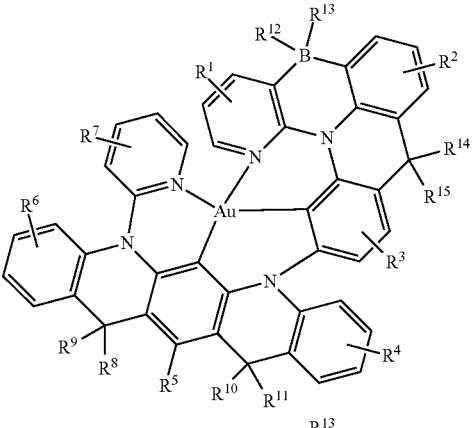
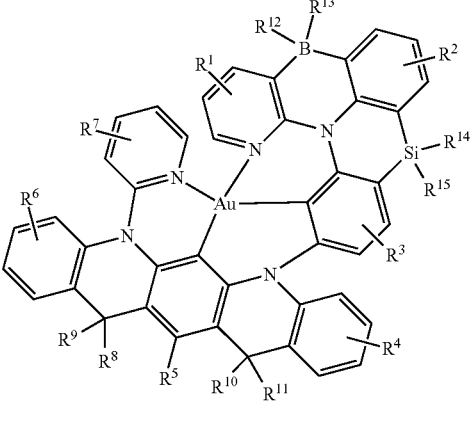
266
-continued
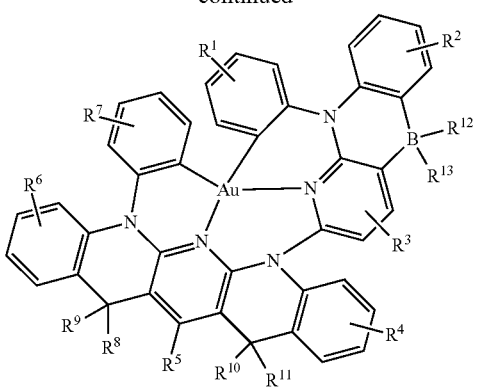
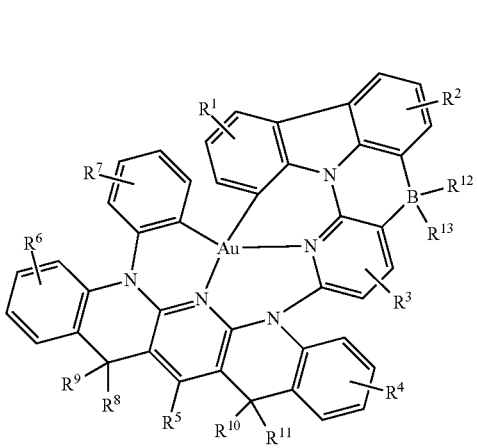
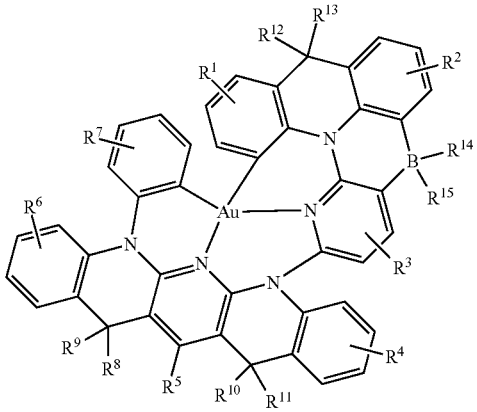
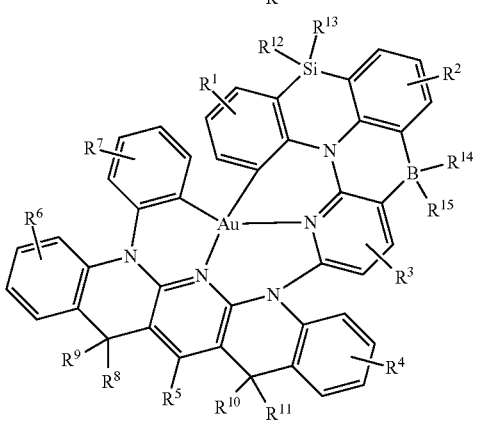

267
-continued
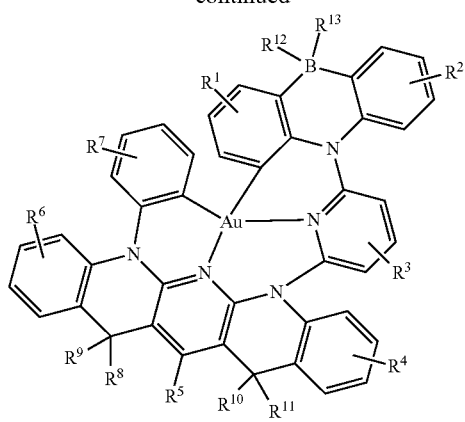
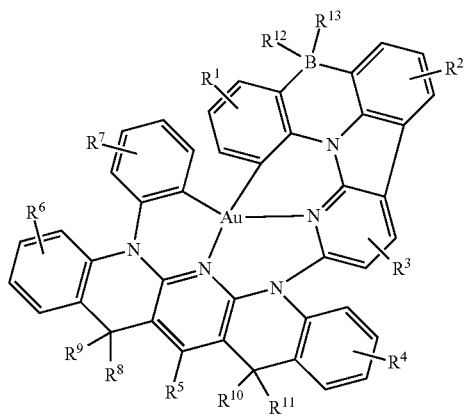
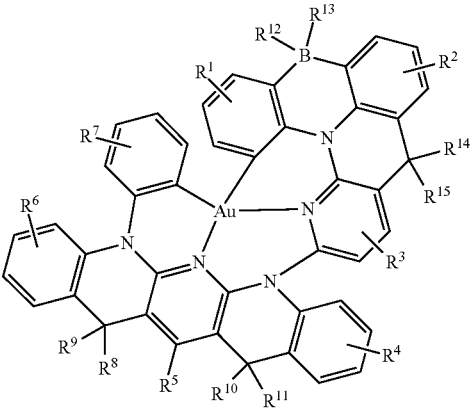
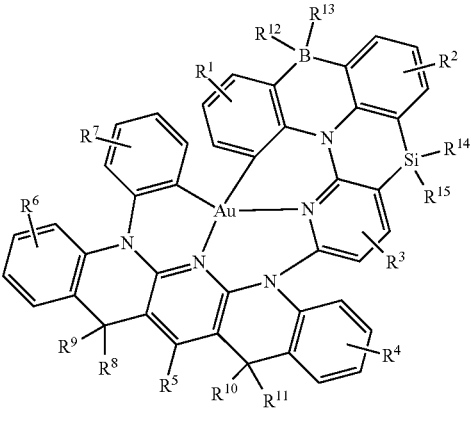
268
-continued
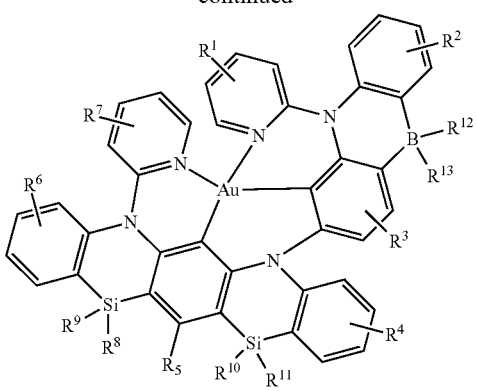
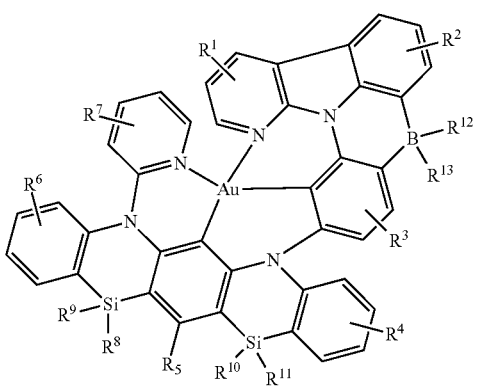
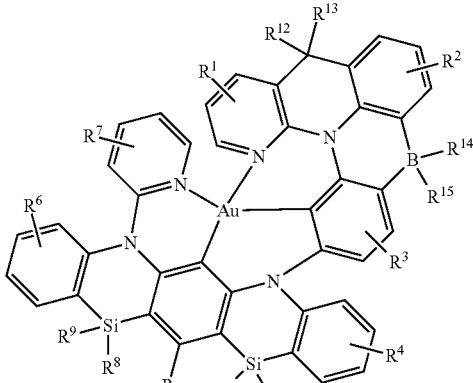
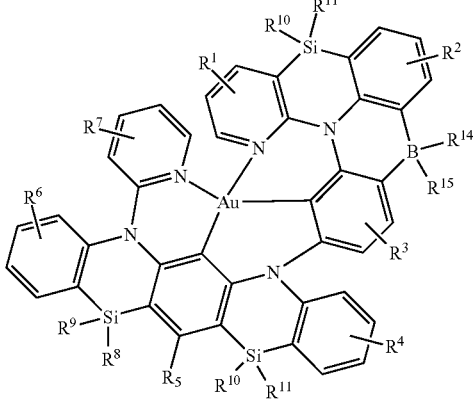

-continued
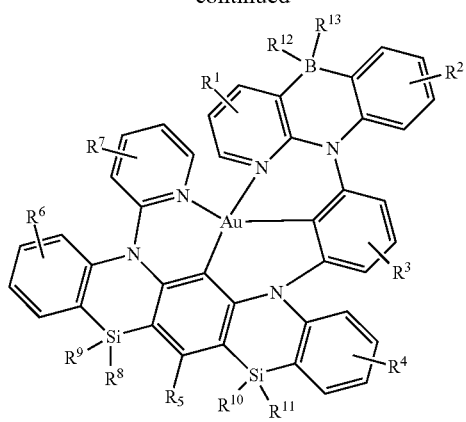
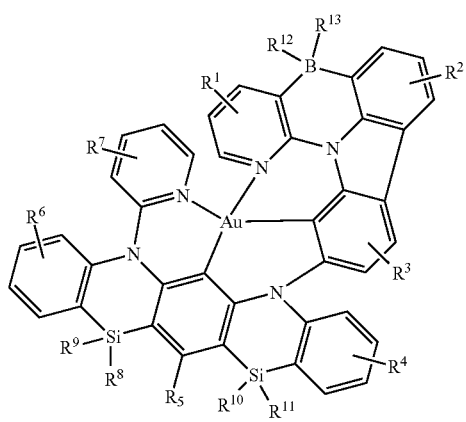
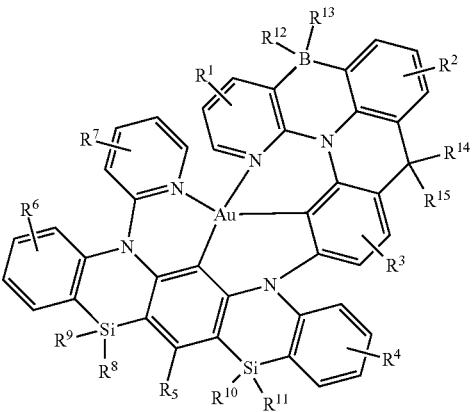
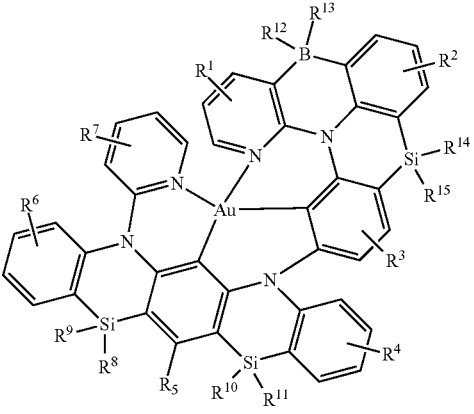
-continued
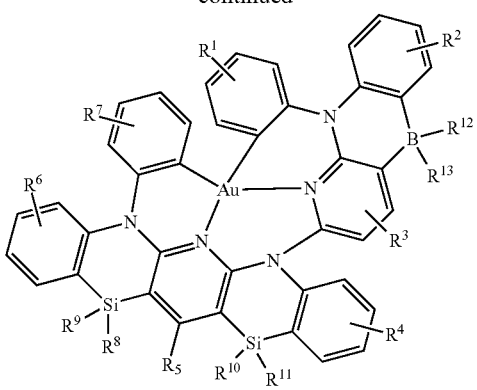
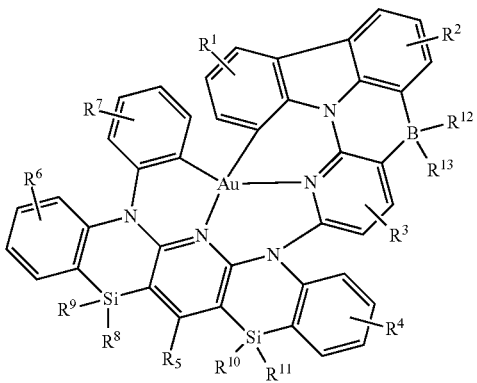
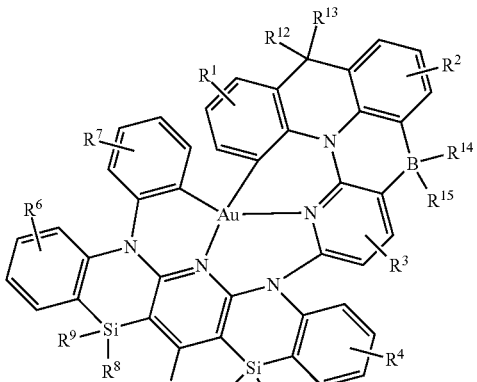
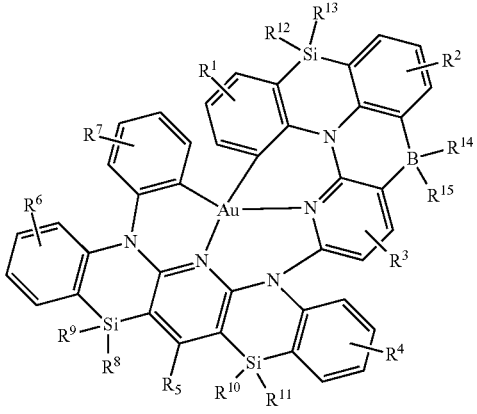

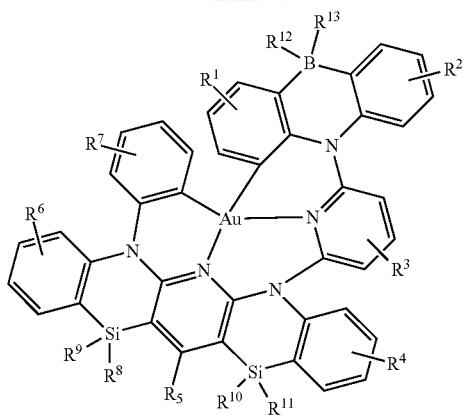
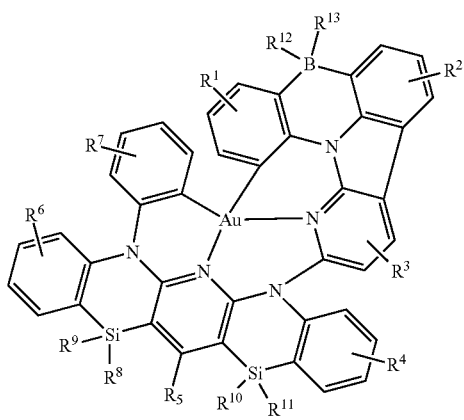
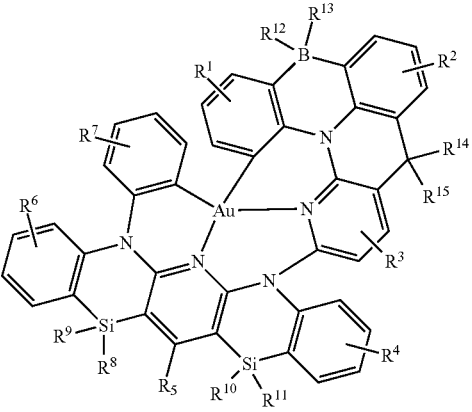
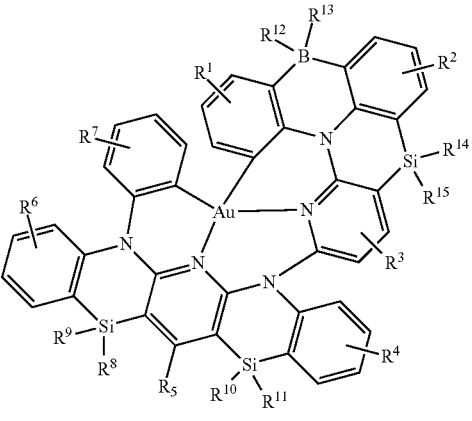
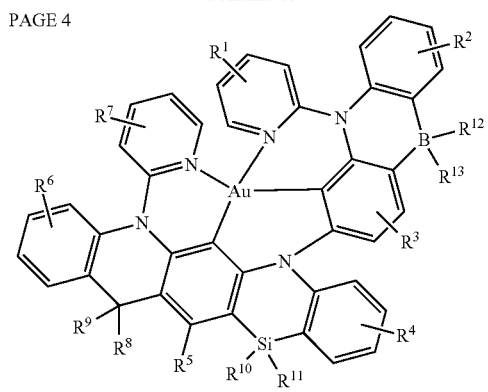
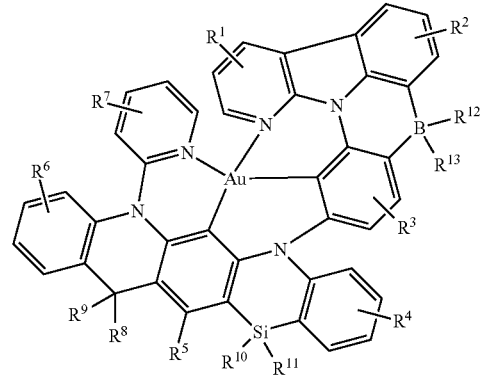
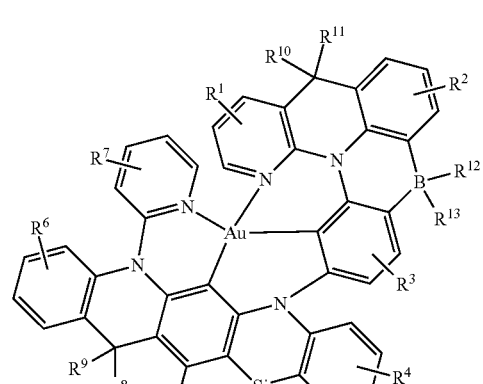
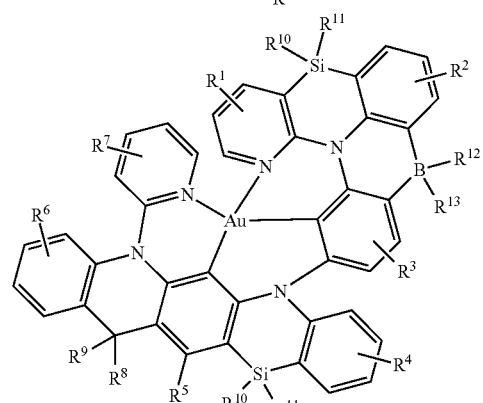

273
-continued
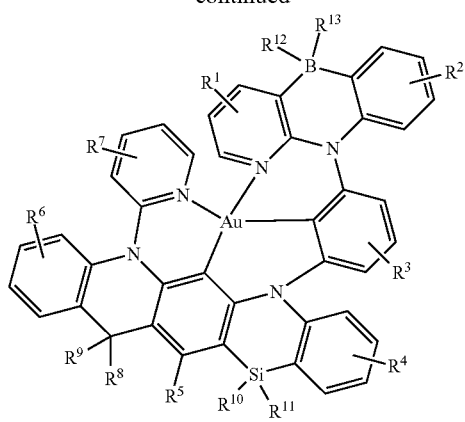
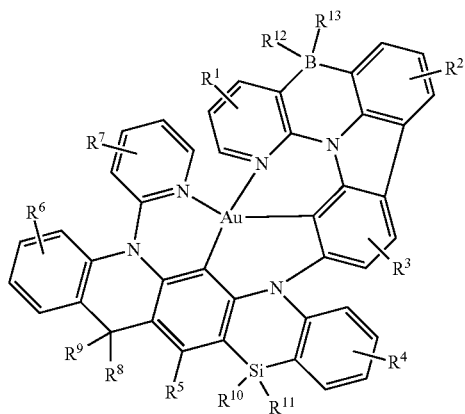
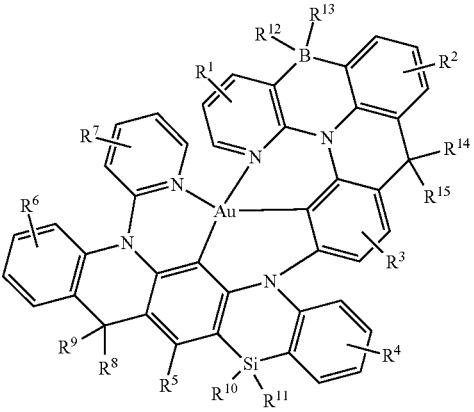
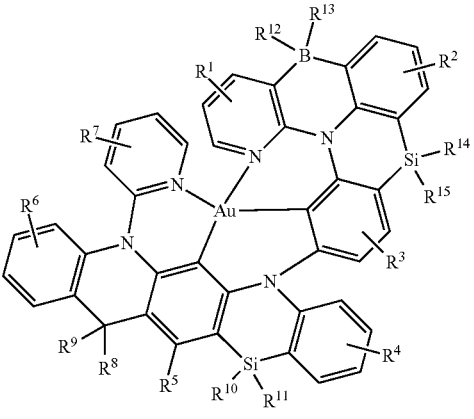
274
-continued
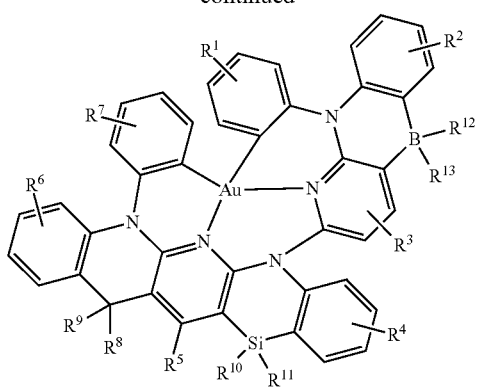
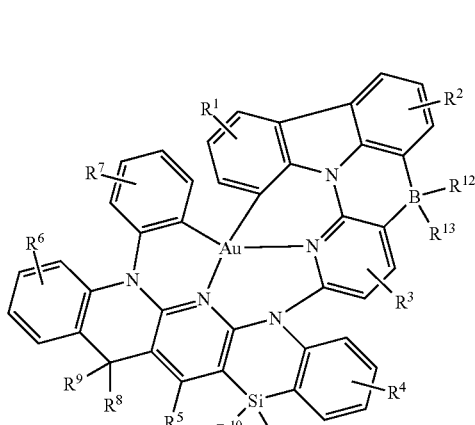
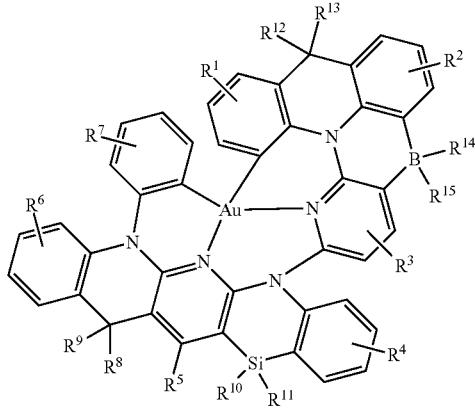
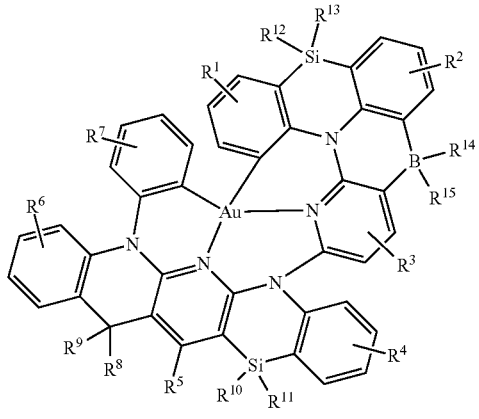

275
-continued
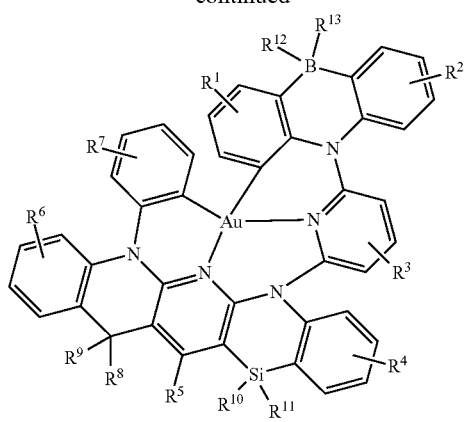
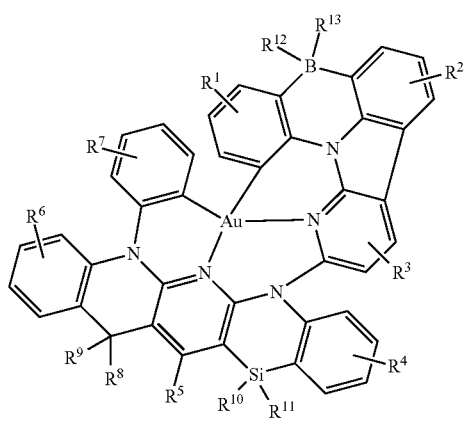
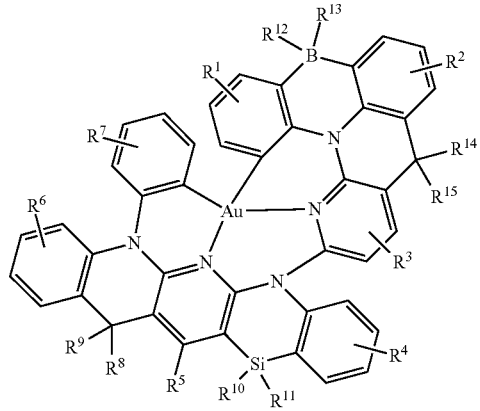
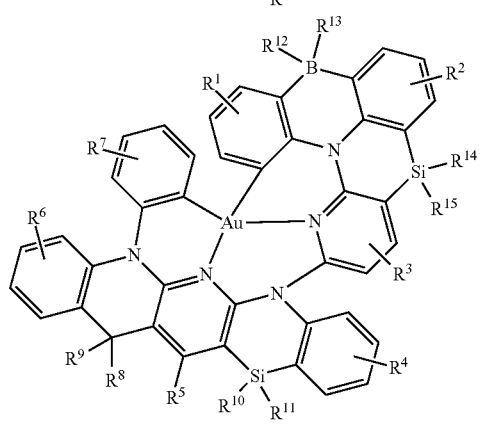
276
-continued
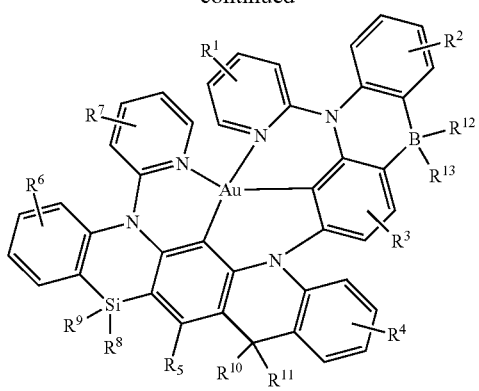
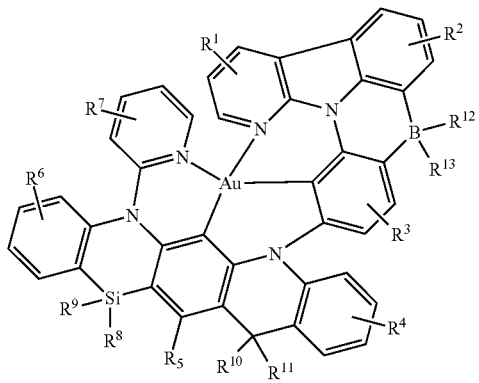
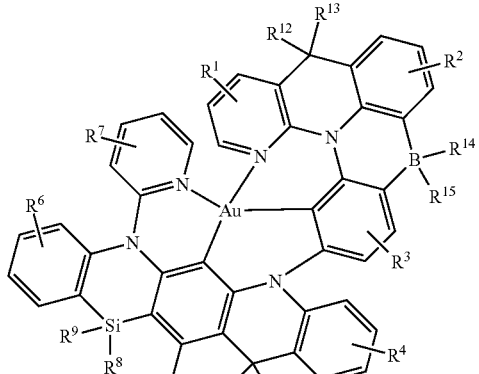
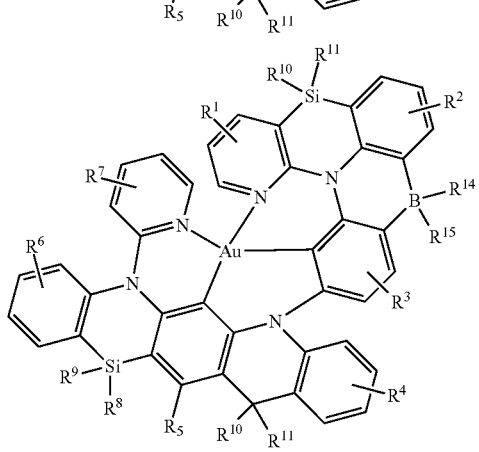

277
-continued

278
-continued

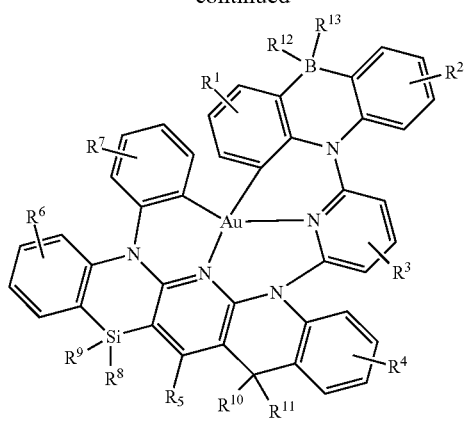
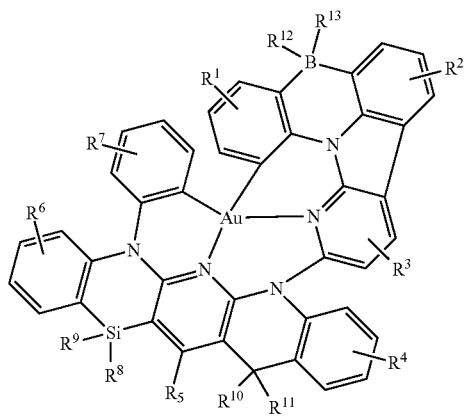
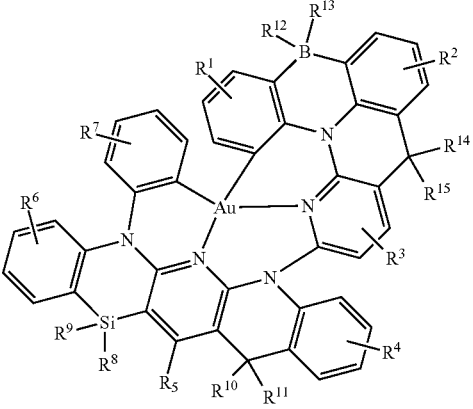
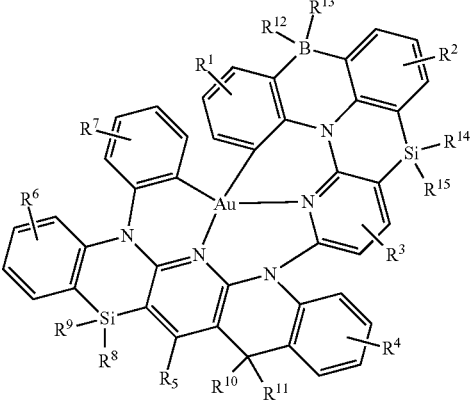
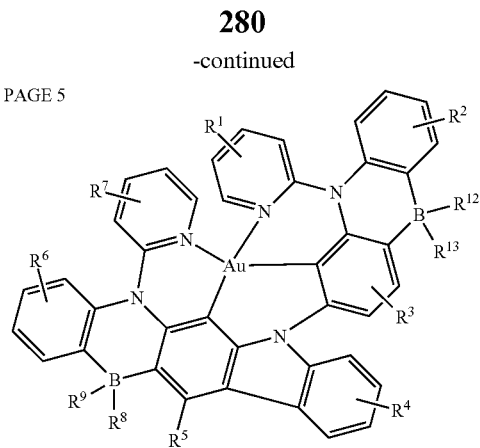
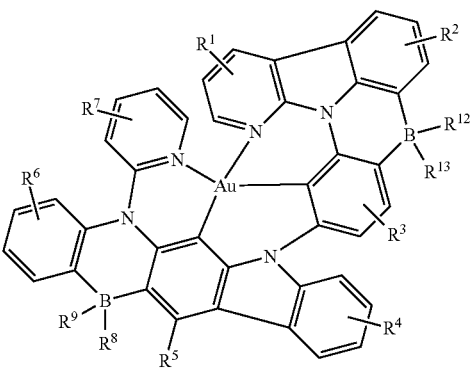
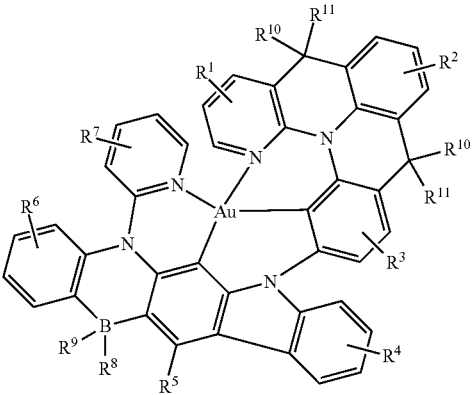
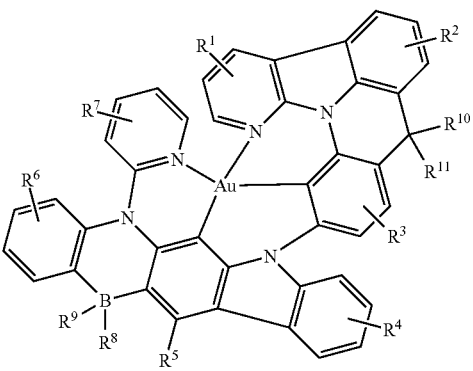

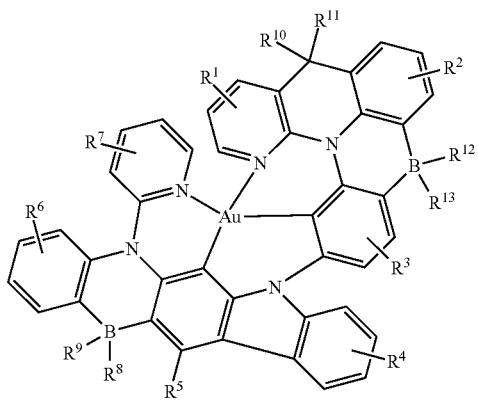
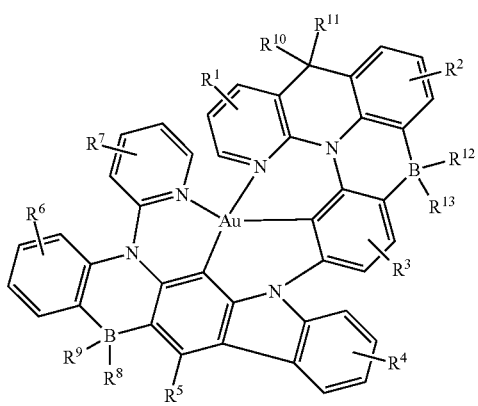
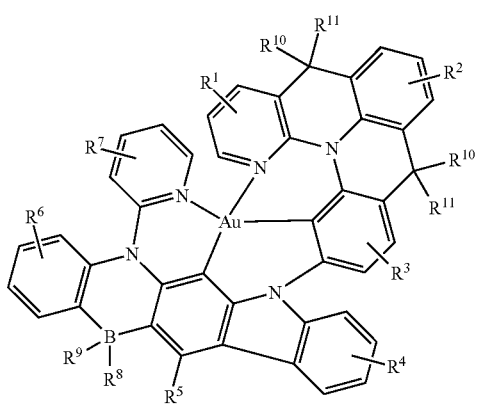
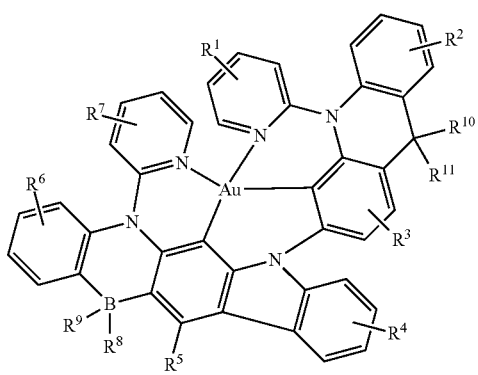
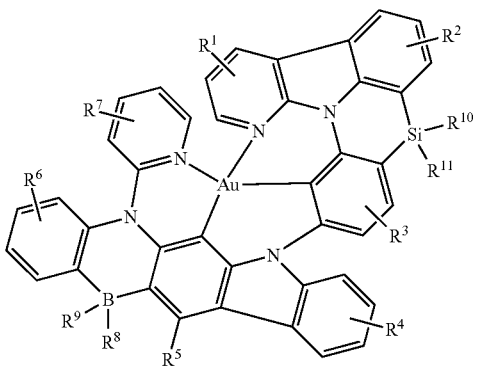
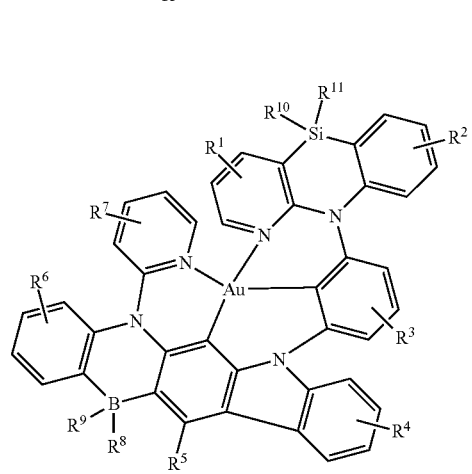
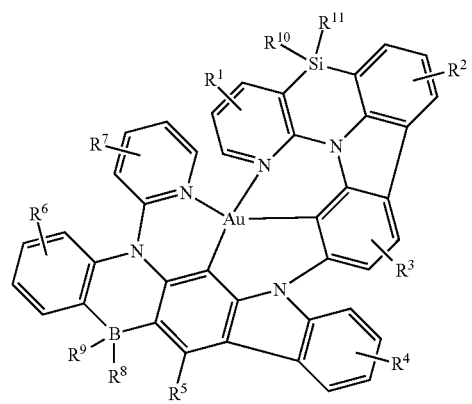
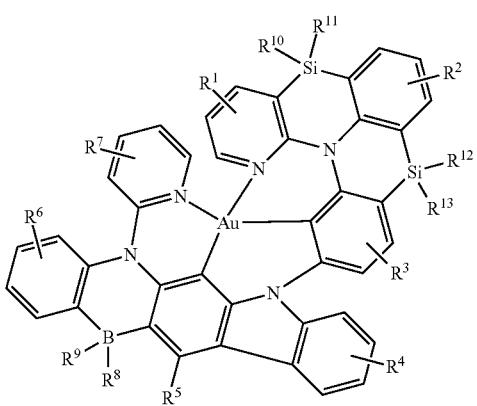

283
-continued
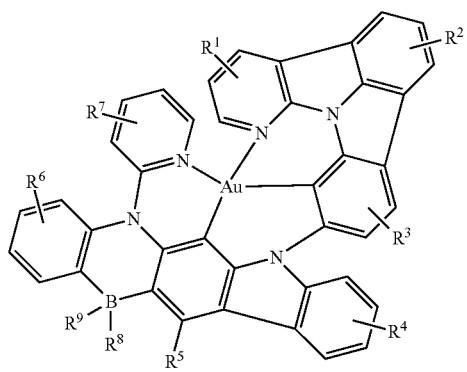
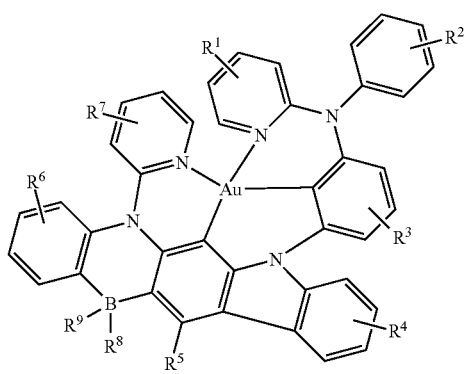
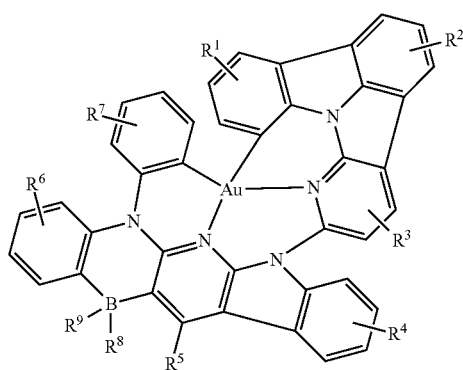
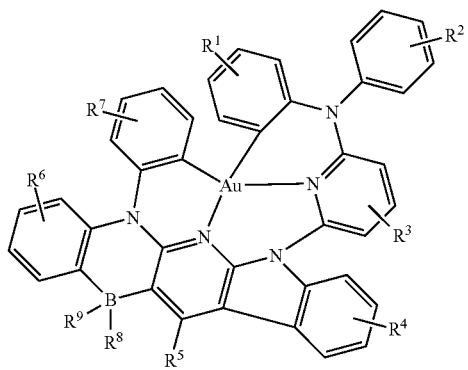
284
-continued
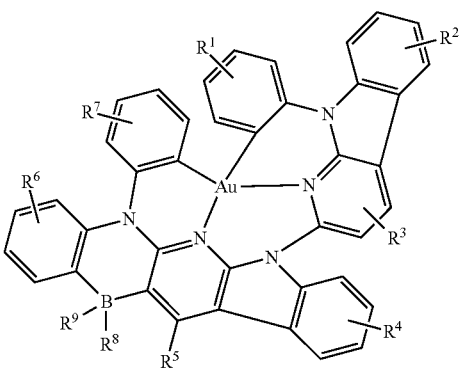
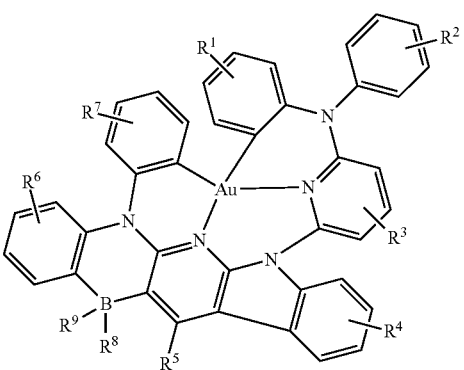
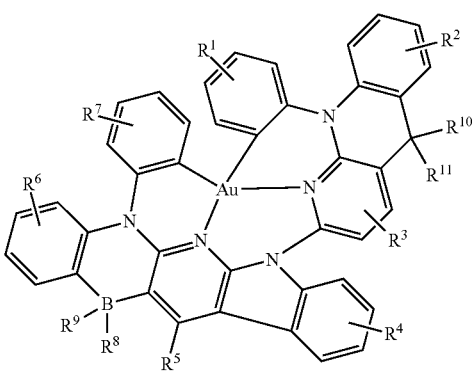
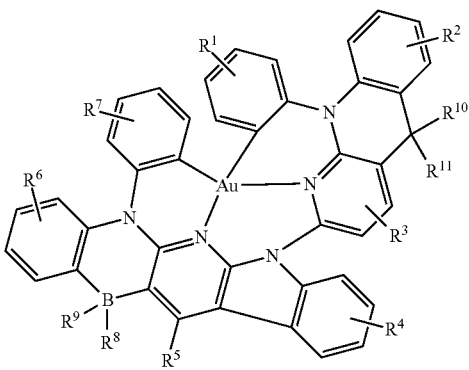

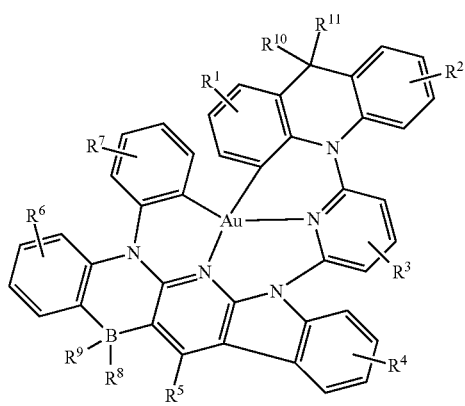
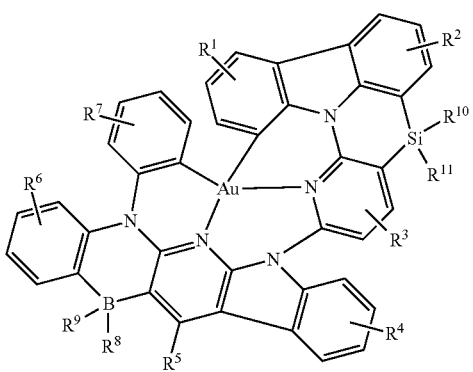
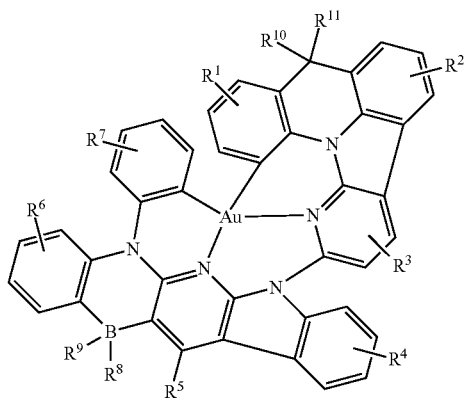
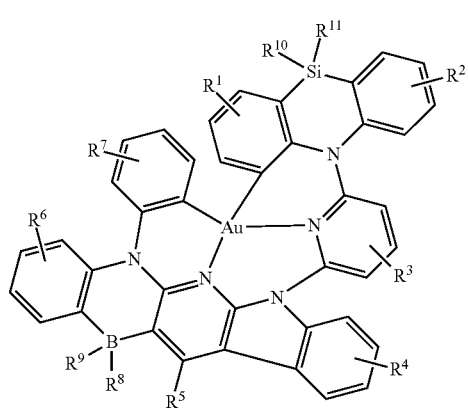
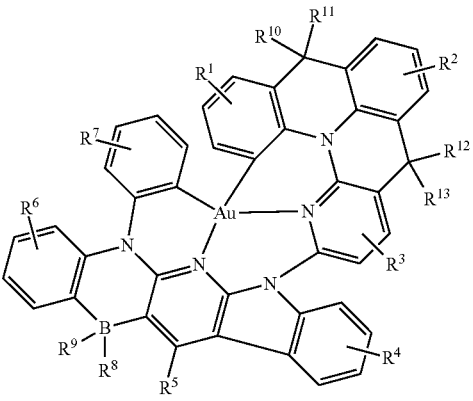
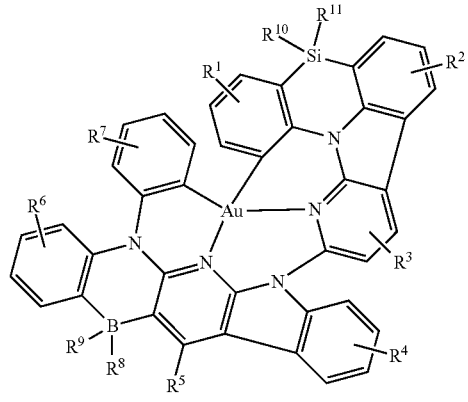
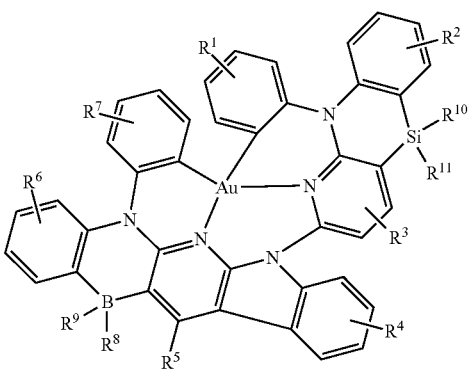
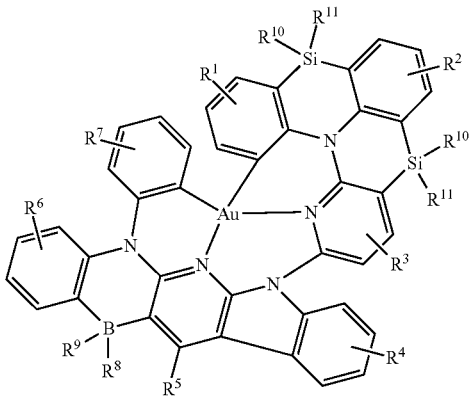

287
-continued
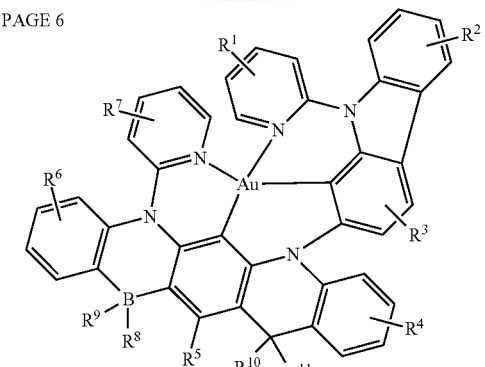
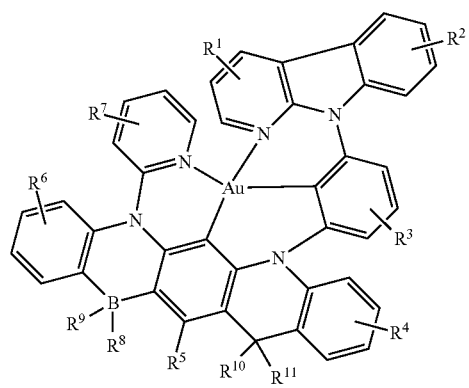
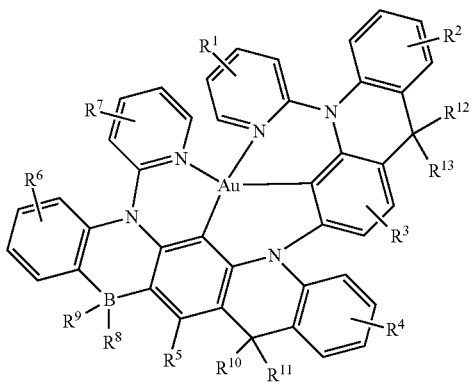
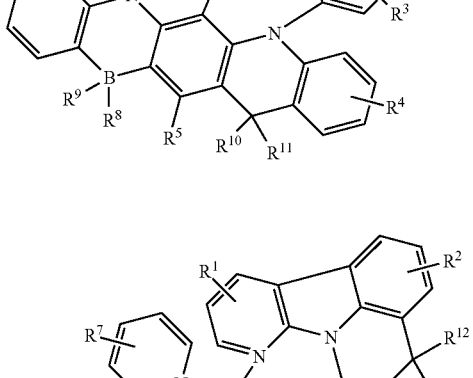
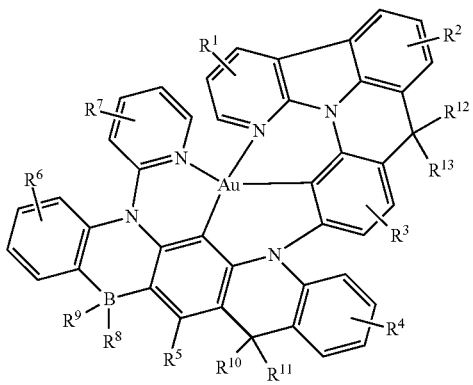
288
-continued
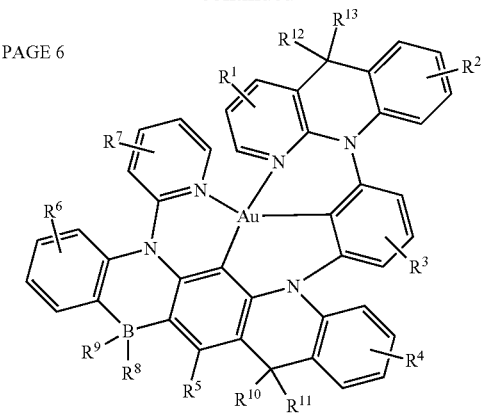
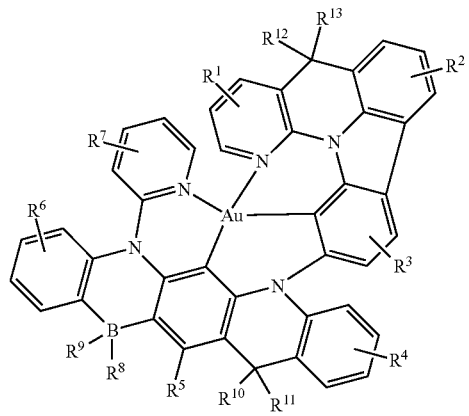
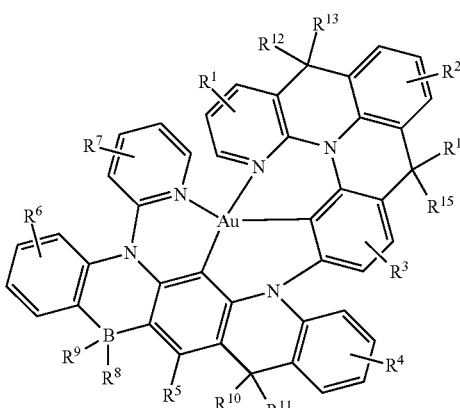
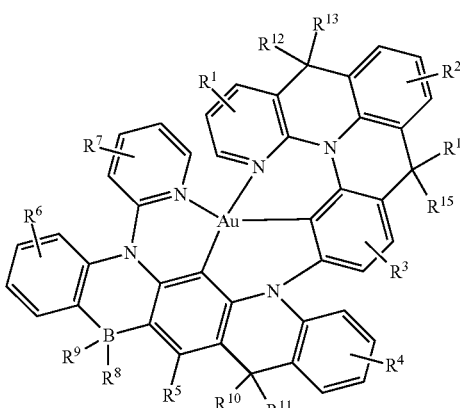
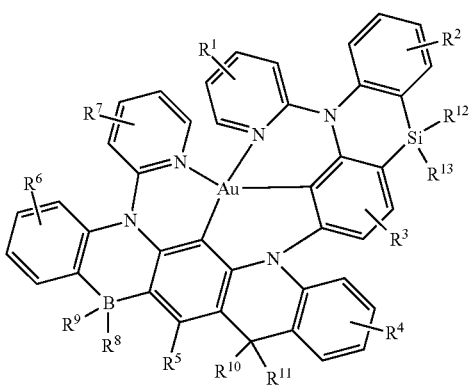

289
-continued
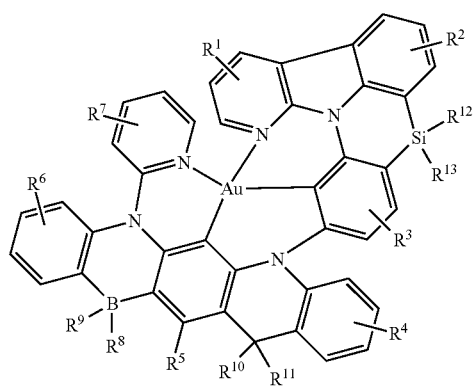
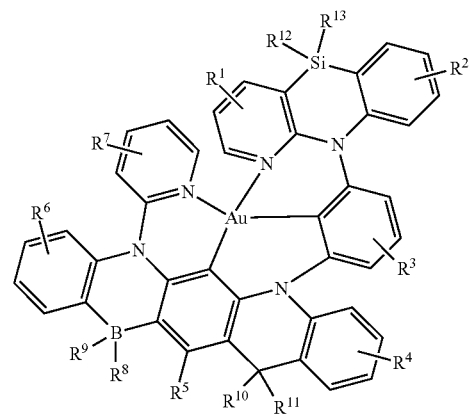
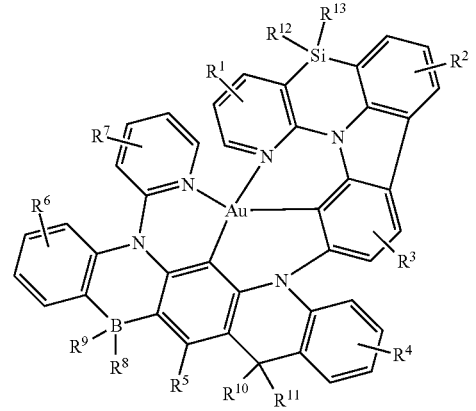
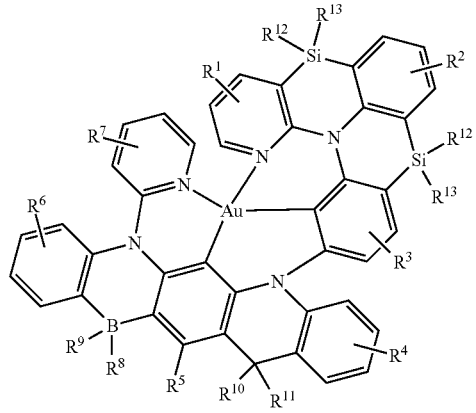
290
-continued
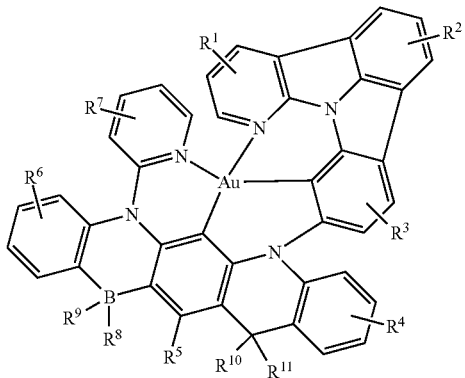
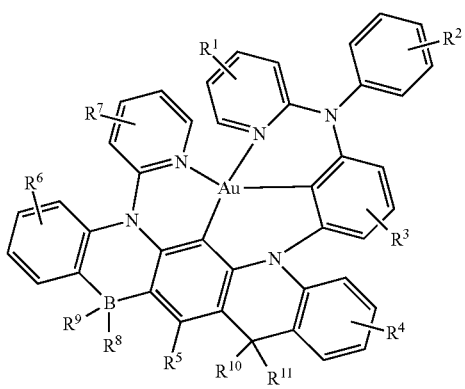
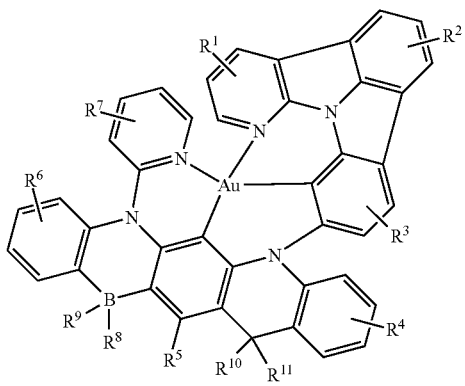
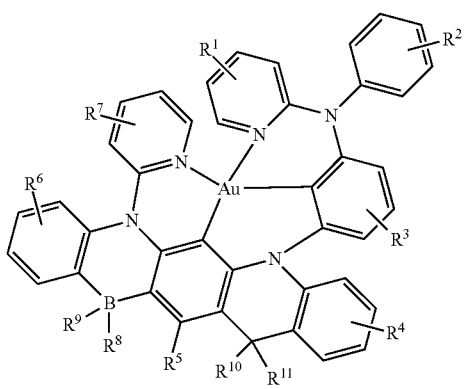

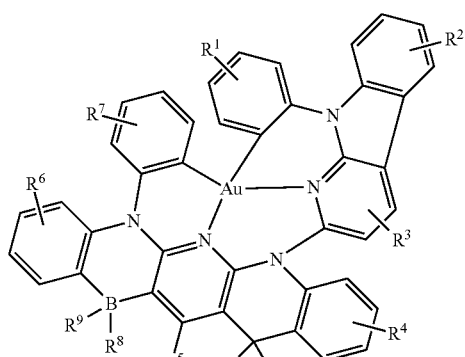
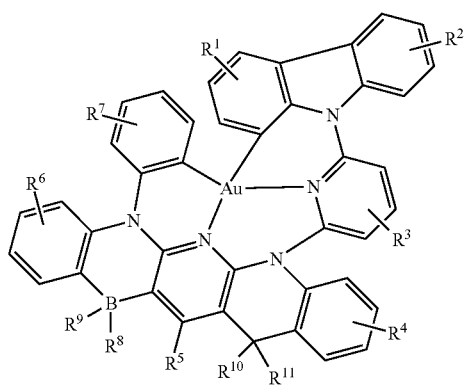
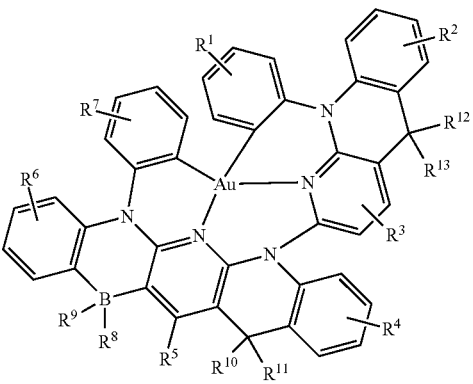
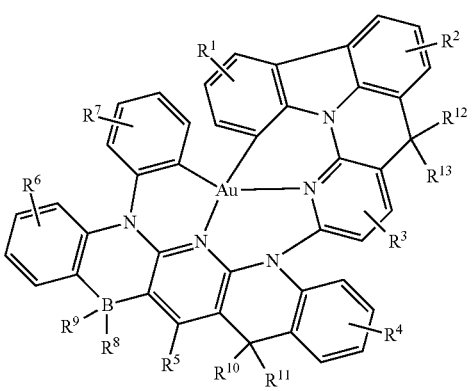
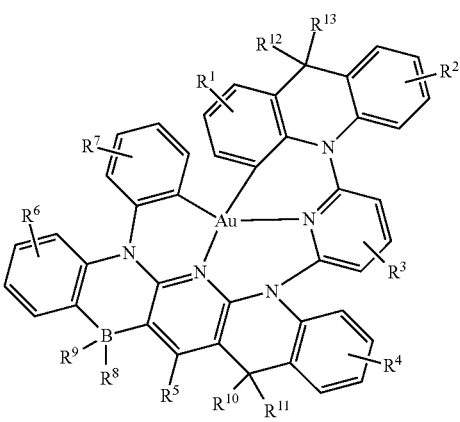
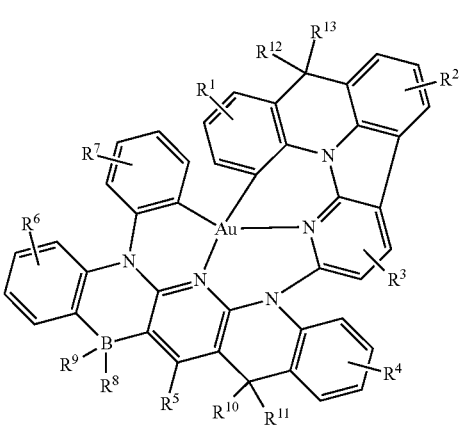
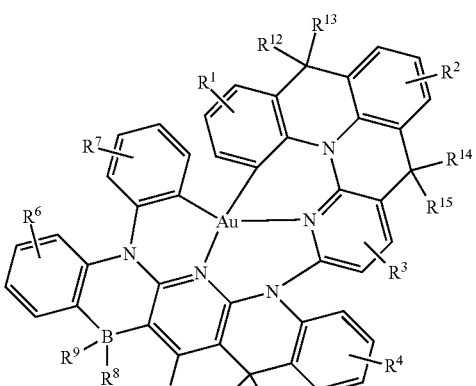
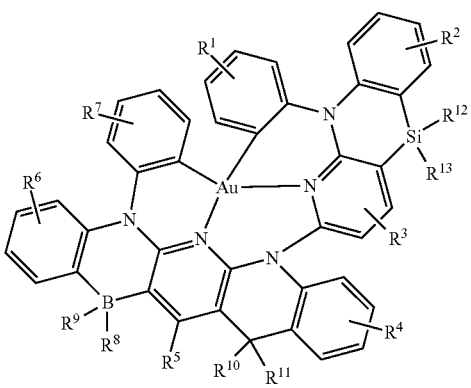

-continued
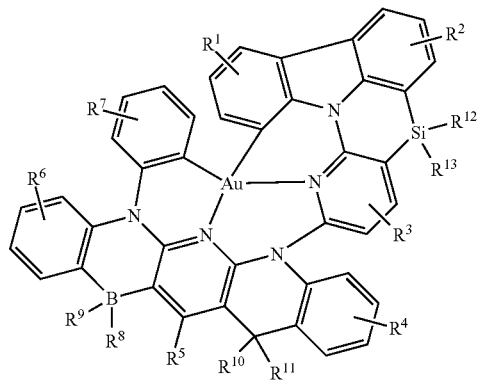
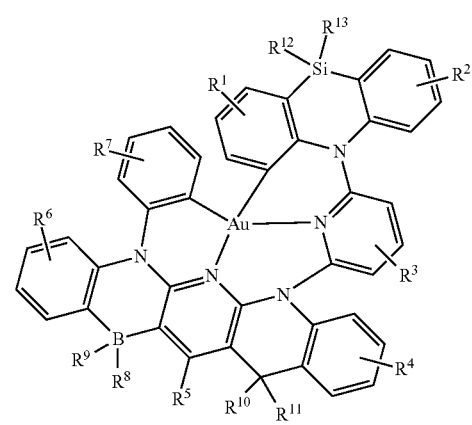
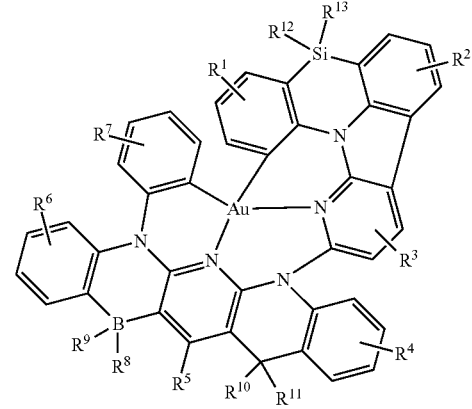
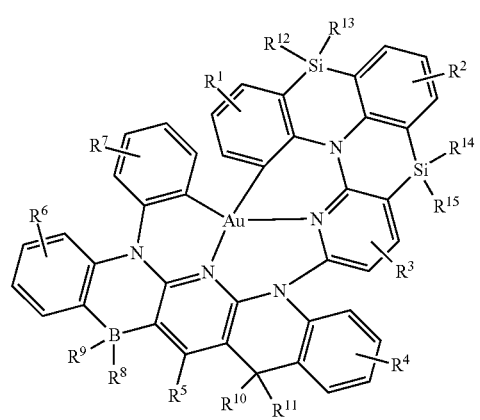
-continued
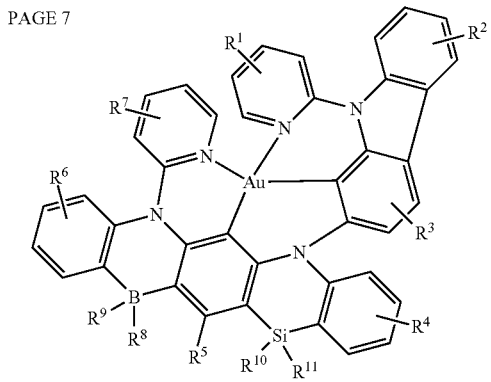
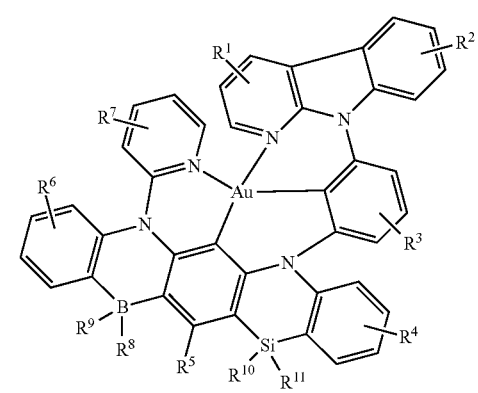
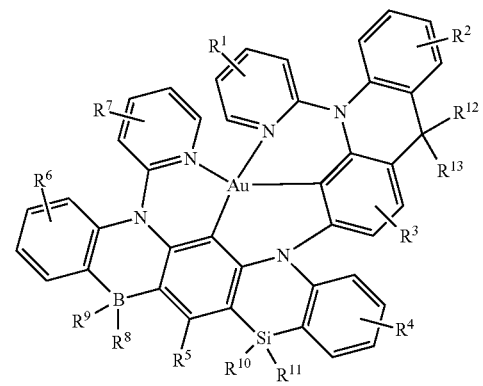
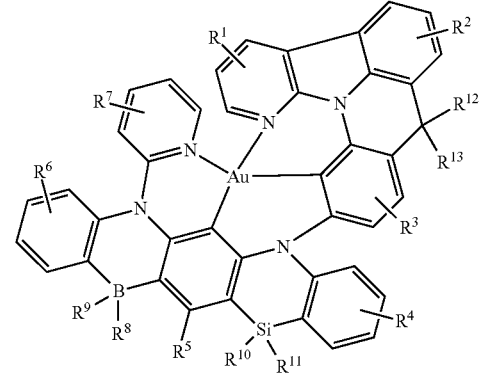

295
-continued
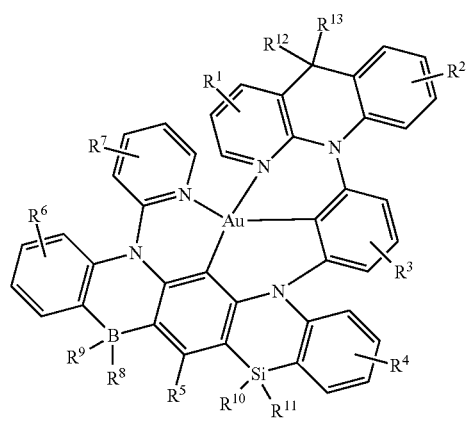
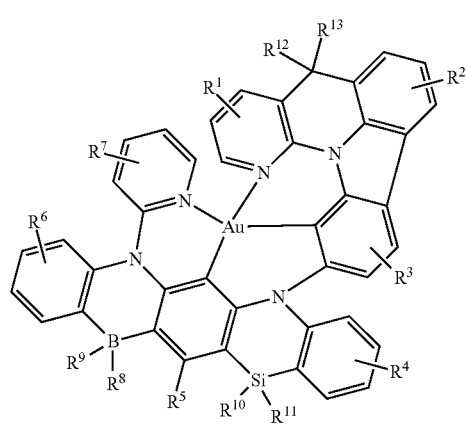
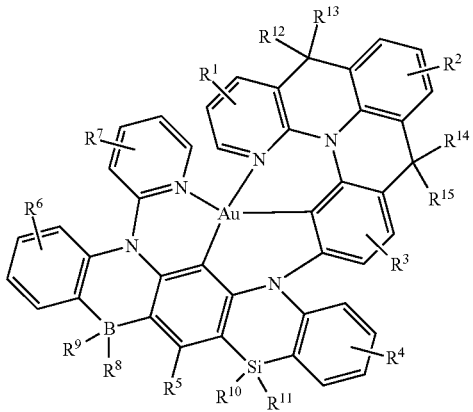
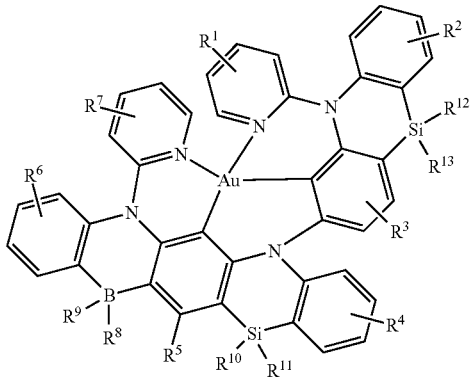
296
-continued
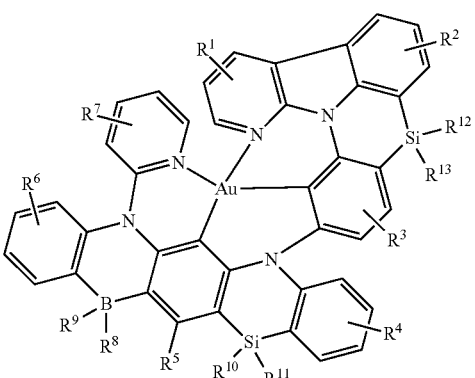
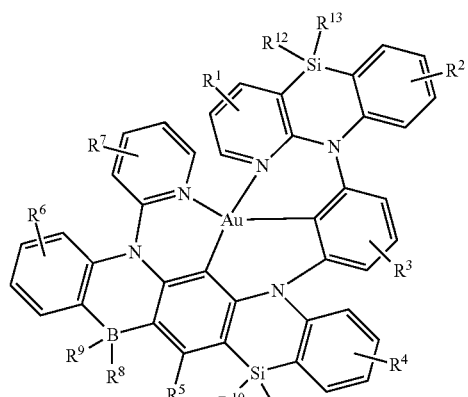
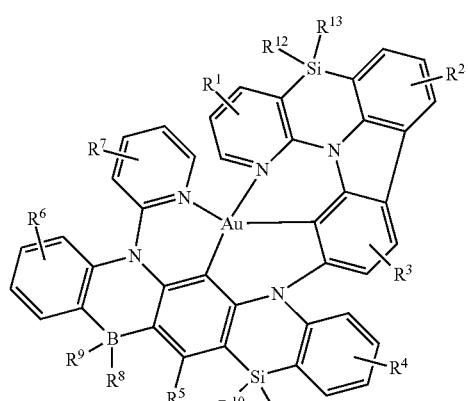
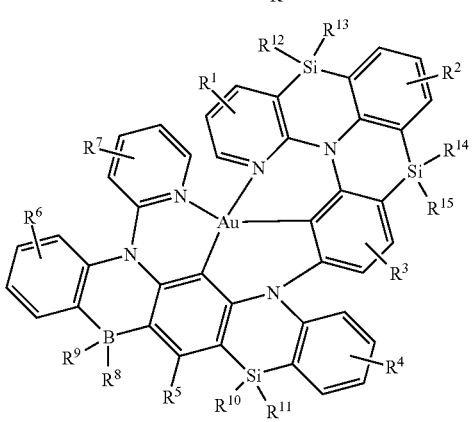

297
-continued
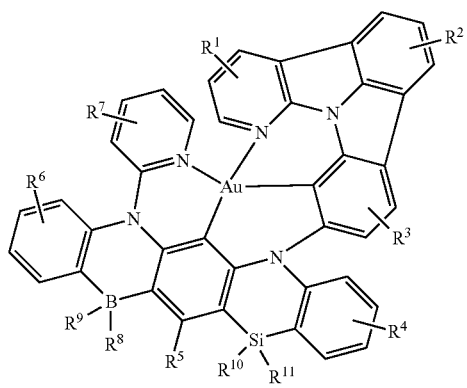
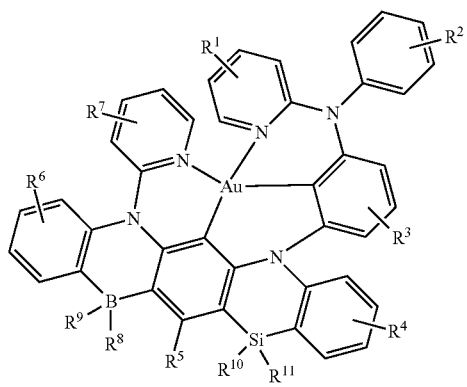
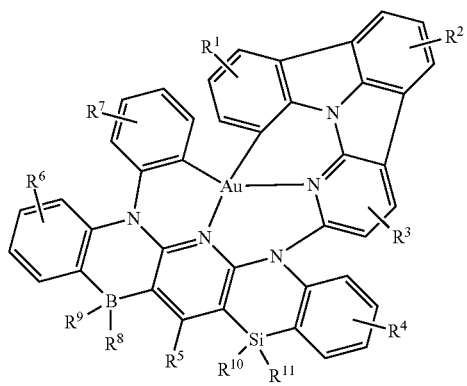
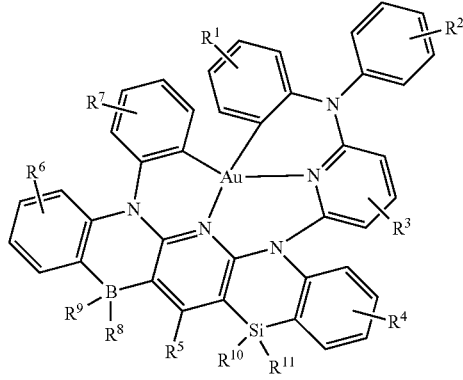
298
-continued
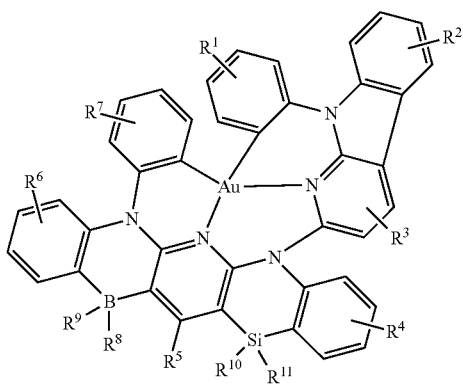
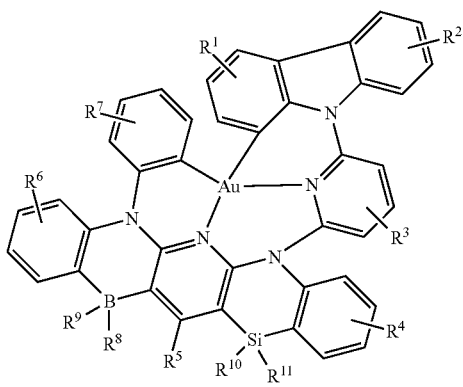
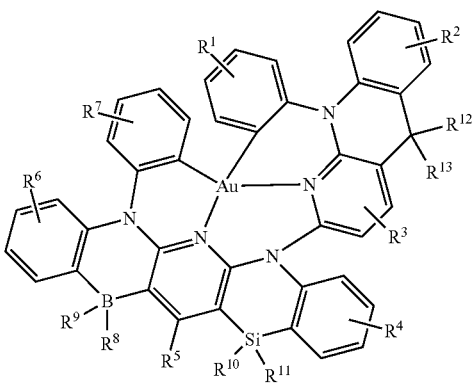
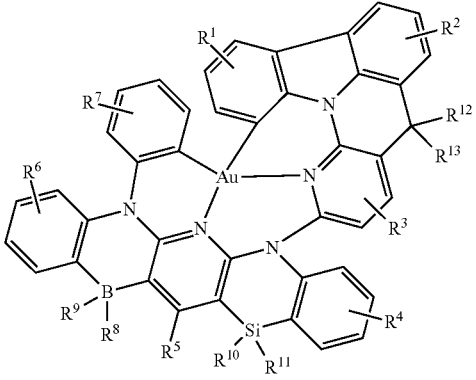

299
-continued
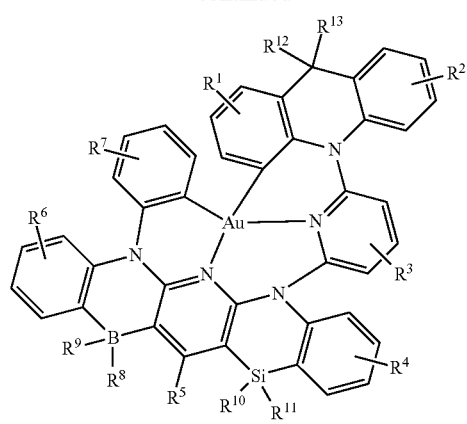
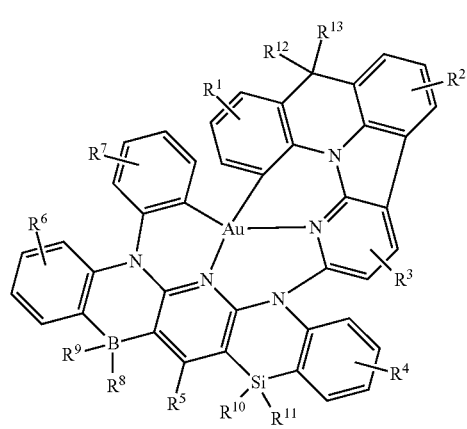
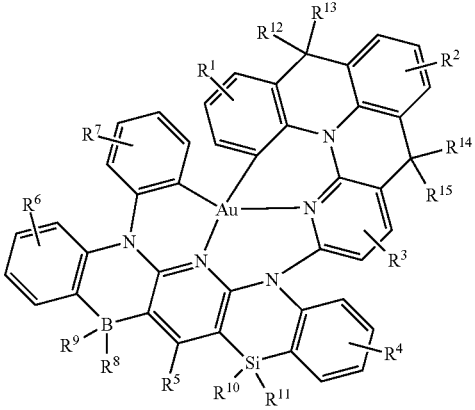
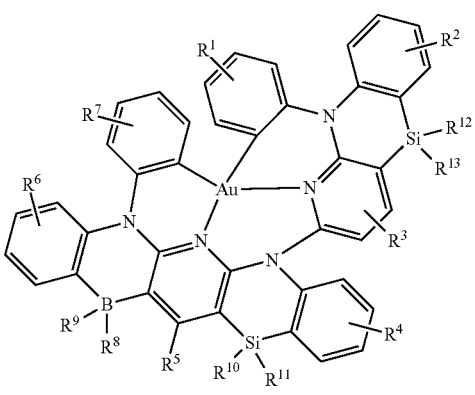
300
-continued
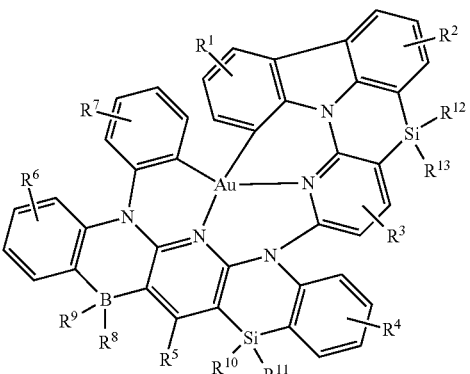
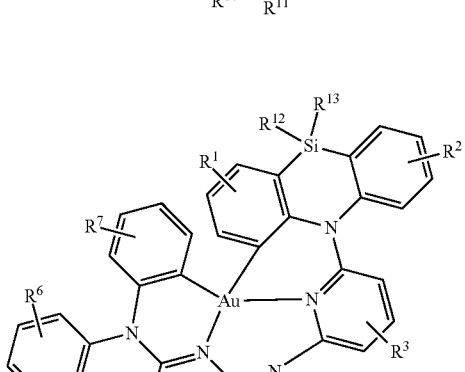
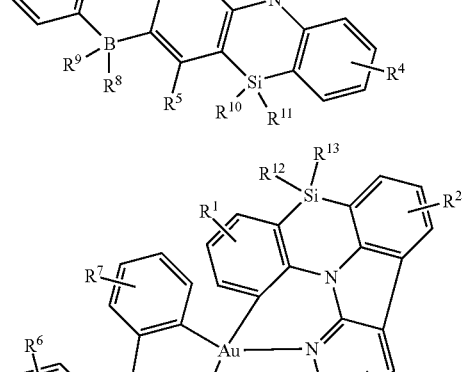
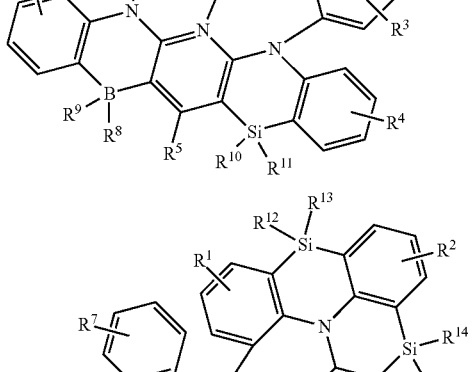

301
-continued
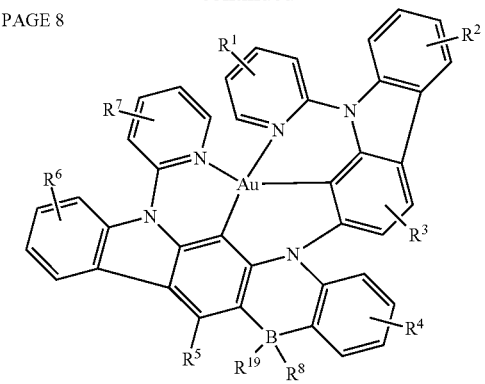
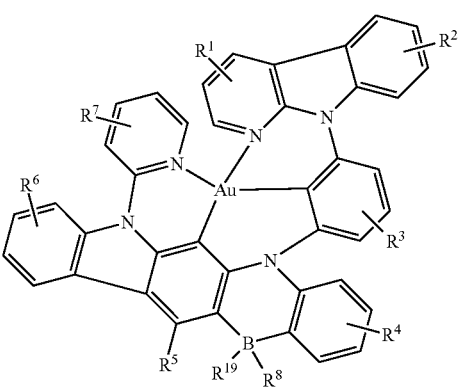
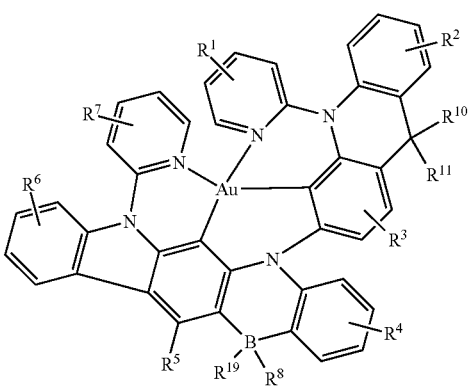
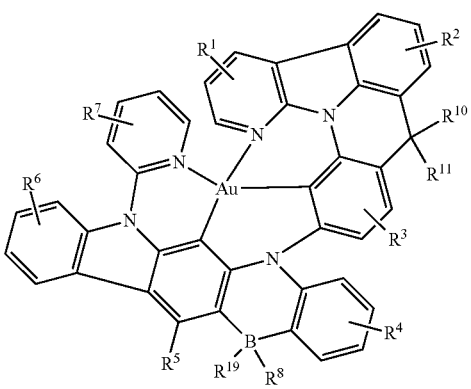
302
-continued
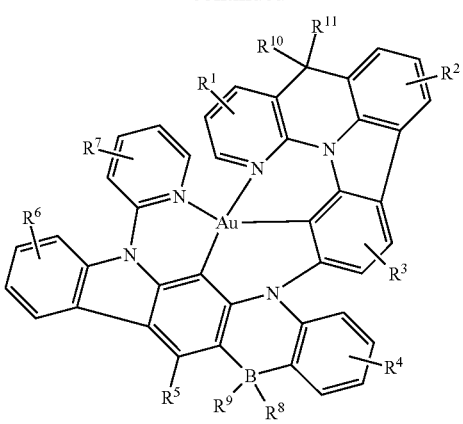
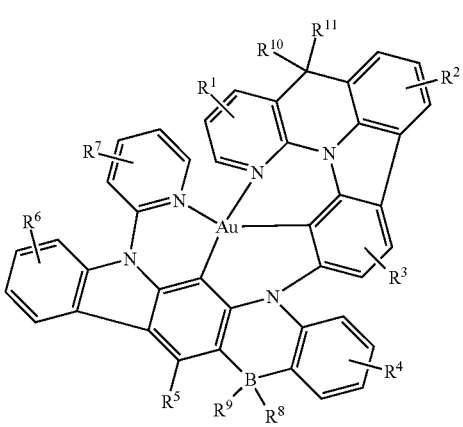
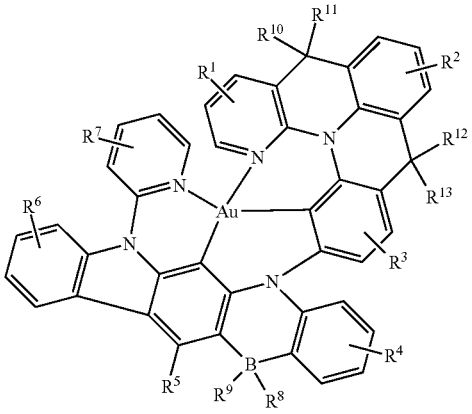
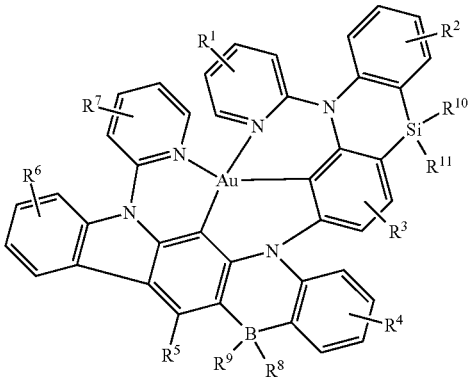

303
-continued
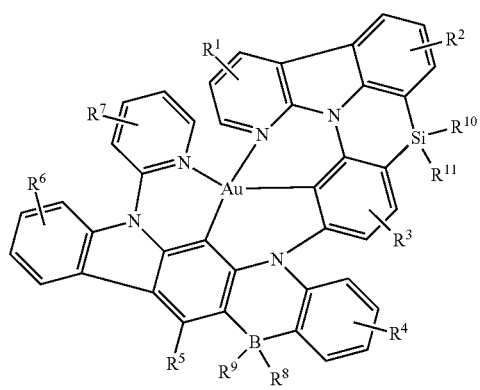
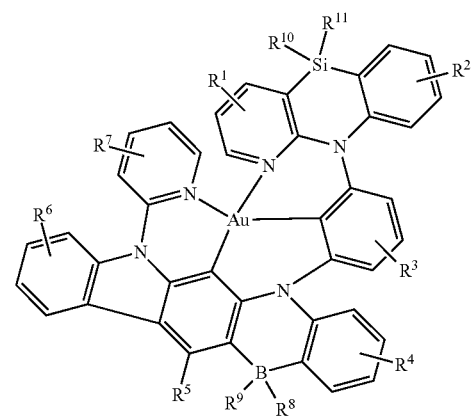
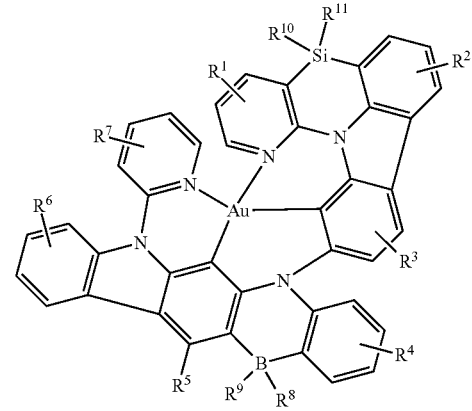
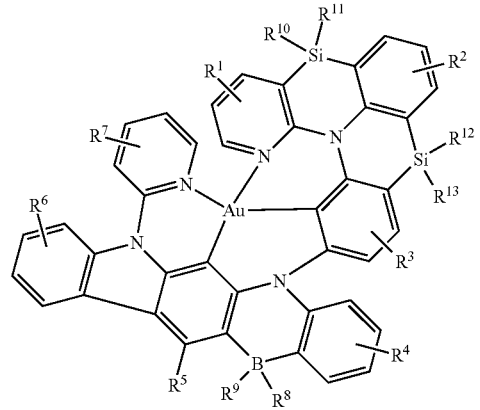
304
-continued
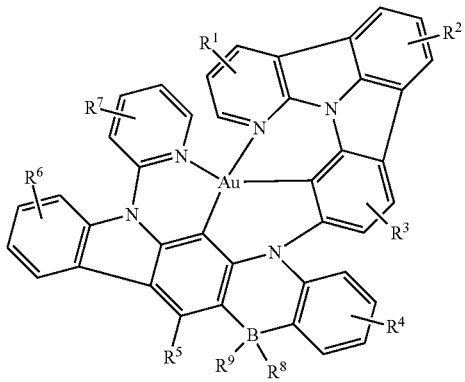
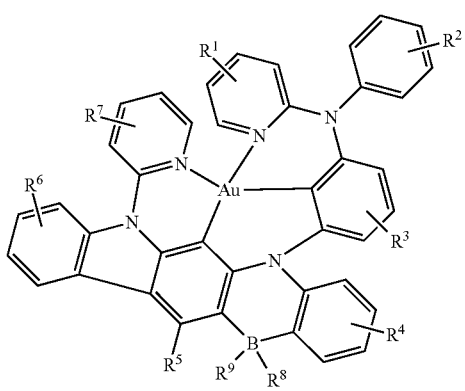
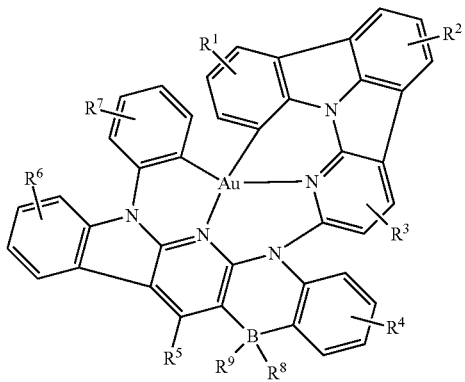
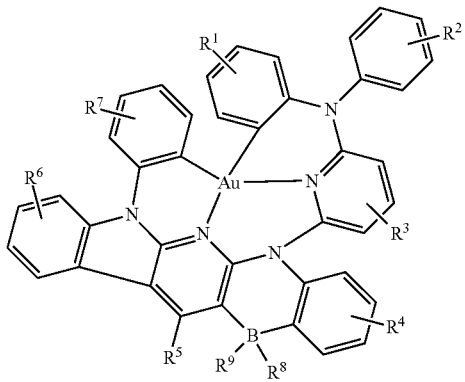

305
-continued
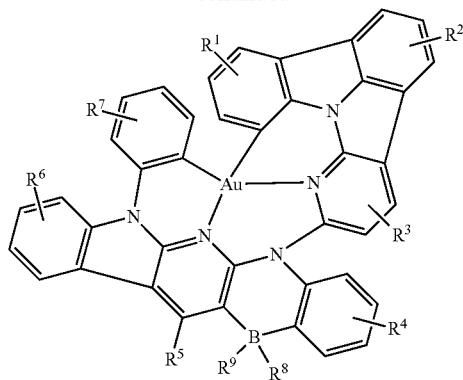
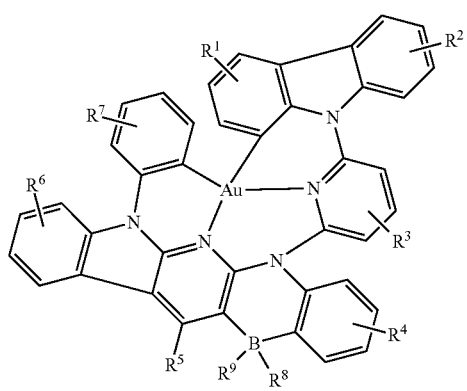
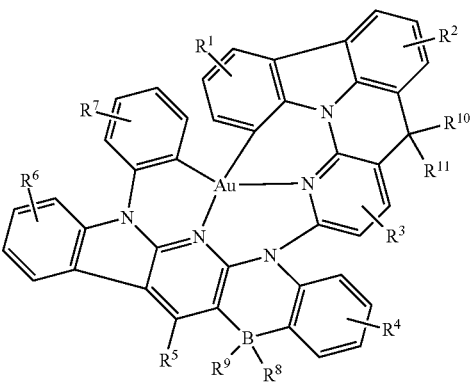
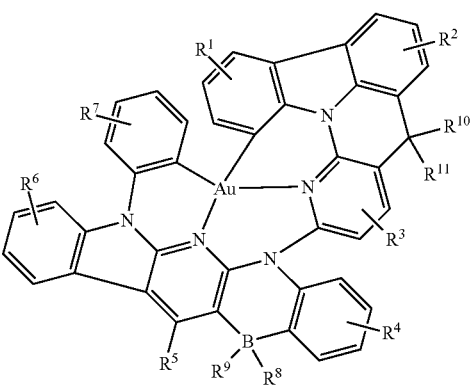
306
-continued
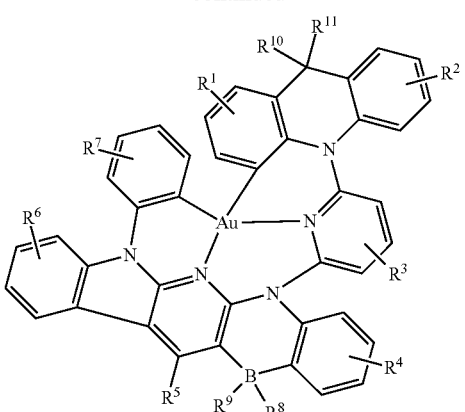
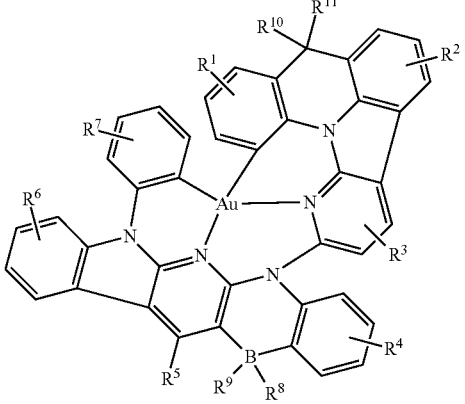
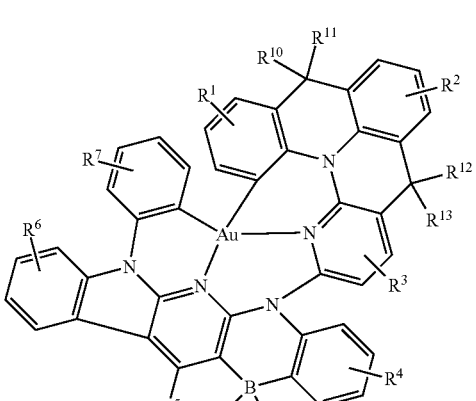
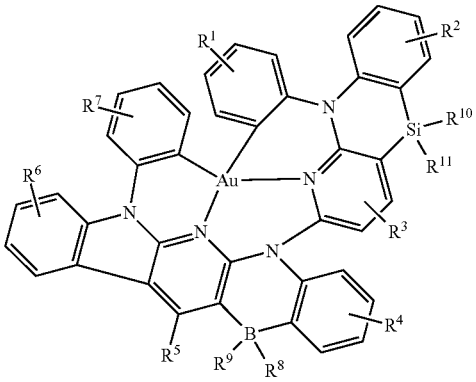

307
-continued
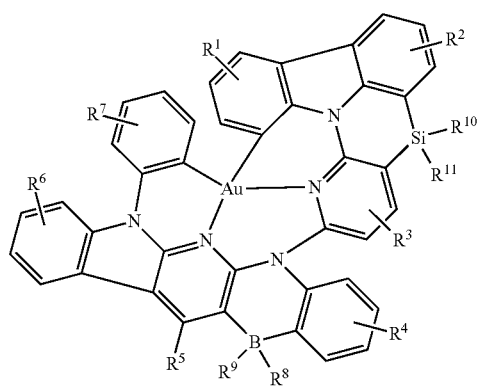
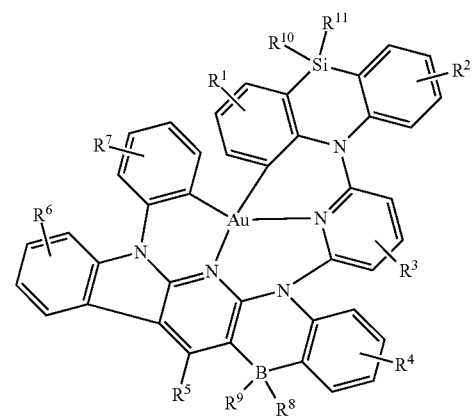
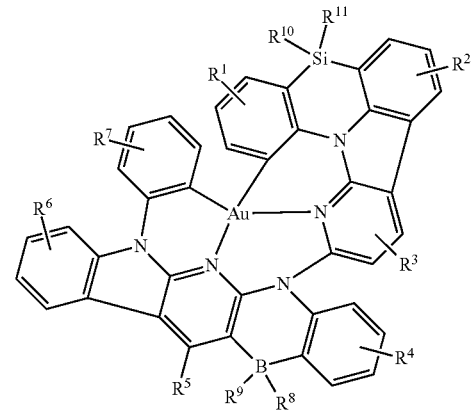
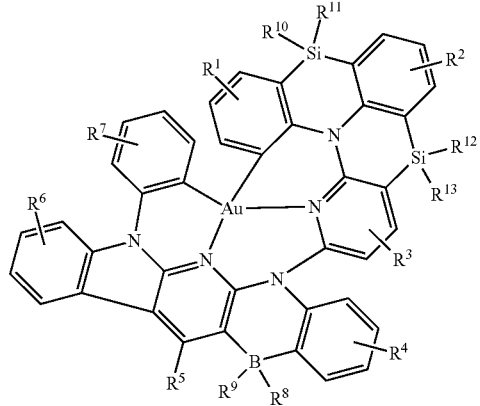
308
-continued
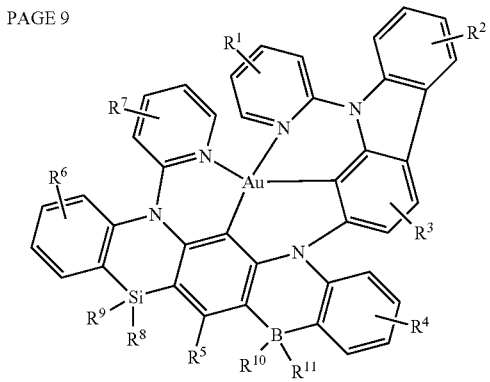
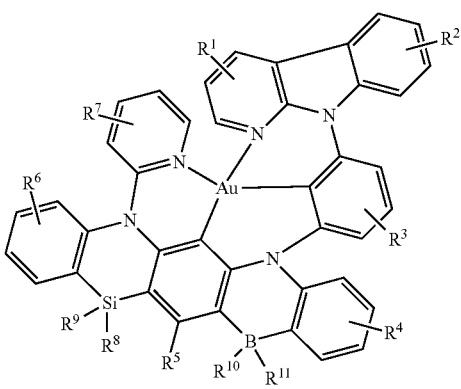
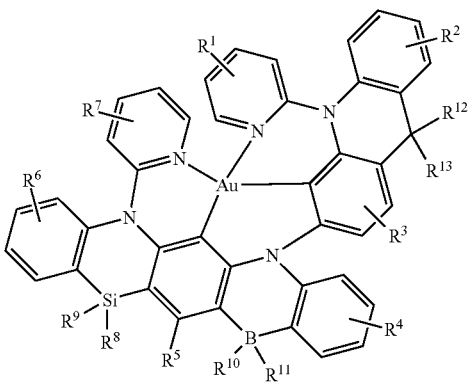
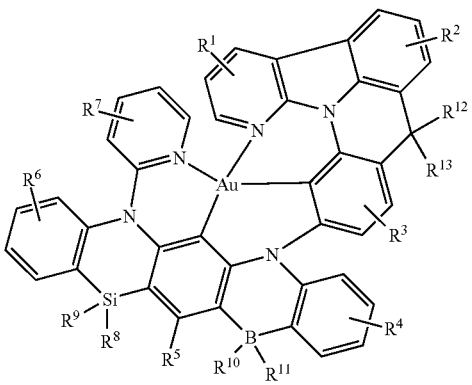

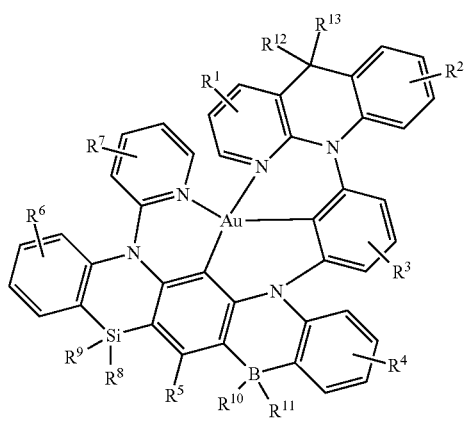
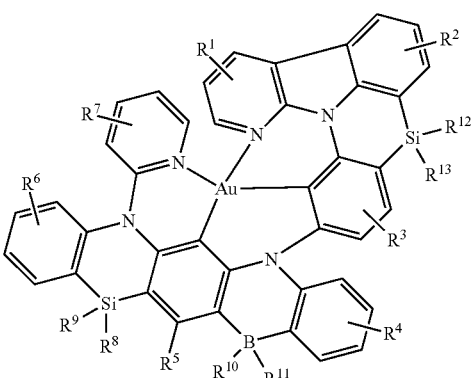
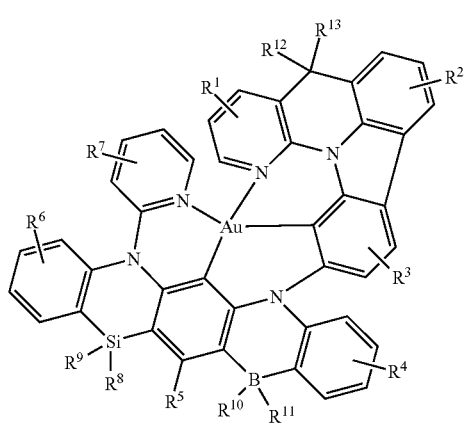
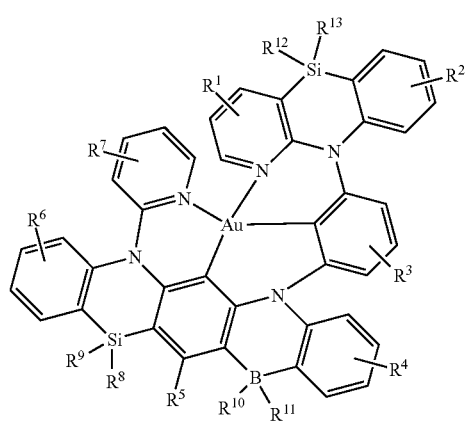
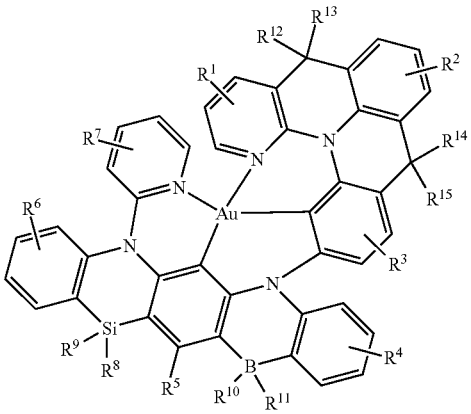
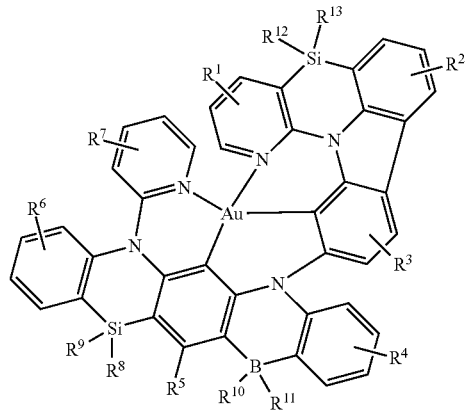
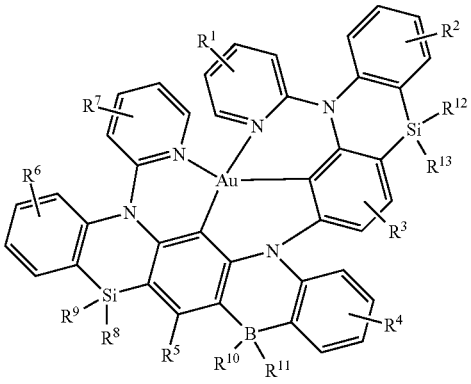
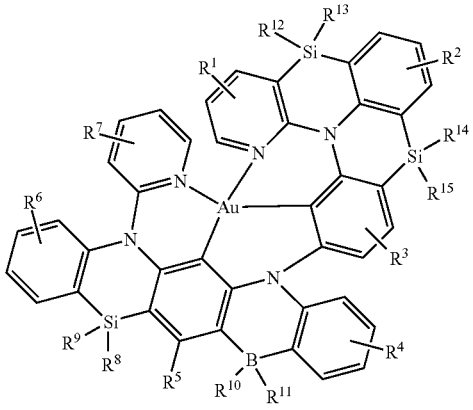

311
-continued
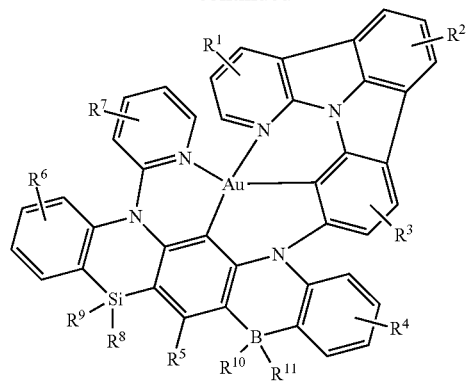
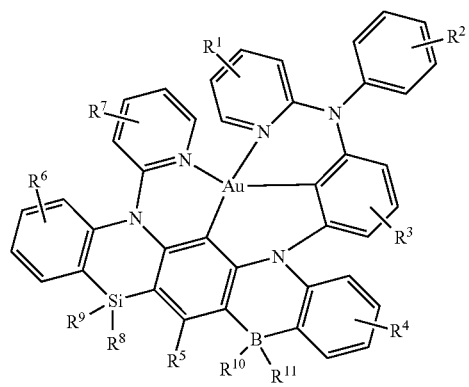
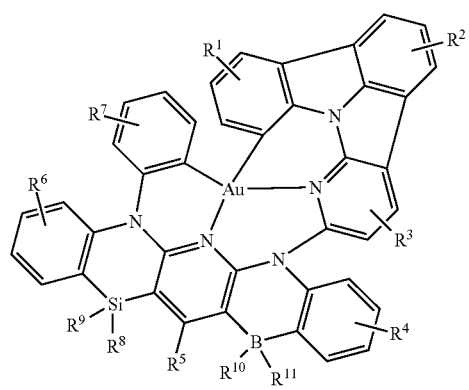
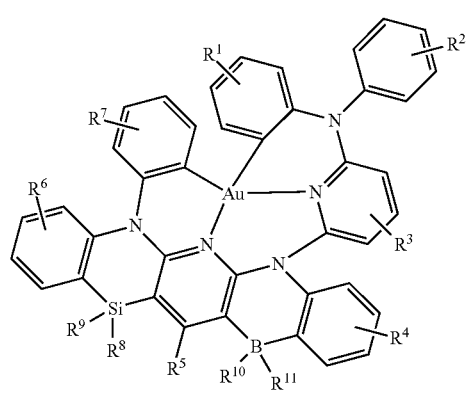
312
-continued
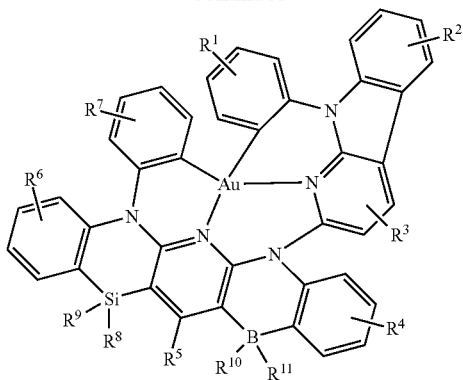
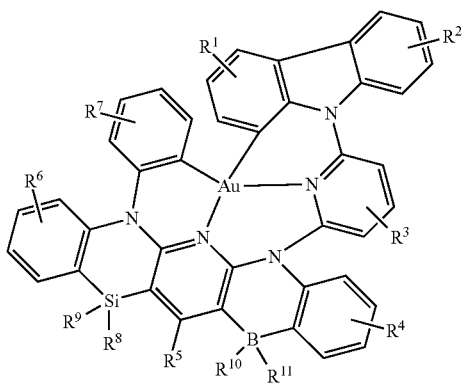
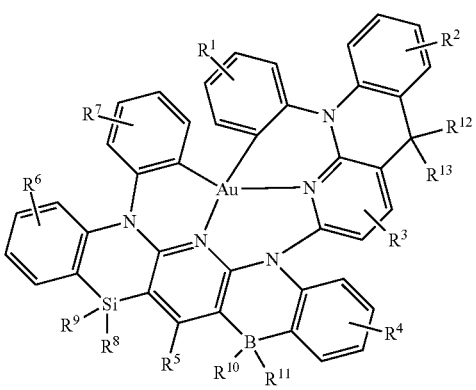
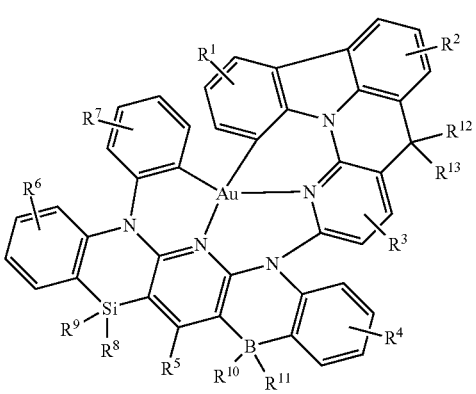

313
-continued
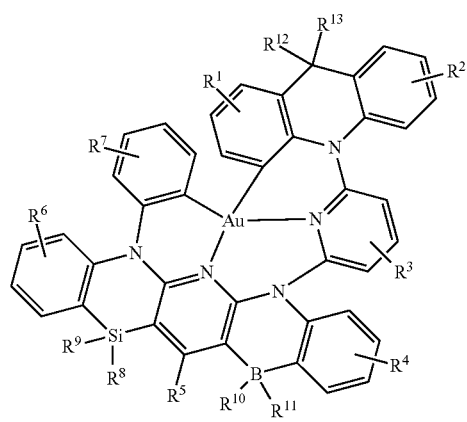
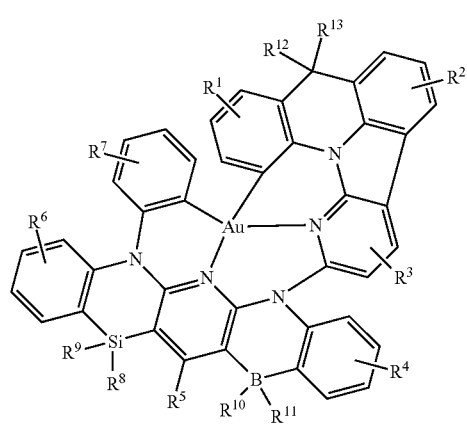
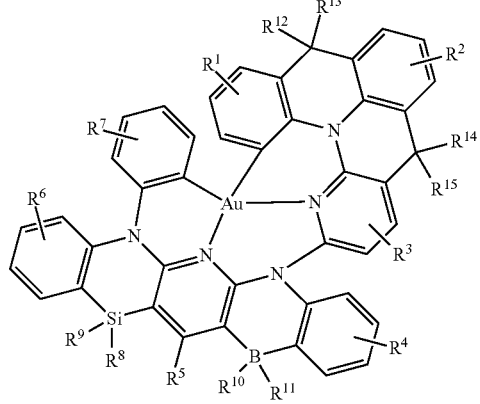
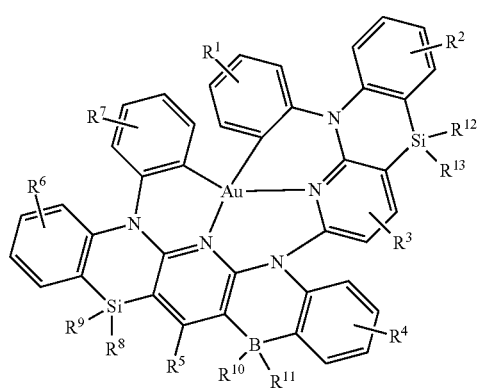
314
-continued
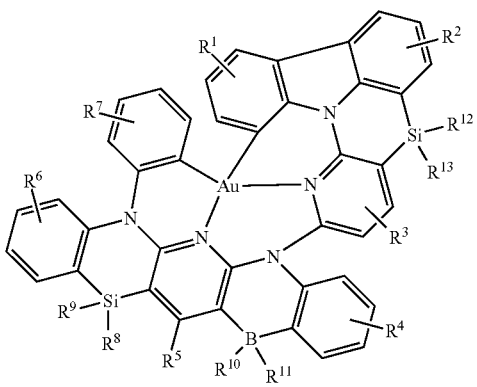
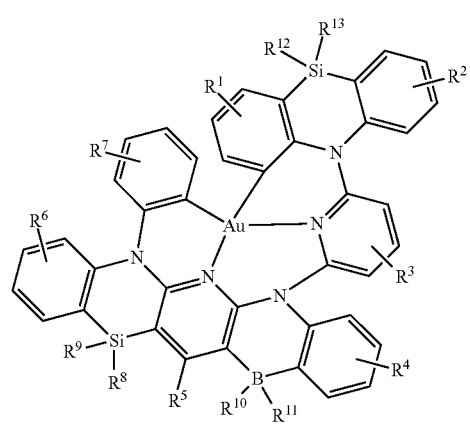
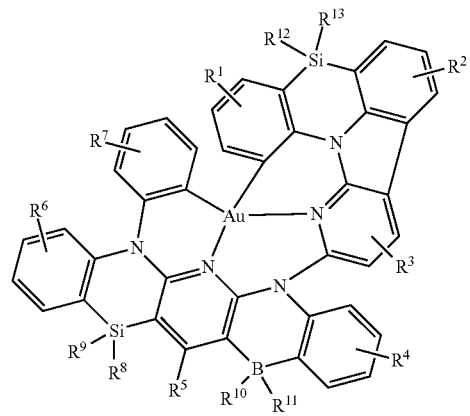
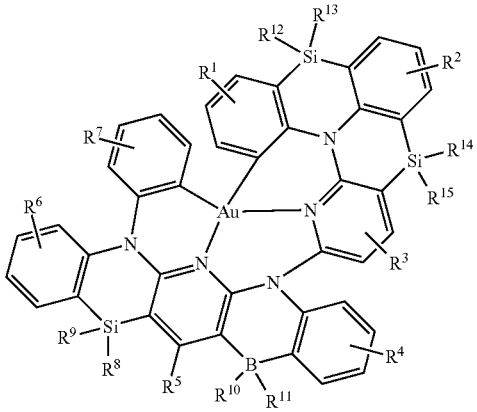

Complexes of Formula II are represented as shown below.

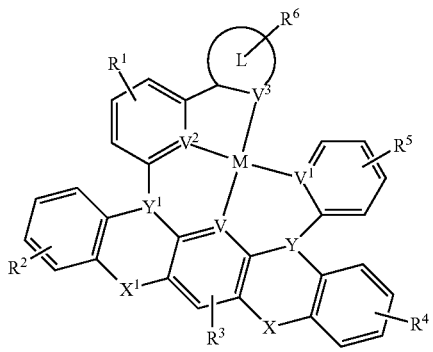

Formula II

In Formula II:
M is Pt (II), Pd (II), or Au (III),
each of V, $V^1$, $V^2$, and $V^3$ is independently N, C, P, or Si,
each of X and $X^1$ is independently present or absent, and each X and $X^1$ present independently represents $CR^7R^8$, C=O, $SiR^7R^8$, $GeR^7R^8$, $NR^7$, $PR^7$, $PR^7R^8$, $R^7P$=O, $AsR^7$, $R^7As$=O, O, S, S=O, $SO_2$, Se, Se=O, $SeO_2$, $BR^7$, $BR^7R^8$, $AlR^7R^8$, $R^7Bi$=O, $BiR^7$, or a single bond,
each of Y and $Y^1$ is independently $CR^9$, $SiR^9$, $GeR^9$, N, P, P=O, As, As=O, B, Bi=O, or Bi,
L is a substituted or unsubstituted aryl, heteroaryl, or N-heterocyclic carbene,
each of $R^1$, $R^2$, $R^3$, $R^4$, $R^5$, and $R^6$ is independently absent or present as a single substituent or multiple substituents, valency permitting, and each $R^1$, $R^2$, $R^3$, $R^4$, $R^5$, and $R^6$ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and
each of $R^7$, $R^8$, and $R^9$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Complexes of Formula II include the following implementations.

When M is Pt or Pd and one of X and $X^1$ is $BR^7R^8$ or $AlR^7R^8$, then one of V, $V^1$, $V^2$, and $V^3$ is C or Si.

When M is Pt or Pd and both of X and $X^1$ are independently $BR^7R^8$ or $AlR^7R^8$, then each of V, $V^1$, $V^2$, and $V^3$ is independently N or P.

When M is Au and one of X and $X^1$ is $BR^7R^8$ or $AlR^7R^8$, then two of V, $V^1$, $V^2$, and $V^3$ are independently C or Si.

When M is Au and both of X and $X^1$ are independently $BR^7R^8$ or $AlR^7R^8$, then one of the V, $V^1$, $V^2$, and $V^3$ is C or Si.

In some implementations of Formula II, V and $V^2$ are C; $V^1$ and $V^3$ are N, Y and $Y^1$ are N; and L is a substituted or unsubstituted pyridyl. In other implementations of Formula II, V and $V^2$ are C; $V^1$ and $V^3$ are N, Y and $Y^1$ are N; L is a substituted or unsubstituted pyridyl; and X is a single bond. In still other implementations of Formula II, V and $V^2$ are C; $V^1$ and $V^3$ are N, Y and $Y^1$ are N; L is a substituted or unsubstituted pyridyl; X is a single bond; and $X^1$ is $CR^8R^9$.

Further implementations of Formula II include the structures below, in which:

M is Pt(II), Pd(II), or Au(III), each U is independently $CR^8R^9$, C=O, $SiR^8R^9$, $GeR^8R^9$, $NR^8$, $PR^8$, $PR^8R^9$, $R^8P$=O, $AsR^8$, $R^8As$=O, O, S, S=O, $SO_2$, Se, Se=O, $SeO_2$, $BR^8$, $BR^8R^9$, $AlR^8$, $AlR^8R^9$, $R^8Bi$=O, or a single bond, each A is independently $BR^8R^9$ or $AlR^8R^9$, and

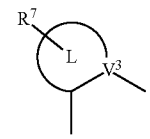

is one of

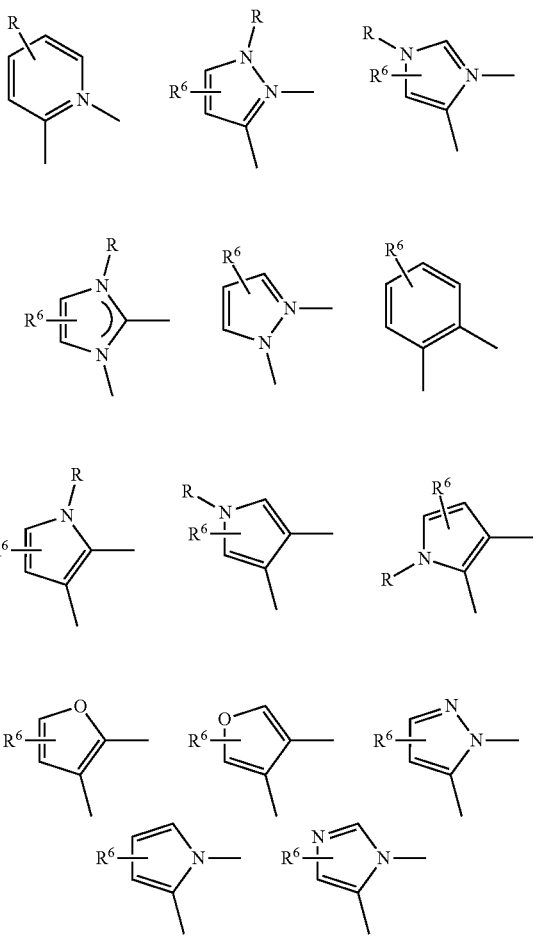

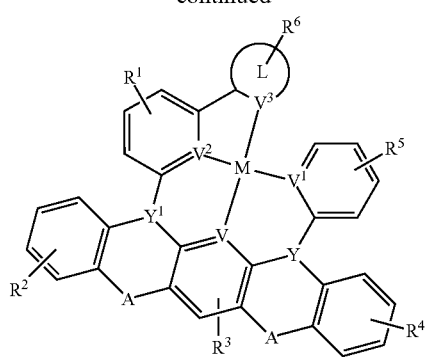
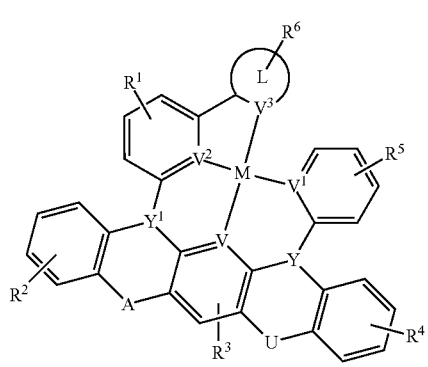
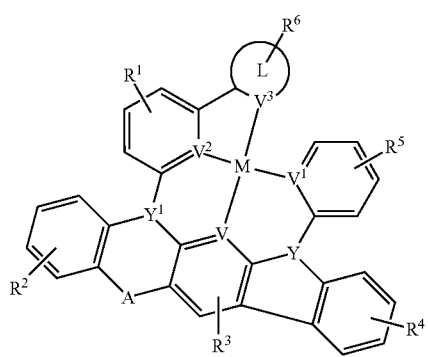
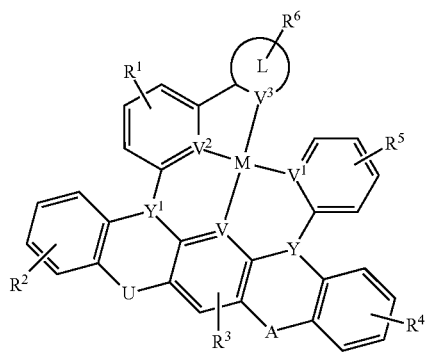
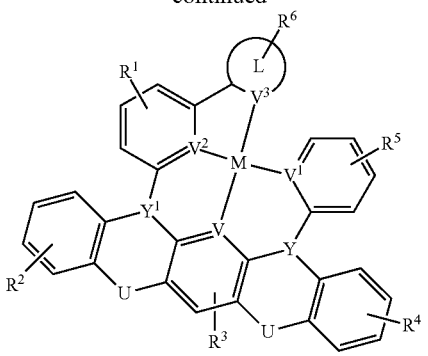
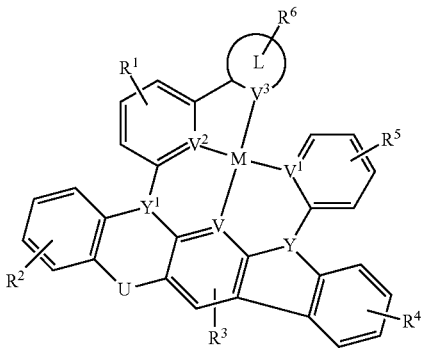
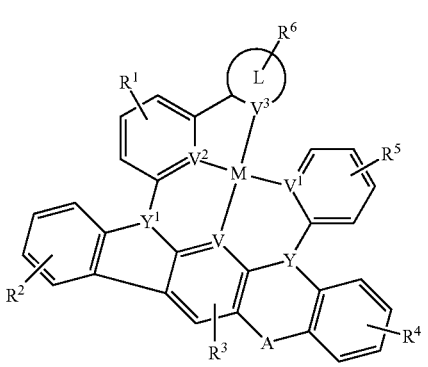
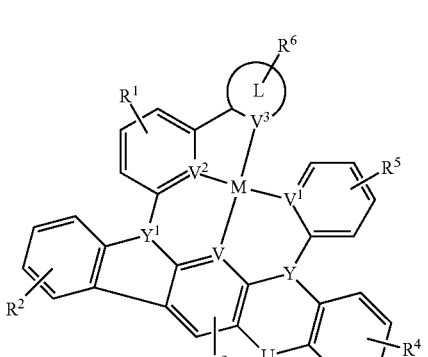
Further implementations of Formula II include the structures below, in which M is Pt(II) or Pt(II).

319
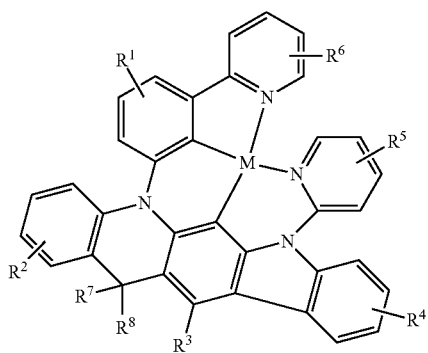
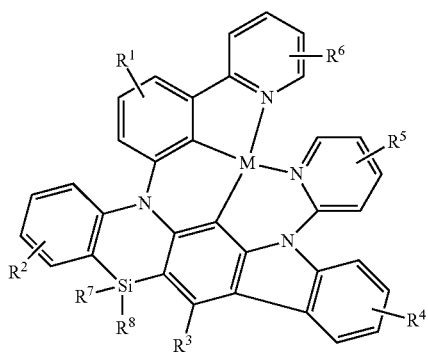
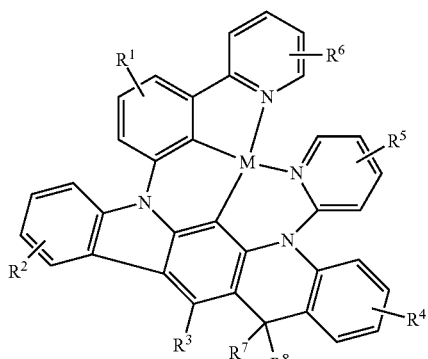
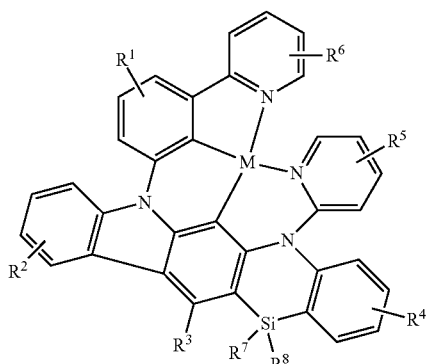
320
-continued
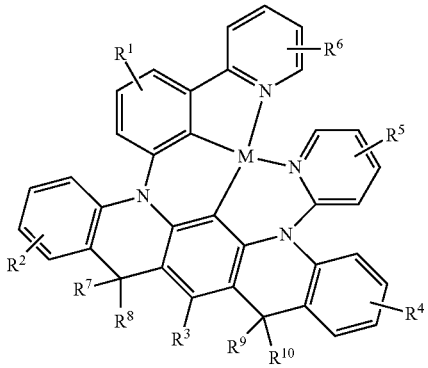
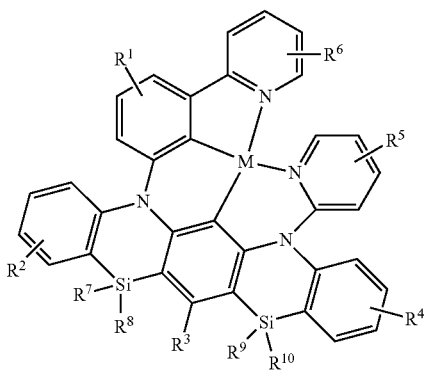
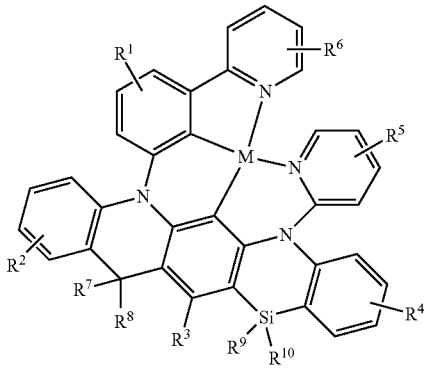
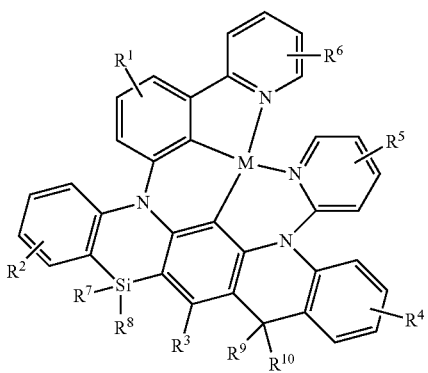

321
-continued
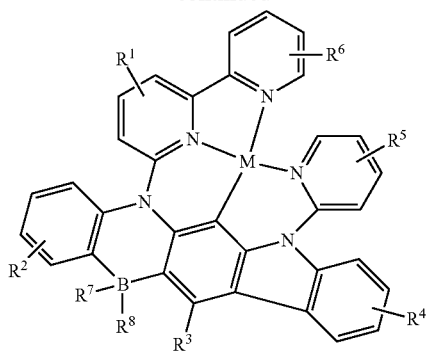
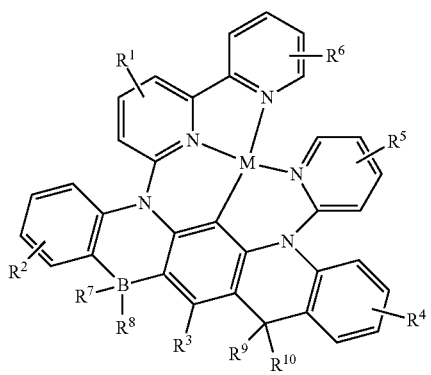
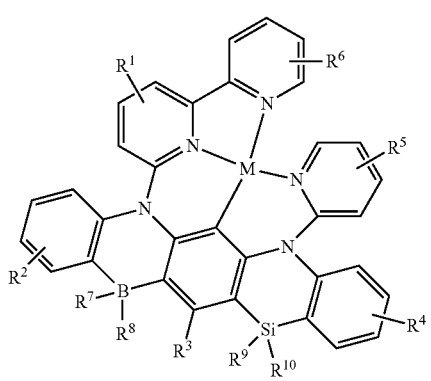
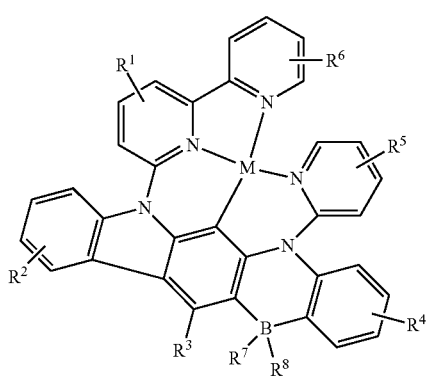
322
-continued
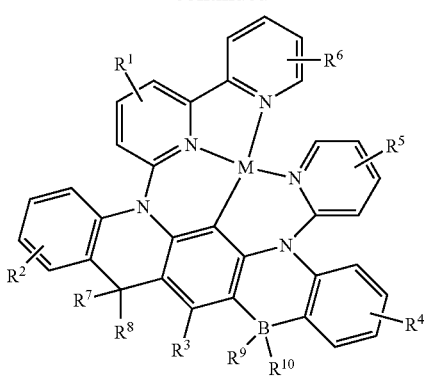
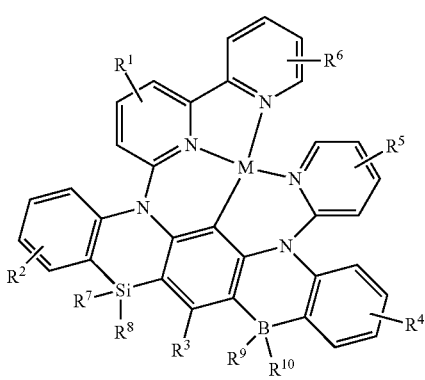
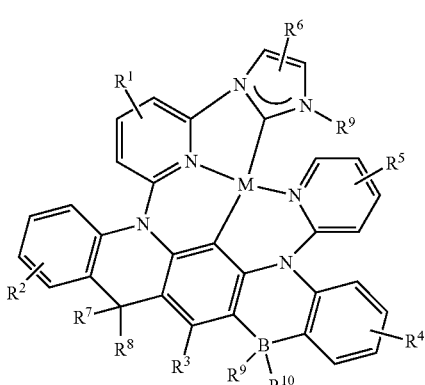
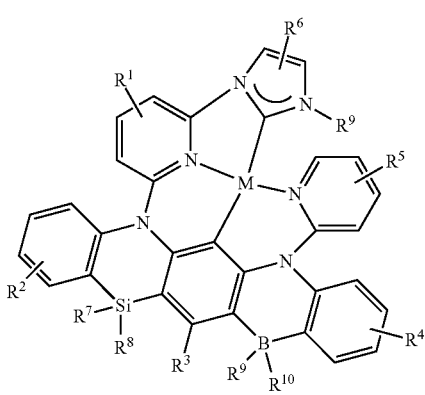

323
-continued
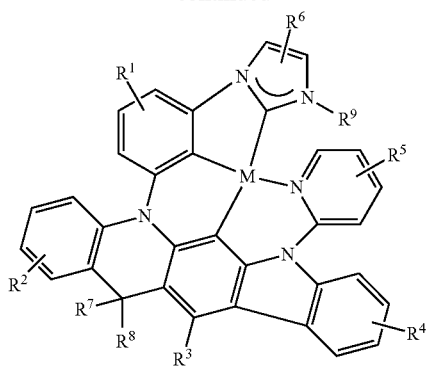
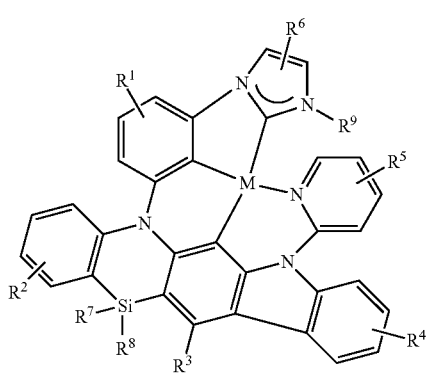
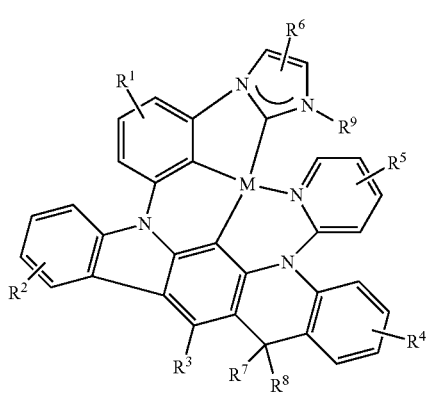
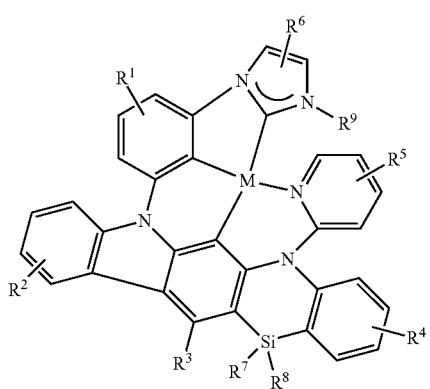
324
-continued
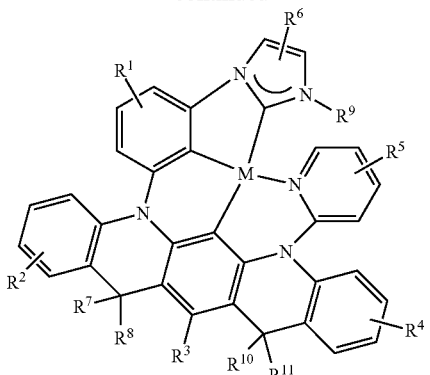
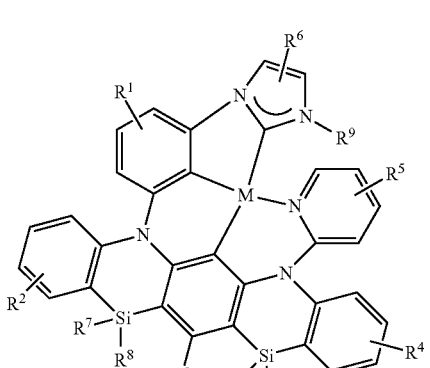
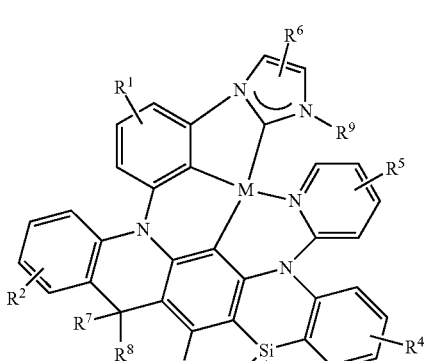
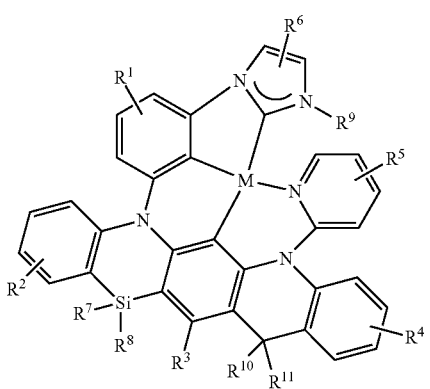

-continued
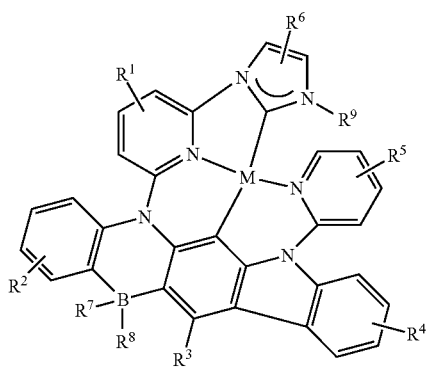
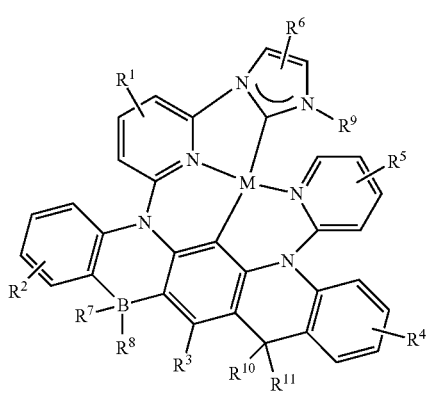
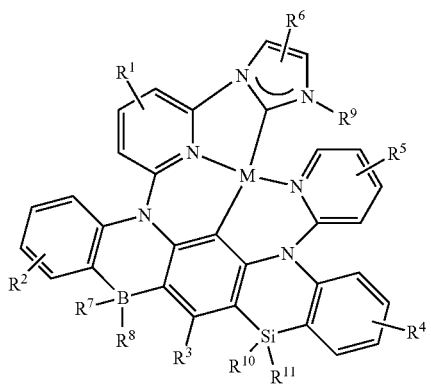
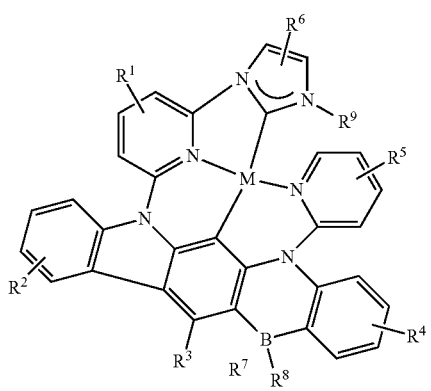
-continued
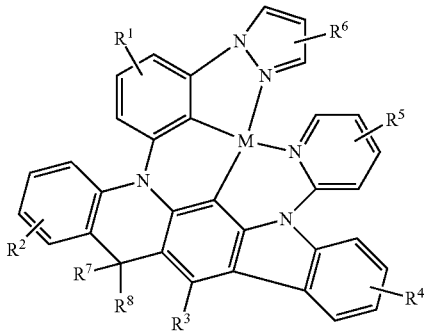
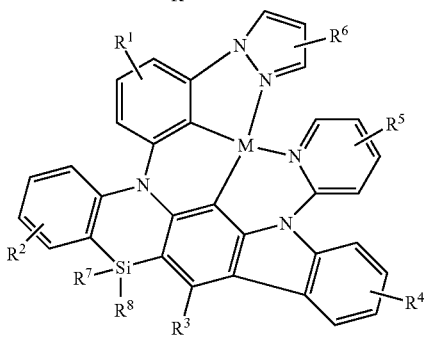
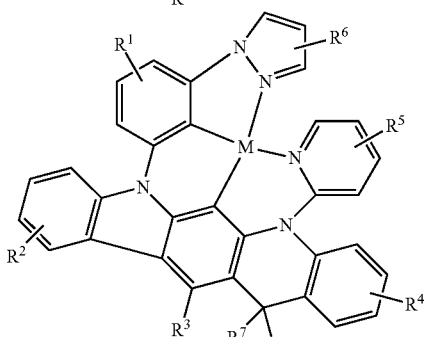
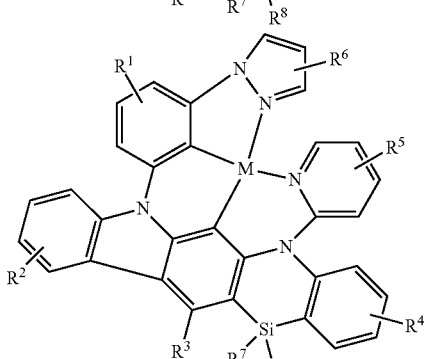
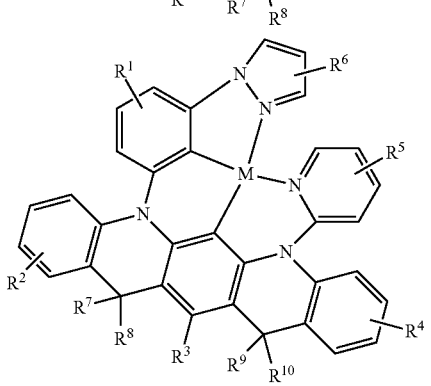

327
-continued
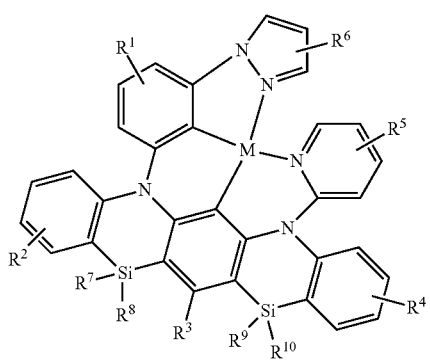
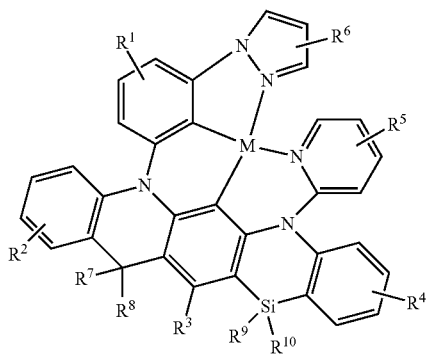
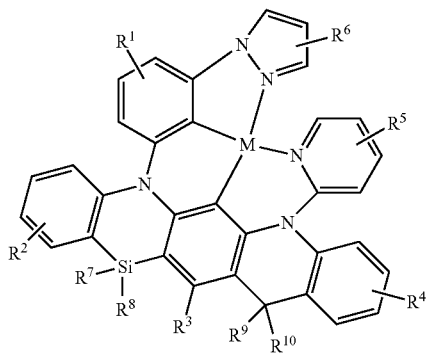
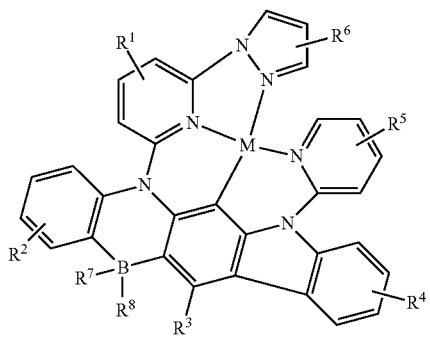
328
-continued
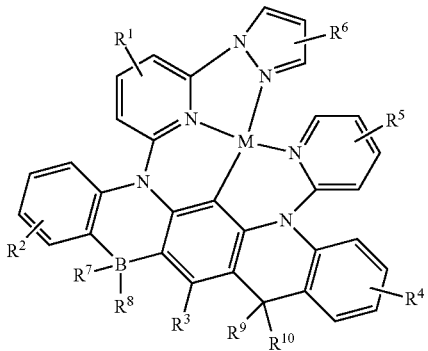
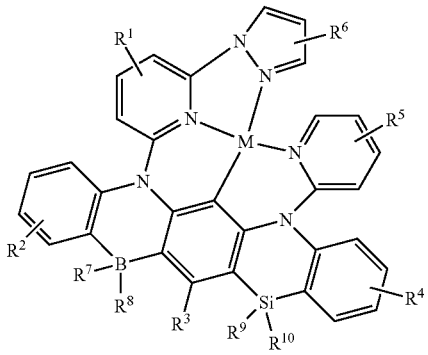
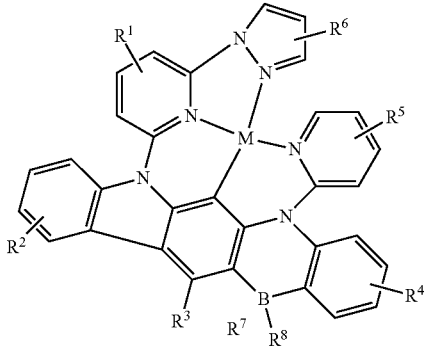
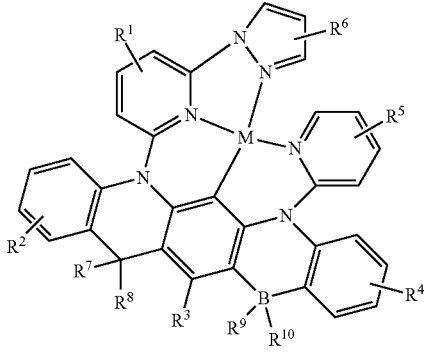

329
-continued
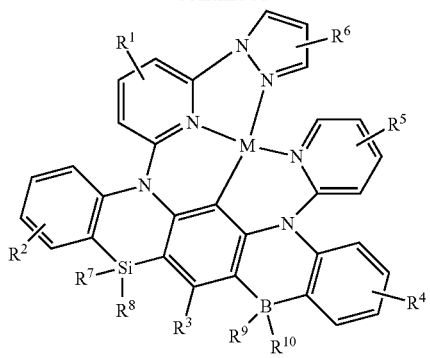
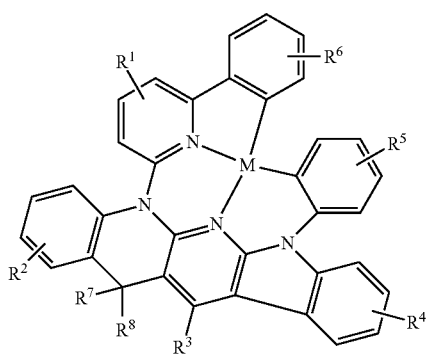
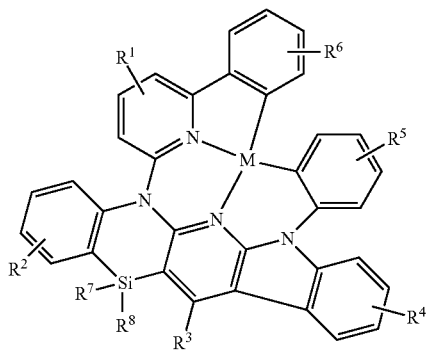
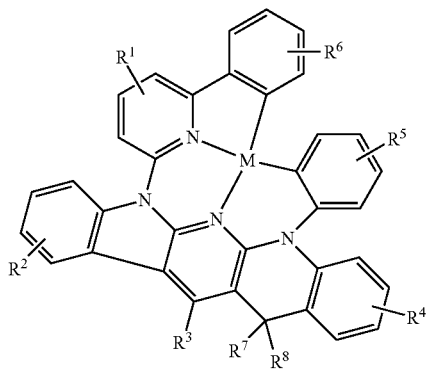
330
-continued
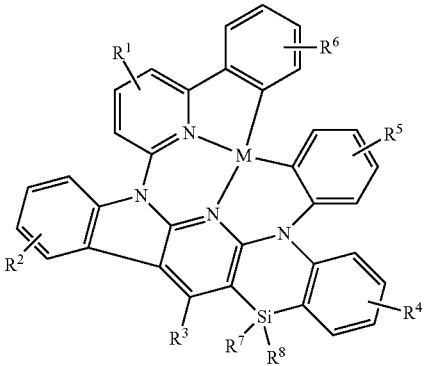
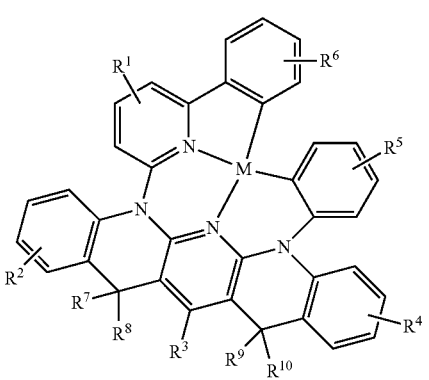
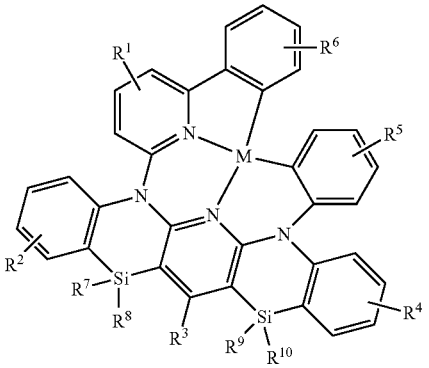
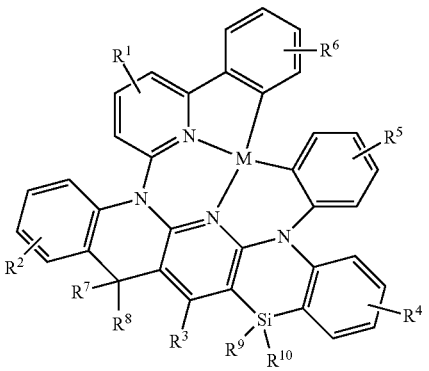

331
-continued
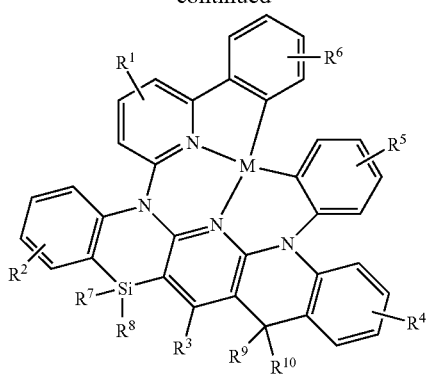
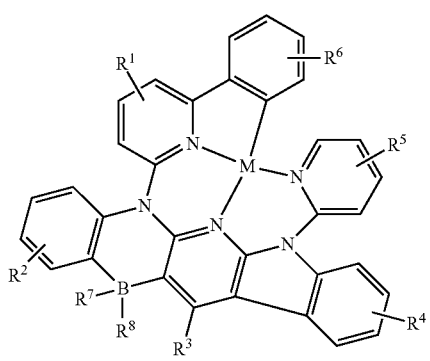
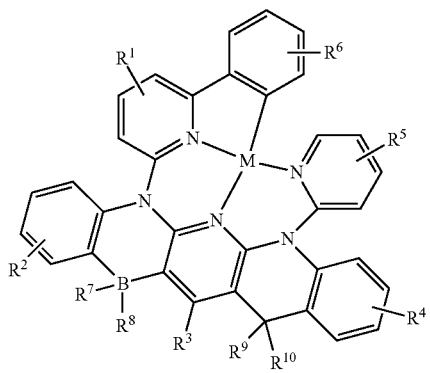
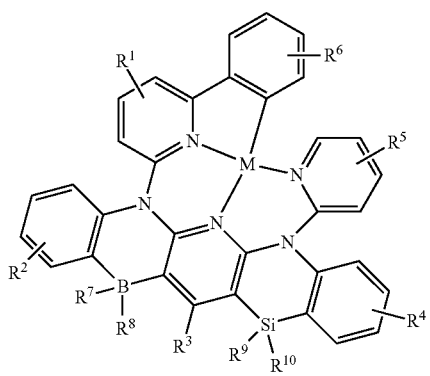
332
-continued
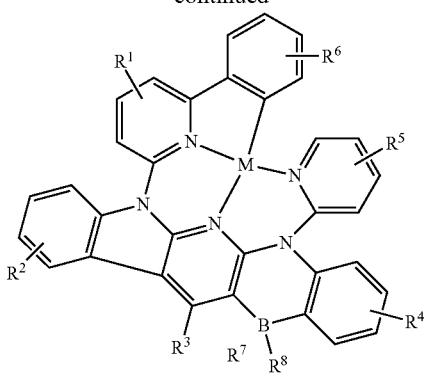
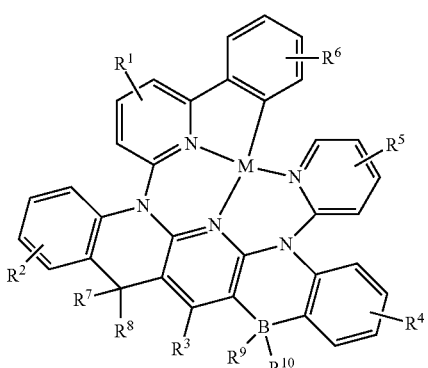
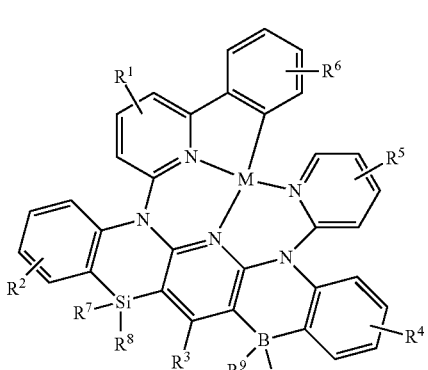
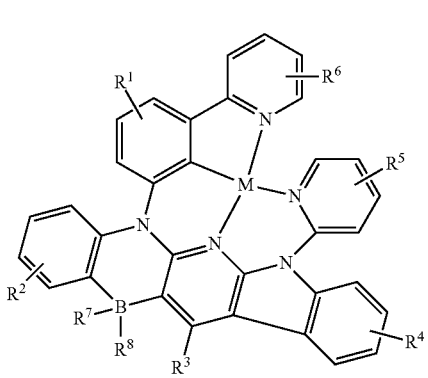

333
-continued
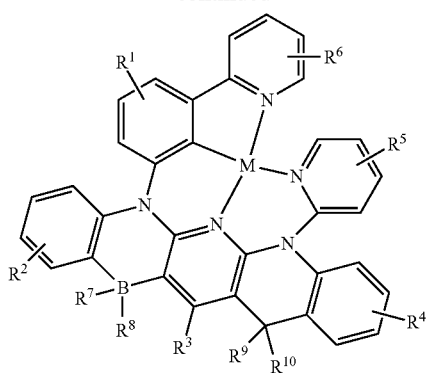
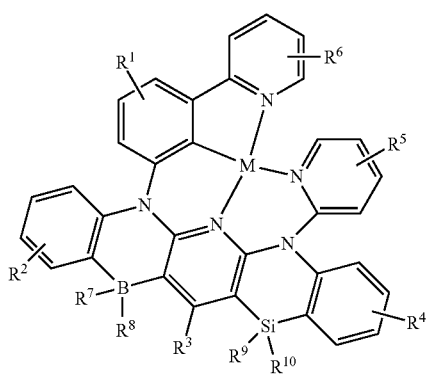
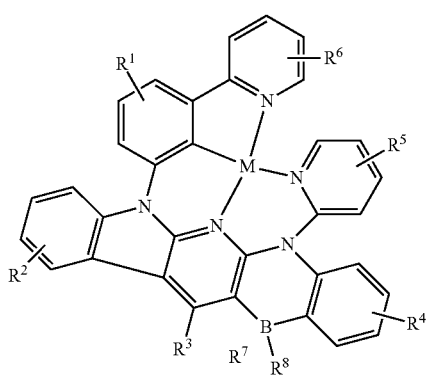
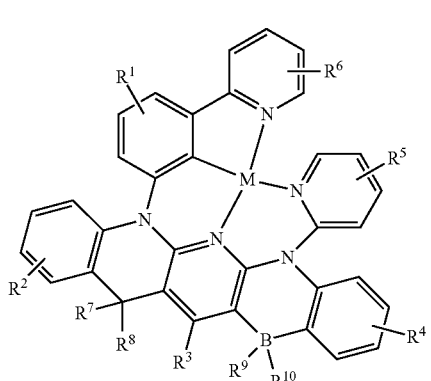
334
-continued
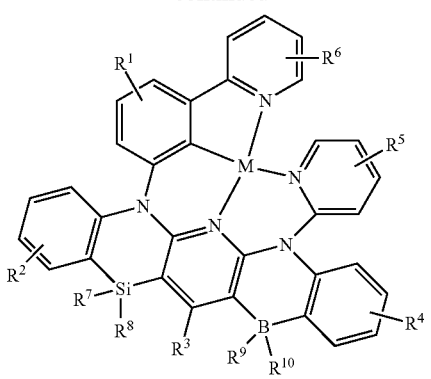
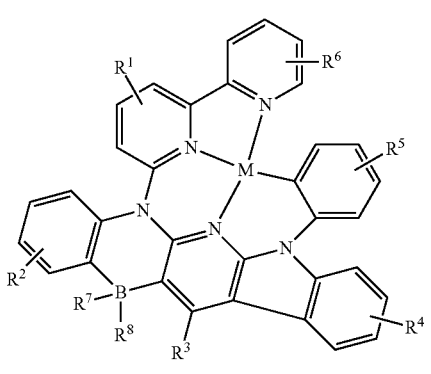
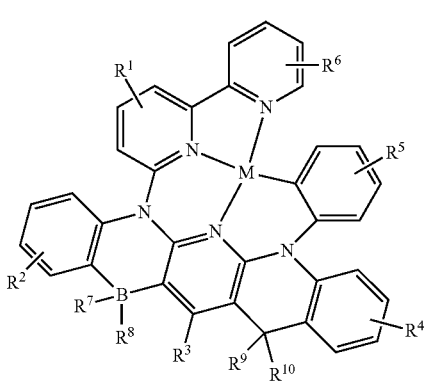
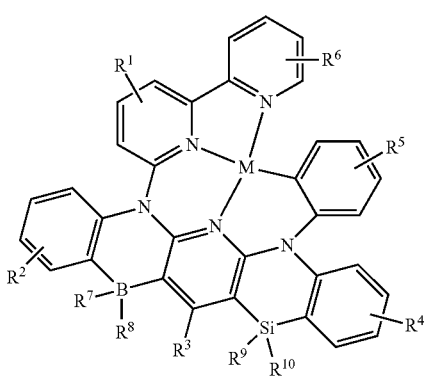

335
-continued
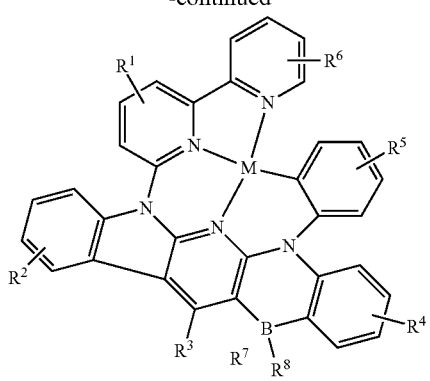
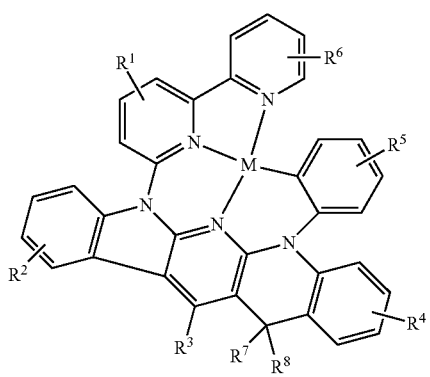
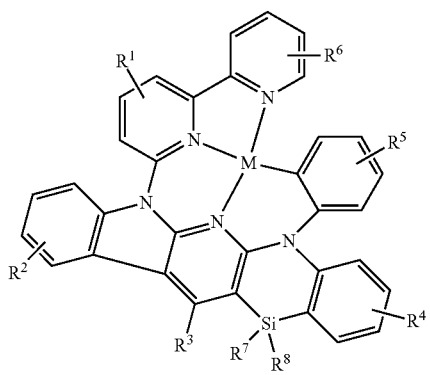
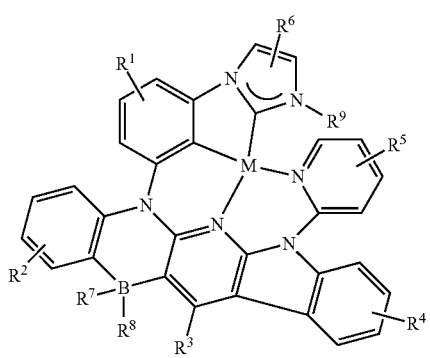
336
-continued
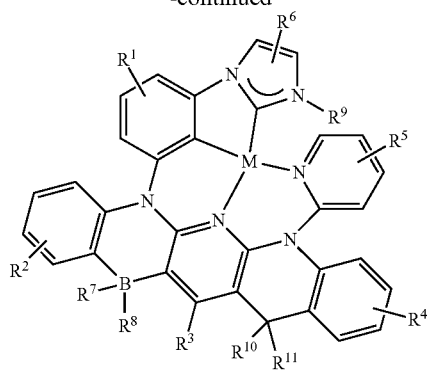
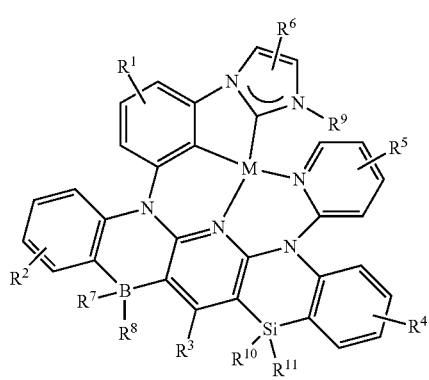
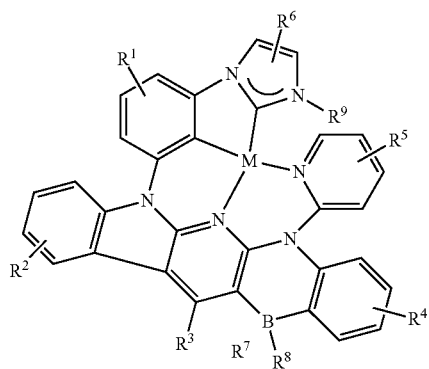
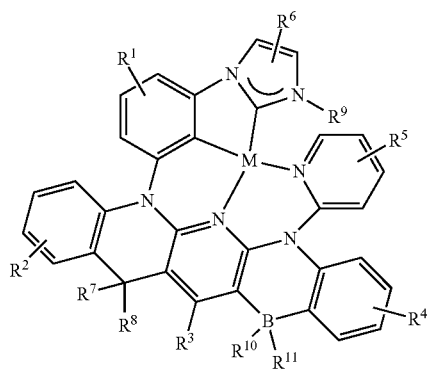

337
-continued
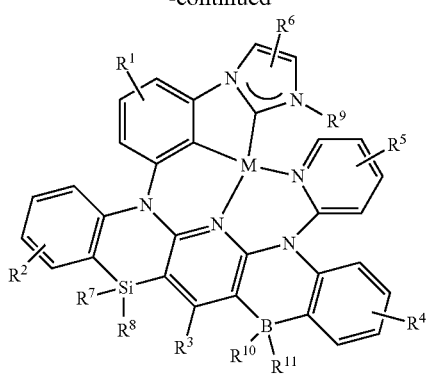
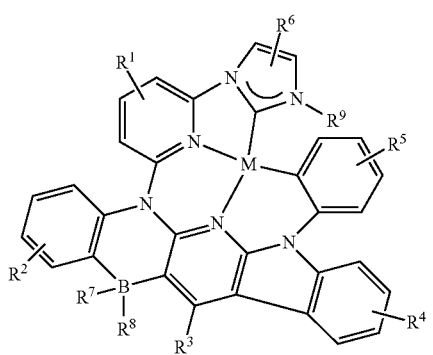
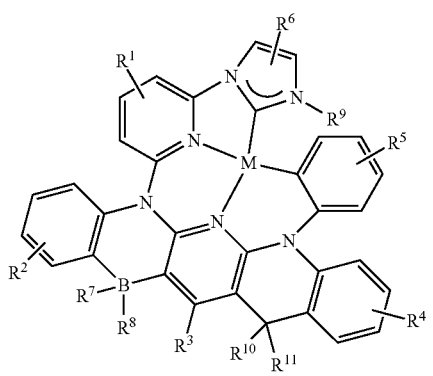
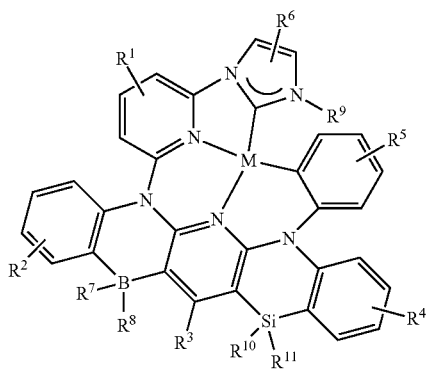
338
-continued
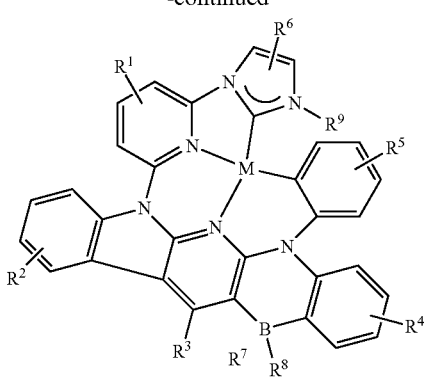
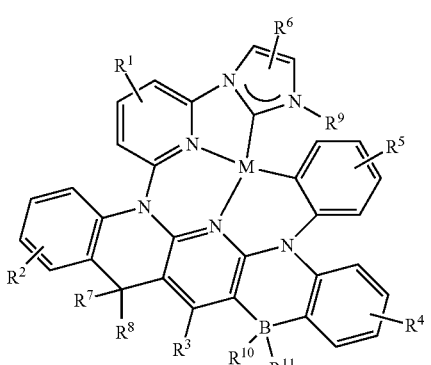
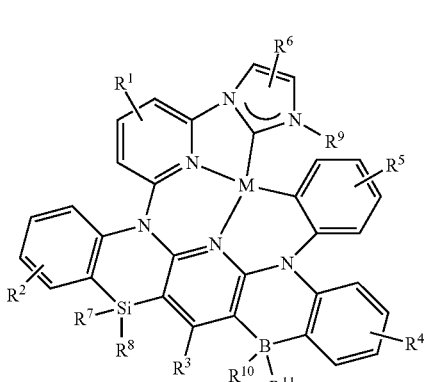
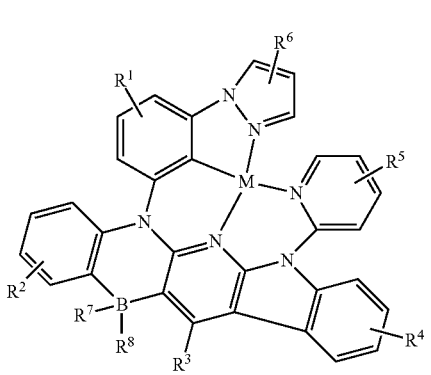

-continued
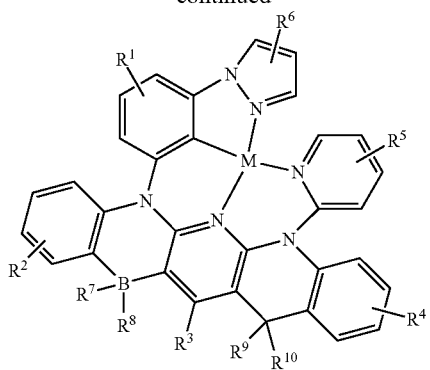
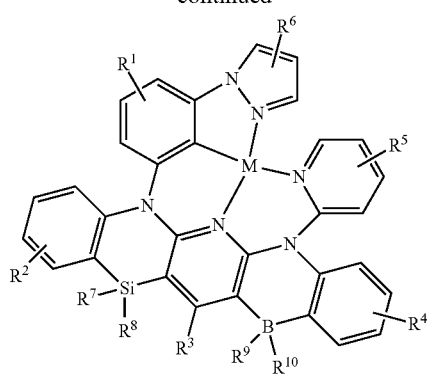
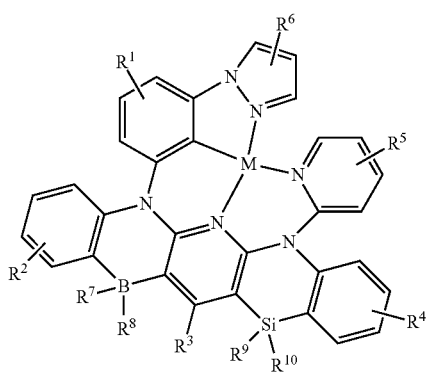
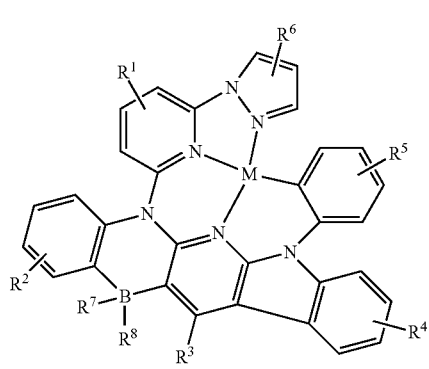
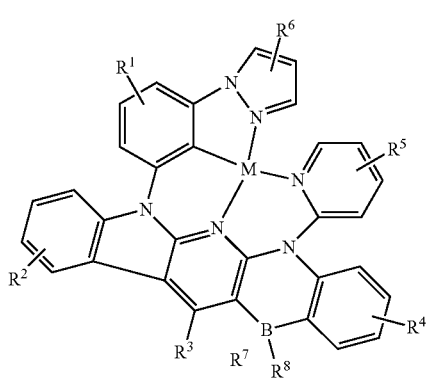
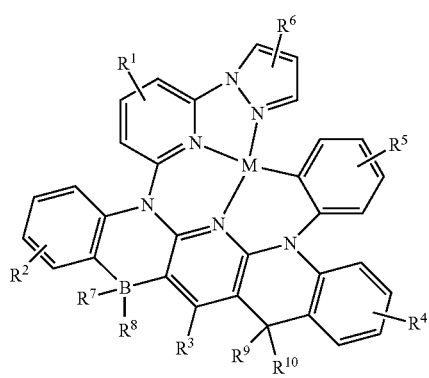
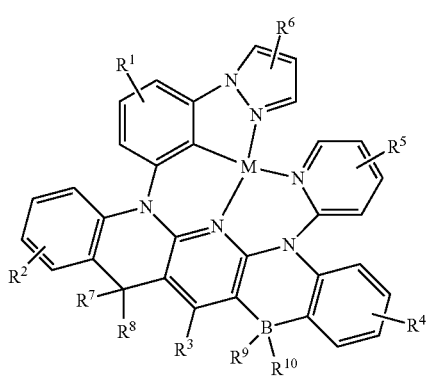
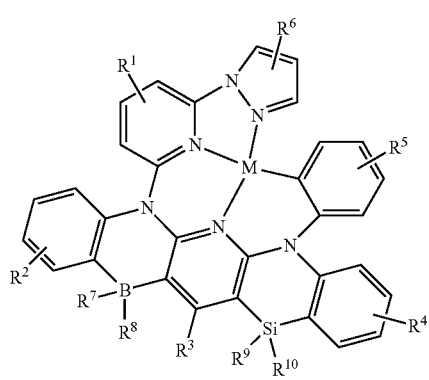

341
-continued
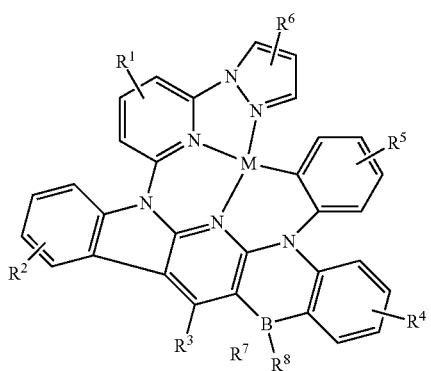
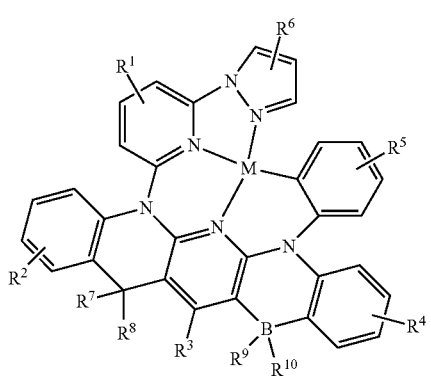
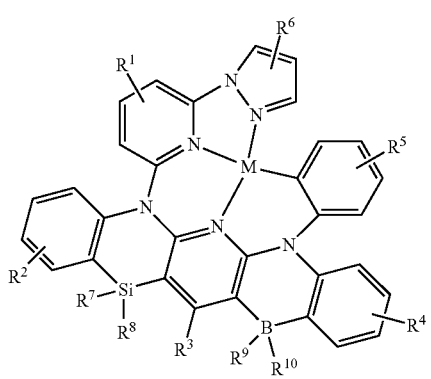
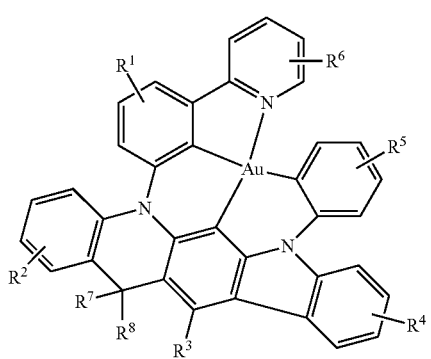
342
-continued
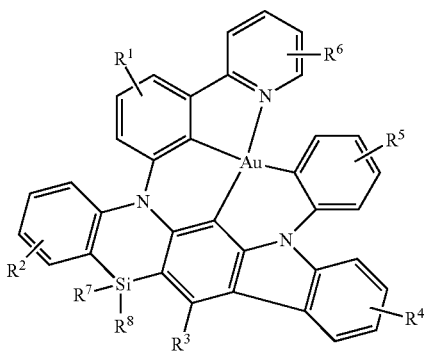
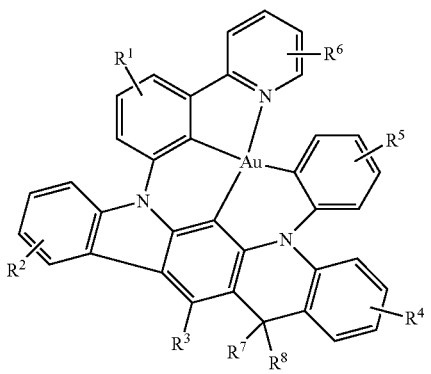
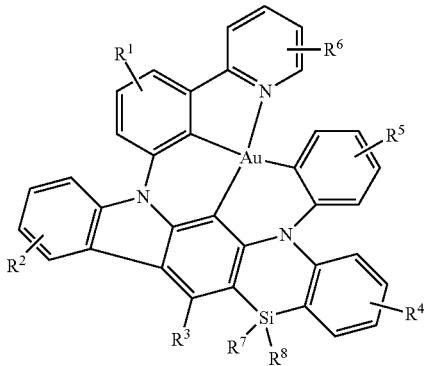
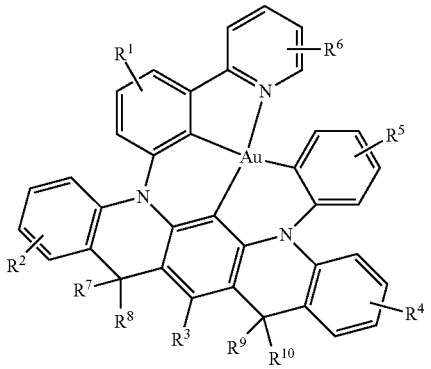

343
-continued
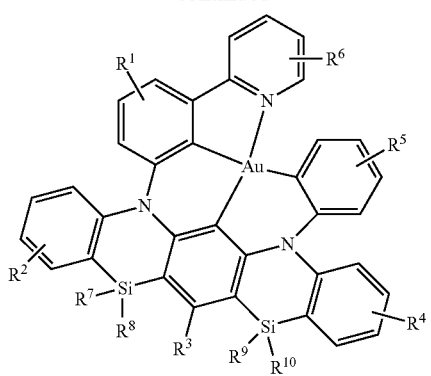
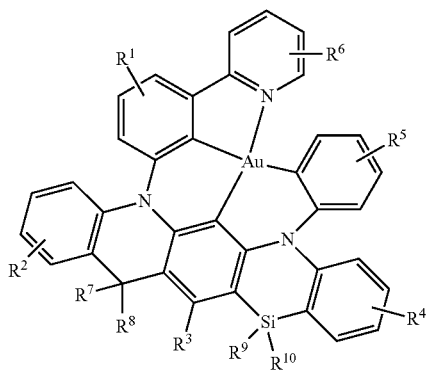
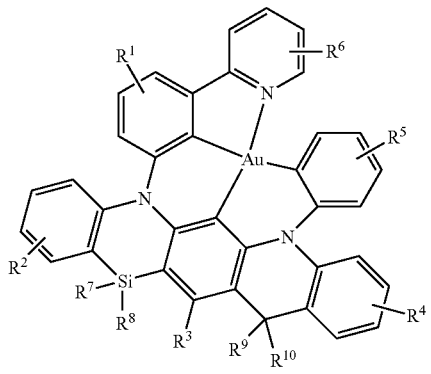
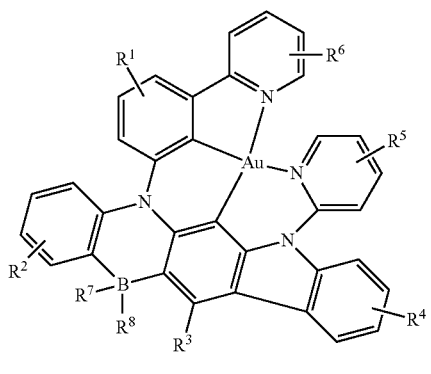
344
-continued
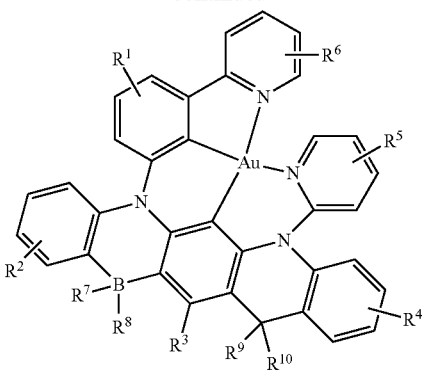
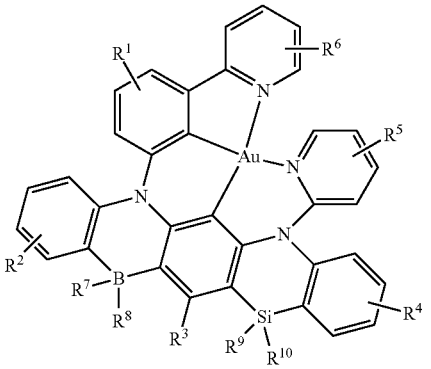
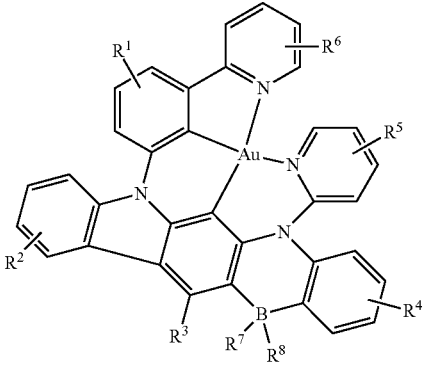
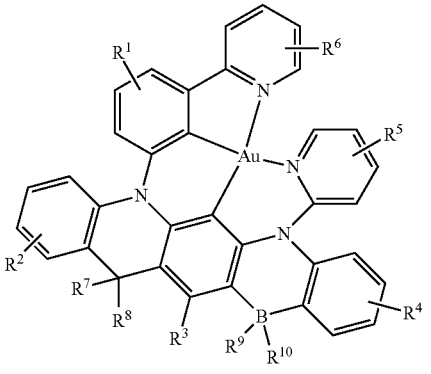

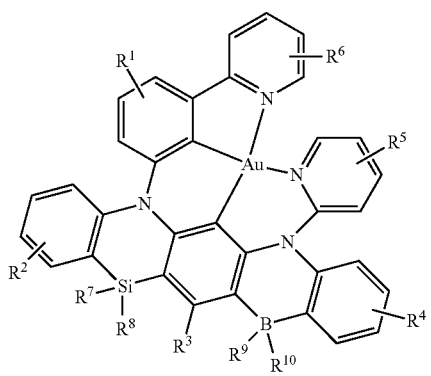
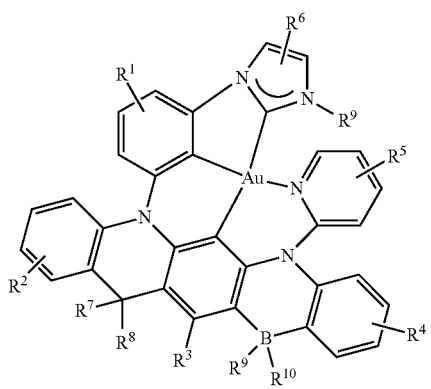
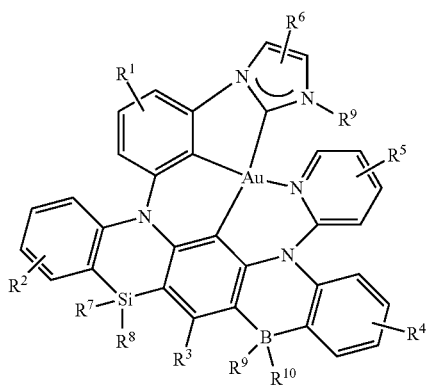
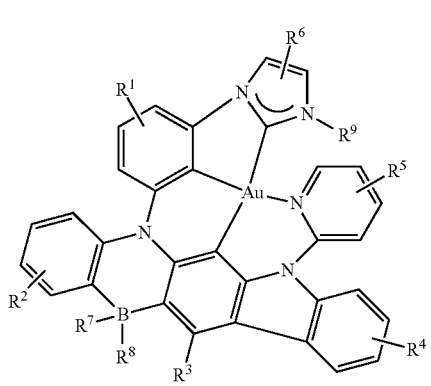
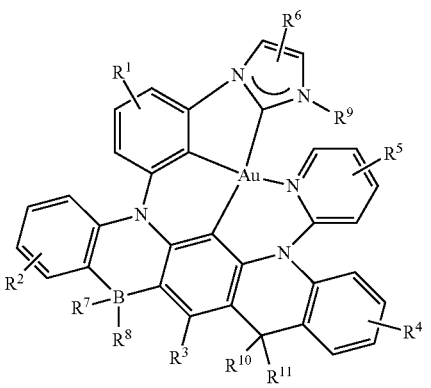
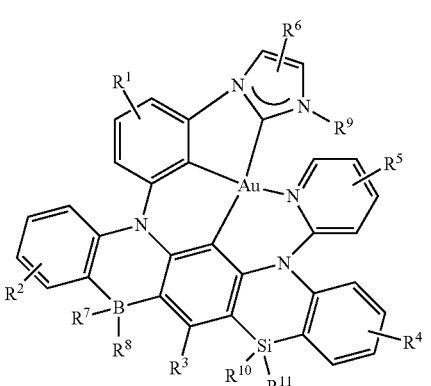
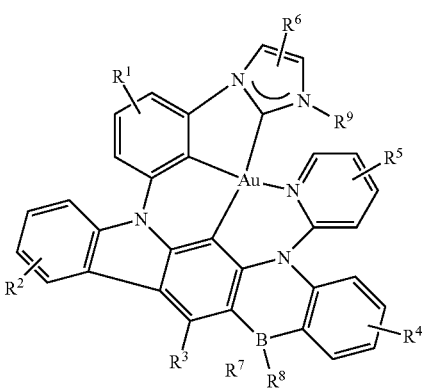
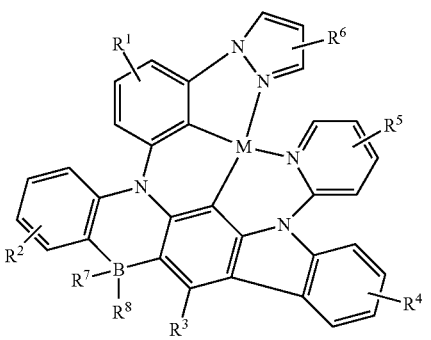

-continued
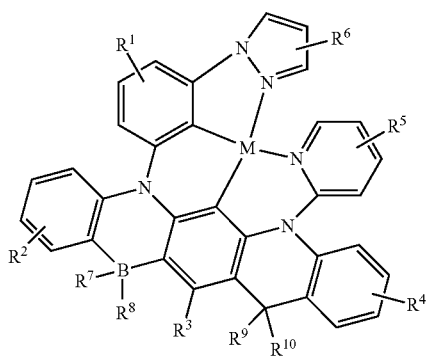
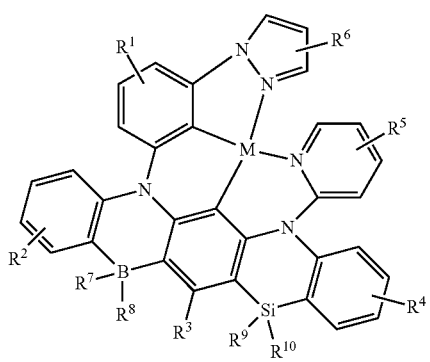
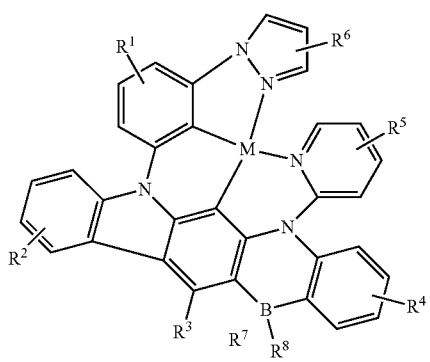
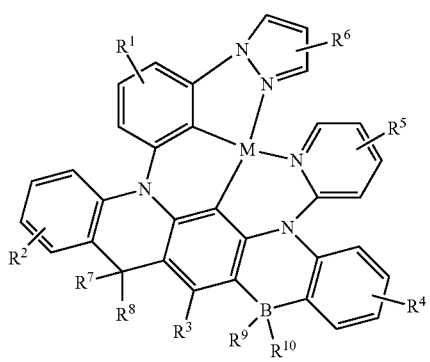
-continued
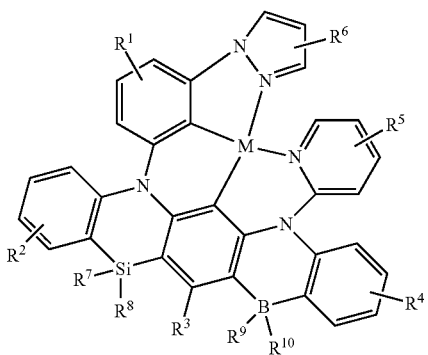
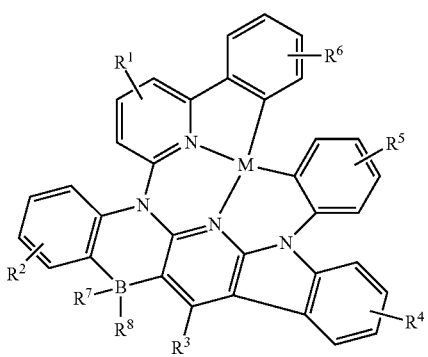
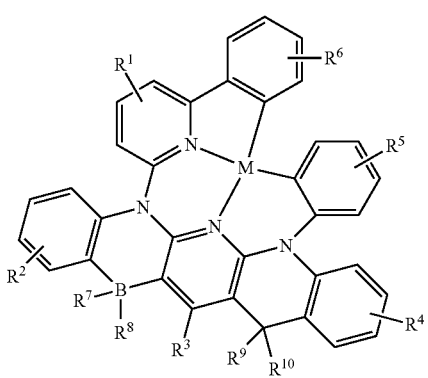
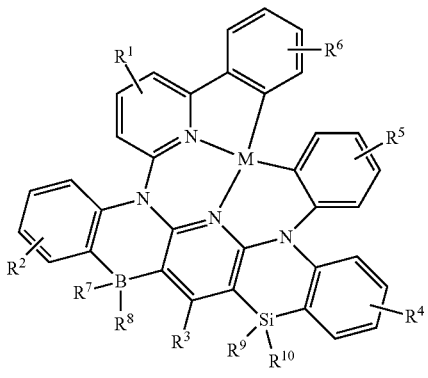

-continued

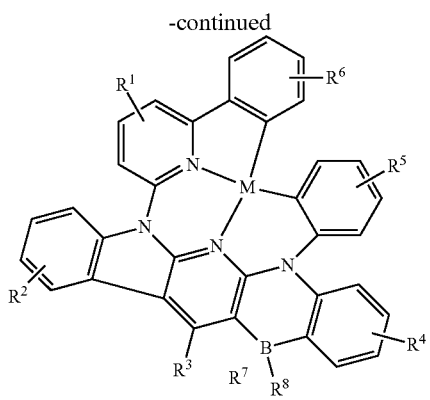

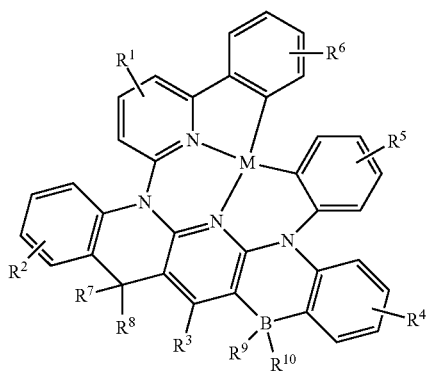

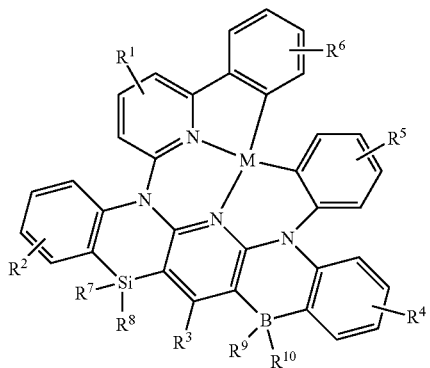

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4' diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane ($\delta$=0.00 ppm) as internal reference; $^{13}$C NMR spectra were recorded with CDCl$_3$ ($\delta$=77.00 ppm) as internal reference. If DMSO-d$_6$ was used as solvent, $^1$H NMR spectra were recorded with residual H$_2$O ($\delta$=3.33 ppm) as internal reference; $^{13}$C NMR spectra were recorded with DMSO-d$_6$ ($\delta$=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Example 1

Synthesis of PdN'—N3

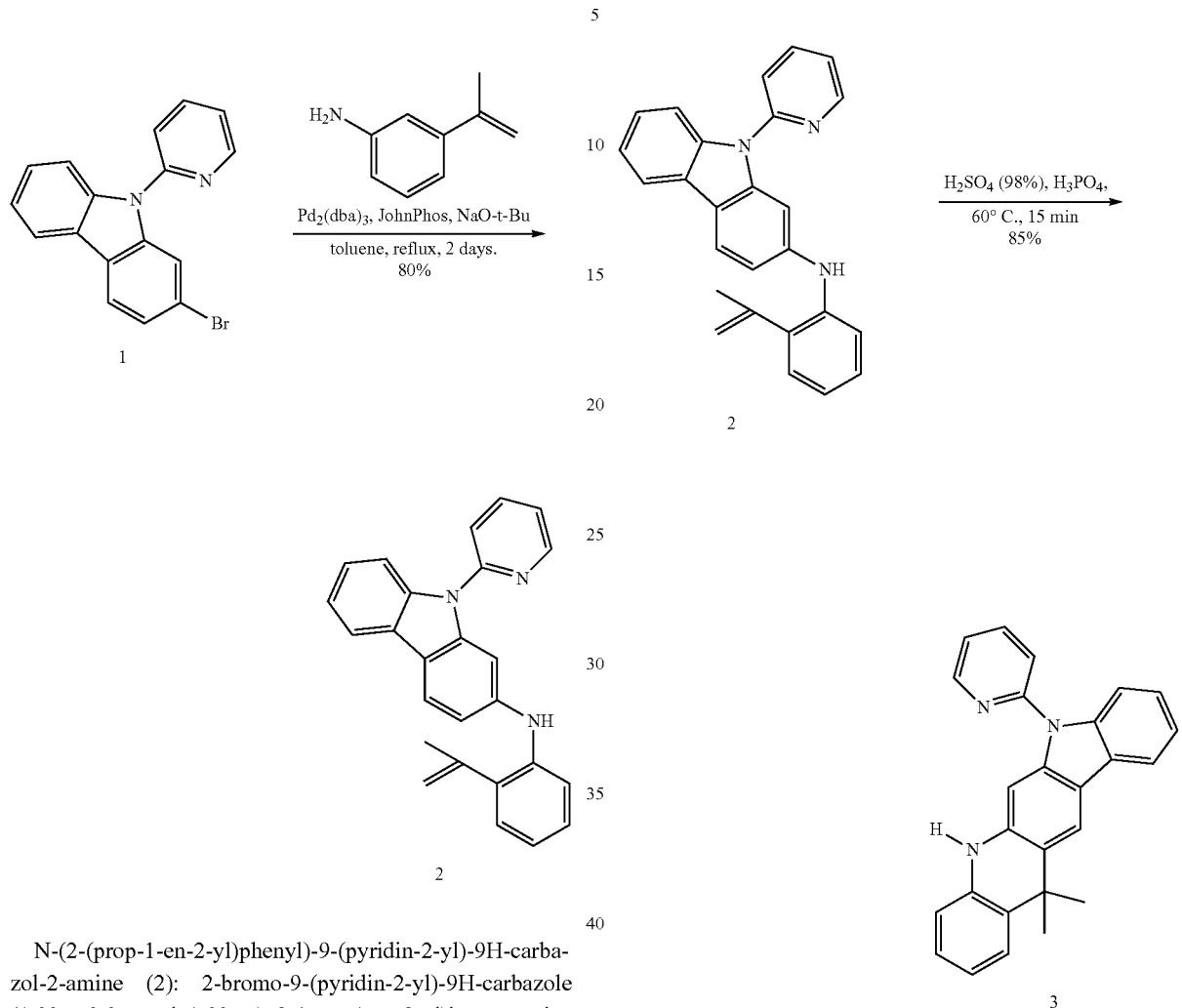

N-(2-(prop-1-en-2-yl)phenyl)-9-(pyridin-2-yl)-9H-carbazol-2-amine (2): 2-bromo-9-(pyridin-2-yl)-9H-carbazole (1.00 g, 3.0 mmol, 1.00 eq), 2-(prop-1-en-2-yl)benzenamine (0.48 g, 3.6 mmol, 1.20 eq), $Pd_2(dba)_3$ (0.14 g, 0.15 mmol, 0.05 eq), and (2-biphenyl)ditert-butylphosphine) (0.09 g, 0.3 mmol, 0.10 eq) was added to a dry pressure tube equipped with a magnetic stir bar. The tube was then taken into a glove box. t-BuONa (0.60 g, 6 mmol. 2.00 eq) and dry toluene (10 mL) were added. The mixture was bubbled with nitrogen for 10 minutes and then the tube was sealed. The tube was taken out of the glove box and heated to 95° C.-105° C. in an oil bath. The reaction was monitored by TLC and about 6 hours later the starting was consumed completely. Then the mixture was cooled to ambient temperature, diluted with ethyl acetate and washed with water. The organic phase was dried over sodium sulfate, then filtered and concentrated under vacuum. The residue was purified by silica gel column chromatography, using a mixture of hexanes and ethyl acetate as an eluent, in a ratio of 1:4 in volume and giving a white solid 0.80 g in yield of 70%. $^1$H NMR (400 MHz, $CDCl_3$): δ 8.69-8.68 (m, 1H), 8.10-8.07 (m, 1H), 8.02 (d, 1H, J=7.5 Hz), 7.96 (d, 1H, J=8.5 Hz), 7.71-7.67 (m, 1H), 7.58 (s, 1H), 7.46-7.44 (m, 1H), 7.32-7.21 (m, 6H), 7.02-6.99 (m, 1H), 6.95-6.93 (m, 1H), 5.11 (s, 1H), 5.02(s, 1H), 1.98 (s, 3H).

7,13-Dihydro-13,13-dimethyl-7-(pyridin-2-yl)-5H-indolo[3,2-b]acridine (3): N-(2-(prop-1-en-2-yl)phenyl)-9-(pyridin-2-yl)-9H-carbazol-2-amine (2) (1.00 g, 2.80 mmol) was added to a mixture of 98% concentrated sulfuric acid (5 mL) and phosphoric acid (5 mL) at 60° C. The resulting dark solution was stirred for 15 min, then cooled to room temperature and quenched with water. A white precipitate was formed and extracted with ethyl acetate. Then the organic phase was separated and dried over sodium sulfate, then filtered and the filtrate was concentrated under vacuum. The residue was purified by silica gel column chromatography using a mixture of ethyl acetate and hexane as an eluent in a ratio of 1:4 in volume, giving a white solid 0.75 g in a yield of 75%. $^1$H NMR ($CDCl_3$): δ, 9.12 (s, 1H), 8.76 (d, 1H, J=4.0 Hz), 8.22 (s, 1H), 8.15 (d, 1H J=3.5 Hz), 7.8 (d, 1H, J=9.0 Hz), 7.73 (d, 1H, J=9 Hz), 7.49-7.47 (m, 1H), 7.43-7.41 (m, 1H), 7.31-7.30 (m, 1H), 7.26-7.24 (m, 2H), 7.09-7.06 (m, 1H), 6.85-6.80 (m, 2H), 1.64 (m, 6H).

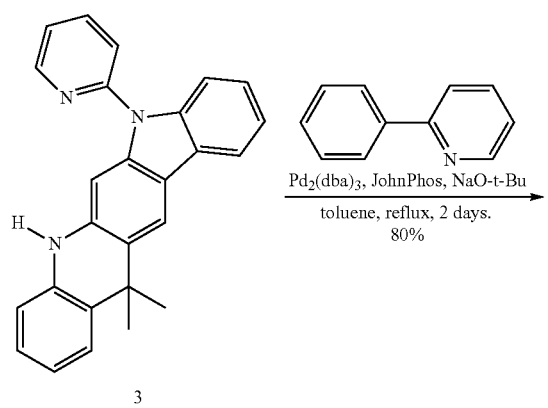

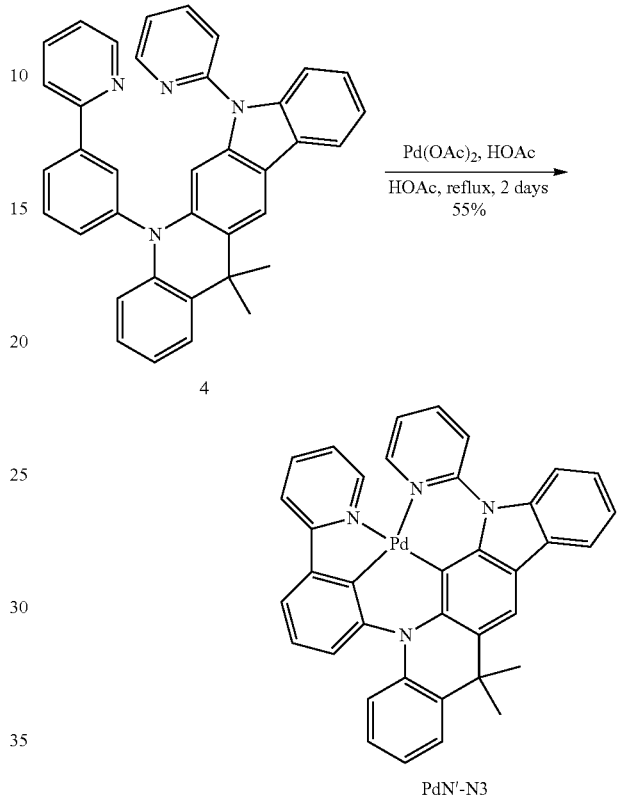

8.04 (d, 1H, J=6.4 Hz), 7.93-7.84 (m, 1H), 7.80-7.66 (m, 2H), 7.56-7.54 (m, 1H), 7.49-7.46 (m, 2H), 7.31-7.19 (m, 4H), 7.00-6.90 (m, 2H), 6.81 (s, 1H), 6.27 (d, 1H), 3.53 (s, 3H), 1.76 (s, 3H).

Figure 2:
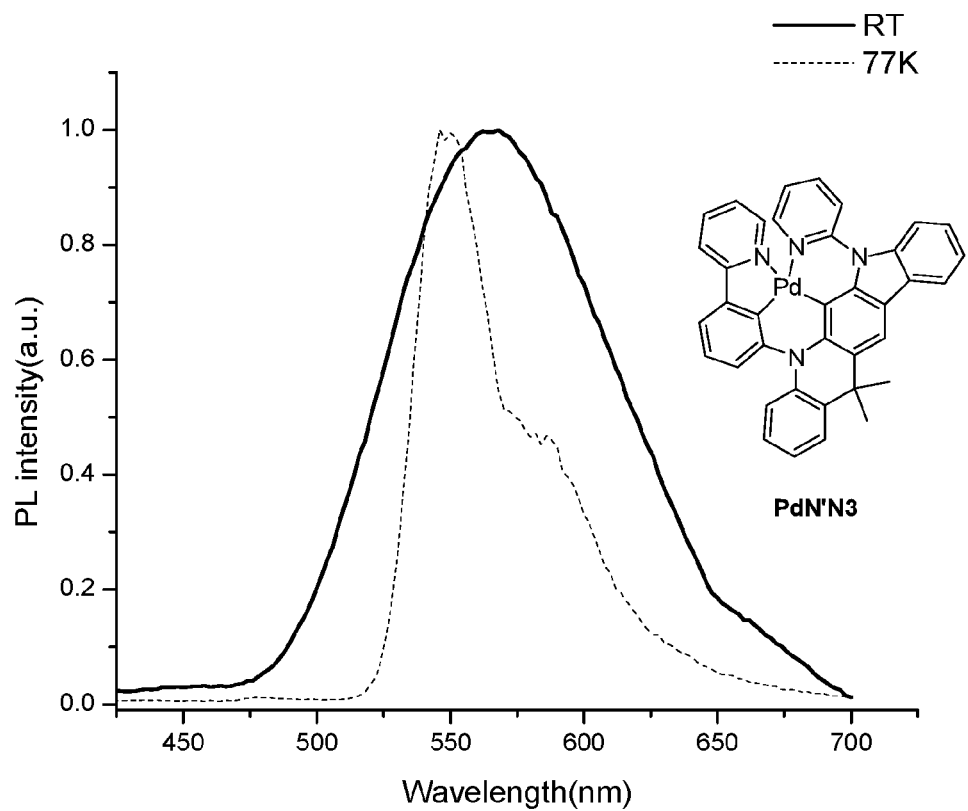
FIG. 2 shows an emission spectrum of PdN'N3 in $CH_2Cl_2$ at room temperature and in 2-methyltetrahydrofuran at 77K.

7,13-Dihydro-13,13-dimethyl-7-(pyridin-2-yl)-5-(3-(pyridin-2-yl)phenyl)-5H-indolo[3,2-b]acridine (4): 7,13-Dihydro-13,13-dimethyl-7-(pyridin-2-yl)-5H-indolo[3,2-b]acridine (3) (0.38 g, 1.00 mmol, 1.0 eq), 2-(3-bromophenyl)pyridine (0.30 g, 1.30 mmol, 1.30 eq), Pd$_2$(dba)$_3$ (0.05 g, 0.05 mmol, 0.05 eq), and (2-biphenyl)ditert-butylphosphine) (0.03 g, 0.10 mmol, 0.10 eq) was added to a dry pressure tube equipped with a magnetic stir bar. The tube was then taken into a glove box. t-BuONa (0.20 g, 2 mmol. 2.00 eq) and dry toluene (5 mL) was added. The mixture was bubbled with nitrogen for minutes and then the tube was sealed. The tube was taken out of the glove box and heated to 95° C.-105° C. in an oil bath. The reaction was monitored by TLC and about 6 hours later the starting was consumed completely. Then the mixture was cooled to ambient temperature, diluted with ethyl acetate and washed with water. The organic phase was dried over sodium sulfate, then filtered and concentrated under vacuum. The residue was purified by silica gel column chromatography, using a mixture of hexanes and ethyl acetate as an eluent, in a ratio of 1:4 in volume and gave the title compound as a white solid 0.30 g in yield of 53%. $^1$H NMR (400 MHz, CDCl$_3$):δ 8.64-8.63 (m, 1H), 8.33 (s, 1H), 8.30-8.29 (m, 1H), 8.27-8.25 (d, 1H, J=8.0 Hz), 8.15 (d, 1H J=6.8 Hz), 8.10 (s, 1H), PdN'—N3:7,13-Dihydro-13,13-dimethyl-7-(pyridin-2-yl)-5-(3-(pyridin-2-yl)phenyl)-5H-indolo[3,2-b]acridine (4) Ligand (50 mg, 0.1 mmol, 1.0 eq), Pd(OAc)$_2$ (22.30 mg, 0.10 mmol, 1.00 eq) and n-Bu$_4$NBr (3.20 mg, 0.01 mmol, 1.00 eq) were added to a dry pressure tube was then taken into a glove box and acetic acid (6 mL) was added. The mixture was bubbled with nitrogen for 30 minutes and then the tube was sealed. The tube was taken out of the glove box and the mixture was stirred at room temperature for 20 hours. Then the mixture was heated to 105° C.-115° C. in an oil bath and stirred at that temperature for 2 days, cooled to ambient temperature and water (30 mL) was added slowly. After stirring at room temperature for 10 minutes, the precipitate was filtered off and washed with water three times. Then the solid was purified through column chromatography on silica gel using dichloromethane as eluent to obtain to obtain the desired product, PdN'—N3 as a yellow solid 47 mg in 65% yield. FIG. 2 shows an emission spectrum of PdN'—N3 in CH$_2$Cl$_2$ at room temperature and in tetrahydro-2-methylfuran at 77K. $^1$H NMR (400 MHz, d$_6$-DMSO):δ 9.04 (d, 1H, J=5.2 Hz), 8.60 (d, 1H, J=4.4 Hz), 8.24 (d, 1H, J=8.4 Hz), 8.17 (d, 1H, J=7.2 Hz), 7.51-7.39 (m, 4H), 7.25-7.22 (m, 2H), 7.13-7.09 (m, 2H), 7.05-7.02 (m, 1H), 2.00 (s, 3H), 1.23(s, 3H).

Example 2

Synthesis of PtN'—N3

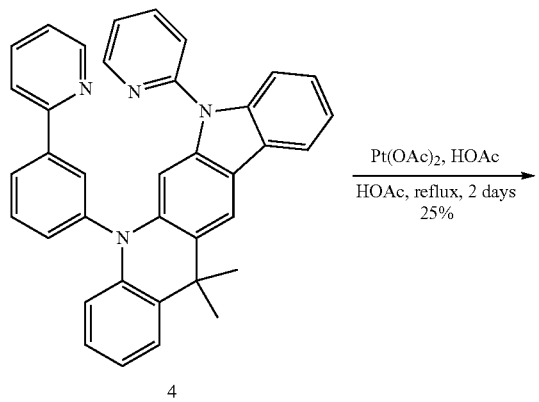

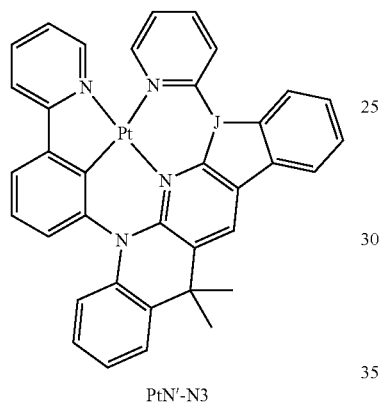

Figure 3:
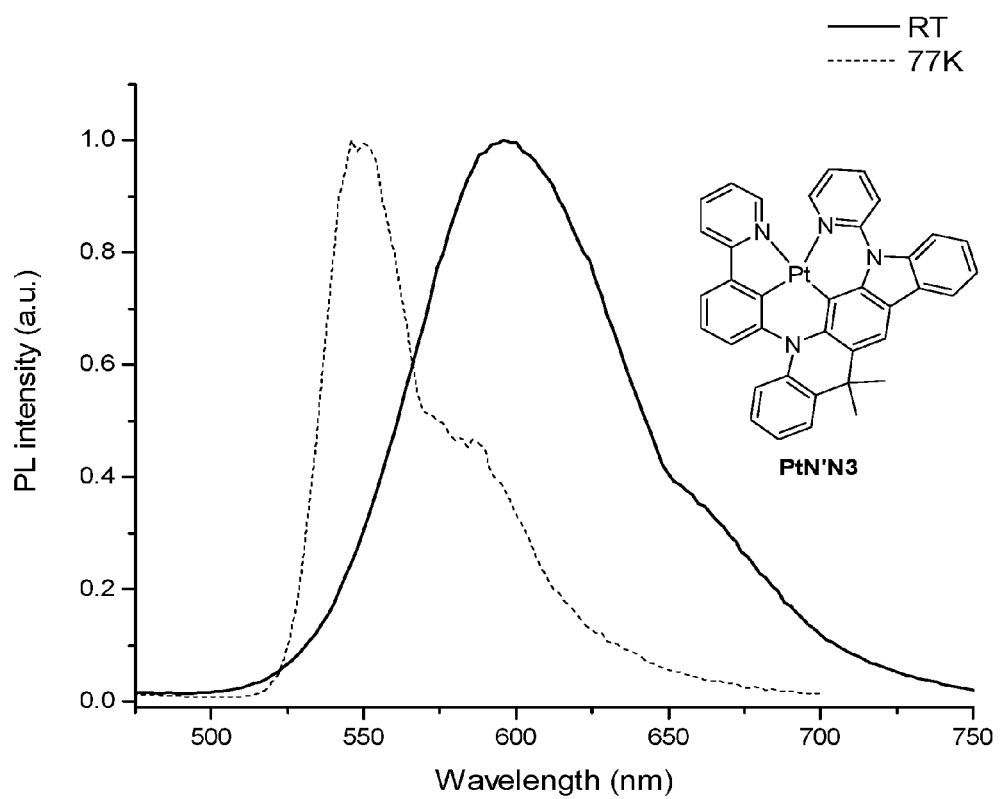
FIG. 3 shows an emission spectrum of PtN'N3 in $CH_2Cl_2$ at room temperature and in 2-methyltetrahydrofuran at 77K.

PtN'-N3   7,13-Dihydro-13,13-dimethyl-7-(pyridin-2-yl)-5-(3-(pyridin-2-yl)phenyl)-5H-indolo[3,2-b]acridine (4) Ligand (200 mg, 0.40 mmol, 1.0 eq), K$_2$PtCl$_4$ (167 mg, 0.40 mmol, 1.00 eq) and n-Bu$_4$NBr (13 mg, 0.04 mmol, 1.00 eq) were added to a dry pressure tube was then taken into a glove box and acetic acid (24 mL) was added. The mixture was bubbled with nitrogen for 30 minutes and then the tube was sealed. The tube was taken out of the glove box and the mixture was stirred at room temperature for 20 hours. Then the mixture was heated to 105° C.-115° C. in an oil bath and stirred at that temperature for 2 days, cooled to ambient temperature and water (30 mL) was added slowly. After stirring at room temperature for 10 minutes, the precipitate was filtered off and washed with water three times. Then the solid was purified through column chromatography on silica gel using dichloromethane as eluent to obtain to obtain the desired product, PtN'N3, as a yellow solid 85 mg in 25% yield. The product (60 mg) was further purified by sublimation in a sublimator, giving a red solid 15 mg. FIG. 3 shows an emission spectrum of PtN'—N3 in CH$_2$Cl$_2$ at room temperature and in 2-methyl tetrahydrofuran at 77K. $^1$H NMR (400 MHz, d$_6$-DMSO):δ 9.04 (d, 1H, J=4.4 Hz), 8.64 (d, 1H, J=5.2 Hz), 8.04 (d, 1H, J=6.6 Hz), 7.94-7.92 (m, 1H), 7.87 (d, 1H, J=8.0 Hz), 7.80-7.73 (m, 3H), 7.69 (s, 1H), 7.44-7.33 (m, 5H), 7.34-7.31 (m, 4H), 7.04-6.93 (m, 4H), 1.96 (s, 3H), 1.42 (s, 9H).

Example 3

Synthesis of PtN—N'N-tBu

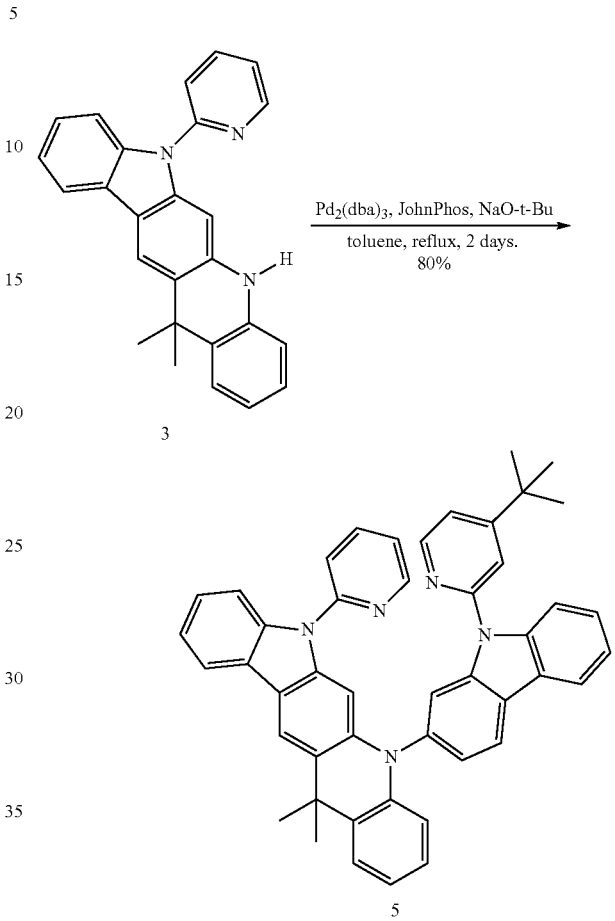

5-(9-(4-Tert-butylpyridin-2-yl)-9H-carbazol-2-yl)-7,13-dihydro-13,13-dimethyl-7-(pyridin-2-yl)-5H-indolo[3,2-b]acridine (5):7,13-Dihydro-13,13-dimethyl-7-(pyridin-2-yl)-5H-indolo[3,2-b]acridine (3): (0.30 g, 0.80 mmol, 1.00 eq), 9-(4-tert-butylpyridin-2-yl)-2-bromo-9H-carbazole (0.30 g, 0.80 mmol, 1.0 eq), Pd$_2$(dba)$_3$ (40 mg, 0.004 mmol, 0.05 eq), and (2-biphenyl)ditert-butylphosphine) (24 mg, 0.08 mmol, 0.10 eq) was added to a dry pressure tube equipped with a magnetic stir bar. The tube was then taken into a glove box. t-BuONa (0.20 g, 6 mmol. 2.00 eq) and dry toluene (4 mL) was added. The mixture was bubbled with nitrogen for minutes and then the tube was sealed. The tube was taken out of the glove box and heated to 95° C.-105° C. in an oil bath. The reaction was monitored by TLC and about 6 hours later the starting was consumed completely. Then the mixture was cooled to ambient temperature and diluted with ethyl acetate and washed with water. The organic phase was dried over sodium sulfate, then filtered and concentrated under vacuum. The residue was purified by silica gel column chromatography, using a mixture of hexanes and ethyl acetate as an eluent, in a ratio of 1:4 in volume and gave the title compound as a white solid 0.30 g in yield of 63%. $^1$H NMR (400 MHz, d$_6$-DMSO):δ 8.56-8.53 (m, 1H), 8.38-8.35 (m, 1H), 8.24-8.18 (m, 1H), 7.83-7.80 (m, 1H), 7.72-7.50 (m, 2H), 7.43-7.36 (m, 2H), 7.15-7.7.12 (m, 1H), 6.96-6.92 (m, 2H), 7.25-7.19 (m, 2H), 6.99-6.92 (m, 2H), 6.84-6.82 (m, 1H), 2.05 (s, 3H), 1.76 (s, 6H), 1.23 (s, 9H).

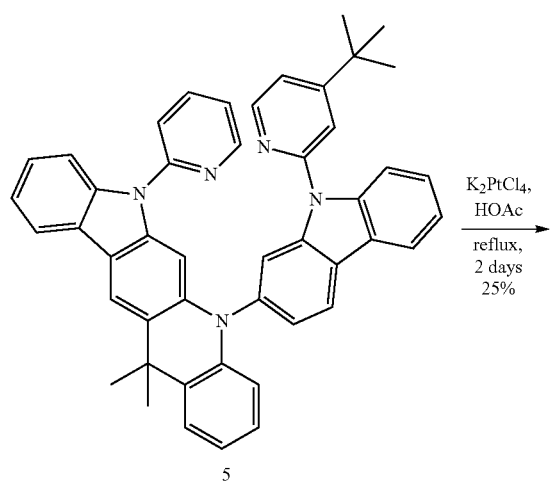

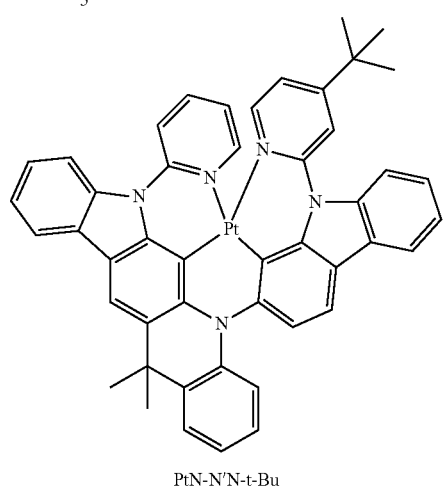

PtN-N'N-t-Bu

Figure 4:
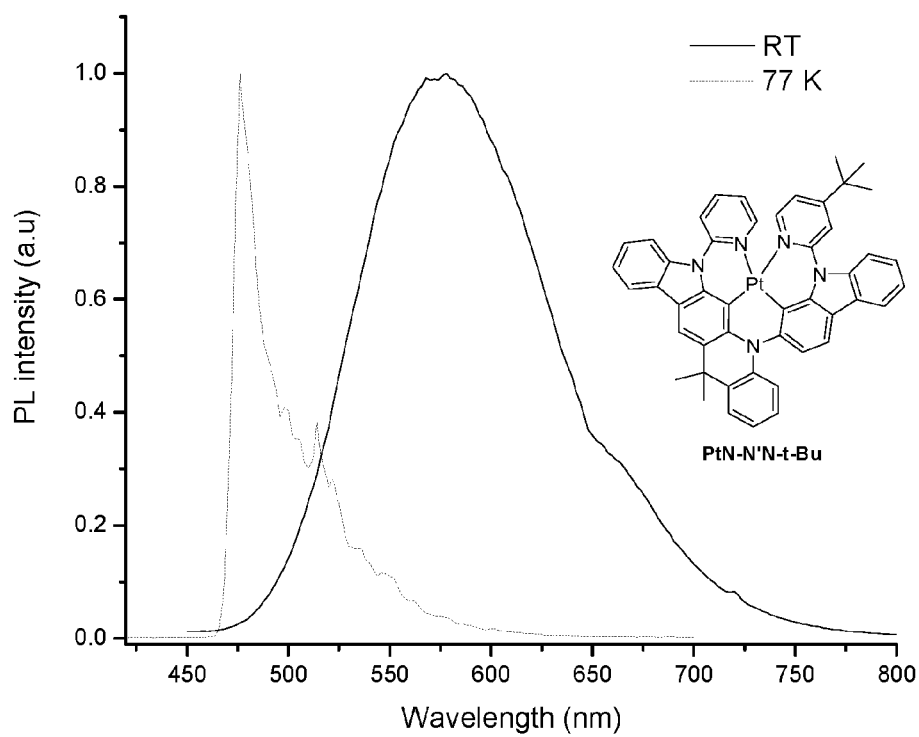
FIG. 4 shows an emission spectrum of PtN—N'N-t-Bu in $CH_2Cl_2$ at room temperature and in 2-methyltetrahydrofuran at 77K.

PtN—N'N-t-Bu: 5-(9-(4-Tert-butylpyridin-2-yl)-9H-carbazol-2-yl)-7,13-dihydro-13,13-dimethyl-7-(pyridin-2-yl)-5H-indolo[3,2-b]acridine (5): Ligand (250 mg, 0.40 mmol, 1.00 eq), $K_2PtCl_4$ (167 mg, 0.40 mmol, 1.00 eq) and n-$Bu_4NBr$ (13 mg, 0.04 mmol, 1.0 eq) were added to a dry pressure tube. The tube was then taken into a glove box and acetic acid (24 mL) was added. The mixture was bubbled with nitrogen for 30 minutes and then the tube was sealed. The tube was taken out of the glove box and the mixture was stirred at room temperature for 20 hours. Then the mixture was heated to 105° C.-115° C. in an oil bath and stirred at that temperature for 2 days, cooled to ambient temperature and water (30 mL) was added slowly. After stirring at room temperature for 10 minutes, the precipitate was filtered off and washed with water three times. Then the solid was purified through column chromatography on silica gel using dichloromethane as eluent to obtain to obtain the desired product, PtN—N'N-t-Bu, as a yellow solid 80 mg in 25% yield. FIG. 4 shows an emission spectrum of PtN—N'N-t-Bu in $CH_2Cl_2$ at room temperature and in tetrahydro-2-methylfuran at 77K. $^1$H NMR (400 MHz, $d_6$-DMSO):δ 8.90 (d, 1H, J=6.4 Hz), 8.18-8.16 (d, 1H, J=8.0 Hz), 8.14-8.07 (m, 4H), 8.04 (m, 1H), 8.01-7.99 (d, 1H, J=8.0 Hz), 7.90 (s, 1H), 7.53-7.49 (m, 1H), 7.44-7.33 (m, 5H), 7.25-7.19 (m, 2H), 6.99-6.92 (m, 2H), 6.84-6.82 (m, 1H), 2.05 (s, 3H), 1.36 (s, 3H), 1.34 (s, 9H).

Example 4

Synthesis of PtN'—NN

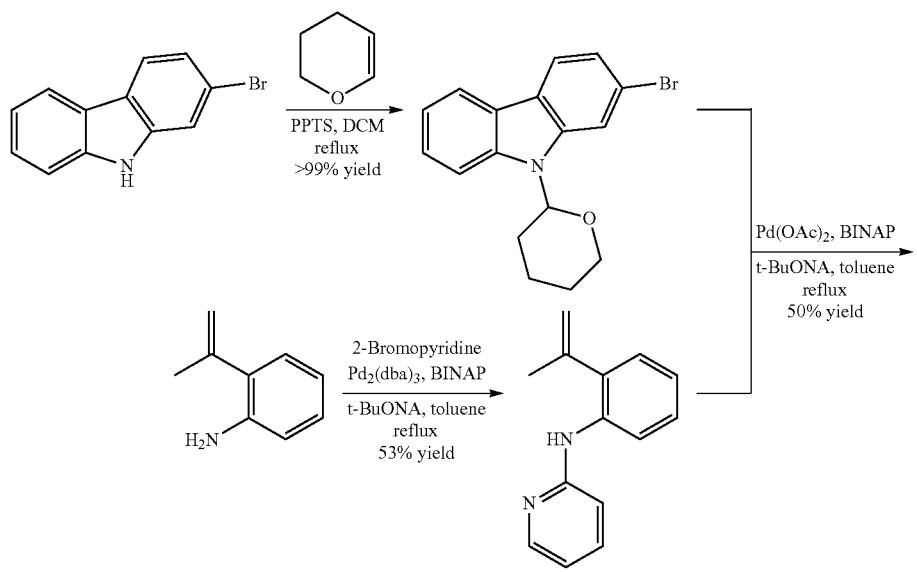

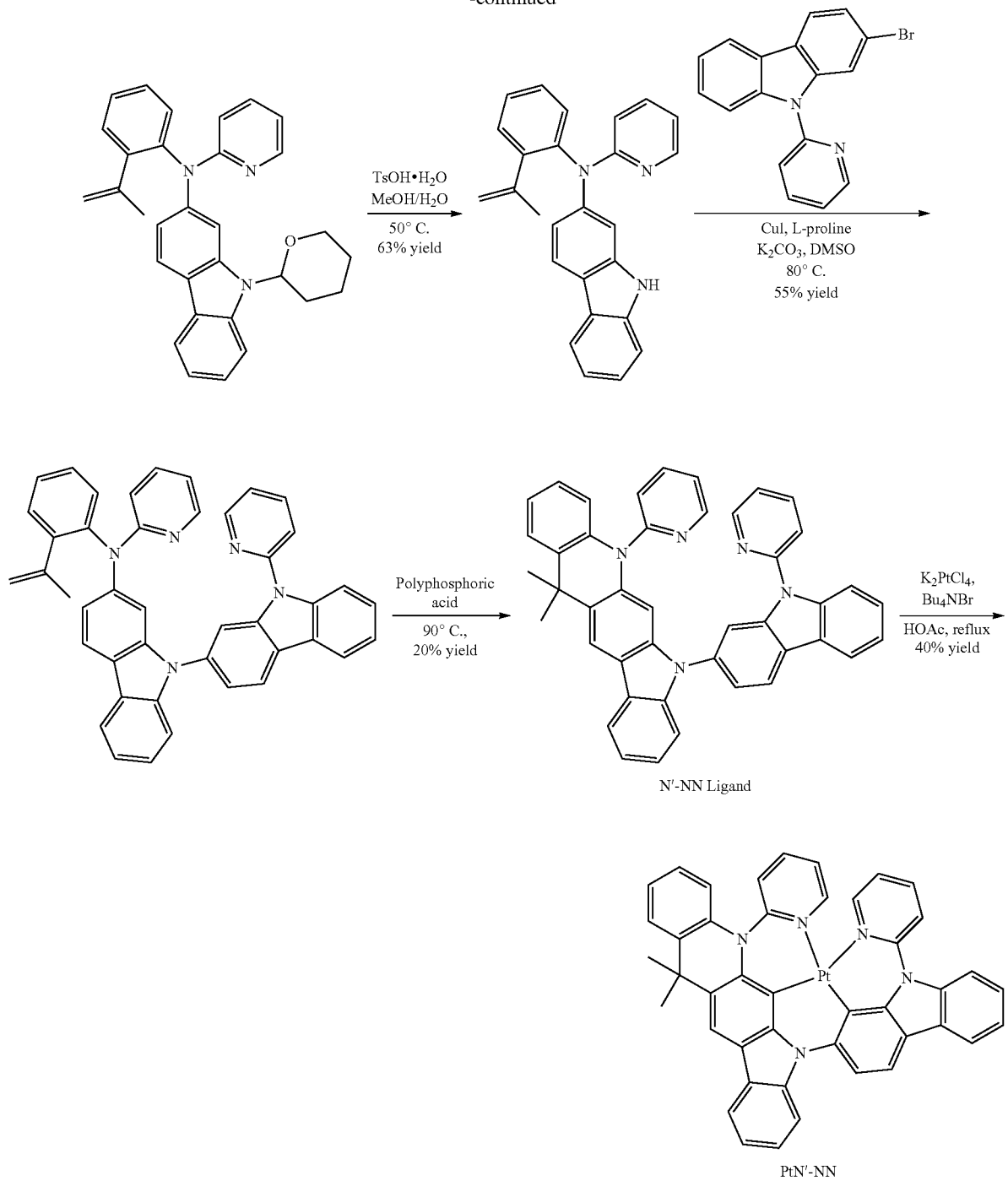

Figure 5:
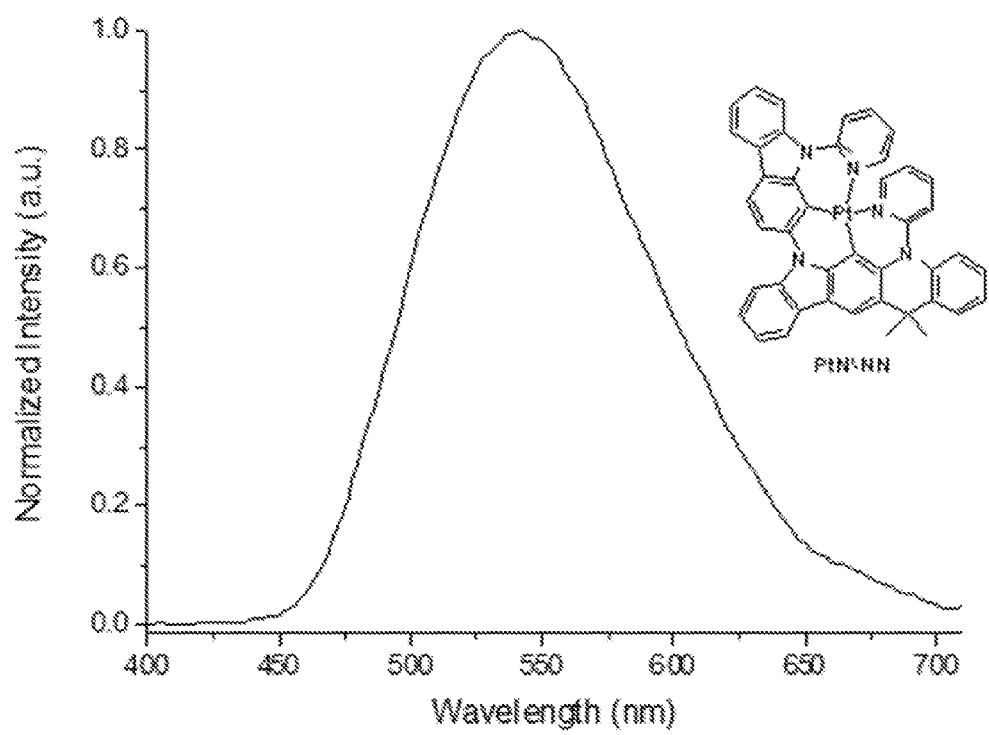
FIG. 5 shows a room temperature emission spectrum of PtN'—NN in a solution of dichloromethane.

PtN'—NN: To a solution of N'—NN ligand (34 mg, 0.055 mmol) in HOAc (5 mL, 0.011 M) were added K₂PtCl₄ (25 mg, 0.0605 mmol) and n-Bu₄NBr (2 mg, 0.0055 mmol). The mixture was heated to reflux and maintained at this temperature for 2 days. The reaction mixture was cooled to room temperature and filtered through a short pad of silica gel. The filtrate was concentrated under reduced pressure. Purification by column chromatography (hexanes:DCM=1:1 to 1:2) gave the PtN'—NN (18 mg, 0.0222 mmol, yield: 40%) as a yellow solid. $^1$H NMR (400 MHz, DMSO-$d_6$, δ): 8.99 (d, J=5.9 Hz, 1 H), 8.79 (dd, J=6.1, 1.4 Hz, 1 H), 8.32-8.19 (m, 5 H), 8.16-8.10 (m, 2 H), 8.07 (d, J=8.4 Hz, 1 H), 8.01 (s, 1 H), 7.99-7.94 (m, 1 H), 7.65-7.59 (m, 1 H), 7.57-7.38 (m, 5 H), 7.38-7.32 (m, 1 H), 7.31-7.23 (m, 3 H), 7.18-7.13 (m, 1 H), 2.12 (s, 3 H), 1.40 (s, 3 H). FIG. 5 shows a room temperature emission spectrum of PtN'—NN in a solution of dichloromethane. $^1$H NMR (400 MHz, DMSO-$d_6$, δ): 8.73-8.68 (m, 1H), 8.43 (d, J=8.2 Hz, 1H), 8.39 (s, 1H), 8.37-8.30 (m, 2H), 8.25 (d, J=7.8 Hz, 1H), 8.14 (td, J=7.8, 1.9 Hz, 1H), 7.90-7.84 (m, 2H), 7.82-7.74 (m, 2 H), 7.60-7.19 (m, 10 H), 7.09-6.98 (m, 2 H), 6.70 (s, 1 H), 6.56-6.49 (m, 1 H), 1.73 (s, 6 H).

Example 5

Synthesis of PtN′—N′N

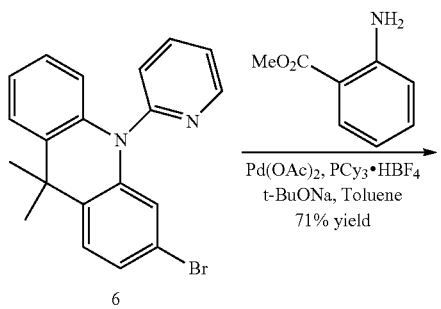

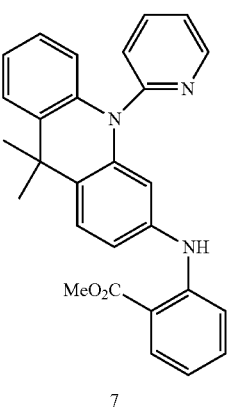

To a solution of 6 (1.205 g, 3.3 mmol) in toluene (20 mL, 0.165 M) were added methyl 2-aminobenzoate (598 mg, 3.96 mmol), Pd(OAc)₂ (74 mg, 0.33 mmol), ligand (122 mg, 0.33 mmol) and t-BuONa (476 mg, 4.95 mmol). The reaction mixture was heated to reflux for 2 days. The mixture was cooled to rt and filtered through a short pad of Celite. The filtrate was concentrated under reduced pressure. Purification by column chromatography (hexanes:EtOAc) gave 7 (1.02 g, yield: 71%) as a light yellow solid. ¹H NMR (500 MHz, DMSO-d₆, δ): 9.16 (s, 1H), 8.71 (m, 1 H), 8.05 (td, J=7.7, 2.0 Hz, 1H), 7.83 (dd, J=8.0, 1.6 Hz, 1H), 7.51 (dd, J=7.7, 1.6 Hz, 1H), 7.49-7.44 (m, 3 H), 7.33 (m, 1 H), 7.11 (d, J=8.4 Hz, 1 H), 7.07-6.97 (m, 2 H), 6.86 (dd, J=8.4, 2.2 Hz, 1H), 6.75 (m, 1 H), 6.43 (dd, J=8.0, 1.5 Hz, 1 H), 6.32 (d, J=1.9 Hz, 1 H), 3.81 (s, 3 H), 1.61 (s, 6 H).

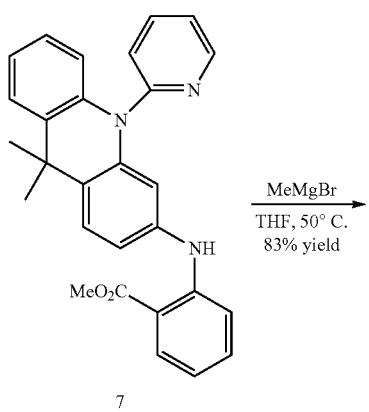

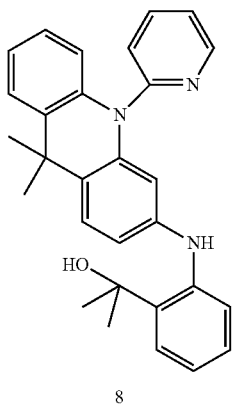

To a solution of 7 (1.02 g, 2.34 mmol) in THF (20 mL, 0.117 M) was slowly added methylmagnesium bromide (9.4 mL, 1 M in THF) at room temperature. The mixture was then heated to 50° C. and maintained at this temperature for 12 hours. The mixture was cooled to rt and quenched with saturated NH₄Cl (aq). The organic layer was then separated and the inorganic phase was extracted with EtOAc for three times. The combined organic phase was then dried over Na₂SO₄ and filtered through a short pad of silica gel. The filtrate was evaporated under reduced pressure. Purification by column chromatography (hexanes:EtOAc) gave 8 (847 mg, yield: 83%). ¹H NMR (500 MHz, DMSO-d₆, δ): 8.71-8.66 (m, 1 H), 8.35 (s, 1 H), 8.03 (t, J=7.8 Hz, 1 H), 7.49 (d, J=7.8 Hz, 1 H), 7.46-7.40 (m, 2 H), 7.34 (d, J=8.3 Hz, 1 H), 7.18 (d, J=7.8 Hz, 1 H), 7.08 (d, J=7.8 Hz, 1 H), 7.02 (t, J=8.1 Hz, 2 H), 6.96 (t, J=7.3 Hz, 1 H), 6.75 (t, J=7.6 Hz, 1 H), 6.61 (dd, J=8.3, 1.9 Hz, 1 H), 6.44 (d, J=8.3 Hz, 1 H), 6.15 (d, J=1.9 Hz, 1 H), 5.70 (s, 1 H), 1.58 (s, 6 H), 1.46 (s, 6 H).

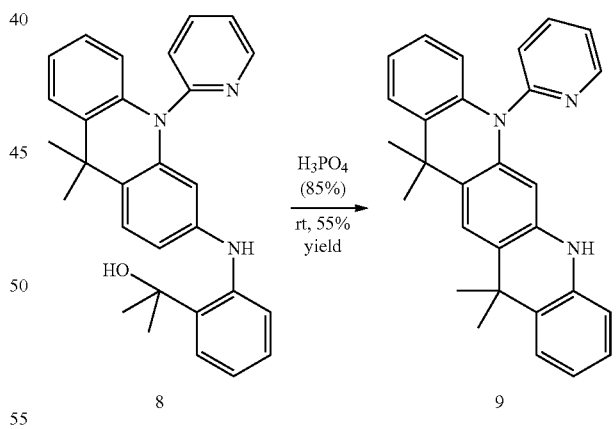

A solution of 8 (847 mg, 1.94 mmol) in 10 mL H₃PO₄ (85%, 0.194 M) was stirred at room temperature. After about 20 mins (monitored by TLC), 20 mL of water was added. The mixture was then slowly quenched with K₂CO₃. The mixture was extracted with EtOAc for three times. The combined organic phase was then dried over Na₂SO₄ and filtered through a short pad of silica gel. The filtrate was evaporated under reduced pressure. Purification by column chromatography (hexanes:EtOAc) gave 9 (445 mg, 55% yield). ¹H NMR (500 MHz, DMSO-d₆, δ): 8.76-8.71 (m, 1 H), 8.59 (s, 1 H), 8.07 (td, J=7.7, 1.5 Hz, 1 H), 7.53-7.45 (m, 2 H), 7.43

(d, J=7.9 Hz, 1 H), 7.40 (s, 1 H), 7.31 (d, J=7.9 Hz, 1 H), 7.02-6.90 (m, 3 H), 6.74 (t, J=7.8 Hz, 1 H), 6.65 (d, J=7.8 Hz, 1 H), 6.37 (d, J=8.3 Hz, 1 H), 5.89 (s, 1 H), 1.60 (s, 6 H), 1.50 (s, 6 H).

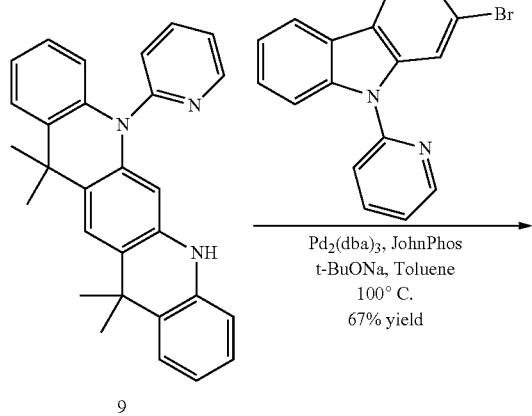

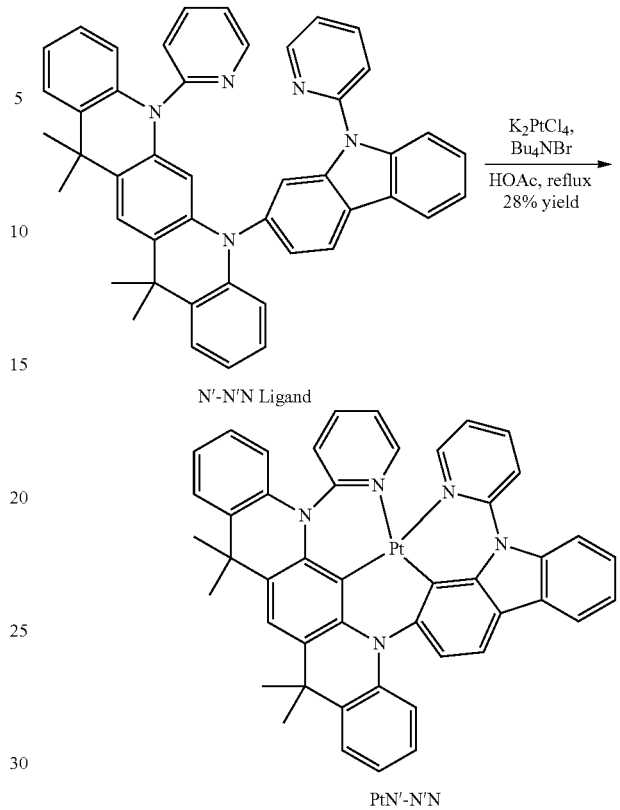

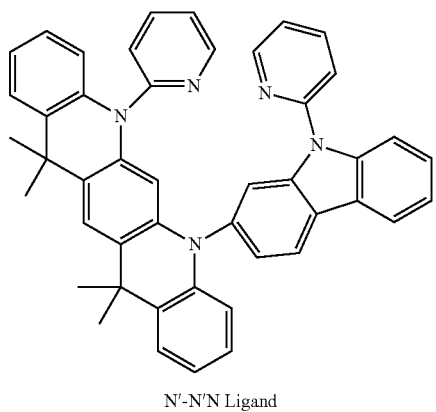

To a solution of 9 (84 g, 0.2 mmol) in toluene (10 mL, 0.02 M) were added 2-bromo-9-(pyridin-2-yl)-9H-carbazole (97 mg, 0.3 mmol), Pd$_2$(dba)$_3$ (9 mg, 0.01 mmol), JohnPhos (6 mg, 0.02 mmol) and t-BuONa (29 mg, 0.3 mmol). The reaction mixture was heated to reflux for 2 days. The mixture was cooled to rt and filtered through a short pad of Celite. The filtrate was concentrated under reduced pressure. Purification by column chromatography (hexanes:EtOAc) gave N'—N'N Ligand (89 mg, yield: 67%). $^1$H NMR (500 MHz, DMSO-d$_6$, δ): 8.74-8.68 (m, 1 H), 8.40-8.33 (m, 2 H), 8.11 (td, J=7.8, 1.5 Hz, 1 H), 7.96-7.90 (m, 2 H), 7.77 (d, J=7.8 Hz, 1 H), 7.59 (t, J=7.7 Hz, 1 H), 7.54-7.36 (m, 7 H), 7.06-6.99 (m, 2 H), 6.95-6.82 (m, 4 H), 6.46-6.39 (m, 1 H), 6.28-6.18 (m, 2 H), 4.95 (s, 1 H), 1.66 (s, 6 H), 1.58 (s, 6 H).

To a solution of N'—N'N ligand (89 mg, 0.055 mmol) in HOAc (5 mL, 0.011 M) were added K$_2$PtCl$_4$ (25 mg, 0.0605 mmol) and n-Bu$_4$NBr (2 mg, 0.0055 mmol). The mixture was heated to reflux and maintained at this temperature for 2 days. The reaction mixture was cooled to room temperature and filtered through a short pad of silica gel. The filtrate was concentrated under reduced pressure. Purification by column chromatography (hexanes:DCM=1:1 to 1:2) gave the PtN'—N'N (32 mg, yield: 28%) as a yellow solid. $^1$H NMR (500 MHz, DMSO-d$_6$, δ): 9.40 (d, J=5.9 Hz, 1 H), 9.15 (d, J=5.4 Hz, 1 H), 8.38 (d, J=8.7 Hz, 1 H), 8.17 (t, J=7.3 Hz, 1 H), 8.09-8.04 (m, 2 H), 7.92 (t, J=8.1 Hz, 1 H), 7.72 (d, J=7.9 Hz, 1 H), 7.59-7.45 (m, 4 H), 7.41-7.31 (m, 4 H), 7.27-7.15 (m, 4 H), 7.13-7.05 (m, 2 H), 7.01 (d, J=8.3 Hz, 1 H), 1.94 (s, 3 H), 1.90 (s, 3 H), 1.30 (s, 3 H), 1.15 (s, 3 H).

Example 6

Synthesis of PdN'—N'N

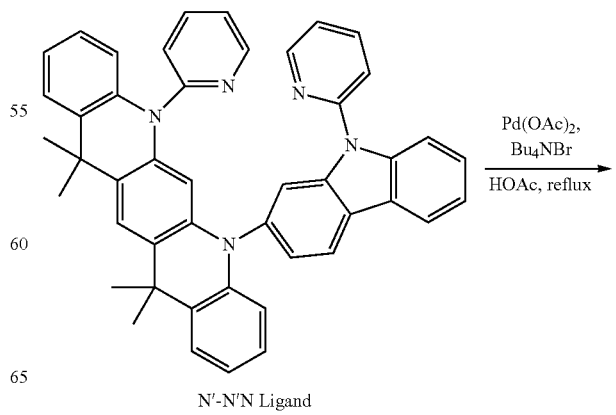

-continued

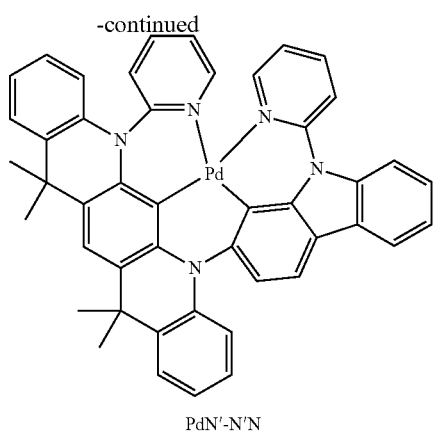

PdN'-N'N

To a solution of N'—N'N ligand (1 eq) in HOAc (5 mL, 0.02 M) were added Pd(OAc)$_2$ (1.05 eq) and n-Bu$_4$NBr (0.1 eq). The mixture was heated to reflux and maintained at this temperature for 2 days. The reaction mixture was cooled to room temperature and filtered through a short pad of silica gel. The filtrate was concentrated under reduced pressure. Purification by column chromatography (hexanes:DCM) gave the PdN'—N'N.

Example 7

Synthesis of PtN'—N'3

To a solution of 9 (1 eq) in toluene (0.02 M) were added 2-(3-bromophenyl)pyridine (1.5 eq), Pd$_2$(dba)$_3$ (0.05 eq), JohnPhos (0.1) and t-BuONa (1.5 eq). The reaction mixture was heated to reflux for 2 days. The mixture was cooled to rt and filtered through a short pad of Celite. The filtrate was concentrated under reduced pressure. Purification by column chromatography (hexanes:EtOAc) gave N'—N'3 Ligand.

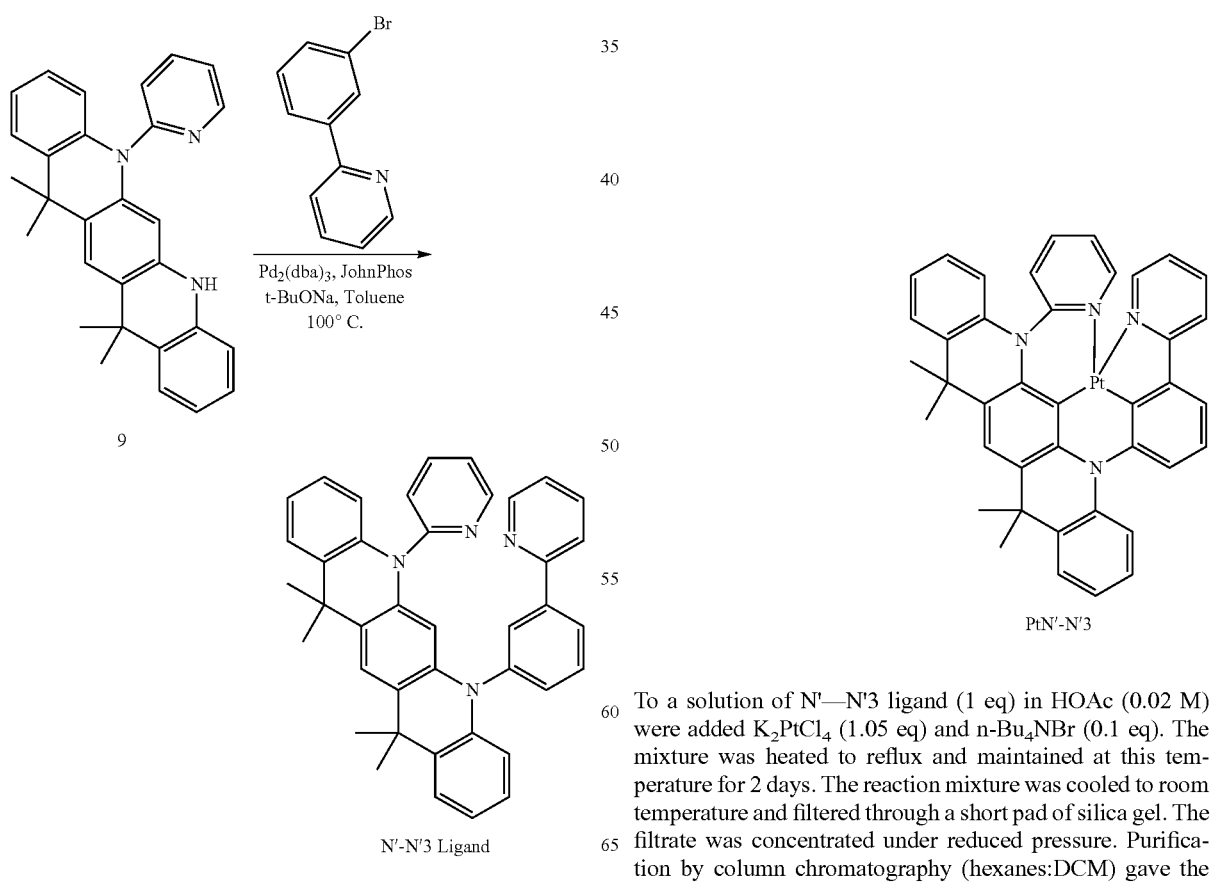

To a solution of N'—N'3 ligand (1 eq) in HOAc (0.02 M) were added K$_2$PtCl$_4$ (1.05 eq) and n-Bu$_4$NBr (0.1 eq). The mixture was heated to reflux and maintained at this temperature for 2 days. The reaction mixture was cooled to room temperature and filtered through a short pad of silica gel. The filtrate was concentrated under reduced pressure. Purification by column chromatography (hexanes:DCM) gave the PtN'—N'3.

Example 8

Synthesis of PdN'—N'3

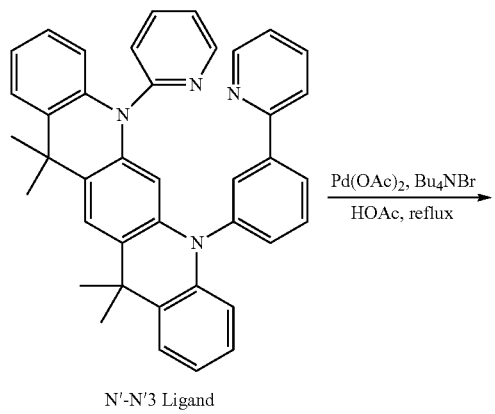

N'-N'3 Ligand

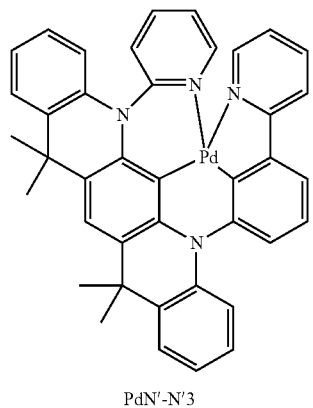

PdN'-N'3

To a solution of N'—N'3 ligand (1 eq) in HOAc (0.02 M) were added Pd(OAc)$_2$ (1.05 eq) and n-Bu$_4$NBr (0.1 eq). The mixture was heated to reflux and maintained at this temperature for 2 days. The reaction mixture was cooled to room temperature and filtered through a short pad of silica gel. The filtrate was concentrated under reduced pressure. Purification by column chromatography (hexanes:DCM) gave the PdN'—N'3.

A number of embodiments have been described. Nevertheless, it will be understood that various modifications may be made without departing from the spirit and scope of this disclosure. Accordingly, other embodiments are within the scope of the following claims.

What is claimed is:

1. A complex of Formula II:

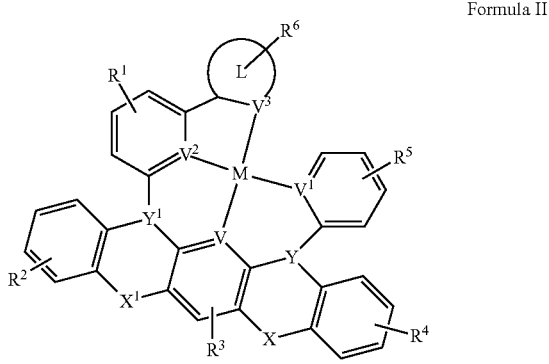

Formula II wherein:

M is Pt (II), Pd (II), or Au (III), each of V, $V^1$, $V^2$, and $V^3$ is independently N, C, P, or Si, each of X and $X^1$ is independently present or absent, and each X and $X^1$ present independently represents $CR^7R^8$, C=O, $SiR^7R^8$, $GeR^7R^8$, $NR^7$, $PR^7$, $PR^7R^8$, $R^7P$=O, $AsR^7$, $R^7As$=O, O, S, S=O, $SO_2$, Se, Se=O, $SeO_2$, $BR^7$, $BR^7R^8$, $AlR^7$, $AlR^7R^8$, $R^7Bi$=O, $BiR^7$, or a single bond, each of Y and $Y^1$ is independently $CR^9$, $SiR^9$, $GeR^9$, N, P, P=O, As, As=O, B, Bi=O, or Bi, L is a substituted or unsubstituted: 5-membered heteroaryl or 5-membered N-heterocyclic carbene, each of $R^1$, $R^2$, $R^3$, $R^4$, $R^5$, and $R^6$ is independently absent or present as a single substituent or multiple substituents, valency permitting, and each $R^1$, $R^2$, $R^3$, $R^4$, $R^5$, and $R^6$ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^7$, $R^8$, and $R^9$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

2. The complex of claim 1, wherein:
V and $V^2$ are C,
$V^1$ and $V^3$ are N,
Y and $Y^1$ are N, and
L is a substituted or unsubstituted 5-membered heteroaryl.

3. The complex of claim 2, wherein X is a single bond.

4. The complex of claim 3, wherein $X^1$ is $CR^8R^9$.

5. The complex of claim 1, wherein M is Pt or Pd; one of X and $X^1$ is $BR^7R^8$ or $AlR^7R^8$; and one of V, $V^1$, $V^2$, and $V^3$ is C or Si.

6. The complex of claim 1, wherein M is Pt or Pd; both of X and $X^1$ are independently $BR^7R^8$ or $AlR^7R^8$; and each of V, $V^1$, $V^2$, and $V^3$ is independently N or P.

7. The complex of claim 1, wherein M is Au; one of X and $X^1$ is $BR^7R^8$ or $AlR^7R^8$; and two of V, $V^1$, $V^2$, and $V^3$ are independently C or Si.

8. The complex of claim 1, wherein M is Au; both of X and $X^1$ are independently $BR^7R^8$ or $AlR^7R^8$; and one of V, $V^1$, $V^2$, and $V^3$ is C or Si.

9. A light emitting device comprising the complex of claim 1.

10. An OLED device comprising the complex of claim 1.

11. The OLED device of claim 10, wherein the device is a phosphorescent OLED device.

12. A photovoltaic device comprising the complex of claim 1.

13. A luminescent display device comprising the complex of claim 1.

14. The complex of claim 1, wherein X and $X^1$ are both $CR^8R^9$.

15. The complex of claim 14, wherein $R^8$ and $R^9$ are both alkyl.

16. The complex of claim 1, wherein M is Pt or Pd; X and $X^1$ are $CR^8R^9$; and each of V, $V^1$, $V^2$, and $V^3$ is independently C or N.

17. The complex of claim 1, wherein L is a substituted or unsubstituted 5-membered N-heterocyclic carbene.

18. The complex of claim 1, wherein each of $R^1$, $R^2$, $R^3$, $R^4$, $R^5$, and $R^6$ is hydrogen.

19. The complex of claim 1, wherein:
V and $V^2$ are C,
$V^1$ and $V^3$ are N,
Y and $Y^1$ are N, and
L is a substituted or unsubstituted 5-membered N-heterocyclic carbene.

* * * * *